US011602118B2

(12) United States Patent
Frederick et al.

(10) Patent No.: US 11,602,118 B2
(45) Date of Patent: Mar. 14, 2023

(54) METHODS AND COMPOSITIONS RELATED TO IMPROVED NITROGEN UTILIZATION EFFICIENCY IN TOBACCO

(71) Applicant: Altria Client Services LLC, Richmond, VA (US)

(72) Inventors: Jesse Frederick, Richmond, VA (US); Chengalrayan Kudithipudi, Midlothian, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 17/116,816

(22) Filed: Dec. 9, 2020

(65) Prior Publication Data

US 2021/0100213 A1  Apr. 8, 2021

Related U.S. Application Data

(63) Continuation of application No. 16/119,366, filed on Aug. 31, 2018, now Pat. No. 10,888,064.

(60) Provisional application No. 62/553,501, filed on Sep. 1, 2017.

(51) Int. Cl.
  *C12N 15/82*  (2006.01)
  *A01H 5/12*  (2018.01)
  *A01H 6/82*  (2018.01)
  *C07K 14/415*  (2006.01)
  *C12N 9/90*  (2006.01)
  *C12N 9/10*  (2006.01)
  *C12N 9/88*  (2006.01)
  *A01H 5/10*  (2018.01)

(52) U.S. Cl.
  CPC ............... *A01H 6/823* (2018.05); *A01H 5/10* (2013.01); *A01H 5/12* (2013.01); *C07K 14/415* (2013.01); *C12N 9/1085* (2013.01); *C12N 9/88* (2013.01); *C12N 9/90* (2013.01); *C12N 15/8227* (2013.01); *C12N 15/8237* (2013.01); *C12N 15/8261* (2013.01); *C12Y 205/01054* (2013.01); *C12Y 402/01033* (2013.01); *C12Y 501/03015* (2013.01)

(58) Field of Classification Search
  None
  See application file for complete search history.

(56) References Cited

U.S. PATENT DOCUMENTS

| | | | |
|---|---|---|---|
| 4,516,590 A | 5/1985 | Teng |
| 4,528,993 A | 7/1985 | Sensabaugh, Jr. et al. |
| 4,660,577 A | 4/1987 | Sensabaugh et al. |
| 4,683,195 A | 7/1987 | Mullis et al. |
| 4,683,202 A | 7/1987 | Mullis |
| 4,732,856 A | 3/1988 | Federoff |
| 4,761,373 A | 8/1988 | Anderson et al. |
| 4,762,785 A | 8/1988 | Comai |
| 4,769,061 A | 9/1988 | Comai |
| 4,800,159 A | 1/1989 | Mullis et al. |
| 4,810,648 A | 3/1989 | Stalker |
| 4,848,373 A | 7/1989 | Lenkey |
| 4,940,835 A | 7/1990 | Shah et al. |
| 4,945,050 A | 7/1990 | Sanford et al. |
| 4,965,188 A | 10/1990 | Mullis et al. |
| 4,975,374 A | 12/1990 | Goodman et al. |
| 4,987,907 A | 1/1991 | Townend |
| 5,004,863 A | 4/1991 | Umbeck |
| 5,013,658 A | 5/1991 | Dooner et al. |
| 5,013,659 A | 5/1991 | Bedbrook et al. |
| 5,104,310 A | 4/1992 | Saltin |
| 5,141,131 A | 8/1992 | Miller, Jr. et al. |
| 5,149,645 A | 8/1992 | Hoekema et al. |
| 5,159,135 A | 10/1992 | Umbeck |
| 5,162,602 A | 11/1992 | Somers et al. |
| 5,164,180 A | 11/1992 | Payne et al. |
| 5,177,010 A | 1/1993 | Goldman et al. |
| 5,231,019 A | 7/1993 | Paszkowski et al. |
| 5,276,268 A | 1/1994 | Strauch et al. |
| 5,316,931 A | 5/1994 | Donson et al. |
| 5,372,149 A | 12/1994 | Roth |
| 5,463,174 A | 10/1995 | Moloney et al. |

(Continued)

FOREIGN PATENT DOCUMENTS

| | | |
|---|---|---|
| EP | 0242246 | 10/1987 |
| JP | H09-503389 | 4/1997 |

(Continued)

OTHER PUBLICATIONS

Wijnker and Jong, 2008, Managing meiotic recombination in plant breeding, Trends in Plant Science 13: 640-646.*

Edwards et al., 2017, A reference genome for Nicotiana tabacum enables map-based cloning of homeologous loci implicated in nitrogen utilization efficiency, BMC Genomics 18:448, pp. 1-14.*

Edwards, K. D., et al. "A reference genome for Nicotiana tabacum enables map-based cloning of homeologous loci implicated in nitrogen utilization efficiency." BMC genomics 18.1 (2017): 1-14. (Year: 2017).*

Brauer et al., "Nitrogen Use Efficiency: re-construction of the Bioengineering Approach," *Botany*, 88(2):103-110 (2010).

(Continued)

*Primary Examiner* — Weihua Fan
(74) *Attorney, Agent, or Firm* — Arnold & Porter LLP

(57) ABSTRACT

The present disclosure provides metabolic signatures and genetic markers for tracking enhanced nitrogen utilization efficiency phenotypes in tobacco plants and for introgressing enhanced nitrogen utilization efficiency phenotypes into tobacco plants. The disclosure also provides tobacco plants comprising enhanced nitrogen utilization efficiency and methods to the creation of tobacco plants comprising enhanced nitrogen utilization efficiency. The disclosure also provides recombinant polynucleotides and polypeptides for enhancing nitrogen utilization efficiency in modified tobacco plants and tobacco plants comprising the provided recombinant polynucleotides and polypeptides.

19 Claims, 6 Drawing Sheets

Specification includes a Sequence Listing.

(56) References Cited

U.S. PATENT DOCUMENTS

| | | | |
|---|---|---|---|
| 5,464,763 | A | 11/1995 | Schilperoort et al. |
| 5,545,565 | A | 8/1996 | De Greve et al. |
| 5,561,236 | A | 10/1996 | Leemans et al. |
| 5,563,055 | A | 10/1996 | Townsend et al. |
| 5,589,367 | A | 12/1996 | Donson et al. |
| 5,659,026 | A | 8/1997 | Baszczynski et al. |
| 5,767,366 | A | 6/1998 | Sathasivan et al. |
| 5,789,156 | A | 8/1998 | Bujard et al. |
| 5,814,618 | A | 9/1998 | Bujard et al. |
| 5,866,785 | A | 2/1999 | Donson et al. |
| 5,879,903 | A | 3/1999 | Strauch et al. |
| 5,879,918 | A | 3/1999 | Tomes et al. |
| 5,886,244 | A | 3/1999 | Tomes et al. |
| 5,889,190 | A | 3/1999 | Donson et al. |
| 5,889,191 | A | 3/1999 | Turpen |
| 5,928,937 | A | 7/1999 | Kakefuda et al. |
| 5,932,782 | A | 8/1999 | Bidney |
| 5,981,840 | A | 11/1999 | Zhao et al. |
| 6,072,050 | A | 6/2000 | Bowen et al. |
| 6,084,155 | A | 7/2000 | Volrath et al. |
| 6,166,302 | A | 12/2000 | Merlo et al. |
| 6,451,732 | B1 | 9/2002 | Beckett et al. |
| 6,451,735 | B1 | 9/2002 | Ottaway et al. |
| 9,322,029 | B2 | 4/2016 | Davenport et al. |
| 10,888,064 | B2 * | 1/2021 | Frederick ............... A01H 6/823 |
| 2001/0016956 | A1 | 8/2001 | Ward et al. |
| 2003/0101487 | A1 | 5/2003 | Kisaka et al. |
| 2003/0110530 | A1 | 6/2003 | Shelp et al. |
| 2004/0118422 | A1 | 6/2004 | Lundin et al. |
| 2005/0178398 | A1 | 8/2005 | Breslin et al. |
| 2006/0191548 | A1 | 8/2006 | Strickland et al. |
| 2012/0024301 | A1 | 2/2012 | Carroll et al. |
| 2012/0031414 | A1 | 2/2012 | Atchley et al. |
| 2012/0031416 | A1 | 2/2012 | Atchley et al. |
| 2014/0223603 | A1 | 8/2014 | Xu et al. |
| 2015/0173319 | A1 | 6/2015 | Frederick et al. |

FOREIGN PATENT DOCUMENTS

| | | |
|---|---|---|
| JP | 2012-501190 | 1/2012 |
| JP | 2013-543377 | 12/2013 |
| WO | WO 2002/038736 | 5/2002 |
| WO | WO 2004/041006 A1 | 5/2004 |
| WO | WO 2007/092704 A2 | 8/2007 |
| WO | WO 2009/054735 | 4/2009 |
| WO | WO 2009/105612 | 8/2009 |
| WO | WO 2010/025465 A1 | 3/2010 |
| WO | WO 2011/025514 A1 | 3/2011 |
| WO | WO 2018/068000 | 4/2018 |

OTHER PUBLICATIONS

Chenna et al., "Multiple Sequence Alignment with the Clustal Series of Programs," *Nucleic Acids Research*, 31(13):3497-3500 (2003).

Davis et al., "Tobacco, Production, Chemistry and Technology," eds., Blackwell Publishing, Oxford, Chapters 4B and 4C, pp. 70-103 (1999).

Dayhoff et al., "22 A Model of Evolutionary Change in Proteins," *Atlas of Protein Sequence and Structure*, 5(Suppl. 3):345-352 (1978).

Fischhoff et al., "Insect Tolerant Transgenic Tomato Plants," *Nature Biotechnology*, 5:807-813 (1987).

GenBank Accession No. AF352732.1 "Nicotiana tabacum glutamate decarboxylase isozyme 1 mRNA, complete cds," 2 pages.

Gut et al., "A Common Structural Basis for PH- and Calmodulin-mediated Regulation in Plant Glutamate Decarboxylase," *Journal of Molecular Biology*, 392(2):334-351 (2009).

Ha et al., "Cis-acting Regulatory Elements Controlling Temporal and Organ-Specific Activity of Nopaline Synthase Promoter," *Nucleic Acids Research*, 11;17(1):215-23 (1989).

Hansen et al., "Wound-inducible and Organ-Specific Expression of ORF13 from *Agrobacterium rhizogenes* 8196 T-DNA in Transgenic Tobacco Plants," *Molecular General Genetics*, 254(3):337-343 (1997).

Hill et al., "Functional Analysis of Conserved Histidines in ADP-glucose Pyrophosphorylase from *Escherichia coli*," *Biochemical and Biophysical Research Communications*, 244(2):573-7 (1998).

Hörtensteiner et al., "Chlorophyll Breakdown in Higher Plants," *Biochimica et Biophysica Acta*, 1807:977-988 (2011).

International Search Report and Written Opinion in International Application No. PCT/US2017/055635, dated Jan. 26, 2018, 16 pages.

Kim et al., "A 20 Nucleotide Upstream Element is Essential for the Nopaline Synthase (nos) Promoter Activity," *Plant Molecular Biology*, 24(1):105-17 (1994).

Kouranov et al., "Analysis of the Interactions of Preproteins with the Import Machinery over the Course of Protein Import into Chloroplasts," *Journal of Cell Biology*, 139(7):1677-1685 (1997).

Kouranov et al., "Tic20 and Tic22 Are New Components of the Protein Import Apparatus at the Chloroplast Inner Envelope Membrane," *Journal of Cell Biology*, 143(4):991-1002 (1998).

Kumar et al., "Comparative Phylogenetic Analysis and Transcriptional Profiling of MADS-box Gene Family Identified DAM and FLC-like Genes in Apple (Malus x domestica)," *Scientific Reports*, 6:20695 (2016).

Li et al., "A Fast Neutron Deletion Mutagenesis-based Reverse Genetics System for plants," *The Plant Journal*, 27(3):235-242 (2001).

Li et al., "Modularly Assembled Designer TAL Effector Nucleases for Targeted Gene Knockout and Gene Replacement in Eukaryotes," *Nucleic Acids Research* 39(14):6315-6325 (2011).

Matsuyama et al., "Characterization of Glutamate Decarboxylase Mediating γ-Amino Butyric Acid Increase in the Early Germination Stage of Soybean," *Journal of Bioscience and Bioengineering*, 107(5):538-543 (2009).

Ruiter et al., "Spontaneous Mutation Frequency in Plants Obscures the Effect of Chimeraplasty," *Plant Molecular Biology*, 53(5):675-89 (2003).

Vaeck et al., "Transgenic Plants Protected from Insect Attack," *Nature*, 328:33-37 (1987).

Wright et al., "High-frequency Homologous Recombination in Plants Mediated by Zinc-Finger Nucleases," *The Plant Journal*, 44:693-705 (2005).

Yevtushenko et al., "Calcium/calmodulin Activation of two Divergent Glutamate Decarboxylases from Tobacco," *Journal of Experimental Botany*, 54(389):2001-2002 (2003).

Yoo et al., "*Arabidopsis* Mesophyll Protoplasts: a Versatile Cell System for Transient Gene Expression Analysis," *Nature Protocols*, 2(7):1565-1572 (2007).

Yu et al., "Overexpression of *Arabidopsis* NLP7 Improves Plant Growth Under Both Nitrogen-limiting and Sufficient Conditions by Enhancing Nitrogen and Carbon Assimilation," *Scientific Reports*, 6(1):113 (2016).

Zhou et al., "The Plant Cyclin-dependent Kinase Inhibitor ICK1 has Distinct Functional Domains for In Vivo Kinase Inhibition, Protein Instability and Nuclear Localization," *The Plant Journal*, 35(4):476-89 (2003).

Allen et al., "microRNA-Directed Phasing During *Trans*-Acting siRNA Biogenesis in Plants," *Cell*, 121:207-221 (2005). U.S. Appl. No. 16/119,366.

Altschul et al., "Basic Local Alignment Search Tool," *J. Mol. Biol.*, 215:403-410 (1990). U.S. Appl. No. 16/119,366.

Altschul et al., "Gapped BLAST and PSI-BLAST: a New Generation of Protein Database Search Programs," *Nucleic Acids Res.*, 25:3389-3402 (1997). U.S. Appl. No. 16/119,366.

Bartel, "MicroRNAs: Genomics, Biogenesis, Mechanism, and Function," *Cell*, 116:281-297 (2004). U.S. Appl. No. 16/119,366.

Bindler et al., "A High Density Genetic Map of Tobacco (*Nicotiana tabacum* L.) Obtained from Large Scale Microsatellite Marker Development," *Theor. Appl. Genet*, 123:219-230 (2011). U.S. Appl. No. 16/119,366.

Bingguang et al., "SNP-based Genetic Linkage Map of Tobacco (*Nicotiana tabacum* L.) Using Next-Generation RAD Sequencing," *J. of Biol. Res-Thessaloniki*, 22:11 (2015). U.S. Appl. No. 16/119,366.

(56) References Cited

OTHER PUBLICATIONS

Canevascini et al., "Tissue-Specific Expression and Promoter Analysis of the Tobacco Itp1 Gene," Plant Physiol., 112(2):513-524 (1996). U.S. Appl. No. 16/119,366.

Christou et al., "Stable Transformation of Soybean Callus by DNA-Coated Gold Particles," *Plant Physiol.*, 87:671-674 (1988). U.S. Appl. No. 16/119,366.

Christensen et al., "Sequence Analysis and Transcriptional Regulation by Heat Shock of Polyubiquitin Transcripts from Maize," *Plant Mol. Biol.*, 12:619-632 (1989). U.S. Appl. No. 16/119,366.

Christensen et al., "Maize Polyubiquitin Genes: Structure, Thermal of Expression and Transcript Splicing, and Promoter Activity Following Transfer to Protoplasts by Electroporation," *Plant Mol. Biol.*, 18:675-689 (1992). U.S. Appl. No. 16/119,366.

Crossway et al., "Micromanipulation Techniques in Plant Biotechnology," *Biotechniques*, 4:320-334 (1986). U.S. Appl. No. 16/119,366.

D'Halluin et al., "Transgenic Maize Plants by Tissue Electroporation," *Plant Cell*, 4:1495-1505 (1992). U.S. Appl. No. 16/119,366.

De Wet et al., "Exogenous Gene Transfer in Maize (*Zea mays*) Using DNA-treated Pollen," The Experimental Manipulation of Ovule Tissues, pp. 197-209 (1985). U.S. Appl. No. 16/119,366.

Fedoroff et al., "Cloning of the *bronze* Locus in Maize by a Simple and Generalizable Procedure Using the Transposable Controlling Element Activator (Ac)," *Proc. Natl. Acad. Sci.*, 81:3825-3829 (1984). U.S. Appl. No. 16/119,366.

Finer et al., "Transformation of Soybean Via Particle Bombardment of Embryogenic Suspension Culture Tissue," *In Vitro Cell Dev. Biol.*, 27P:175-182 (1991). U.S. Appl. No. 16/119,366.

Gatz et al., "Regulation of a Modified CaMV 35S Promoter by the Tn 10-encoded Tet repressor in Transgenic Tobacco," Mol. Gen. Genet., 227:229-237 (1991). U.S. Appl. No. 16/119,366.

Goldman et al., "Female Sterile Tobacco Plants are Produced by Stigma-Specific Cell Ablation," *EMBO Journal*, 13:2976-2984 (1994). U.S. Appl. No. 16/119,366.

Griffiths-Jones et al., "Rfam: anRNA Family Database," *Nucleic Acids Res.*, 31:439-441 (2003). U.S. Appl. No. 16/119,366.

Guevara-Garcia et al., "Tissue-Specific and Wound-Inducible Pattern of Expression of the Mannopine Synthase Promoter is Determined by the Interaction Between Positive and Negative cis-regulatory Elements," *Plant J.*, 4(3):495-505 (1993). U.S. Appl. No. 16/119,366.

Hildering et al., "The Use of Induced Mutations in Plant Breeding," Pergamon Press, pp. 317-320 (1965). U.S. Appl. No. 16/119,366.

Hoekema et al., "A Binary Plant Vector Strategy Based on Separation of vir-and T-region of the *Agrobacterium tumefaciens* Ti-plasmid," *Nature*, 303:179-180 (1983). U.S. Appl. No. 16/119,366.

Horsch et al., "A Simple and General Method for Transferring Genes into Plants," *Science*, 227:1229-1231 (1985). U.S. Appl. No. 16/119,366.

International Search Report and Written Opinion in International Application PCT/US2018/049156 dated Jan. 28, 2019. U.S. Appl. No. 16/119,366.

Kaeppler et al., "Silicon Carbide Fiber-mediated DNA Delivery into Plant Cells," *Plant Cell Reports*, 9:415-418 (1990). U.S. Appl. No. 16/119,366.

Kaeppler et al., "Silicon Carbide Fiber-mediated Stable Transformation of Plant Cells," *Theor. Appl. Genet.*, 84:560-566 (1992). U.S. Appl. No. 16/119,366.

Kawamata et al., "Temporal and Spatial Pattern of Expression of the Pea Phenylalanine Ammonia-Lyase Gene 1 Promoter in Transgenic Tobacco," Plant Cell Physiol. 38(7):792-803 (1997).

Ladha et al. "Efficiency of Fertilizer Nitrogen in Cereal Production Retrospects and Prospects," *Advances in Agronomy*, 87:85-156 (2005). U.S. Appl. No. 16/119,366.

Lam, "8 Analysis of Tissue-Specific Elements in the CaMV 35S Promoter," *Results Probl. Cell Differ.*, 20:181-196 (1994). U.S. Appl. No. 16/119,366.

Last et al., "pEmu: an Improved Promoter for Gene Expression in Cereal Cells," *Theor. Appl. Genet.*, 81:581-588 (1991). U.S. Appl. No. 16/119,366.

Lin-Hui et al., "Overexpression of *Arabidopsis NLP7* Improves Plant Growth Under Both Nitrogen-limiting and -sufficient Conditions by Enhancing Nitrogen and Carbon Assimilation," *Scientific Reports*, 6:27795, 1-13 (2016). U.S. Appl. No. 16/119,366.

Matsuoka et al., "Tissue-Specific Light-Regulated Expression Directed by the Promoter of a C4 Gene, Maize Pyruvate, Orthophosphate Dikinase, in a C3 Plant, Rice," Proc. Natl. Acad. Sci. USA, 90(20):9586-9590 (1993). U.S. Appl. No. 16/119,366.

Mayo et al., "Genetic Transformation of Tobacco NT1 Cells with *Agrobacterium tumefaciens*," Nat. Protoc., 1:1105-11 (2006). U.S. Appl. No. 16/119,366.

McCabe et al., "Stable Transformation of Soybean (Glycine Max) by Particle Acceleration," *Biotechnology*, 6:923-926 (1988). U.S. Appl. No. 16/119,366.

McCallum et al., "Targeted Screening for Induced Mutations," *Nat. Biotechnol.*, 18:455-457 (2000). U.S. Appl. No. 16/119,366.

McNellis et al., "Glucocorticoid-Inducible Expression of a Bacterial Avirulence Gene in Transgenic *Arabidopsis* Induces Hypersensitive Cell Death," *Plant J.* 14(2):247-257 (1998). U.S. Appl. No. 16/119,366.

Nicotiana tomentosifoimis kirola-like (LOC104105589), GenBank accession No. XM_009613937 (2016). U.S. Appl. No. 16/119,366.

Odell et al., "Identification of DNA Sequences Required for Activity of the Cauliflower Mosaic Virus 35S Promoter," *Nature*, 313:810-812 (1985). U.S. Appl. No. 16/119,366.

Orozco et al., "Localization of Light-Inducible and Tissue-Specific Regions of the Spinach Ribulose Bisphosphate Carboxylase/Oxygenase (subisco) Activase Promoter in Transgenic Tobacco Plants," *Plant Mol. Biol.*, 23(6): 1129-1138 (1993). U.S. Appl. No. 16/119,366.

Parizotto et al., "In vivo Investigation of the Transcription, Processing, Endonucleolytic Activity, and Functional Relevance of the Spatial Distribution of a Plant miRNA," *Genes Dev.*, 18:2237-2242 (2004). U.S. Appl. No. 16/119,366.

Paszkowski et al., "Direct Gene Transfer to Plants," *EMBO J.*, 3(12):2717-2722 (1984). U.S. Appl. No. 16/119,366.

Poehlman, "Breeding Field Crops," Van Nostrand Reinhold, New York (3.sup.rded.), (1987). U.S. Appl. No. 16/119,366.

Porta et al., "Use of Viral Replicons for the Expression of Genes in Plants," Molecular Biotechnology, 5:209-221 (1996). U.S. Appl. No. 16/119,366.

Reynolds et al., "Rational siRNA Design for RNA Interference," Nature Biotechnol., 22:326-330 (2004). U.S. Appl. No. 16/119,366.

Riggs et al., "Stable Transformation of Tobacco by Electroporation: Evidence for Plasmid Concatenation," Proc. Natl. Acad. Sci. USA, 83:5602-5606 (1986). U.S. Appl. No. 16/119,366.

Rinehart et al., "Tissue-Specific and Developmental Regulation of Cotton Gene FbL2A, " Plant Physiol., 112(3):1331-1341 (1996). U.S. Appl. No. 16/119,366.

Russell et al., "Tissue-Specific Expression in Transgenic Maize of Four Endosperm Promoters from Maize and Rice," Transgenic Res., 6(2): 157-168 (1997). U.S. Appl. No. 16/119,366.

Schena et al., "A Steroid-Inducible Gene Expression System for Plant Cells," Proc. Natl. Acad. Sci. USA, 88:10421-10425 (1991). U.S. Appl. No. 16/119,366.

Search Report dated Mar. 28, 2022 in Chinese Appln. 2018800665073 along with English translation of related Office Action. U.S. Appl. No. 16/119,366.

Shillito et al., "Direct Gene Transfer to Protoplasts of Dicotyledonous and Monocotyledonous Plants by a Number of Methods, Including Electroporation," *Meth. Enzymol.*, 153:313-336 (1987). U.S. Appl. No. 16/119,366.

Sierro et al., "Reference genomes and transcriptomes of Nicotiana sylvestris and *Nicotiana tomentosiformis*," *Genome Biology* 14:R50:1-17 (2013). U.S. Appl. No. 16/119,366.

Singh et al., "Cytological Characterization of Transgenic Soybean," *Theor. Appl. Genet.*, 96:319-324 (1998). U.S. Appl. No. 16/119,366.

Tanaka et al., "Studies on Biological Effects of Ion Beams on Lethality, Molecular Nature of Mutation, Mutation Rate, and Spectrum of Mutation Phenotype for Mutation Breeding in Higher Plants," *J. Radiat. Res.*, 51:223-233 (2010). U.S. Appl. No. 16/119,366.

Thompson et al., "Clustal W: Improving the Sensitivity of Progressive Multiple Sequence Alignment through Sequence Weighting,

(56) References Cited

OTHER PUBLICATIONS

Position-Specific Gap Penalties and Weight Matrix Choice," *Nucl. Acids Res.*, 22:4673-4680 (1994). U.S. Appl. No. 16/119,366.

Tomes et al., "16 Direct DNA Transfer into Intact Plant Cells Via Microprojectile Bombardment," *Plant Cell, Tissue, and Organ Culture Fundamental Methods*, pp. 197-198 (1995). U.S. Appl. No. 16/119,366.

Van Camp et al., "Tissue-Specific Activity of Two Manganese Superoxide Dismutase Promoters in Transgenic Tobacco," Plant Physiol., 112(2):525-535 (1996). U.S. Appl. No. 16/119,366.

Verkerk, "Chimerism of the Tomato Plant After Seed Irradiation with Fast Neutrons," *Neth. J. Agric. Sci.*, 19:197-203 (1971). U.S. Appl. No. 16/119,366.

Velten et al., "Isolation of a Dual Plant Promoter Fragment from the Ti Plasmid of *Agrobacterium tumefaciens*," EMBO J., 3:2723-2730 (1984). U.S. Appl. No. 16/119,366.

Weising et al., "Foreign Genes in Plants: Transfer, Structure, Expression, and Applications," *Annu. Rev. Genet.*, 22:421-477 (1988). U.S. Appl. No. 16/119,366.

Wemsman et al., "Principles of cultivar development," Chapter Seventeen: Tobacco, MacMillan Publishing Company, New York, 2:669-698 (1987). U.S. Appl. No. 16/119,366.

Yamamoto et al., "The Promoter of a Pine Photosynthetic Gene Allows Expression of a js-Glucuronidase Reporter Gene in Transgenic Rice Plants in a Light-Independent but Tissue-Specific Manner," Plant Cell Physiol., 35(5):773-778 (1994). U.S. Appl. No. 16/119,366.

Yamamoto et al., "Light-Responsive Elements of the Tobacco PSI-D Gene are Located both Upstream and within the Transcribed Region," Plant J., 12(2):255-265 (1997). U.S. Appl. No. 16/119,366.

\* cited by examiner

SEQUENCE LISTING

<160> NUMBER OF SEQ ID NOS: 65

<210> SEQ ID NO 1
<211> LENGTH: 128
<212> TYPE: PRT
<213> ORGANISM: Nicotiana tabacum

<400> SEQUENCE: 1

```
Met Gly Leu Lys Gly Lys Leu Ile Ser Gln Met Glu Met Lys Cys Ala
1               5                   10                  15

Gly Asp Leu Leu His Glu His Phe Lys Ser Asn Pro His Gln Thr Ser
            20                  25                  30

Thr Met Ser Pro Asp Lys Ile Thr Asn Phe Thr Leu His Glu Gly Gln
        35                  40                  45

Leu Gly Asn Thr Gly Ser Val Val Ser Trp Lys Tyr Val Leu Gly Gly
    50                  55                  60

Lys Glu Arg His Ala Lys Gln Ala Leu His Ile Asp Asp Ala Lys Lys
65                  70                  75                  80

Ser Ile Thr Phe Asn Phe Leu Glu Gly Tyr Met Asn Glu Leu Tyr Lys
                85                  90                  95

Ser Met Thr Pro Gln Tyr Arg Ile Asn Asn Asn Leu Glu Cys His Lys
            100                 105                 110

Ser Arg Asn His Pro Met Gln Val Thr Ser Pro Asn His Thr Gln Ile
        115                 120                 125
```

<210> SEQ ID NO 2
<211> LENGTH: 540
<212> TYPE: PRT
<213> ORGANISM: Nicotiana tabacum

<400> SEQUENCE: 2

```
Met Lys Ala Glu Gly Ser Ala Leu Ser Ser Ala Gly Ser Tyr His Arg
1               5                   10                  15

Leu Ala Tyr His Glu Val Ile Asn Asp Asp Asn Gln Asn Lys Ile Phe
            20                  25                  30

Thr Ser Asp Asp Ser Arg Leu Arg Gln Leu Gly Tyr Lys Gln Glu Leu
        35                  40                  45

Tyr Arg Gly Leu Ser Phe Ile Ala Asn Phe Ser Phe Thr Phe Ala Ile
    50                  55                  60

Val Ser Val Leu Thr Gly Ile Ser Thr Leu Tyr Asn Gln Ala Leu Thr
65                  70                  75                  80

Phe Gly Gly Pro Ile Thr Leu Val Tyr Gly Trp Pro Ile Val Ser Leu
                85                  90                  95

Met Thr Leu Ile Val Gly Leu Ala Met Ala Glu Ile Cys Ser Ala Tyr
            100                 105                 110
```

```
Pro Thr Ser Ala Gly Leu Tyr Tyr Trp Ser Ala Lys Leu Ser Gly Asn
        115                 120                 125

Tyr Phe Gly Pro Phe Ala Ser Trp Ile Thr Gly Trp Phe Asn Ile Val
    130                 135                 140

Gly Gln Trp Ala Val Thr Ala Ser Ile Asp Phe Ser Leu Ala Gln Leu
145                 150                 155                 160

Val Gln Val Met Ile Leu Leu Ser Thr Gly Gly Leu Asn Gly Gly Gly
                165                 170                 175

Tyr Gln Ala Ser Lys Tyr Val Val Ile Ala Leu His Gly Gly Ile Leu
                180                 185                 190

Leu Leu His Ala Ile Leu Asn Ser Leu Pro Ile Ser Trp Leu Ser Phe
        195                 200                 205

Phe Gly Gln Leu Ala Ala Ala Trp Asn Val Leu Gly Val Phe Leu Leu
    210                 215                 220

Met Ile Leu Ile Pro Met Val Ser Thr Glu Arg Ala Ser Ala Lys Phe
225                 230                 235                 240

Val Phe Thr Asn Phe Asn Thr Asp Asn Gly Asp Gly Ile Asn Asn Asn
                245                 250                 255

Leu Tyr Ile Phe Val Leu Gly Leu Leu Met Ser Gln Tyr Thr Leu Thr
        260                 265                 270

Gly Tyr Asp Ala Ser Ala His Met Thr Glu Glu Thr Lys Asn Ala Asp
    275                 280                 285

Lys Asn Gly Pro Lys Gly Ile Val Ser Ala Ile Gly Ile Ser Val Leu
290                 295                 300

Ala Gly Trp Ala Tyr Ile Leu Gly Ile Thr Phe Ala Val Thr Asp Ile
305                 310                 315                 320

Pro His Leu Leu Asn Lys Asn Asn Asp Ser Gly Gly Tyr Ala Ile Ala
                325                 330                 335

Gln Ile Phe Tyr Asp Ala Phe Lys Asn Arg Tyr Gly Ser Gly Val Gly
        340                 345                 350

Gly Ile Ile Cys Leu Gly Val Ile Ala Ile Ala Val Phe Phe Cys Gly
    355                 360                 365

Met Ser Ser Leu Thr Ser Asn Ser Arg Met Ala Tyr Ala Phe Ser Arg
370                 375                 380

Asp Gly Ala Met Pro Tyr Ser Ser Phe Trp His Lys Val Asn Lys Gln
385                 390                 395                 400

Glu Val Pro Leu Asn Ala Val Trp Met Ser Ala Phe Ile Ala Phe Cys
                405                 410                 415

Met Ala Leu Thr Ser Leu Gly Ser Leu Val Ala Phe Gln Ala Met Thr
        420                 425                 430

Ser Ile Ala Thr Ile Gly Leu Tyr Ile Ala Tyr Ala Leu Pro Ile Leu
    435                 440                 445

Phe Arg Val Thr Leu Ala Arg Lys Ser Phe Thr Pro Gly Pro Phe Asn
450                 455                 460

Leu Gly Ser Tyr Gly Leu Val Val Gly Trp Val Ala Ile Phe Trp Val
465                 470                 475                 480

Ala Leu Ile Ser Val Leu Phe Ser Leu Pro Val Ala Tyr Pro Ile Thr
                485                 490                 495

Asp Gln Thr Leu Asn Tyr Thr Pro Val Ala Val Gly Gly Leu Leu Ile
        500                 505                 510

Leu Val Val Ser Ser Trp Ile Phe Ser Ala Ile His Trp Phe Lys Gly
    515                 520                 525
```

```
Pro Ile Thr Asn Leu Gly Asn Ser Ser Glu Glu Ala
    530                 535                 540
```

<210> SEQ ID NO 3
<211> LENGTH: 145
<212> TYPE: PRT
<213> ORGANISM: Nicotiana tabacum

<400> SEQUENCE: 3

```
Met Ala Ser Thr Gln Gln Ala Val Ser Ser Gly Ser Asp Ala Asp Gln
1               5                   10                  15

Arg Tyr Ala Lys Phe Asp Glu Arg Lys Arg Lys Arg Met Glu Ser Asn
            20                  25                  30

Arg Glu Ser Ala Arg Arg Ser Arg Met Arg Lys Gln Gln Arg Leu Gly
        35                  40                  45

Glu Leu Met Ser Glu Thr Thr Gln Leu Gln Asn Gln Asn Ser Ile Cys
    50                  55                  60

Arg Glu Arg Ile Asp Ser Val Glu Arg Asn Tyr Cys Ala Ile Asp Ala
65                  70                  75                  80

Glu Asn Asn Val Leu Arg Ala Gln Ile Ala Glu Leu Thr Glu Arg Leu
                85                  90                  95

Asn Ser Leu Asn Ser Leu Thr Gln Phe Trp Ala Asp Ala Thr Gly Phe
            100                 105                 110

Pro Val Asp Leu Pro Glu Ile Pro Asp Thr Leu Leu Glu Pro Trp Gln
        115                 120                 125

Leu Pro Cys Pro Ile Gln Pro Ile Asp Ala Ser Ser Asp Met Leu Leu
    130                 135                 140

Phe
145
```

<210> SEQ ID NO 4
<211> LENGTH: 654
<212> TYPE: PRT
<213> ORGANISM: Nicotiana tabacum

<400> SEQUENCE: 4

```
Met Pro Gly Val Tyr Leu Glu Thr Ala Ser Leu Pro Lys Gly Arg Gly
1               5                   10                  15

Leu Glu Cys Gln Glu Ser Gln Ala Val Arg Tyr Phe Phe Arg Gly Arg
            20                  25                  30

Asn Lys Val Asp Asp Ser Leu Thr Ile Glu Ile Phe Asn Leu Phe Pro
        35                  40                  45

Trp Ile Phe Phe Thr Ile Leu Ala Met Asp Lys His His Gln Leu
    50                  55                  60

Pro Leu Thr Lys Ser Thr Ser Arg Gln Arg Tyr Asn Glu Trp Val Phe
65                  70                  75                  80

Arg Asp Val Pro Ser Asp Ile Thr Ile Glu Val Asp Gly Gly Ile Phe
                85                  90                  95

Ser Leu His Lys Phe Pro Leu Val Ser Arg Ser Gly Arg Ile Arg Arg
            100                 105                 110

Leu Val Ala Glu His Arg Asp Ser Asp Ile Ser Arg Ile Glu Leu Val
        115                 120                 125

Ser Leu Pro Gly Gly Thr Glu Ser Phe Glu Leu Ala Ala Lys Phe Cys
    130                 135                 140

Tyr Gly Val Asn Phe Glu Ile Thr Ala Ala Asn Val Ala Gln Leu Cys
145                 150                 155                 160
```

```
Cys Val Ser Asp Tyr Leu Glu Met Ser Glu Asp Tyr Ser Lys Asn Asn
            165                 170                 175

Leu Gly Ser Arg Ala Glu Glu Tyr Leu Asp Ser Ile Val Cys Lys Asn
        180                 185                 190

Leu Glu Met Cys Val Glu Val Leu Arg Gln Cys Glu Asn Leu Leu Pro
        195                 200                 205

Leu Ala Asp Glu Leu Lys Val Val Ser Arg Cys Ile Asp Ala Val Ala
        210                 215                 220

Ser Lys Ala Cys Val Glu Gln Ile Ala Ser Ser Phe Ser Arg Leu Glu
225                 230                 235                 240

Tyr Ser Ile Ser Gly Gly Arg Leu His Met Ser Lys Gln Ala Asn Cys
                245                 250                 255

Glu Leu Asp Trp Trp Ile Glu Asp Ile Ser Met Leu Arg Ile Asp Leu
            260                 265                 270

Tyr Gln Arg Val Ile Thr Ala Met Lys Phe Arg Gly Val Arg Pro Glu
        275                 280                 285

Ser Ile Ala Ala Ser Leu Val Asn Tyr Ala Gln Lys Glu Leu Ile Gln
        290                 295                 300

Lys Thr Leu Ser Gly Ser Asn Ile Gln Glu Lys Leu Val Val Glu Thr
305                 310                 315                 320

Ile Val Ser Leu Met Pro Val Glu Lys Phe Val Val Pro Leu Thr Phe
                325                 330                 335

Leu Phe Gly Leu Leu Arg Ser Ala Val Met Leu Asp Cys Thr Val Ala
            340                 345                 350

Cys Arg Leu Asp Leu Glu Arg Arg Ile Gly Ser Gln Leu Asp Thr Ala
        355                 360                 365

Thr Leu Asp Asp Ile Leu Ile Pro Ser Phe Arg His Ala Gly Asp Thr
        370                 375                 380

Leu Phe Asp Val Asp Thr Val His Arg Ile Leu Val Asn Phe Ser Gln
385                 390                 395                 400

Gln Glu Gly Asp Ser Asp Asp Met Glu Asp Val Ser Val Phe Glu
                405                 410                 415

Ser Asp Ser Pro Thr Thr Thr Pro Ser Gln Thr Ala Leu Phe Lys Val
            420                 425                 430

Ser Lys Leu Val Asp Asn Tyr Leu Ala Glu Ile Ala Leu Asp Ala Asn
        435                 440                 445

Leu Lys Leu Asn Lys Phe Ile Ala Val Ala Glu Thr Leu Pro Ala His
        450                 455                 460

Ala Arg Thr Val His Asp Gly Leu Tyr Arg Ala Ile Asp Leu Tyr Leu
465                 470                 475                 480

Lys Ala His Gln Thr Leu Ser Asp Pro Asp Lys Arg Arg Leu Cys Lys
                485                 490                 495

Leu Ile Asp Phe Gln Lys Leu Ser Gln Glu Ala Gly Ala Gln Ala Ala
            500                 505                 510

Gln Asn Glu Arg Leu Pro Leu Gln Ser Ile Val Gln Val Leu Tyr Phe
        515                 520                 525

Glu Gln Leu Arg Leu Arg Asn Ala Leu Phe Cys Ser Tyr Pro Asp Asp
        530                 535                 540

Asp Ile Lys Pro Thr His Gln Ser Trp Arg Ile Asn Ser Gly Ala Leu
545                 550                 555                 560

Ser Ala Ala Met Ser Pro Lys Asp Asn Tyr Ala Ser Leu Arg Arg Glu
                565                 570                 575
```

```
Asn Arg Glu Leu Lys Leu Glu Leu Ala Arg Met Arg Met Arg Leu Asn
            580                 585                 590

Asp Leu Glu Lys Asp His Val Cys Met Lys Arg Asn Met Gln Lys Ser
            595                 600                 605

Ser Ser Arg Arg Phe Met Lys Ser Phe Ser Lys Arg Ile Gly Lys Lys
610                 615                 620

Phe Asn Ile Phe Gly His Asn Phe Ser Arg Asp Cys Ser Ser Pro Ser
625                 630                 635                 640

Ser Gln Ser Glu Arg Thr Glu Ser Lys Ile Thr Glu Arg Thr
            645                 650

<210> SEQ ID NO 5
<211> LENGTH: 303
<212> TYPE: PRT
<213> ORGANISM: Nicotiana tabacum

<400> SEQUENCE: 5

Met Glu His Ser Ala Ala Asp Arg Asp Pro Lys Ala Val Glu Phe Ala
1               5                   10                  15

Lys Asp Lys Asn Gly Val Gly Gln Val Leu Leu Arg Asn Pro Arg Gly
            20                  25                  30

Ala Ser Val Arg Val Ser Leu His Gly Gly Gln Val Leu Ser Trp Lys
        35                  40                  45

Asn Asp His Gly Glu Glu Leu Leu Phe Ile Ser Ser Lys Ala Thr Phe
    50                  55                  60

Lys Pro Pro Thr Ala Val Arg Gly Gly Ile Pro Ile Cys Phe Pro Gln
65                  70                  75                  80

Phe Gly Asn Arg Gly Ser Leu Glu Gln His Gly Phe Ala Arg Asn Arg
                85                  90                  95

Met Trp Ile Ile Asp Asp Asn Pro Pro Leu His Pro Asn Asp Ser
            100                 105                 110

Asn Gly Lys Ala Phe Thr Asp Leu Leu Leu Lys Ser Ser Asp Asp Asp
            115                 120                 125

Leu Lys Val Trp Pro His Gly Phe Glu Phe Arg Leu Arg Val Thr Leu
    130                 135                 140

Ala Val Asp Gly Ser Leu Thr Leu Ile Ser Arg Ile Arg Asn Val Asn
145                 150                 155                 160

Cys Lys Pro Phe Ser Phe Ser Ile Ala Tyr His Thr Tyr Phe Ala Leu
                165                 170                 175

Ser Asp Ile Ser Glu Val Arg Val Glu Gly Leu Glu Thr Leu Asp Tyr
            180                 185                 190

Leu Asp Asn Leu Cys Asn Arg Glu Arg Phe Thr Glu Gln Gly Asp Ala
            195                 200                 205

Leu Thr Phe Glu Thr Glu Val Asp Arg Val Tyr Leu Ser Ser Ser Asp
    210                 215                 220

Val Ile Ala Ile Phe Asp His Glu Lys Lys Arg Thr Phe Val Ile Lys
225                 230                 235                 240

Arg Glu Gly Leu Pro Asp Val Val Trp Asn Pro Trp Glu Lys Lys
                245                 250                 255

Ser Lys Thr Ile Ala Asp Phe Gly Asp Asp Glu Tyr Arg His Met Leu
            260                 265                 270

Cys Val Asp Gly Ala Ala Ile Glu Lys Pro Ile Thr Leu Lys Pro Gly
            275                 280                 285
```

Glu Glu Trp Thr Gly Arg Leu Glu Leu Ser Val Met Pro Ser Ser
    290                 295                 300

<210> SEQ ID NO 6
<211> LENGTH: 578
<212> TYPE: PRT
<213> ORGANISM: Nicotiana tabacum

<400> SEQUENCE: 6

Met Glu Val Met Lys Lys Glu Asn Thr Ser Arg Lys Met Lys Gly
1               5                   10                  15

Gly Met Ile Thr Met Pro Phe Ile Phe Ala Asn Glu Ile Cys Glu Lys
                20                  25                  30

Leu Ala Val Val Gly Phe Gly Ala Asn Met Ile Ile Tyr Leu Thr Asn
                35                  40                  45

Glu Leu His Leu Pro Leu Thr Lys Ala Ala Asn Thr Leu Thr Asn Phe
    50                  55                  60

Gly Gly Thr Ala Ser Leu Thr Pro Leu Leu Gly Ala Phe Ile Ala Asp
65                  70                  75                  80

Thr Phe Ala Gly Arg Phe Trp Thr Ile Thr Ile Ala Ser Ile Ile Tyr
                85                  90                  95

Gln Ile Gly Met Ile Ile Leu Thr Val Ser Ala Ile Leu Pro Gln Leu
                100                 105                 110

Arg Pro Pro Ser Cys Lys Gly Asp Glu Phe Cys Lys Glu Ala Asn Ser
                115                 120                 125

Gly Gln Leu Ala Ile Leu Tyr Ile Ser Leu Leu Leu Thr Ala Phe Gly
    130                 135                 140

Ser Gly Gly Ile Arg Pro Cys Val Val Ala Phe Gly Ala Glu Gln Phe
145                 150                 155                 160

Asp Glu Thr Asp Pro Asn Gln Lys Thr Gln Thr Trp Lys Phe Phe Asn
                165                 170                 175

Trp Tyr Tyr Phe Ser Met Gly Phe Ser Met Leu Ile Ala Val Thr Val
                180                 185                 190

Ile Val Tyr Ile Gln Asp Asn Ile Gly Trp Gly Ile Gly Phe Gly Val
                195                 200                 205

Pro Thr Ile Ala Met Leu Ile Ser Ile Ile Val Phe Ile Phe Gly Tyr
    210                 215                 220

Pro Leu Tyr Arg Asn Leu Asp Pro Ala Gly Ser Pro Phe Thr Arg Leu
225                 230                 235                 240

Leu Gln Val Cys Val Ala Ala Tyr Lys Lys Arg Lys Leu Asp Met Val
                245                 250                 255

Ser Asp Pro Ser Phe Leu Tyr Gln Asn Glu Glu Leu Asp Ser Ala Ile
                260                 265                 270

Ser Thr Ala Gly Lys Leu Val His Thr Lys Gln Met Lys Phe Leu Asp
                275                 280                 285

Arg Ala Ala Ile Val Thr Glu Glu Asp Asn Arg Lys Ser Pro Asn Leu
    290                 295                 300

Trp Arg Leu Asn Thr Val His Arg Val Glu Glu Leu Lys Ser Ile Ile
305                 310                 315                 320

Arg Met Gly Pro Ile Trp Ala Ser Gly Ile Ile Leu Ile Thr Ala Tyr
                325                 330                 335

Ala Gln Gln His Thr Phe Ser Val Gln Gln Ala Lys Thr Met Asp Arg
                340                 345                 350

```
His Leu Ile Asn Ser Phe Glu Ile Pro Ala Ala Ser Met Thr Val Phe
            355                 360                 365

Thr Leu Thr Ala Met Leu Cys Thr Ile Cys Phe Tyr Asp Arg Val Phe
        370                 375                 380

Val Pro Ile Ala Arg Lys Phe Thr Gly Leu Glu Arg Gly Ile Ser Phe
385                 390                 395                 400

Leu Ser Arg Met Ala Ile Gly Phe Ser Ile Ser Val Leu Ala Thr Leu
                405                 410                 415

Val Ala Gly Phe Ile Glu Val Lys Arg Lys Glu Ala Ala Leu Thr His
            420                 425                 430

Gly Leu Ile Asp Lys Gly Lys Ala Ile Val Pro Ile Ser Val Phe Trp
            435                 440                 445

Leu Val Pro Gln Tyr Cys Leu His Gly Val Val Ala Phe Met Ser Ile
        450                 455                 460

Gly His Leu Glu Phe Phe Tyr Asp Gln Ala Pro Glu Ser Met Arg Ser
465                 470                 475                 480

Thr Ala Thr Ala Leu Phe Trp Thr Ser Ile Ser Ala Gly Asn Tyr Leu
                485                 490                 495

Ser Thr Leu Leu Val Ser Leu Val His Lys Phe Thr Ser Gly Ser Gly
            500                 505                 510

Gly Ser Asn Trp Leu Pro Asp Asn Asn Leu Asn Lys Gly Lys Leu Glu
        515                 520                 525

Tyr Phe Tyr Trp Leu Ile Thr Ile Leu Gln Val Val Asn Leu Ile Tyr
        530                 535                 540

Tyr Leu Phe Cys Ala Lys Phe Tyr Thr Phe Lys Pro Ile Gln Val His
545                 550                 555                 560

Lys Thr Glu Asp Leu Asp Ser Lys Lys Asp Ser Ile Glu Leu Val Asn
                565                 570                 575

Asn Val

<210> SEQ ID NO 7
<211> LENGTH: 517
<212> TYPE: PRT
<213> ORGANISM: Nicotiana tabacum

<400> SEQUENCE: 7

Met Ala Leu Ser Asn Thr Leu Ser Leu Ser Ser Ser Lys Ser Leu Val
1               5                   10                  15

Gln Ser His Leu Leu His Asn Pro Ser Leu Pro Gln Pro Arg Ile Pro
            20                  25                  30

Val Phe His Asn Pro Gln His Gly Arg Arg His Pro Ile Ser Ala Val
        35                  40                  45

His Ala Ala Glu Pro Ala Lys Thr Ala Thr Ala Ser Gln Pro Leu Lys
    50                  55                  60

Lys Thr Gln Trp Ser Leu Asp Ser Trp Lys Ser Lys Lys Ala Leu Gln
65                  70                  75                  80

Leu Pro Glu Tyr Pro Asp Glu Lys Glu Leu Glu Ser Val Leu Glu Thr
                85                  90                  95

Leu Glu Ser Asn Pro Pro Leu Val Phe Ala Gly Glu Ala Arg Asn Leu
            100                 105                 110

Glu Glu Arg Leu Gly Glu Ala Ala Leu Gly Lys Ala Phe Leu Leu Gln
        115                 120                 125

Gly Gly Asp Cys Ala Glu Ser Phe Lys Glu Phe Asn Ala Asn Asn Ile
    130                 135                 140
```

Arg Asp Thr Phe Arg Ile Leu Leu Gln Met Ser Val Leu Met Phe
145                 150                 155                 160

Gly Gly Gln Val Pro Val Ile Lys Val Gly Arg Met Ala Gly Gln Phe
                165                 170                 175

Ala Lys Pro Arg Ser Asp Pro Phe Glu Glu Ile Asp Gly Val Lys Leu
            180                 185                 190

Pro Ser Tyr Lys Gly Asp Asn Ile Asn Gly Thr Phe Asp Glu Lys
        195                 200                 205

Ser Arg Ile Pro Asp Pro His Arg Leu Ile Arg Ala Tyr Met Gln Ser
    210                 215                 220

Ala Ala Thr Leu Asn Leu Leu Arg Ala Phe Ala Thr Gly Gly Tyr Ala
225                 230                 235                 240

Ala Met Gln Arg Val Thr Glu Trp Asn Leu Asp Phe Val Glu Asn Ser
                245                 250                 255

Glu Gln Gly Asp Arg Tyr Gln Glu Leu Ala His Arg Val Asp Glu Ala
            260                 265                 270

Leu Gly Phe Met Ala Ala Gly Leu Thr Val Asp His Pro Ile Met
        275                 280                 285

Ala Thr Thr Asp Phe Trp Thr Ser His Glu Cys Leu Leu Pro Tyr
290                 295                 300

Glu Gln Ala Leu Thr Arg Glu Asp Ser Thr Ser Gly Leu Phe Tyr Asp
305                 310                 315                 320

Cys Ser Ala His Met Ile Trp Val Gly Glu Arg Thr Arg Gln Leu Asp
                325                 330                 335

Gly Ala His Val Glu Phe Leu Arg Gly Val Ala Asn Pro Leu Gly Ile
            340                 345                 350

Lys Val Ser Gln Lys Met Asp Pro Asn Glu Leu Val Lys Leu Ile Asp
        355                 360                 365

Ile Leu Asn Pro Thr Asn Lys Pro Gly Arg Ile Thr Val Ile Val Arg
370                 375                 380

Met Gly Ala Glu Asn Met Arg Val Lys Leu Cys His Leu Ile Arg Ala
385                 390                 395                 400

Val Arg Gly Ala Gly Gln Ile Val Thr Trp Val Cys Asp Pro Met His
                405                 410                 415

Gly Asn Thr Ile Lys Ala Pro Cys Gly Leu Lys Thr Arg Ala Phe Asp
            420                 425                 430

Ser Ile Leu Ala Glu Val Arg Ala Phe Phe Asp Val His Glu Gln Glu
        435                 440                 445

Gly Ser His Pro Gly Gly Ile His Leu Glu Met Thr Gly Gln Asn Val
450                 455                 460

Thr Glu Cys Ile Gly Gly Ser Arg Thr Val Thr Tyr Asp Asp Leu Gly
465                 470                 475                 480

Ser Arg Tyr His Thr His Cys Asp Pro Arg Leu Asn Ala Ser Gln Ser
                485                 490                 495

Leu Glu Leu Ser Phe Ile Val Ala Glu Arg Leu Arg Lys Arg Arg Met
            500                 505                 510

Ala Ser Gln Arg Leu
        515

<210> SEQ ID NO 8
<211> LENGTH: 254
<212> TYPE: PRT
<213> ORGANISM: Nicotiana tabacum

<400> SEQUENCE: 8

Met Ala Ala Ser Ser Thr Leu Ser Ser Ser Ile Thr Thr Phe Lys Leu
1               5                   10                  15

Ser Pro Cys Gln Pro Arg Ala Ser Ser Thr Thr Ala Ser Val Lys Ile
            20                  25                  30

Pro Ser Ile Pro Pro Ile Thr Leu Ser Ile Leu Leu Ile Ser His Phe
        35                  40                  45

Gly Pro Thr Pro Lys Asn Pro Thr Val Ala Pro Leu Arg Cys Ser Ala
    50                  55                  60

Thr Ser Thr Thr Pro Glu Thr Thr Thr Thr Ser Thr Pro Phe His
65                  70                  75                  80

Asp Leu Cys Tyr Val Val Gly Asp Asn Ile Asp Asn Asp Gln Ile Ile
                85                  90                  95

Pro Ala Lys Tyr Leu Thr Leu Val Ser Ser Asn Pro Glu Tyr Lys
            100                 105                 110

Lys Leu Gly Ser Tyr Ala Leu Cys Gly Leu Pro Leu Ser Tyr Gln Thr
        115                 120                 125

Arg Phe Val Asp Pro Asp Glu Phe Ser Ser Lys Tyr Ser Ile Ile Ile
130                 135                 140

Gly Gly Glu Asn Phe Gly Cys Gly Ser Ser Arg Glu His Ala Pro Val
145                 150                 155                 160

Ala Leu Gly Ala Ala Gly Val Ala Glu Ser Tyr Ala Arg Ile Phe Phe
                165                 170                 175

Arg Asn Ser Val Ala Thr Gly Glu Val Tyr Pro Leu Glu Ser Glu Val
            180                 185                 190

Arg Ile Cys Glu Glu Cys Lys Thr Gly Asp Val Val Ala Val Glu Leu
        195                 200                 205

Ala Glu Ser Arg Leu Ile Asn His Met Thr Gly Lys Glu Tyr Lys Leu
    210                 215                 220

Lys Ser Ile Gly Asp Val Gly Pro Val Ile Glu Ala Gly Gly Ile Phe
225                 230                 235                 240

Ala Tyr Ala Arg Lys Ala Gly Met Ile Pro Ser Arg Glu Ala
                245                 250

<210> SEQ ID NO 9
<211> LENGTH: 386
<212> TYPE: DNA
<213> ORGANISM: Nicotiana tabacum

<400> SEQUENCE: 9
atgggtctca aaggcaagtt gatctctcaa atggagatga agtgtgctgg agatttgctt      60
catgaacact tcaaatcaaa tccacaccaa acctccacca tgtctcctga taagataaca     120
aatttcacgt acatgagggg tcagttgggt aatactggtt ctgttgtcag ctggaagtat     180
gttctcggag gaaagagag gcatgcgaag caggccctac acatagatga tgcaaaaaaa     240
tcaatcacct tcaattttct tgaaggttat atgaatgaat tatacaagtc catgacacca     300
caatatagaa tcaataataa tctagaatgc cataagtctc gaaccatcc aatgcaagtt     360 acaagtccta accatacgca aatctg                                           386

<210> SEQ ID NO 10
<211> LENGTH: 1622
<212> TYPE: DNA
<213> ORGANISM: Nicotiana tabacum

<400> SEQUENCE: 10

```
atgaaagcag aaggctcagc attatcatca gctggttctt atcatcgact tgcttatcat    60
gaagttatta atgatgataa tcaaaacaaa attttacaa gtgatgactc tcgtctcaga   120
caattgggtt acaaacaaga actctatcgt ggcctttcgt tcattgcgaa cttctcattt   180
acattcgcca ttgtatcagt tcttacgggc atatccacat tgtataatca ggccttaact   240
tttggtgggc ctataactct tgtttacggt tggcccatag ttagcttaat gacacttatt   300
gtgggcctgg ccatggctga atatgttca gcttatccaa cttcagctgg gctttactat   360
tggagtgcta aattgtctgg aaattacttc ggcccatttg cttcttggat tactggctgg   420
tttaacattg ttggtcagtg ggctgtcacg gcaagtatag attttccctt ggcgcagtta   480
gttcaggtga tgattctcct tagcactggt ggattaaatg aggtggata ccaagcctct   540
aaatacgttg ttatcgcact ccacggtgga attctgcttt acatgctat attaaacagt   600
cttcctatct catggttgtc cttctttgga caactagccg ctgcatgaa tgttttaggt   660
gtctttcttc ttatgatttt gatcccaatg gtctcaacag aaagagccag cgctaaattt   720
gtgtttacta atttcaatac tgacaatggg gatggaatta acaataacct ctacatcttc   780
gtcctcggac ttcttatgag ccagtatacg ttgacaggtt atgacgcttc tgctcatatg   840
acagaagaaa cgaaaaatgc agataagaat gggccaaaag aatagtaag tgctattggc   900
atatcagttc ttgctggctg gcttatata cttggtataa ccttcgcagt tacagatatc   960
ccgcatctat tgaataaaaa caatgattct gggggttatg ctattgctca aatcttttac  1020
gatgcattca agaatagata cggcagtggt gttggtggaa tcatttgctt aggtgtaatt  1080
gctattgccg tattcttttg tggtatgagc tcactaacta gcaactcgag gatggcttat  1140
gcattctcca gagatggagc gatgccatat tcgtcgttct ggcataaagt aaacaagcaa  1200
gaggttccac taaatgcagt ctggatgtcg gcctttatag catttgcat ggcattgacg  1260
tctcttggaa gcttggtagc atttcaagcc atgacatcga tagcaacaat tgggctctat  1320
attgcttatg ccttgccaat cctatttcga gtgactctag ctcgaaagtc tttcactcca  1380
ggtccttta acttgggaag ctatgggctc gttgtaggtt gggttgcaat attttgggtt  1440
gcactcattt ctgtactctt ctcttttgcct gttgcatacc ctattacaga tcaaactctc  1500
aactatactc ctgtcgcgtt cggtggcctt ctcattcttg ttgtttcttc ttggatcttc  1560
agtgctatac attggtttaa aggtcctatt accaatttag gaaactctag tgaggaagca  1620
ta                                                                 1622
```

<210> SEQ ID NO 11
<211> LENGTH: 437
<212> TYPE: DNA
<213> ORGANISM: Nicotiana tabacum

<400> SEQUENCE: 11

```
atggcttcta ctcagcaagc ggtgagttct ggttctgatg cagaccagcg gtatgcaaag    60
tttgatgaac ggaaaaggaa gagaatggaa tccaaccgtg agtctgctcg taggtcacgg   120
atgaggaagc agcagcgatt gggggagttg atgagcgaaa caacacagct acagaaccag   180
aacagtatct gccgcgagag gattgattct gttgaaagaa attattgtgc catcgatgca   240
gagaacaatg tgttgagggc tcagattgct gaattgactg aacgtttgaa ttcactgaac   300
tcgctcactc aattttgggc tgatgctact ggatttcctg ttgacctccc tgaaattccc   360
```

```
gacactttgc ttgagccatg gcagctgcct tgccctattc aacctatcga tgcttcttct    420
gatatgttgc tgttttg                                                    437

<210> SEQ ID NO 12
<211> LENGTH: 1965
<212> TYPE: DNA
<213> ORGANISM: Nicotiana tabacum

<400> SEQUENCE: 12
atgccggggg tctatttgga acagcctct ctacccaagg gtaggggtct ggaatgtcaa      60
gaatcacaag ctgttaggta tttctttcga gggagaaata aagtcgatga ttcattgact   120
attgagattt tcaatctttt cccttggatt ttcttcacca tattggccat ggacaagcac   180
caccatcaac tacctctaac caagtctact tcgcgccagc gttataacga atgggtattt   240
cgagatgttc ctagtgatat aacaatagaa gtggatggtg gcatattttc actccacaag   300
tttccccttg tttcgagaag cggacgaatc cggaggctag tagcagagca cagagattct   360
gatatatcaa gaattgagct tgttagttta ccaggtggaa cagaatcatt cgagctagca   420
gccaaattct gttatggtgt caactttgag atcacagcag caaatgttgc tcagcttttgt  480 tgcgtatccg attatctcga gatgtcagag gactactcga aaacaatctc ggttcaaga    540 gctgaagaat atcttgacag cattgtttgc aagaatcttg aaatgtgtgt tgaagtcttg   600
agacaatgtg aaaacttact tccacttgct gatgagctga agttgttag ccggtgtatc    660 gatgctgtag catcgaaagc ttgtgtcgag caaatcgcct caagtttctc gcgattggag   720
tatagtatct caggtggaag actacatatg agtaaacaag ccaattgcga attggactgg   780
tggattgagg atatttcaat gcttcgtatc gacttgtacc aacgtgtcat aaccgcgatg   840
aagtttcgtg gggttaggcc tgagagtatt gctgcatcac tagtgaacta tgcacagaag   900
gaattgatac aaaagaccct ttctggttca aatatccaag aaaaactagt ggttgagacg   960
atcgtgagcc tgatgccagt tgaaaaattc gtcgtgccct tgacctttct ttttggattg   1020
ttgcgaagtg cagtgatgtt agattgcacg gttgcttgta ggcttgatct cgagaggcgg   1080
ataggatctc aattggatac ggctaccctg gacgatatac tgattccttc ctttcgacat   1140
gctggtgata cattgtttga tgttgacaca gtgcatcgaa tattggttaa ctttttcacag  1200 caagagggcg atagcgatga tgatatggaa gatgtatcgg ttttttgaatc cgatagccct   1260 actacgacgc catcacaaac tgcattgttc aaagtatcaa agttggttga caattaccta   1320
gctgaaattg cactagatgc aaatctaaag ctgaacaagt tcattgctgt tgcagaaaca   1380
ttaccagcac atgcgcgtac tgtccacgat ggactttatc gagcaatcga cctttacctc   1440
aaggctcatc aaactttatc agatccagac aagaggagac tatgcaaatt gattgatttc   1500
caaaagctct cacaggaagc tggtgcacag gctgcacaaa atgagcgcct tcccctccaa   1560
tcaatcgttc aagttctta tttcgagcaa ttgaggctac gaaacgcctt gttttgttcg    1620
taccctgatg atgacattaa gccaacgcac cagtcttgga ggatcaatag tggtgctctt   1680
agtgctgcaa tgtctcccaa ggacaattat gcttcgttga cgcgagaaaa tagagagcta   1740
aaacttgaac tagcgcggat gaggatgaga ttaaatgacc tggaaaaaga tcatgtttgt   1800
atgaagagga atatgcaaaa atctagctcg agacgattca tgaaatcctt ctccaaaagg   1860
attggcaaaa agttcaatat tttcggacat aatttttcca gggattgtag ttctcccctca  1920 agtcagtcag aaagaactga atctaaaata actgaaagaa cttga                   1965
```

```
<210> SEQ ID NO 13
<211> LENGTH: 911
<212> TYPE: DNA
<213> ORGANISM: Nicotiana tabacum

<400> SEQUENCE: 13
atggagcatt ctgcagcaga tagggatcct aaagctgtag aatttgcaaa ggataagaat      60
ggagttggtc aagttttgct tcgaaatcca cgtggcgcct ctgttcgagt tagcctgcat     120
ggaggacagg ttctttcttg gaagaatgac catggtgaag aattactttt tataagcagt     180
aaggcaactt ttaagccgcc aacagctgtg agaggaggaa ttccaatttg ttttccacag     240
tttggaaacc ggggctccct cgagcaacat ggatttgcca gaataggat gtggatcatt      300 gatgataatc ctcctcctct acaccctaat gattccaatg gcaaagcatt caccgattta     360
ctacttaaat catctgatga tgatcttaaa gtctggcctc atggttttga atttcggctg     420
agagtaactt tggctgttga tggatctctt accctgatat cacgcatcag aaatgtcaac     480
tgcaagccgt ttagtttctc cattgcatac catacatatt ttgctctctc agatatcagt     540
gaagtgagag tggaaggctt ggagactctt gactaccttg acaacttgtg caacagagaa     600
cgtttcactg agcaaggaga tgccttaaca tttgaaaccg aggtggatcg agtttatctt     660
agttcatcag atgtgatagc aattttgat cacgagaaaa agcggacttt tgtgataaag     720
agggaagggc ttcctgatgt tgtggtttgg aatccatggg agaagaaatc taaaaccata     780
gcagattttg gagatgacga gtacagacat atgctttgtg tagacggagc agcaattgag     840
aaaccaatca ccttgaagcc aggtgaagaa tggactggaa ggttggaact gtccgtcatg     900
ccttcaagtt g                                                          911

<210> SEQ ID NO 14
<211> LENGTH: 1736
<212> TYPE: DNA
<213> ORGANISM: Nicotiana tabacum

<400> SEQUENCE: 14
atggaagtaa tgaagaagaa agaaaacacc tctagaaaaa tgaagggtgg aatgattacc      60
atgcccttca tatttgcaaa tgagatatgt gagaagttgg cagtggtggg atttggtgca     120
aatatgataa tatacttgac aaatgagctc catcttccat tgactaaagc agctaatact     180
cttacaaact ttggtggcac tgcaagtttg actccattac ttggagcttt cattgctgat     240 accttgcag gaaggttttg gaccataaca attgcttcta tcatctacca atcggtatg       300 atcattttaa cagtatcagc aatacttcct caactaaggc caccttcttg caaggtgat      360 gaattttgca agaagcaaa ttctggccaa ctagccattc tctatatatc attactccta     420
acagcatttg gatcaggagg aattaggcct tgtgttgtag catttggagc agaacaattt     480
gatgaaactg atccaaatca aaaacacaa acatggaaat tcttcaattg gtattatttc     540
agtatgggat tttccatgct aatagctgtg acagtaattg tttatatcca agataatatt     600
ggatggggta ggatttggg agtcccaact attgctatgc ttatttcaat tattgttttc     660
atatttggat acctttata tagaaacttg gatcctgctg gtagtccttt tactaggcta     720
ttgcaagttt gtgttgctgc ttacaagaaa agaaaattgg acatggtttc tgatcctagt     780 ttccttgtacc aaaatgaaga gcttgattct gctatttcta ctgctggcaa gcttgttcac     840
actaagcaaa tgaagttctt ggacagagca gcaatagtga cagaggaaga caatcgaaaa     900
tctccgaatc tatggaggct aaacacagtt catcgcgtag aagagctaaa atcgatcata     960
```

| agaatgggac caatatgggc atctggaata attctaatca cagcatatgc tcaacaacac | 1020 |
| acattctcag ttcaacaggc aaaaacaatg acagacact taataaattc cttcgaaatc | 1080 |
| ccagctgcat caatgacagt cttcacatta acagcaatgt tatgcaccat ttgcttctat | 1140 |
| gaccgcgtat ttgtgcctat agcacgtaaa ttcactggtc tagaacgagg catatcgttt | 1200 |
| cttagcagaa tggctattgg gttctctatt tcagttctag ccacattagt agctggattt | 1260 |
| atagaagtta aacgaaaaga agcagcctta actcatggac tgatcgataa aggtaaggcg | 1320 |
| attgttccca tttcagtatt ttggcttgtg cctcagtatt gtttacatgg tgtggtggca | 1380 |
| tttatgtcaa ttggacatct tgaatttttc tatgatcaag caccagagag tatgagaagt | 1440 |
| acagctactg cattattttg gacatcaatt tcagctggga attatttgag tacacttttg | 1500 |
| gtttcattag tgcataaatt tacttcagga tctggaggat caaattggtt acctgataat | 1560 |
| aatttgaata agggaaaatt agagtatttt tattggttaa tcacaattct acaagtggtt | 1620 |
| aacttgattt actatctgtt ttgtgcaaaa ttctatactt ttaagcctat tcaggtacac | 1680 |
| aagacagaag atttggactc taaaaaagat agtattgaac ttgtaaataa tgttta | 1736 |

<210> SEQ ID NO 15
<211> LENGTH: 1553
<212> TYPE: DNA
<213> ORGANISM: Nicotiana tabacum

<400> SEQUENCE: 15

| atggctttat caaacacctt atcattgtca tcatcaaaat cccttgttca atctcacctt | 60 |
| ctccacaatc cctccttacc ccagcctcgt attcccgttt tcacaaccc ccaacatggg | 120 |
| cggcgccacc ccatctccgc cgtacacgcg gcggagcccg ccaaaacagc aactgcttca | 180 |
| cagccgttga aaaaacccca atggagtctt gattcttgga aaagcaaaaa ggctttgcaa | 240 |
| ttacctgaat acccagatga aaagaactt gaatctgtgc ttgaaactct tgaatctaat | 300 |
| cctccacttg tgtttgctgg tgaagctagg aatttagaag agagacttgg tgaagctgct | 360 |
| ttaggaaaag cttttttatt acaaggtggt gattgtgctg agagttttaa ggaatttaat | 420 |
| gctaataata ttcgtgatac ttttaggatt cttcttcaga tgagtgttgt tcttatgttt | 480 |
| ggtggtcaag ttcctgtgat taaggttgga agaatggcgg gtcagtttgc gaaaccaaga | 540 |
| tcagatccgt ttgaggagat tgatggagtg aagctgccaa gttacaaggg tgataacatt | 600 |
| aatggcgata catttgatga aagtcaaga attccagacc tcataggct tattagggct | 660 |
| tacatgcaat ctgctgcgac tcttaacctt cttagggctt ttgctactgg aggttatgct | 720 |
| gcaatgcaga gggtcaccga tggaatcttt gattttgtgg agaacagtga gcaaggagat | 780 |
| aggtatcaag aactagctca cagagtcgat gaagccttgg gattcatggc tgctgctgga | 840 |
| ctcacagtag accaccctat catggcaaca actgattttt ggacatctca cgagtgcttg | 900 |
| cttcttcctt atgaacaagc acttacaagg gaggattcaa cttctggtct tttctatgat | 960 |
| tgttccgctc acatgattg ggttggggaa cgaaccaggc aacttgacgg tgctcatgtt | 1020 |
| gagttcttga gaggagtagc aaacccactt ggcataaagg tgagccaaaa gatggatcca | 1080 |
| aatgagctcg ttaaactcat tgacatcctg aacccaacca ataagcccgg aagaattact | 1140 |
| gtaattgtga gaatgggtgc tgagaatatg agagtgaagc tttgccactt gatcagggca | 1200 |
| gttcgaggag ctggacagat tgttacctgg gtttgtgacc cgatgcacgg caacaccata | 1260 |
| aaggcaccat gcggactcaa aacccgtgct ttcgattcaa tcctggctga ggtccgagct | 1320 |
| ttcttcgatg tgcatgagca agaagggagc caccctggtg gtatccatct agaaatgaca | 1380 |

```
gggcaaaatg tgactgaatg cattggcgga tcacgaacag taacctacga cgatttgggc   1440
tctcgctacc acacacattg tgacccaaga ttgaacgctt ctcaatctct agaactttcc   1500
ttcatcgtag ctgaacgact aagaaaacga agaatggcct ctcaacgtct gta          1553

<210> SEQ ID NO 16
<211> LENGTH: 764
<212> TYPE: DNA
<213> ORGANISM: Nicotiana tabacum

<400> SEQUENCE: 16
atggcggctt catcaactct ttccagttcc atcaccacct tcaaactgtc tccgtgccaa     60
ccacgcgcct cctctactac cgcctccgtc aaaatccctt caattcctcc aataacccct    120
tcaatccttt taatttctca ttttggccca actcccaaaa accctaccgt cgcaccactc    180
cgttgttccg ctacctccac cacaccagaa actaccacaa cgacttccac accattccac    240
gacctttgct acgtcgtcgg ggacaacatc gacaatgacc aaatcatccc tgcaaaatac    300
ctaaccctag tttcgtcaaa cccagacgag tacaaaaaac tcgggtccta cgcgctgtgc    360
ggactcccct tatcatacca aacccgtttc gtcgacccag atgaattctc atccaagtac    420
tccatcatca taggcggtga aaacttcggg tgcgggtcgt cgcgggagca cgcgccggtt    480
gctttaggag ctgcgggtgt ggcggagtcg tacgcgagga tattcttcag gaactcggtt    540
gcgactggcg aagtttatcc ccttgaatca gaagtgagga tttgtgagga gtgtaagacg    600
ggtgatgtgg tggctgttga actagcgagg agtaggttga ttaatcatat gactgggaaa    660
gagtataaat tgaagtcaat tggtgatgtt ggtcctgtca ttgaagctgg tggcattttt    720
gcttatgcaa gaaaggctgg aatgattcct tcccgagaag ctta                     764

<210> SEQ ID NO 17
<211> LENGTH: 2500
<212> TYPE: DNA
<213> ORGANISM: Nicotiana tabacum

<400> SEQUENCE: 17
tctgacatat ctatagcatt tcatttcact acaagtcact tcatgtcgtc accgtttaat     60
gtgcttaata tgtcgaaacc atgactagtg atatagacat tctcaaattt cttaaagagg    120
cataaggaac ttttgcatgg attgaaagag agcatatata atttatttct agcatccatt    180
gcctaaaatg agatgactct ctctccactt taatttccat acaatctcaa ggaagacatt    240
ggatagtaga tatataagct ccattttgtg aactcctgta agatcattgc ctcatgtgct    300
atattgcacg gactttccga aatgctgttg tattcatgtc agatcctcta aaaatatatt    360 actttggag aatctgacac acatctagag acattttcgg aaaatctgag caatgtagct    420
ctagtgtgcc ggagaaagca taggtcaatt agtcttgcaa ttgactaatt gcaatctgct    480
aatagaagta tatatgtaag agtacatcga catggtaagc actaaactat cagataggct    540 atctttttc atatacctaa gtcttggtgc acaaactcgg tacttatgct ggtgagaagt    600
aatacctatc cagtgaaata gtcgaggtgc cggaaaatca gtctacgcac tacttagtta    660
aaaaagttct aaatcatcta aaaggagcag gagcttttgg gaaagaaaca ggtataaggc    720
aatgtgcaat ggtgactgtc gacaacatta ttatgcaaa ggtgagaaat atcatctctt    780
tattgtaaat ataagtgac acacacgagc agtatgaaa atctaataaa gttgatgctc    840
gtgcaacaaa ttcatttgga atttctttgg tgaattattc ttttggttgt caatgtgtaa    900
```

```
gtgtttagag tagacatgaa ttgataactg aagaaaagtt tgagtaactt gttggaccct      960
gccaaattat tgtgaatgtg taagtatttc cacaatgtca ctgatcatac tgttgcagat     1020
acacatacgg ccagaattca ataatagcaa taactaaaaa tttctaccaa actgaaaatg     1080
caaaattgag gcagataaaa tttgtaagat tgtggtatgg ggcgtgaagt tgttgactta     1140
tagccactgg tgcaattgat ttaagatagg accttatctc ttctcatcca ctacctttt      1200 cgtttgcctt tcatttacct tgctccattc attttcttta tgtatatcca gattttttaa     1260
tttgaatttg cagttcgttt aagtataact tcagcagctg ctgacacatg tcacgttagt     1320
tacctctttt atttgtggga tgtggcgagc agtgatctga taagggatat ttgaccttta     1380
tcgaacacat gacatgaaaa aaaaaggtt aattgattta gttgaagata agtgaagctc      1440
taaaggcaat tgaaggaatt taaatttact aaaatccaaa aacacgatat taattatatg     1500
ttccgtgcat gcttaactca cgcgtactag agatttaat ccttctaatt ctattacgtt      1560
tattctaata cttgcattgg atttttacta gccaaaactc gacgcagatt gatctcctta    1620
ttctcactaa agataagagg agccaaaagt ggagtaagaa atctttacaa actaaagggg    1680
ttagatgaaa aggaagaatc caatacttcg gattcaacat gttaacaaaa gcaatttttt    1740
aaccgacttt gtcactacag ggaaaaaaaa tattttaca ctattcaggc agtctaaatt      1800
ttcaacgaac ggaattcaat taaactctct acgtcacatg tacatctgtg atcagcaata    1860
attgttgagt tgatttggaa ttaagtaaat tagttctgat cactccggaa gtgaaactgc    1920
aaatgtgcaa taacacgaac aaaagactat gattccatgg tttcaacata gcccacaaac    1980
aagctaattg agattatggc gattaataga agatcattag gtttaatttg gcgaggcgaa    2040
tagccattgc atgtatagtc caaaccatga aaatgacaca acaaaccata cgacaaccta    2100
aaaaagaatg caaatatagg tggaacttga tattgaggat taaataactg ccccacaaga    2160
aaaaacaaca tgccccatat tcaaccataa cgatcactcg tatttaatta ttctctcctt    2220
taattcaaat aaaaaaaaat cttaggttct tggcttctta gccatatgct tttagttcca    2280
ggcaaaagta ctgcaacatt caatctccaa cgtacaaact ctcatctaca atggattgaa    2340
gctctcattt gcttagcaat cactttcaac tctgttataa tactgttata tgtaagagac    2400
ccgacccatg atcaagaccc attccacaac tatataatat atactagtga gtgaggagta    2460
ataaaagcaa gcaaaagcta aaaggaagtt cttgagccaa                           2500
```

<210> SEQ ID NO 18
<211> LENGTH: 1406
<212> TYPE: DNA
<213> ORGANISM: Nicotiana tabacum

<400> SEQUENCE: 18

```
ccttatagaa attgtctgct tctttcttct cgaaactcaa aaccccgatc gaaaaattag       60
tttttggggt tagaacatgg atgggattga gtttaaaaac gtaaagatca tagagcctag     120
agggaaaaga atctgatgtc atgtcgtaaa ggaaaaggaa agcaaataac agtgtccagc     180
ctcgaggcaa aggaagaaaa gatgcccgg aaacaggaag ctttaggct caaattaagc       240 acactcaatt cactcctctg tttaattaga atttccatgt ttcctcctct cgcggacacc     300
cccatcttag tttcttccac aacatttata attcaatgtc ctaaatttgg aagcgacata    360
ttgcattata cctctagtaa tcagttggat tagccgatta ggtaaacgta agagatacac    420
tatgtaagta tattcttcaa ggtatatgag aatatgttta cgtaacagaa tgatttaaat    480
gaactgatta ttgattctgt attatcatgc ttatgctttc gatgattaat tagccacatc    540
```

```
tagctaaaact ttttcttcca tatcttttt ttttttttg tgatttacaa gaatagatcg      600
tgtcatttgt ttcttaaag tacctatgtc aacatcatgg atgacatgga ataacaagtg      660
catggaggtc gataagaaaa aaacaagcag ctccttggat ttttcgaagt ttggactttt     720
tagagcctca atttgctga aatatcgaaa tttggagacg tgagattcac ccagtcaccg      780
cttacgattt aatttatata cactgacaag tataaataaa ttataatatt ataaatttaa    840
tttgacagtt atatcatgtt atatgcttta tttttcgagt aactccttca acttattgtg    900
agcattacct atggttattt tgaatttaag gtattacatt gacgctttaa agttctatta    960
cacagtagtg tatagaagtt aaactcgac tgttttcacc ctttgttcac actccaattt    1020
tgaaaaactg attaacaagg actatccaac ttctatttaa gaagaaacta atccttgttt   1080
gatttaatca atcttgaatt tctgtgaacg gtacaaattc cgtgaccaaa ctggaccatc   1140
atctaaactc caactaacgc acggaataat atcaagcttt atgctttaga ttttgtatt    1200 tctaacataa agatcctaga gaaacagacc acataaaaga catttacga cgtgcatgtc   1260 cagcagtggc tataaaaatg ataagaaatg tgcgctcaat agtcgttcca tgctctgttt   1320
atatatatgt accttctcat acattaaaca tcatatcata caaagatca ctaaaacaga   1380 aggaaaaaag aaaagatctt cagaat                                           1406
```

```
<210> SEQ ID NO 19
<211> LENGTH: 2500
<212> TYPE: DNA
<213> ORGANISM: Nicotiana tabacum

<400> SEQUENCE: 19
```

```
gcgcaatatc caggacggtg gtcttgcacc gcatcccacc cgggagggat caactcgacg       60
tgatcgggaa ggccgtattt agccttaagc tctaataaat cagcctcctt cattgccgac     120 ttaaggttt cgggttcgac ttcaggcaat tttgagaaat cggacctgga tcgtacgagg     180
aactatctct tccatcgtca ggaagcttct gtcctcaaca gcagtgggaa tgctctcagc    240
atgaggagga aaactatcg ctagagggac cgggtcactt ccctcgctgg actcagaagg     300
tacattagac atgttttaaa cgaaagagag gaaggtatca acaacggag gattaaaaac    360 gatgaggatc gctggaacaa agggaaaaga tgcacaacaa tggaaaagga agaagaagat    420
ataaggtttc gatgtaggaa gtctgtaaag tttgggatta caccctcata tccctattta   480
taggaattca ggcgccagaa ccaagaaatt ggctcatcat tacctagcat cggaattgaa    540
gtggcaggac caatcaggag ccccatgcaa aataaagcga cgcatcggga atacgcatca    600
tgatgatgca cgaggtcatg acgtcaccct gattcatgga caacacaact ccaaaatttg    660
cagctcacga agggccactt ttctagctcg cctcaatcat cacgagccga tcagctcgtc    720
taatcgtttt gaccgtaatg aacataattc gctcatcagg cccgcctgag gtcggcctca    780
ataagcggag gggctaactg tatgggtcaa aatctgtcct aaaatatta agataagata    840 atactaaaga aagaattctc gagccgtcgt tagtcgaggt ggactaggaa ggagcgaaac    900
ttatagtcga agaatcgacg agagccatgg tcgagatgtc aataatggtc gaagtcgagc    960
accgttgata aagctgtaac aactagtttt cgaatagga tattaaagag aatattctag   1020
tggattctct gcacttgtac tattaaggtt tactaggaat atgtctcata taaatagaaa  1080
aagagacaat gatatgaggc atgtgatatt catttgtaac aagatacttt gacaaaaaag   1140
attctctctc tctctctctc tctcactaag atacaaacac cacctttca ctaagattct    1200
```

```
tgtctgtatt attccatact ttttcatcag atccgagaat aattcaagca ttcaaggatt      1260
tgtgtgtcac tcatcattgt caagaggaac aaccatcccg ttcatccttt attgggtgaa      1320
tcattcctcc tatttactta agtgtcattt attgttattc attgccatta aatgccacat      1380
tattattcat gattttttgga atagttattg catactgtta tcactattcg accaaatcta     1440
tgtgacttta tcacacccctt ggaagctacg tctagaaata ttattgttaa ctaatttttaa    1500 cccataatca cataaatttg attatttgaa ccgagagtca tatttttggt caaacatata     1560
ctttattaat aagttatcat aatcgctttg tttttaaagg attgcacgcc gaaatttgtc      1620
gctaataatt gacatatcta aaacgttgtg tccccgttgc actcaaattc cgggtccgcc      1680
tctagaccta ctaacatttt taccactata gtgagtatct tgcatgtttc acgtacattt      1740
tgtgcatctg cacactcact aatctttctt aaaatatgtg acgacaaata cattcttttct    1800 tagaagcttg aagacagcag gatttctctg agataaaatg aaactaaaga aaaagaaaaa      1860
gcaatgcttt gggcttaggc tcattcagaa tatagagtca gtaaattcaa aatgaatatg      1920
atcttaatac atttattatt ttaattattt tagaacatac gtaaacaata tatataataa     1980
gttcaattga actaagaaaa cttgtctctc tatttgtgta tgccaatatt gaacgagact     2040
accatcatga aataaaaaaa tccagtccac tcgtatgtcg tatgactatt taactctaat     2100 gcttctttttc atagatattc atatgattca tgtcgaaaat ataatgttcg atcggttgaa    2160
ttcttagctg acaatagcag acatttgaaa atgtatactc cccttagtta ttccaacttc     2220
caaaagtcac taaactctaa tagcatgaca ggaagcgtaa caatgccatg ccaaaatcca     2280
aattgcctag taggagtaaa aacaaaatga aatgggtcac cattcatcgg caattaggta     2340
accatatctc ttttgatatt tgagccacaa atatacgagt gatactcatt attttaatct     2400
catccacgtg gcaccatccc attaactgct tatctcaggc tgaaacccctta gtatcttgca   2460 tatttttcttc ttcctcagtg taaaaccctta attcacaata                         2500

<210> SEQ ID NO 20
<211> LENGTH: 2500
<212> TYPE: DNA
<213> ORGANISM: Nicotiana tabacum

<400> SEQUENCE: 20
gaacacatct aaacaacttg gaatcacctc aaatatcgca cagaagttgc aaatgacata       60
acaaacctat tttaactcct agaacaataa tccaaactcg ataacatcaa agtcaactcc      120
cgatcaaacc tatgaacttt tcaaaccttc aaattgccaa cttttaccaa ttatagccaa      180
aaccttctag aaatattcaa atgtaaatct gggcatacat ccaagtccaa aattgccata      240
cggacctacc agaaccatca aaactcagat ccatggtcaa atacataaaa gtcaaacttg      300
gtcaattctt ccgacttaaa actttctatc taagaatcat tctctcgaat caattccgaa      360
ccgcttaaaa actaaaatcg acgatatccg taggtcataa taaatcatac gaagctactc      420
gtgccctcaa accaccgaac gaagcacaaa tgctcaaaat cactacttgg gtcgttacat      480
ttttgagttg gtcacactat ttattttttgt acttgttgaa ttgatgaaac tatataggtt     540
atagcaagtt ttacttatat ttgttgcctc ttttacctcg ccgagggtag ttatgatact      600
tgctgagtac gttgggtcgg ttgtactgat actacactct gcacttaatt gtacaaatcc      660
aggtgtcaga cccagacatt agtagctgag gctagcagaa gagttgattg ctgagcgacg      720
aggtagaact gcattcttga tcgcagtctt ggcgtctctt ttcttaatta ctgttgtctt      780
tatttcagac agtattgtac ttggtcattt cagactttat ttccgtatta gagcttatga      840
```

```
ctctgtattt accagtttct acgggatata tcatgtatta gcggtatttt gctatattga      900
agttttagac atatgttatt tctataaatt atgttatttt ggttctttat tgttatgtcc      960
ggcttgccta gcaaatgtgt taggcgtcat catgactggt tgggattttg ggtcgtgaca     1020
catatcttct ctaaatgcta tcaccgtaat gtatacatgt cttttattca tatcttctct     1080
atatgttgct ttacatgatg aaataattca cggtatatat cttctctata tattaatctg     1140
tattacctga cttatttatc catgcatatc ttttctatat gcaactgttg actggttctt     1200
tgaactgtta gtttgtttac aatgcttgtg catgtcttgt ctatatatat cgatggcctt     1260
acttgtactt catgcttaga tttttgttatt gttcttgtgc acatgtacat tcatgaacat     1320
ttcaggtttc ataaaattag tatcttttga cttaaattct cattactact tcactgagat     1380
tagtcaagag atttactaag tacatgtggt tagttatact catactatac ttttgcacct     1440
tgcgtgcaga tttcagagtt gagctgctgt gatgatgaag ccagcattg aagaggtacc      1500 ggtgttctag atacaagttg tcacttgttc atggttgttt acgttttata ttatatttat     1560
gtaaatttta aatagatgct gtaatctctg ttcatattag agttgcactc gtaatcttgt     1620
tcttaatcgt tcatgacttg tactaccagt ccttgggata attatgtgaa ttttctcaat     1680
cttatttatt atttattgat aatctttcat tcgagttgtg ttatttgttg tttggcttac     1740
ctagcatacc atagttaggt gccagtactc gtaacatttg ttcttacttt ctagacttt      1800 agtgtatatt aaaaatattt attttatgt actgctttgc attagtaaga ggatctttta     1860
ggtataatgc tctttcttac ttttaataac tatcgtcttg tattaataaa attttcttgc     1920
aaattttaaa agcaatgaca tattaatgga gaaattatac acaatataaa gatataatca     1980
atttaaaaaa gcaacatgta aaagttgta gacgagataa gatgcctatt atttatattt     2040
ggtacatgaa tgtcattttc catgaaagtt tttcaaaacc aataatttgt atatgttagt     2100
tgaaatgtca cttttgtttt gttcaatcag aaccagtaat ttgtatttaa taatactaat     2160
gtcattttta tccgactcaa ttaactactc cctcttttac aacaaggaaa gaaaagcttg     2220
ttactctccc tataagtttt tcacgaaggc aatacaattg ttgcaacttc tttttcataa     2280
tcgtagtttt tcttcattga tcataatggg tggaaagagt tctccaacga tgttttgttt     2340
ggttctagcc ttcttacttt atgcatctat ttagtataat tttattatat ataaatgttc     2400 ggattttct ctcactactt tctcccccctt acttcaaccc aactatcaaa agagattatt      2460
tttagatatc aaaataatta acacaaactt tattacaaat                           2500
```

<210> SEQ ID NO 21
<211> LENGTH: 2500
<212> TYPE: DNA
<213> ORGANISM: Nicotiana tabacum

<400> SEQUENCE: 21

```
caaaatactc tataatgaaa taatgagga gaaagaaaga gaagagtgaa aagtcttgaa      60
ttggtgtgtt tactaatgag gagaaactcc tctatttata gcaagaaatc cttagcctaa     120
taatggatat tatgtcatgc aaatgtcatg atctacaaat ttgttataat ggatattatg    180
tcatggcaaa tgtcatggac caaaatttgt tataatggat attatgtcat ggcaaatgtc    240
atgaaccaca aatttgttat aatggtatta tatcatggca aatgtcatga aaatttggcc    300
atattacata ggatcacttt tcgaagacaa acacaattat atggataata caatgatgt     360 aaattcatcg tgtttaaagc atattccatt tcggatgcct ccaaatctga aaatatgtaa    420
```

```
cgccaaatat tgtttatttt aaaaaatgcc aattatacaa ggctctatcc atgcaaagta    480
acttatccac acgtaaaagc aatacaacgt taattaggcc aagaattagc ataagttagt    540
gcaattttaa agttttgtac tcacctttta tgcctcaaat atctgtccaa ataaagtagt    600
aaaatttaac aaattgatat cacagagaaa caaagaaatt atttggaatc attctagtgt    660
actttcaaat attcactaaa tttatctcga agttatgcat aatttgcgca ccttgagcta    720
aaataattga tttgtttcta ttatatacgt ttatacatta ccagtgcttt ttgtttttttt    780 ggtctacttg ttcggcacaa ttattacact taacaatgca ataataattg agaatacggt    840
aaagggccaa aattatccct agactattcg atttggtata aaattgtcct ccgttcatct    900
attgagtcaa aaatgtctat attgttattt tagtggctca ataatgcctt tattactaac    960
cgacttattt gaaaaaaata attaataaat atccacgtgt caccgtccat ggctaaata    1020 aaatacttac taaactttta aaaagaatc accataacct aggttttgat tggcgccgca    1080
cgattataaa cctgtaatcc aaatctttta ttcttaatag acaatgtaac ttattcttct    1140
tcctctttta attaagttca gttctgcaaa tgggagaatt tatgtcacca caacaacaag    1200
aaaagtaaca atttaagcaa gaaaatgttg attttgggaa taaatgaagt gggtatggga    1260
ataaaatttc ggatcttgac ttaggaagta attcaattaa atgagagtaa attcattaat    1320
gaaaacaaat gggtatgaca tgggtgaaaa taattcatta tctcctcctc taattcgatt    1380
tcatggagat gggagaagaa agagggagtt ggcagctagg cgggtccttt ttggggccgg    1440
tccgatgaaa acccaggtta tggttttctt cttttttaaa aaaatataaa ttggtaagga    1500
tttatattta gaccaatggg acggtgatat gtggatatta attaattttt ttagataagt    1560
tcgttggtaa taaggacata attgaaccac taaataacgg taaggacatt tctagctcaa    1620
taggtagacg gggatatttt tgcaccaaat cgaatagtgt agggtagttt tgacccttct    1680
ccgtactaga agcaaggaga ttagtaacat agcaaaatta ttttgttaat accaaatcaa    1740
acaaagcgac caacatcaca gttgaggacc acggcgcctt agttcatcat attctatgat    1800
gataactgtt ttaatactaa taaataagta tgattataat tgtttaaaca ataaagaaaa    1860
ccaagaatat gtccagttac gttataatga taagactcta ccaaacaaca catgtcaact    1920
tcatcgctaa tttgaattgc tcatagctaa caaaattttt gataatttat cgtaaatcta    1980 taactaatt ggattagcga cgattttgtt cagctacaaa atttgtccgt agctaattcc    2040
tgttttttag tagtaaaact agcctagtac aactttgttg gttgtgtgac ataaaaaata    2100
aaatttctcg tattcaacta attaatcaca ttccaaattc ttcataaata ctaaatagat    2160 tctcttttc cataactgaa gcaccaatta ctcgagaaaa gaaaattaaa gtaaatatgg    2220
gttccgaaac tatcaagctt cctaatatag acttctccaa tgtgacctaa agccaggcac    2280
acttgtatgg aaccaagtga aaagccaagt ccacaaagct ctagtaaact atggcgtttt    2340
gaagcatcat ttgataaaat cctatacacc ttcgaaaatc cttttgaat ccttaaaaga    2400 gcttttcgat ctccctttac aaaccaaaat aagaaacatt tcaaccaaac ctttccatgg    2460
ctacgttgga cagtatccag cagttccact ctatgaaagt                         2500

<210> SEQ ID NO 22
<211> LENGTH: 2500
<212> TYPE: DNA
<213> ORGANISM: Nicotiana tabacum
```

<400> SEQUENCE: 22

```
ttaaggatat gttttaaata attccttaaa aaaaatactc tgagcattat tggtacttta      60
agcttacaaa aaattatact tttatttttc atcaaatatt taacaaacgc tatttgtcga     120
aattgtgggg ggaaaaaaag aatttaacta gtaacgctag aaaagttcca taaaatttca     180
gaaactacag tgcaaaattg cactagacac aaaaaggtaa actaaaaata gcaaaacttg     240
catctcataa attgcaccaa attctagaaa atagaccaaa aatagaagaa ctgtaaaaat     300
tgtacccttta aatgtgagtt ctagctaaat tctttgtatt tcacagttcc ctcaaagacg     360
gagtttgttt actatttgac aatgaaagaa aatagtaaaa atagtacgat atagtcagtt     420
ttcggactgg tcattcaaaa atagtcagcg tttaccaagt caataaaaat agccactatt     480
ttgctgcaaa agagaccgat ccagcataat atactggagt tcggtgcacc tgtgtatgaa     540
ctccagcata ttatgctgga ccgatatact ttgctggctc agtataata tactggagac     600
tggagcaccg gtgctccaaa ctccagtata ttatgatgga ccggtatact tgctggaact     660
ccagtatatt atgctggagt tctagtgtac ttatgttgga actccatcat attatgctgg     720
agttccggca tacttatctc ggaactccag tataatatgc tggagttcaa gtatacttat     780
gctggaactc cagcataata tactgacgta ttttccgggt tttgaacagt attttcgctc     840
agatttatct ttcatgaaa agtggctaaa tttcgattac ttttgaaact gggctatttt     900
tgaacgacca gttgtaaatc tggctatttt tgaatttctc ccaagaaaat atcctaactt     960
aaataacaaa aaatgctcga aaggtatatt tgaagtacta ctttttttgaa cctattccaa    1020
acttacaagt agggggtgtac aaacggaacc ggaaaatcgc accaaactga aaagtcaaac    1080
caaaccgatt aaaagacccg actaggtttg gtttgatttg gtttggtatt gagtaaaaaa    1140
atcataacca aactgacata taaatatata attttttatat atacttttaa gattttatat    1200
aaaattttct ttaaagaata tctaaaatat ttgggattct cttgtgggat ataaatattta    1260
atatgatcca taattattaa ccttaaataa tgggttatat gatcgcgttc tcatcaagtg    1320
ttactgaaat gcgtcaatct ctatgtccgt ccatattcat atcatatgtt aagatctatt    1380
atattcttat atctttttttc gaatgtgaag tgataattag tattatttag gtatcatatt    1440
ggtttttata tttaattact aattcggtta accttgaaaa tatatatcaa caaaaaatta    1500
ttgtcaaacg aataaaaaaa ataactatta tgtgttacta agaaaattct cccttaaaaa    1560
tattttaata gataatttgt caattttttta tattttttact aaacatatat ttacttatca    1620
aaaatttaat aaagtaaaat taaaataata tttaattaac aaaaaacctg aaaaatcgaa    1680
aaaatccgac aaaacaaaat caatccaaac cgatagggtt gggttggtac acccctactt    1740
acaagctcat ctctattatt ttctcaagtt tgtattgaag gttcaaattt caaggattat    1800
aattataatg attgcaaaac gacaatctta atataggtga ttaattctga tatggacaaa    1860
attttgcgtc gtatccatga tcgaccaact accaataatt ttcaaatgct caagggtttc    1920
aagtgcgtgt ttatgttctg aaattgtagc tagttggata tattccatca atcttgtaa    1980
agctaataat gtttcttgac cttttttaaat atactagtga tcctttcatg agatattgag    2040
atcagttttt tctatctgct tggaattgaa taatatagaa tataaacata tgatatattg    2100
ggggcaaata cggacataaa atttaaagtg agtcacttac tttatatgtt aaactatgtc    2160
aagattaatg accacaatcc gaagccgaag gaatataata cgaacgatga attttgttta    2220
cgattaggtg gaatgattga tattaaaaaa gaatgtaaaa gcaaataaga aaaggtgaat    2280
```

| | | | | |
|---|---|---|---|---|
| aatgcatatt | aacaatctat | attttatacg | attaggtagg | aagataatat gattgatatt | 2340 |
| taaacgtaaa | tattttaaag | tacgttgctg | tctttgtgac | ccctctggcc ataccattac | 2400 |
| ccattattta | tattccctcg | tatcaacatt | cagtagcaag | taaaaagaga taattttttgt | 2460 |
| tgattatttg | ttgttgaact | tgataaattt | tgctgaaaaa | | 2500 |

<210> SEQ ID NO 23
<211> LENGTH: 2500
<212> TYPE: DNA
<213> ORGANISM: Nicotiana tabacum

<400> SEQUENCE: 23

| | | | | | |
|---|---|---|---|---|---|
| gagacgcata | ttgtaagaag | aagaaagagg | ggataagata | ggtgggtcga ggaccgggag | 60 |
| actgcatatg | taagctttca | attttcttta | agtattataa | tttactttta taaaatttta | 120 |
| aatactattt | aatttaaaat | aatatagggt | cgctaccaaa | gtaacgtgga ggaattcatc | 180 |
| gtagtcacca | gctggtgaat | cgggtgagcc | aacccaacct | tcggacgagg atgctgaaag | 240 |
| aatatggttg | gagtctgttg | gcggtccaaa | atggggaagg | tatacgggct tcctactaaa | 300 |
| aattccatcg | ctataagtgt | ggaatgcagg | aatagggact | tcctgcaggc gagaacttaa | 360 |
| tagggagagc | ctctcgctat | gcgggagaca | gtacaaagct | acatcgagct agaagcggcc | 420 |
| aaggaaagag | aaaggcttag | agatgctcaa | ttccttggca | tgcaagctca gatcagaact | 480 |
| ctcctatcta | tggagctttt | ccgttgcccg | tctcgtgagt | catcccaggg tcgactccac | 540 |
| gtgatcgttc | ctcctccttg | tgatcgttcc | tccgtcctcc | ccgtgatcgt ttcccgtcct | 600 |
| ccacaagaat | tctctatacg | tcttgtagat | gaaagttcat | cagatggtga tgatgttgta | 660 |
| gaaaatacccc | cttgaccaat | actttgatat | actttgaact | agactaatag aactgttttg | 720 |
| aattagattg | aacaatttg | aacttgttgt | aattagtttt | tgcttggttt tggattgtga | 780 |
| ggttcaagtg | aactttaatt | tgttagtttt | aaggtattaa | ttggatgttt ggttgttgtt | 840 |
| gttggatatt | tagttagatt | tgtggtgaat | taggggttgt | atatggtgaa ttaggggtta | 900 |
| ttagatgtga | attgggggta | ttggtatgct | gttttatttt | gacaggtggt atagctacca | 960 |
| aaacaggcat | tttctgccaa | aattaaaccc | agaaaaccga | ccaacatttg tcagtaacta | 1020 |
| aaaaaaaaaa | attaaattgc | acattcacaa | ccaatgttgg | ttggttaatg tacaatgaat | 1080 |
| ttccagaaat | tcaacattac | cgaccgaatt | tagtcggctt | gttgcctgcc ctgtccagtt | 1140 |
| taccgaccaa | ttttggtcgg | tattttaaa | ttttaattat | ttataaaaaa aatatatttt | 1200 |
| ccaataccga | ccaaagttgg | tcggtatttt | taaattttaa | ttatttataa aaataatata | 1260 |
| ttttccaata | ctgaccaaag | gcaaaattaa | taaatttaat | acaccgacca agtttggttg | 1320 |
| gtaaaattaa | attaataaat | aatattccga | ctaattttga | tcggtaagtc aattaaattg | 1380 |
| tcagatagtc | gtgtagagca | taccgaccaa | cattggtcgg | taatttccga gtaactttgg | 1440 |
| tcgctatgcc | cttccgatct | tcaaaatact | gttcacacgt | gaatgatcgc gttttgaacg | 1500 |
| gttattgacc | tttaccgact | tactttgatc | gttttttgg | acgatatttt tcgaatttct | 1560 |
| aatagtgact | gtcatctatt | tcttttgaa | aaagaaaaa | aagaatcaaa cttgagcttg | 1620 |
| gaagcacggg | ggaaataaca | tggcgatttc | ttttgtcata | aaagaagaca acaaacaact | 1680 |
| cctcgaattc | tgcttttaac | ttttaagtt | gacttcccaa | atcccaacta ctcaggaaac | 1740 |
| agttgagctt | gtttgcctag | atctaacaca | atatataatg | catcgacccc cataacaaaa | 1800 |
| tctgtatttt | cacgttttatt | acactgaaaa | aaaaagata | aacattata tagcagacaa | 1860 |
| gataaaacct | tctttgtcaa | aacaaaatac | aaaatatgta | ctaagagaaa atcaccaaca | 1920 |

```
tatcgttacg gattcacttg tttgataaag atgatcttct tttgtggata tttacataaa    1980
taattgatcg aatttattgt ttatacataa attatacact gattatataa gggtatataa    2040
ctattataca tccgtcgact agttcgtttc agcaattagt tgaacaacta cttaaattaa    2100
ttcttttttt aatataagta ttgaaattca attgtcttca ttcttttata acagtaaaat    2160
taatgctcat aattttgtga gccttacatt aattaaggac cgcgtagtcg taaaccaact    2220
ataaaatgaa tataataagc tgtaaattta tctacagcat ttttagttag cgtgcgtacg    2280
taaaaattca aatcgagaga caaacttata acttactaca acctaattat atacgaaatg    2340
aactaacact aaccttcgtc cccactaatt aaaaatcgtg gatcatgttt tatactagct    2400
ttgcatacag ctaattaaaa tctatataga ctacaacttt tgaacatttt ctcacaccac    2460
tttcttttca caacttttag ctactccgaa aaaagtaatt                          2500

<210> SEQ ID NO 24
<211> LENGTH: 2500
<212> TYPE: DNA
<213> ORGANISM: Nicotiana tabacum

<400> SEQUENCE: 24
ctgaccataa aagtttctcta atgacactat tccataact caagaccaga accaacttaa     60
attacattgt aattttacgg atgattattc aacttttact tgttacatc gaagtcacta    120 aatttttgaa actttgctac tttcttcctc ctttattcga ggtagaagaa gacagtgcaa    180
tagttgactt attagacagc tttactcata tcacgagagc ttaaaggagc tttgtctaat    240
tccatgatct taatctgtcc atatgtcctt gtatttgatt ttcaagaaag gaattctttt    300
tatttcagag gcggatccag aattttaatt ttatggattc aggattatat tagagcctat    360
tttagtaata cagttagagt ctgcagtacc atttgaaaag tctcatttta aggcttttca    420
ctttgaaatt ccttatccca ttttcaagt ttttgcttct ggagccactc cttttctgag    480
cctgcaagtt caagtgagcg ttactgcagt tcaagaatga caaaaaggg ttgtgataag    540 ctgcaatgga ttgaagtgaa cgtcaaataa ttaatgctgt gactattgca acttttgcag    600
cttctttagg ctttgtctga agtgaatgtc ttcattcgaa atgaatagac ttcagcaagc    660
tatgttgcta agattctccg aaaatgtcac gaggtccatg tcagatcctt caaaagtaat    720 gcattttga aggatctgat acgggtgcgg caacattttg gagagtacgc gcaacatagc    780
cagccaacaa gtcgatactt acggtctaat agtttgaaga tctcctatcc aaccaagatt    840
attgaacatg tttcgattgc catttagctc aaatgacaaa atgaatgaat atttcctttt    900
taagtacacg tctctaatac atttatatag tcactccgga aaccctgtta catatattag    960
tatctacata taggttaatt ggaagccact gaaacaacct taatacttta aaagctaata   1020
aatctacaga aaagagctaa aactacccct aacctattcg cttaggttta aaaatatcct   1080
tcgtccacct attttgtaaa aattgcccct aacatcaact tttcggccca ctcataccct   1140
agaaactaac gacccccattt tgattaagat aatttttta ttacttatta tgtgtcaatt   1200
tcctaatggc ttaaattaaa acctcattcc acatcctatt agcccgctcc ataacccaaa   1260
atatccatac tcgaccccatg accggctttt taaaatgcct taacttcacc tctcatcttc   1320 tcctcttttca tccctacccct cccactctat attttctcta atcatcctcc tccatggcca   1380
aagtacaata actcgccatt ggtaactgag gactaccgtc ggcttcaact ttaagatctt   1440 caccccttcaa cacccacgga tcttcctctc ccactcagat ttttcggcct taatttaatt   1500
```

-continued

```
tttaaattaa tatttttttg ttaaatcaat tttttgagtg aaatctggta ttctttggaa      1560
ttaaattaat ggttcattta aagatttat ggtttaataa gttatgtttc cgccaaagtt       1620 atatttttg taccaccatg tagctttttt ggagttcgac ggcggtgatt tggttaggaa       1680
actgttggcg gagattaagt tgggaaagaa aaacagggaa agggataagg taccaaataa      1740
taaattaata aaaagaaaaa tatgaaattt tgatatatga aaccaaaata acgattggat      1800
catgagtccg gtatggaatc gggtgtttga ggggctaaaa agggattaac gagttggaac      1860
gactaagatg gattgcgagt ggcttattta cggatcagtt ctgggttaga gtgagatttt      1920
taattttgac caataagcaa ttgccacatc atatataacc aaaaaaattt tattcagcaa      1980
aggtccgtca gaaataaggg catgaatgag ccaaattttt aacgatgaag acagttttta      2040 caaataggt ggacagatgg tatttttaaa cccaaacgaa taggttaggg gcagttttgg       2100 ccctttttg ataaatctaa tatcactcca gtaatgacaa agctagaatc tacatatatc       2160
tgtctttatt ttcaacatat agattcctta cacatcattg tcacaaatct tgcttaaatg      2220
gaatctcaga gttaaataga gatagatttc actcaattat cagatcataa ctaaactacc      2280
taaagatgga tttaggagga attatcttaa tcttcctttt cagtaccctc tgcctctatc      2340
tcctttggac aatcattaaa ctcctttatt taatatggtg gatgccactt caaatacaaa      2400
atagaatgag ttttcaggga atcaaaggcc cccttatag ctttcccat gggaatacca        2460 aagaaatctc actaatgaga agccaaacta tggacaacct                            2500
```

<210> SEQ ID NO 25
<211> LENGTH: 318
<212> TYPE: PRT
<213> ORGANISM: Nicotiana tabacum

<400> SEQUENCE: 25

```
Met Cys Val Tyr Ser Asn Cys Asn Lys Lys Arg Gly Arg Gly Arg Glu
1               5                   10                  15

Arg Gly Val Val Ile Gln Gly Lys Thr Ala Val Gly Asn Asn Lys Thr
            20                  25                  30

Thr Asn Tyr Tyr Leu Tyr Phe Leu Ile Phe Ala Pro Ser Leu Thr Ser
        35                  40                  45

Thr Ala His Arg Phe Ser Asp Pro Lys Lys Val Ala Lys Met Asn Asp
    50                  55                  60

Ala Asp Val Ser Lys Gln Ile Gln Gln Met Val Arg Phe Ile Arg Gln
65                  70                  75                  80

Glu Ala Glu Glu Lys Ala Tyr Gly Phe Pro Ser Pro Lys Lys Tyr
                85                  90                  95

Trp Pro Ile Ser Tyr Ser Ile Asp Gln Leu Ala Leu Val Arg Leu Ile
            100                 105                 110

Leu Ser Asn Asn Val Arg Ile Glu Glu Phe Asn Ile Glu Lys Leu
        115                 120                 125

Gln Leu Val Glu Leu Glu Lys Lys Ile Arg Gln Glu Tyr Glu Arg
    130                 135                 140

Lys Glu Lys Gln Val Asp Val Arg Lys Ile Glu Tyr Ser Met Gln
145                 150                 155                 160

Leu Asn Ala Ser Arg Ile Lys Val Leu Gln Ala Gln Asp Asp Leu Val
                165                 170                 175

Asn Ser Met Lys Glu Ala Ala Ser Lys Glu Leu Leu Asn Val Ser His
            180                 185                 190
```

His Gln Asn His His Ile Tyr Lys Lys Leu Leu Gln Asp Leu Ile Val
            195                 200                 205

Gln Ser Leu Leu Arg Leu Lys Glu Pro Cys Val Leu Leu Arg Cys Arg
    210                 215                 220

Glu Asp Asp Val Ser Leu Val Glu Gly Val Leu Asp Ala Ala Lys Glu
225                 230                 235                 240

Glu Tyr Ala Glu Lys Ala Gln Val His Ser Pro Glu Val Ile Ile Asp
            245                 250                 255

Gln Ile Tyr Leu Pro Ser Ala Pro Ser His His Asn Ala His Gly Ser
            260                 265                 270

Ser Cys Tyr Gly Gly Val Val Leu Ala Ser Arg Asp Gly Lys Ile Val
            275                 280                 285

Cys Glu Asn Thr Leu Asp Ala Arg Leu Glu Val Val Phe Arg Lys Lys
            290                 295                 300

Leu Pro Glu Ile Arg Lys Cys Leu Phe Gly Gln Val Ala Ala
305                 310                 315

<210> SEQ ID NO 26
<211> LENGTH: 659
<212> TYPE: PRT
<213> ORGANISM: Nicotiana tabacum

<400> SEQUENCE: 26

Met Ile Thr Pro Lys Leu Ser Leu Leu Cys Ile Gln Asn Pro Gly Thr
1               5                   10                  15

Gln Thr Arg Ser Pro Ser Gly Tyr Ala Asn Glu Ser His Thr Thr Gly
            20                  25                  30

Ser Glu Asn Leu Thr Gln Leu Arg Leu Leu Leu Ser Gly Met Gly Lys
            35                  40                  45

Pro Arg Ile Met His Asn Ser Arg Glu Gly Asn Glu Val Ala His Leu
        50                  55                  60

Leu Ala Lys Lys Thr Ile Asn Gln Ser Asn Met Asp His Leu Val Tyr
65              70                  75                  80

Leu Ala Ile Ser Pro Ser Leu Val Glu Thr Lys Val Leu Ser Asp Lys
            85                  90                  95

Asp Gly Glu Ser Ser Leu Lys Phe Val Val Asp Ala Cys Arg Met
                100                 105                 110

Ser Asn Met Asp Phe Met Lys Val Phe Asp Gln Thr Val Arg Glu Ile
            115                 120                 125

Lys Arg Glu Val Asn Leu Lys Val Leu Lys Val Pro Glu Ile Glu Gln
        130                 135                 140

Lys Val Leu Asp Ala Thr Asp Asp Glu Pro Trp Gly Pro His Gly Thr
145                 150                 155                 160

Ala Leu Ala Glu Ile Ala Gln Ala Thr Lys Lys Phe Ser Glu Cys Gln
                165                 170                 175

Met Val Met Asn Val Leu Trp Thr Arg Leu Thr Glu Thr Gly Lys Asn
            180                 185                 190

Trp Arg Tyr Val Tyr Lys Ser Leu Ala Val Val Glu Tyr Leu Val Ala
        195                 200                 205

His Gly Ser Glu Arg Ala Val Asp Glu Ile Val Glu His Thr Tyr Gln
    210                 215                 220

Ile Ser Ser Leu Thr Ser Phe Glu Tyr Val Glu Pro Asn Gly Lys Asp
225                 230                 235                 240

```
Met Gly Ile Asn Val Arg Lys Lys Ala Glu Asn Ile Val Ala Leu Leu
                245                 250                 255

Asn Asn Lys Glu Lys Ile Glu Asp Ala Arg Asn Lys Ala Ala Ala Asn
                260                 265                 270

Arg Asp Lys Tyr Phe Gly Leu Ser Ser Ser Gly Val Thr Phe Lys Ser
                275                 280                 285

Ser Ser Ala Ser Leu Asn Ser Ser Asn Phe Gln Ser Gly Asp Arg
            290                 295                 300

Tyr Gly Gly Phe Gly Asn Lys Ser Asp Gly Asp Ser Phe Lys Asp Ser
305                 310                 315                 320

Tyr Arg Glu Lys Asp Arg Tyr Gly Glu Asp Lys Phe Asp Gln Phe Lys
                325                 330                 335

Ser Lys Lys Gly Ser Ser Arg Tyr Gly Ser Asn Val Gln Asp Thr Val
                340                 345                 350

Ser Ser Ser Gly Ser Lys Thr Ser Lys Arg Val Gly Lys Pro Asp Lys
            355                 360                 365

Ala Thr Ser Asn Pro Pro His Ser Ala Ala Val Ser Ser Ser Lys Tyr
            370                 375                 380

Glu Glu Asp Phe Asp Asp Phe Asp Pro Arg Gly Thr Ser Ser Thr Lys
385                 390                 395                 400

Pro Ser Thr Glu Lys Ser Asp Gln Val Asp Leu Phe Gly Gln Asn Leu
                405                 410                 415

Ile Gly Asp Leu Leu Asp Val Pro Thr Pro Val Pro Ala Asp Asn Ser
                420                 425                 430

Thr Val Ser Ser His Pro Ser Glu Val Asp Leu Phe Ala Asp Ala Asn
            435                 440                 445

Phe Ala Leu Ala Lys Pro Gln Ser Glu Ile Ser Val Asp Leu Phe Ala
            450                 455                 460

Ser Gln Pro Ala Ser Ser Ala Ala Pro Ser Thr Ile Asp Phe Phe
465                 470                 475                 480

Ser Ala Pro Asp Pro Val Val Gln Ser Asp Ile Arg Ser Pro Lys Ser
                485                 490                 495

Asp Lys Ile Asn Ala Thr Thr Val Asp Pro Phe Ala Ala Val Pro Leu
            500                 505                 510

Asn Thr Phe Asp Ser Ser Asp Pro Phe Gly Thr Phe Val Ser His Ala
            515                 520                 525

Asp Pro Val Ser Val Ala Ser Glu Asn Ala Asn Arg Gly Gly Asn Gln
            530                 535                 540

Glu Glu Thr Pro Ser Lys Leu Asp Lys Ser Ser Val Glu Ala Lys Pro
545                 550                 555                 560

Ala Pro Lys Lys Asp Asp Phe Gln Val Arg Ser Gly Ile Trp Ala Asp
                565                 570                 575

Ser Leu Ser Arg Gly Leu Ile Asp Leu Asn Ile Ser Ala Pro Lys Lys
            580                 585                 590

Val Asn Leu Ala Asp Ile Gly Ile Val Gly Gly Leu Thr Asp Gly Ser
            595                 600                 605

Asp Val Lys Glu Lys Gly Pro Thr Thr Phe Tyr Met Gly Arg Ala Met
            610                 615                 620

Gly Gln Gly Thr Gly Leu Gly Gln Ser Gly Phe Thr Ser Thr Ser Thr
625                 630                 635                 640
```

Gly Gly Asp Asp Phe Phe Ser Ser His Gln Asn Tyr Gln Phe Gly Ser
            645                 650                 655

Phe Gln Lys

<210> SEQ ID NO 27
<211> LENGTH: 284
<212> TYPE: PRT
<213> ORGANISM: Nicotiana tabacum

<400> SEQUENCE: 27

Met Ala Met Asp Asp Asn Phe His Arg Gln Arg Leu Gly Ala His Ala
1               5                   10                  15

Pro Pro Gly Tyr Phe Val Arg Leu Glu Asn Gly Arg Ala Lys Asp Asp
            20                  25                  30

Leu Tyr Leu Arg Lys Gly Gly Arg Met Arg Lys Trp Leu Cys Cys Thr
        35                  40                  45

Cys Gln Val Glu Glu Ser Asp Pro Ser His Glu Asn Glu Leu His Lys
    50                  55                  60

Ser Pro Lys Asn Asn Phe Asp Gly Tyr Gln Lys Gly Ser Lys Ala Ser
65                  70                  75                  80

Val Pro Ala Lys Ala Glu Val Gln Lys Ala Ile Pro Thr Ile Glu Val
                85                  90                  95

Pro Ala Leu Ser Leu Asp Glu Leu Lys Glu Thr Asp Asn Phe Gly
            100                 105                 110

Ser Lys Ala Leu Ile Gly Glu Gly Ser Tyr Gly Arg Val Tyr Tyr Ala
        115                 120                 125

Asn Leu Asn Asn Gly Lys Ala Val Ala Val Lys Lys Leu Asp Val Ser
    130                 135                 140

Ser Glu Pro Glu Thr Asn Val Asp Phe Leu Ser Gln Val Ser Met Val
145                 150                 155                 160

Ser Arg Leu Lys His Val Asn Leu Val Asp Leu Leu Gly Tyr Cys Val
                165                 170                 175

Glu Gly Asn Leu Arg Val Leu Ala Tyr Glu Lys Gly Val Gln Gly Ala
            180                 185                 190

Gln Pro Gly Pro Thr Leu Asp Trp Met Gln Arg Val Lys Ile Ala Val
        195                 200                 205

Asp Ala Ala Arg Gly Leu Glu Tyr Leu His Glu Lys Val Gln Pro Pro
    210                 215                 220

Ile Ile His Arg Asp Ile Arg Ser Ser Asn Val Leu Leu Phe Glu Asp
225                 230                 235                 240

Tyr Lys Ala Lys Leu Leu Ile Leu Ile Cys Gln Ile Ser Leu Leu Thr
                245                 250                 255

Trp Leu Leu Ala Phe Ile Leu His Glu Phe Trp Glu His Leu Val Ile
            260                 265                 270

Met His Gln Ser Asn Val Leu His Leu Thr Leu Leu
        275                 280

<210> SEQ ID NO 28
<211> LENGTH: 485
<212> TYPE: PRT
<213> ORGANISM: Nicotiana tabacum

<400> SEQUENCE: 28

Met Pro Pro Pro Pro Ser Thr Ile Ser Asp Asp Asp Ser Ser Tyr Phe
1               5                   10                  15

His Val Ser Thr Leu Leu Pro Leu Tyr Arg Ala Arg Leu Arg Lys Lys
                20                  25                  30

Leu Asn Leu Arg Arg Leu Arg Asn Gly Thr Cys Arg Ala Glu Phe Ala
        35                  40                  45

Asn Asp Ala Pro Ile Ala Val Ala Ile Gly Ala Cys Ile Phe Ser Ser
50                  55                  60

Leu Val Phe Pro Thr Thr Tyr Thr Glu Asp Asp Gly Asp Ser Val
65                  70                  75                  80

Ile Asp Ser Ala Asp Ala Arg Phe Ala Val Met Gly Ile Ile Ser Phe
                85                  90                  95

Ile Pro Tyr Phe Asn Trp Met Ser Trp Val Phe Ala Trp Leu Asp Thr
                100                 105                 110

Gly Lys Gln Arg Tyr Ala Val Tyr Ala Leu Val Tyr Leu Ala Pro Tyr
            115                 120                 125

Leu Arg Thr Asn Leu Ser Leu Ser Pro Glu Asp Ser Trp Leu Pro Ile
    130                 135                 140

Ala Ser Ile Leu Leu Cys Ile Phe His Ile Gln Leu Glu Val Ser Ile
145                 150                 155                 160

Lys Asn Gly Asp Phe Gln Ala Leu Asn Lys Phe Thr Gly Thr Gly Glu
                165                 170                 175

Glu Leu Ser Ser Val Ser Arg Lys Lys Asp Asp Ser Ile Ser Glu Glu
                180                 185                 190

Asp Met Ile Ala Gly Asp Val Val Asn Pro Asp His Ile Asp Val Gly
            195                 200                 205

Phe Asp Ser Ile Gly Gly Leu Gly Gly Ile Lys Asp Thr Leu Phe Gln
    210                 215                 220

Leu Ala Ile Leu Pro Leu Arg Arg Pro Glu Leu Phe Cys His Gly Lys
225                 230                 235                 240

Leu Leu Gly Pro Met Lys Gly Val Leu Leu Tyr Gly Pro Pro Gly Thr
                245                 250                 255

Gly Lys Thr Met Leu Ala Lys Ala Ile Ala Lys Glu Ser Gly Ala Val
            260                 265                 270

Phe Ile Asn Val Lys Val Ser Thr Leu Met Ser Lys Trp Phe Gly Asp
    275                 280                 285

Ala Gln Lys Leu Val Ala Ala Ile Phe Gly Leu Ala Tyr Lys Leu Gln
290                 295                 300

Pro Ala Ile Ile Phe Ile Asp Glu Val Asp Ser Phe Leu Gly Gln Arg
305                 310                 315                 320

Arg Ala Ser Glu Thr Glu Met Leu Thr Ser Met Lys Thr Glu Phe Met
                325                 330                 335

Ala Leu Trp Asp Gly Phe Thr Thr Asp Gln Asn Ala Arg Val Met Val
            340                 345                 350

Leu Ala Ala Thr Asn Arg Pro Thr Asp Leu Asp Glu Ala Ile Leu Arg
    355                 360                 365

Arg Phe Ser Gln Ser Phe Glu Ile Gly Lys Pro Ser Leu Ser Asp Arg
370                 375                 380

Thr Lys Ile Phe Lys Val Val Leu Lys Gly Glu Arg Ile Glu Asp Asn
385                 390                 395                 400

Val Asp Phe Asp Arg Leu Ala Gly Leu Cys Glu Gly Tyr Thr Gly Ser
                405                 410                 415

Asp Ile Leu Glu Ala Cys Lys Leu Ala Ala Phe Ile Pro Leu Arg Glu
            420                 425                 430

Tyr Leu Gln Asp Glu Lys Lys Gly Lys Gln Ser Gln Ala Pro Arg Pro
            435                 440                 445

Leu Ser Gln Ser Asp Leu Glu Thr Ala Leu Ala Gln Ser Lys Lys Thr
            450                 455                 460

Lys Ile Thr Ala Arg Lys Pro Ala Val Val Ser Phe Arg Leu Asp Asp
465                 470                 475                 480

Tyr Glu Asp Leu Asp
                485

<210> SEQ ID NO 29
<211> LENGTH: 444
<212> TYPE: PRT
<213> ORGANISM: Nicotiana tabacum

<400> SEQUENCE: 29

Met Ser Ser His Asp Ile Arg Arg Pro Phe Lys Arg Pro Ala Ile Ser
1               5                   10                  15

Asp Gln Gln Arg Arg Glu Leu Ser Leu Leu Arg Gln Cys Gln Asn
            20                  25                  30

Arg Arg Asp Ala Gln Leu Gln Ala Arg Arg Leu Ala Ser Thr Val Leu
            35                  40                  45

Ser Leu Gln Pro Thr Gln Asp Asp Tyr Lys Ser Ala Ser Glu Glu
50                  55                  60

Gln Gln Leu Asp Ile Glu Val Ala Ser Val Pro Glu Val Asp Ser Phe
65                  70                  75                  80

Pro Asp Glu Thr Asp Ala Asp Phe Gly His Pro Arg Asp Ala His Asp
            85                  90                  95

Ile Arg Gln Ala Thr Lys Leu Arg Gly Pro Glu Ala Arg Gln Trp Phe
            100                 105                 110

Ala Lys Gln Leu Met Leu Pro Glu Trp Met Ile Asp Val Pro Asp Asn
            115                 120                 125

Leu Asn Thr Asp Trp Tyr Val Phe Ala Arg Pro Ala Gly Lys Arg Cys
130                 135                 140

Phe Val Val Ser Ser Asn Gly Thr Thr Ile Ser Arg Leu Arg Asn Gly
145                 150                 155                 160

Ile Arg Leu His Arg Phe Pro Ser Ala Leu Pro Asn Gly Ala Arg Ile
            165                 170                 175

Asn Asn Ser Lys Ser Ala Gln Ser Tyr Cys Ile Leu Asp Cys Ile Phe
            180                 185                 190

His Glu Ser Asp Glu Thr Tyr Tyr Val Ile Asp Gly Val Cys Trp Ala
            195                 200                 205

Gly Leu Ser Leu Tyr Glu Cys Thr Ala Glu Phe Arg Phe Phe Trp Leu
210                 215                 220

Asn Ser Lys Leu Ala Glu Thr Gly Ala Cys Asp Ala Pro Ser Thr Tyr
225                 230                 235                 240

His Arg Tyr Lys Phe Ser Thr Leu Pro Val Tyr Asn Cys Asp Lys Glu
            245                 250                 255

Gly Leu His Thr Ala Tyr Val Gly Gln Val Pro Tyr Val Lys Asp Gly
            260                 265                 270

Leu Leu Phe Tyr Asn Lys His Ala His Tyr Gln Thr Gly Asn Thr Pro
            275                 280                 285

Leu Thr Leu Val Trp Lys Asp Glu Asn Cys Ser Gln Tyr Val Ile Asp
290                 295                 300

```
Thr Asp Asn Arg Gly Gln Val Pro Ser Gln Gln Val Val Leu Glu
305                 310                 315                 320

Leu Leu Asp Asp Ser Arg Leu Ala Thr Ser Asp Asp Pro Pro Val Ile
                325                 330                 335

Phe Gly Cys Leu Leu Gly Glu Phe Ile Gln Lys Thr Glu Leu Gln Arg
            340                 345                 350

Gly Asp Leu Ile Lys Phe Ala Ile Gly Glu Gly Gly Leu Val Phe Val
                355                 360                 365

Asp Ser Lys Leu Glu Lys Ala Asp Leu Gln Tyr Leu Gly Lys Ser Asn
            370                 375                 380

Arg Ala Arg Ala Phe Ala Asp Ser Tyr Ser Lys Val Leu Phe Gln Tyr
385                 390                 395                 400

Ala Ala Arg His Ser Pro Leu Arg Ile Glu His Leu Phe Ala Ser Ile
                405                 410                 415

Ser Ser Cys Val Glu Asp Gly Arg Ser Asn Ser Arg Cys Arg Tyr Gly
                420                 425                 430

Trp Leu Lys Cys His Ala Arg Glu Thr Phe Phe Asn
                435                 440
```

<210> SEQ ID NO 30
<211> LENGTH: 829
<212> TYPE: PRT
<213> ORGANISM: Nicotiana tabacum

<400> SEQUENCE: 30

```
Met Ala Gln Pro Leu Leu Lys Lys Asp Asp Arg Asp Asp Glu Ala
1               5                   10                  15

Glu Tyr Ser Pro Phe Met Gly Ile Glu Lys Gly Ala Val Leu Gln Glu
                20                  25                  30

Ala Arg Val Phe Asn Asp Pro Gln Leu Asp Ala Arg Arg Cys Ser Gln
            35                  40                  45

Val Ile Thr Lys Leu Leu Tyr Leu Leu Asn Gln Gly Glu Thr Phe Thr
    50                  55                  60

Lys Val Glu Ala Thr Glu Val Phe Phe Ala Val Thr Lys Leu Phe Gln
65                  70                  75                  80

Ser Lys Asp Leu Gly Leu Arg Arg Met Val Tyr Leu Met Ile Lys Glu
                85                  90                  95

Leu Ser Pro Ser Ala Asp Glu Val Ile Ile Val Thr Ser Ser Leu Met
            100                 105                 110

Lys Asp Met Asn Ser Ser Thr Asp Met Tyr Arg Ala Asn Ala Ile Arg
        115                 120                 125

Val Leu Cys Arg Ile Thr Asp Gly Thr Leu Leu Thr Gln Ile Glu Arg
    130                 135                 140

Tyr Leu Lys Gln Ala Ile Val Asp Lys Asn Pro Val Val Ala Ser Ala
145                 150                 155                 160

Ala Leu Val Ser Gly Ile His Leu Leu Gln Thr Asn Pro Glu Ile Val
                165                 170                 175

Lys Arg Trp Ser Asn Glu Val Gln Glu Ala Val Gln Ser Arg Ala Ala
            180                 185                 190

Leu Val Gln Phe His Ala Leu Ala Leu Leu His Gln Ile Arg Gln Asn
        195                 200                 205

Asp Arg Leu Ala Val Ser Lys Leu Val Thr Ser Leu Thr Arg Gly Thr
    210                 215                 220
```

```
Val Arg Ser Pro Leu Ala Gln Cys Leu Leu Ile Arg Tyr Thr Ser Gln
225                 230                 235                 240

Val Ile Arg Glu Ala Ala Met Ser Asn Gln Thr Gly Asp Arg Pro Phe
                245                 250                 255

Tyr Asp Tyr Leu Glu Gly Cys Leu Arg His Lys Ala Glu Met Val Ile
            260                 265                 270

Phe Glu Ala Ala Arg Ala Ile Thr Glu Leu Ser Gly Val Thr Ser Arg
        275                 280                 285

Glu Leu Thr Pro Ala Ile Thr Val Leu Gln Leu Phe Leu Ser Ser Ser
    290                 295                 300

Lys Pro Val Leu Arg Phe Ala Ala Val Arg Thr Leu Asn Lys Val Ala
305                 310                 315                 320

Met Thr His Pro Met Ala Val Thr Asn Cys Asn Ile Asp Met Glu Ser
                325                 330                 335

Leu Ile Ser Asp Gln Asn Arg Ser Ile Ala Thr Leu Ala Ile Thr Thr
            340                 345                 350

Leu Leu Lys Thr Gly Asn Glu Ser Ser Val Asp Arg Leu Met Lys Gln
        355                 360                 365

Ile Thr Asn Phe Met Ser Asp Ile Gly Asp Glu Phe Lys Ile Val Val
    370                 375                 380

Val Glu Ala Ile Arg Ser Leu Cys Leu Lys Phe Pro Leu Lys Tyr Arg
385                 390                 395                 400

Ser Leu Met Asn Phe Leu Ser Asn Ile Leu Arg Glu Glu Gly Gly Phe
                405                 410                 415

Glu Tyr Lys Lys Ala Ile Val Asp Ser Ile Val Ile Leu Ile Arg Asp
            420                 425                 430

Ile Pro Asp Ala Lys Glu Ser Gly Leu Leu His Leu Cys Glu Phe Ile
        435                 440                 445

Glu Asp Cys Glu Phe Thr Tyr Leu Ser Thr Gln Ile Leu His Phe Leu
    450                 455                 460

Gly Asn Glu Gly Pro Lys Thr Ser Asp Pro Ser Lys Tyr Ile Arg Tyr
465                 470                 475                 480

Ile Tyr Asn Arg Val Ile Leu Glu Asn Ala Thr Val Arg Ala Ser Ala
                485                 490                 495

Val Ser Thr Leu Ala Lys Phe Gly Ala Leu Val Asp Ser Leu Lys Pro
            500                 505                 510

Arg Ile Phe Val Leu Leu Lys Arg Cys Leu Phe Asp Gly Asp Asp Glu
        515                 520                 525

Val Arg Asp Arg Ala Thr Leu Tyr Leu Asn Thr Leu Gly Gly Asp Gly
    530                 535                 540

Ala Val Val Glu Thr Asp Asp Glu Val Lys Glu Phe Leu Phe Gly Ser
545                 550                 555                 560

Leu Gly Val Pro Leu Thr Asn Leu Glu Thr Ser Leu Lys Asn Tyr Glu
                565                 570                 575

Pro Ser Glu Glu Ala Phe Asp Ile Phe Ser Val Pro Lys Glu Val Lys
            580                 585                 590

Ser Gln Pro Leu Ala Glu Lys Lys Ala Pro Gly Lys Lys Pro Thr Gly
        595                 600                 605

Leu Gly Ala Pro Pro Val Gly Pro Thr Ser Thr Val Asp Ser Tyr Glu
    610                 615                 620

Arg Leu Leu Ser Ser Ile Pro Glu Phe Ala Ser Tyr Gly Lys Leu Phe
625                 630                 635                 640
```

-continued

```
Lys Ser Ser Ala Pro Val Glu Leu Thr Glu Ala Glu Thr Glu Tyr Ala
                645                 650                 655

Val Asn Val Val Lys His Ile Phe Asp Ser His Val Val Phe Gln Tyr
            660                 665                 670

Asn Cys Thr Asn Thr Ile Pro Glu Gln Leu Leu Glu Asn Gly Arg His
            675                 680                 685

Leu Trp Leu Leu Arg Lys Pro Glu Gly Val Pro Ala Val Gly Lys Phe
690                 695                 700

Ser Asn Thr Leu Arg Phe Ile Val Lys Glu Val Asp Pro Thr Thr Gly
705                 710                 715                 720

Glu Ala Glu Asp Asp Gly Val Glu Asp Glu Tyr Gln Leu Glu Asp Leu
                725                 730                 735

Glu Val Val Thr Ala Asp Tyr Met Leu Lys Leu Gly Val Ser Asn Phe
            740                 745                 750

Arg Asn Ala Trp Glu Ser Leu Gly Pro Asp Cys Glu Arg Gly Thr Glu
            755                 760                 765

Val Val Pro Ser Asn Ser Arg Ser His Thr Cys Leu Leu Ser Gly Val
770                 775                 780

Tyr Ile Gly Ser Lys Val Leu Val Arg Leu Ser Phe Gly Leu Asp
785                 790                 795                 800

Gly Ala Lys Glu Val Ala Met Lys Leu Ala Val Arg Ser Glu Asp Ile
                805                 810                 815

Ser Val Ser Asp Ala Ile His Glu Val Val Ala Ser Gly
            820                 825

<210> SEQ ID NO 31
<211> LENGTH: 566
<212> TYPE: PRT
<213> ORGANISM: Nicotiana tabacum

<400> SEQUENCE: 31

Met Lys Met Arg Gly Tyr Ser Phe Phe Thr Ala Thr Leu Ile Leu Val
1               5                   10                  15

Ala Val Ser Ile Phe Leu Ser Ser Ile His Thr Asp Ala Leu Pro Arg
            20                  25                  30

Asp Thr Phe Lys Ser Ile Leu Gly Glu Gly Asn Leu Glu Ser Trp Lys
        35                  40                  45

Asn Gly Val Leu Asp Ser Ala Gly Met Ala Gln Ala Pro Gly Pro Ala
    50                  55                  60

Asp Gly His Val Gly Thr Leu Val Leu Ala Gly Asn Arg Thr Arg Arg
65                  70                  75                  80

Pro Asp Phe Leu Ser Gly Phe His Lys Tyr Arg Gly Gly Trp Asp Ile
                85                  90                  95

Ala Asn Lys His Tyr Trp Ala Ser Val Gly Phe Thr Gly Leu Ala Gly
            100                 105                 110

Ile Ile Leu Ala Leu Leu Trp Phe Ile Ser Phe Gly Leu Ala Leu Val
        115                 120                 125

Val His Tyr Cys Cys Gly Trp Lys Phe Asn Ile Arg Gly Arg Glu Trp
    130                 135                 140

His Phe Ser Gln Asn Ile Cys Leu Gly Val Leu Ile Val Leu Thr Cys
145                 150                 155                 160

Ala Ala Ala Ile Gly Cys Val Leu Leu Ser Val Gly Gln Asp Asp Phe
                165                 170                 175

His Ala Glu Ala Leu Asp Thr Leu Lys Tyr Val Val Asn Gln Ser Asp
            180                 185                 190
```

Tyr Thr Val Gln Thr Leu Arg Asn Val Thr Gln Tyr Leu Leu Leu Ala
            195                 200                 205

Lys Thr Val Asn Val Ala Gln Ile Phe Leu Pro Ser Asp Val Lys Asp
            210                 215                 220

Asp Ile Asp His Leu Asn Gly Asp Leu Asp Ser Ala Ala Asp Lys Leu
225                 230                 235                 240

Glu Asp Lys Thr Asn Glu Asn Ser Gly Lys Ile Arg Arg Val Phe Asn
            245                 250                 255

Ala Val Arg Ser Ala Leu Ile Thr Ile Ala Ile Val Met Leu Leu Ile
            260                 265                 270

Ser Ile Leu Gly Leu Cys Leu Ser Ile Leu Gly His Gln His Ala Ile
            275                 280                 285

His Ile Phe Ile Ile Ser Gly Trp Leu Leu Val Ala Val Thr Phe Val
            290                 295                 300

Leu Tyr Gly Val Phe Val Ile Ile Asn Ser Ala Ile Ser Asp Thr Cys
305                 310                 315                 320

Met Ala Met Gly Glu Trp Val Asp Asn Pro His Ala Glu Ser Ala Leu
            325                 330                 335

Ser Asn Ile Leu Pro Cys Val Asp Pro Arg Thr Thr Asn Arg Thr Leu
            340                 345                 350

Phe Lys Ser Lys Gln Val Thr Val Asp Leu Val Asn Ile Val Asn Gly
            355                 360                 365

Phe Ile Asp Thr Tyr Ala Asn Ser Asn Pro Ser Asn His Ala Asn Ser
            370                 375                 380

Asn Tyr Tyr Asn Gln Ser Gly Pro Val Met Pro His Leu Cys Tyr Pro
385                 390                 395                 400

Tyr Asp Ser Gln Leu Gln Asp Leu Pro Cys Pro Ala Asp Gln Val Ser
            405                 410                 415

Met Ala Asn Ser Ser Met Val Trp Gln Asn Phe Thr Cys Asn Val Ser
            420                 425                 430

Ala Ala Ala Ile Cys Thr Ser Val Gly Arg Leu Thr Pro Asp Met Tyr
            435                 440                 445

Gly Gln Leu Val Ala Thr Val Asn Ile Ser Tyr Ala Leu Glu His Tyr
            450                 455                 460

Ala Pro Pro Leu Leu Asn Leu Gln Asn Cys Asp Phe Val Arg Asp Thr
465                 470                 475                 480

Phe Arg Asn Ile Thr Val Asn His Cys Pro Pro Leu Glu His His Leu
            485                 490                 495

Arg Val Val Asn Ala Gly Leu Ala Val Ile Ser Val Gly Val Met Leu
            500                 505                 510

Ser Leu Ala Leu Trp Ile Val Tyr Ala Asn Arg Pro Gln Arg Glu Glu
            515                 520                 525

Val Phe Ala Lys Leu Ser Ser Arg Ile Lys Ser Ser Cys Asn Gly Lys
            530                 535                 540

Asn Ile Ser Cys Ser Asn Ser Asn Ile Asp Leu Ser Ser Arg Gly Thr
545                 550                 555                 560

Thr Pro Lys Thr Gly Val
            565

<210> SEQ ID NO 32
<211> LENGTH: 280
<212> TYPE: PRT
<213> ORGANISM: Nicotiana tabacum

<400> SEQUENCE: 32

Met Leu Asp Ala Ser Ala Val Ala Tyr Ile Gln Ile Ala Ser Ile Ala
1               5                   10                  15

Ile Ala Asp Gln Val Ala Arg Gly Gln Ile Glu Leu Ala Lys Asn Val
                20                  25                  30

Arg Gln Arg Leu Thr Ser Pro Ser Val Ala Ala Pro Pro Leu Ser Thr
            35                  40                  45

Gly Lys Gln Lys Gly Gly Ser Ser Ser Cys Cys Lys Leu Ala Ala Ser
50                  55                  60

Thr Ser Ser Ala Gln Met Leu Thr Ser Val Leu Ser Ser Leu Val Ala
65                  70                  75                  80

Glu Glu Ala Ala Ser Leu Ser Ser Gly Leu Lys Ser Ala Gly Phe Ser
                85                  90                  95

Ser Ser Leu Pro Phe Ala Ser Pro Glu Lys Arg Leu Lys Leu Asp Lys
                100                 105                 110

Pro Met Thr Phe Ser Asp Met Asn Ser Glu Gly Gly Asn Ser Thr
            115                 120                 125

Tyr Phe Thr Ser Ser Gln Gln Pro Ile Thr Ser Ile Pro Leu Ala Pro
130                 135                 140

Ser Ser Gly Leu Gln Ser Ser Asn Gln Ile Gln Ala Pro Phe Pro Pro
145                 150                 155                 160

Pro Pro Pro Pro Pro Pro Leu Pro Pro Ala Asn Ser Pro Gly Ser
                165                 170                 175

Gln Leu Gly Gln Ser Ala Ala Met Met Met Gly Met Met Pro Tyr Gly
            180                 185                 190

Tyr Ser Ala Gly Ser Leu Gln Pro Pro Gln Ile Ala Met Gly Leu Arg
            195                 200                 205

Pro Pro Pro Pro Leu Pro Gln Gln Ala Gln Gln Leu His Leu Gln Thr
            210                 215                 220

Gln Gln Pro Gln Ser Gln Gln Pro Ala Asn Gly Gly Phe Tyr Arg
225                 230                 235                 240

Pro Leu Val Leu Asp Ser Met Asp Arg Pro Ile Ser Arg Gln His Gln
                245                 250                 255

Gln His Pro Gly Ser Lys Ser Leu Trp Asn Arg Glu His Met Leu His
            260                 265                 270

Cys Thr Leu Ile Val Lys Val Asp
            275                 280

<210> SEQ ID NO 33
<211> LENGTH: 225
<212> TYPE: PRT
<213> ORGANISM: Nicotiana tabacum

<400> SEQUENCE: 33

Met Glu Ser Asp Ala His Phe Leu Ala Lys Glu Asp Gly Ile Ile Ala
1               5                   10                  15

Gly Ile Ala Leu Ala Glu Met Ile Phe Ala Glu Val Asp Pro Ser Leu
                20                  25                  30

Lys Glu Met Ala Asp Ala Ala His Pro Ala Tyr Ile Leu Glu Thr Arg
            35                  40                  45

Lys Thr Ala Pro Gly Leu Arg Leu Val Asp Lys Trp Ala Val Leu Ile
        50                  55                  60

Gly Gly Gly Lys Asn His Arg Met Gly Leu Phe Asp Met Val Met Ile
65                  70                  75                  80

```
Lys Asp Asn His Ile Ser Ala Ala Gly Gly Val Gly Lys Ala Leu Lys
                85                  90                  95

Ser Val Asp Gln Tyr Leu Glu Gln Asn Lys Leu Gln Ile Gly Val Glu
           100                 105                 110

Val Glu Thr Arg Thr Ile Glu Glu Val Arg Glu Val Leu Asp Tyr Ala
           115                 120                 125

Ser Gln Thr Lys Thr Ser Leu Thr Arg Ile Met Leu Asp Asn Met Val
130                 135                 140

Val Pro Leu Ser Asn Gly Asp Ile Asp Val Ser Met Leu Lys Glu Ala
145                 150                 155                 160

Val Glu Leu Ile Asn Gly Arg Phe Asp Thr Glu Ala Ser Gly Asn Val
                165                 170                 175

Thr Leu Glu Thr Val His Lys Ile Gly Gln Thr Gly Val Thr Tyr Ile
           180                 185                 190

Ser Ser Gly Ala Leu Thr His Ser Val Lys Ala Leu Asp Ile Ser Leu
           195                 200                 205

Lys Ile Asp Thr Glu Leu Ala Leu Glu Val Gly Arg Arg Thr Lys Arg
210                 215                 220

Ala
225

<210> SEQ ID NO 34
<211> LENGTH: 717
<212> TYPE: PRT
<213> ORGANISM: Nicotiana tabacum

<400> SEQUENCE: 34

Met Thr Glu Val Ala Thr Ser Asn Val Val His Asp Val Leu Gly Arg
1               5                   10                  15

Arg Ala Glu Asp Val Asp Gln Pro Ile Ile Asp Tyr Ile Ile Asn Val
            20                  25                  30

Leu Ala Asp Glu Asp Phe Asp Phe Gly Leu Asp Gly Glu Gly Ala Phe
        35                  40                  45

Glu Ala Leu Gly Glu Leu Leu Val Asp Ser Gly Cys Val Ala Asp Phe
50                  55                  60

Pro Glu Cys Arg Ala Val Cys Ser Lys Leu Ser Glu Lys Leu Glu Lys
65                  70                  75                  80

His Gly Leu Val Lys Pro Gln Pro Thr Val Arg Ser Leu Lys Met Pro
                85                  90                  95

Leu Arg Met Tyr Asp Gly Met Asp Glu Glu Ala Pro Lys Asn Lys
            100                 105                 110

Lys Pro Glu Pro Val Asp Gly Pro Leu Leu Thr Glu Arg Asp Lys Ile
            115                 120                 125

Lys Ile Glu Arg Arg Lys Arg Lys Asp Glu Arg Leu Arg Glu Ala Glu
130                 135                 140

Tyr Gln Ala His Leu Lys Glu Val Glu Val Lys Ala Gly Met Pro
145                 150                 155                 160

Leu Val Cys Val Asn His Asp Gly Gln Gly Asp Gly Pro Thr Val Lys
                165                 170                 175

Asp Ile Arg Met Glu Asn Phe Asn Ile Ser Val Ala Gly Arg Asp Leu
            180                 185                 190

Ile Val Asp Gly Ser Val Thr Leu Ser Phe Gly Arg His Tyr Gly Leu
        195                 200                 205

Ile Gly Arg Asn Gly Thr Gly Lys Thr Thr Leu Leu Arg His Met Ala
210                 215                 220
```

-continued

```
Met His Ala Ile Asp Gly Ile Pro Lys Asn Cys Gln Ile Leu His Val
225                 230                 235                 240

Glu Gln Glu Val Val Gly Asp Asp Thr Ser Val Leu Gln Cys Ile Leu
                245                 250                 255

Asn Thr Asp Met Glu Arg Thr Gln Leu Leu Glu Glu Gly Arg Leu
            260                 265                 270

Leu Glu Leu Gln Arg Glu Ile Asp Leu Glu Gly Glu Ala Gly Lys Ser
        275                 280                 285

Asp Lys Leu Asn Gly Glu Ile Asp Lys Asn Ala Leu Ala Lys Arg Leu
        290                 295                 300

Glu Glu Ile Tyr Lys Arg Leu Asp Phe Ile Asp Ala Tyr Ser Ala Glu
305                 310                 315                 320

Ser Arg Ala Ala Thr Ile Leu Ser Gly Leu Ser Phe Thr Thr Glu Met
                325                 330                 335

Gln Lys Arg Ala Thr Lys Thr Phe Ser Gly Gly Trp Arg Met Arg Ile
                340                 345                 350

Ala Leu Ala Arg Ala Leu Phe Ile Glu Pro Asp Leu Leu Leu Leu Asp
            355                 360                 365

Glu Pro Thr Asn His Leu Asp Leu His Ala Val Leu Trp Leu Glu Thr
        370                 375                 380

Tyr Leu Val Lys Trp Pro Lys Thr Phe Ile Val Val Ser His Ala Arg
385                 390                 395                 400

Glu Phe Leu Asn Thr Val Val Thr Asp Ile Ile His Leu Gln Asn Gln
                405                 410                 415

Lys Leu Ser Thr Tyr Lys Gly Asp Tyr Asp Thr Phe Glu Arg Thr Arg
            420                 425                 430

Asp Glu Gln Val Lys Asn Gln Lys Ala Phe Glu Ala Asn Glu Arg
        435                 440                 445

Thr Arg Ala His Met Gln Thr Phe Ile Asp Lys Phe Arg Tyr Asn Ala
        450                 455                 460

Lys Arg Ala Ser Leu Val Gln Ser Arg Ile Lys Ala Leu Glu Arg Ile
465                 470                 475                 480

Gly Arg Val Asp Glu Val Ile Asn Asp Pro Asp Tyr Lys Phe Glu Phe
                485                 490                 495

Pro Ser Pro Asp Asp Arg Pro Gly Ala Pro Ile Ile Ser Phe Ser Asp
            500                 505                 510

Ala Ser Phe Gly Tyr Pro Gly Gly Pro Leu Leu Phe Lys Asn Leu Asn
        515                 520                 525

Phe Gly Ile Asp Leu Asp Ser Arg Val Ala Met Val Gly Pro Asn Gly
        530                 535                 540

Ile Gly Lys Ser Thr Ile Leu Lys Leu Ile Ser Gly Glu Leu Gln Pro
545                 550                 555                 560

Thr Ser Gly Thr Val Phe Arg Ser Ala Lys Val Arg Ile Ala Val Phe
                565                 570                 575

Ser Gln His His Val Asp Gly Leu Asp Leu Ser Ser Asn Pro Leu Leu
            580                 585                 590

Tyr Met Met Arg Cys Phe Pro Gly Val Pro Glu Gln Lys Leu Arg Gly
        595                 600                 605

His Leu Gly Ser Phe Gly Ile Thr Gly Asn Leu Ala Leu Gln Pro Met
        610                 615                 620

Tyr Thr Leu Ser Gly Gly Gln Lys Ser Arg Val Ala Phe Ala Lys Ile
625                 630                 635                 640
```

-continued

```
Thr Phe Lys Lys Pro His Ile Leu Leu Asp Glu Pro Ser Asn His
            645                 650                 655

Leu Asp Leu Asp Ala Val Glu Ala Leu Ile Gln Gly Leu Val Leu Phe
        660                 665                 670

Gln Gly Gly Val Leu Met Val Ser His Asp Glu His Leu Ile Ser Gly
    675                 680                 685

Ser Val Asp Gln Leu Trp Ala Val Ser Glu Gly Arg Val Thr Pro Phe
690                 695                 700

Asp Gly Thr Phe Gln Asp Tyr Lys Lys Ile Leu Gln Ser
705                 710                 715

<210> SEQ ID NO 35
<211> LENGTH: 384
<212> TYPE: PRT
<213> ORGANISM: Nicotiana tabacum

<400> SEQUENCE: 35

Met Gly Ala Gln Ile Ser Val Ser Lys Leu Ala Asn Leu Ser Phe Val
1               5                   10                  15

Pro Arg Ile Arg Val Pro Val Pro Asn Ile Ser Val Pro Ser Pro Ser
            20                  25                  30

Ile Ser Ser Gly Phe Val Ser Asn Leu Ser Cys Ser Ala Ile Gly Ile
        35                  40                  45

Ser Ser Val Leu Val Asn Phe Tyr Gln Ser Ala Ser Leu Ala Lys Ser
    50                  55                  60

Ala Asn Pro Ser Thr Tyr Thr Tyr Thr Val Pro Ser Ser Pro Ser Glu
65                  70                  75                  80

Val Leu Tyr Arg Trp His Leu Pro Glu Pro Asn Val Val Asp Ile Ser
                85                  90                  95

Gly Asn Tyr Asp Cys Ser Ser Val Lys Ser Arg Thr Val Val Val Leu
            100                 105                 110

Leu Gly Trp Leu Gly Ala Lys Gln Lys His Leu Lys Arg Tyr Ala Glu
        115                 120                 125

Trp Tyr Ala Ser Ala Gly Tyr His Val Ile Thr Phe Thr Phe Pro Met
    130                 135                 140

Ser Glu Ile Leu Ser Tyr Gln Val Gly Gly Lys Ala Glu Gln Asp Ile
145                 150                 155                 160

Glu Leu Leu Val Asn His Leu Val Asp Trp Leu Glu Glu His Gly
                165                 170                 175

Lys Asn Leu Val Phe His Thr Phe Ser Asn Thr Gly Trp Leu Thr Tyr
            180                 185                 190

Gly Val Ile Leu Glu Lys Phe Gln Lys Gln Asp Pro Val Leu Met Thr
        195                 200                 205

Arg Ile Lys Gly Cys Ile Val Asp Ser Ala Pro Val Ala Ala Pro Asp
    210                 215                 220

Pro Gln Val Trp Ala Ser Gly Phe Ser Ala Ala Phe Leu Lys Lys Asn
225                 230                 235                 240

Ser Val Ala Thr Lys His Ile Met Thr Ile Asn Asn Lys Asp Ala Asp
                245                 250                 255

Val Thr Ile Glu Thr Lys Thr Ser Ser Asp Ala Thr Pro Ala Val Thr
            260                 265                 270

Glu Ala Ala Leu Leu Val Val Leu Glu Lys Phe Phe Glu Val Val Leu
        275                 280                 285

Ser Leu Pro Ala Val Asn Arg Arg Leu Ser Asp Val Leu Asp Leu Leu
    290                 295                 300
```

```
Thr Ser Gln Gln Pro Ser Cys Pro Gln Leu Tyr Ile Tyr Ser Ser Ala
305                 310                 315                 320

Asp Arg Val Ile Pro Ala Ile Ser Val Glu Ser Phe Val Glu Glu Gln
                325                 330                 335

Arg Arg Ile Gly Arg Asn Val Arg Ala Cys Asn Phe Ile Ser Thr Pro
                340                 345                 350

His Val Asp His Phe Arg Asn Asp Pro Glu Leu Tyr Thr Leu Gln Leu
                355                 360                 365

Thr Gln Phe Leu Glu Asp Ser Val Leu Ser Ser Cys Lys Gln Ser Ser
370                 375                 380

<210> SEQ ID NO 36
<211> LENGTH: 547
<212> TYPE: PRT
<213> ORGANISM: Nicotiana tabacum

<400> SEQUENCE: 36

Met Gly Gly Ala Glu Asp Ala Glu Pro Pro Ser Lys Arg Val Lys Val
1               5                   10                  15

Ser Ser Gly Lys Pro Gly Asp Leu Ser Asn Gly Thr Phe Pro Arg Asp
                20                  25                  30

Pro Ala Ser Cys Ser Leu Asn Asp Leu Met Ala Arg Pro Leu Val Cys
                35                  40                  45

Gln Gly Asp Asp Glu Val Val Gly Thr Lys Gly Val Ile Lys Lys Val
            50                  55                  60

Glu Phe Val Arg Ile Leu Ala Glu Ala Leu Tyr Ser Leu Gly Tyr Asn
65                  70                  75                  80

Lys Thr Gly Ala His Leu Glu Glu Glu Ser Gly Ile Pro Leu Gln Ser
                85                  90                  95

Ala Val Val Lys Leu Phe Met Gln Gln Val Leu Asp Gly Lys Trp Asp
                100                 105                 110

Glu Ser Val Ala Thr Leu Arg Lys Ile Gly Leu Val Asp Glu Lys Val
                115                 120                 125

Val Gln Leu Ala Ser Phe Leu Ile Leu Glu Gln Lys Phe Phe Glu Leu
            130                 135                 140

Leu Asp Glu Lys Lys Val Met Asp Ala Leu Lys Thr Leu Ser Thr Glu
145                 150                 155                 160

Ile Gly Pro Leu Cys Ile Asn Thr Asp Arg Val Arg Glu Leu Ser Leu
                165                 170                 175

Cys Ile Leu Ser Pro Leu Gln Gln Val Arg Ala Val Val Ser Gly Gln
                180                 185                 190

Val Val Val Arg Ala Lys Pro Arg Arg Lys Leu Leu Glu Glu Leu Gln
            195                 200                 205

Lys Leu Leu Pro Pro Thr Val Ile Ile Pro Glu Gln Arg Leu Ile Arg
210                 215                 220

Leu Val Glu Gln Ala Leu Asp Leu Gln Leu Asp Ala Cys Arg Phe His
225                 230                 235                 240

Asn Ser Leu Val Gly Glu Met Ser Leu Leu Thr Asp His Gln Cys Gly
                245                 250                 255

Arg Asp Gln Ile Pro Ser Gln Thr Leu Gln Val Lys Leu Asp Gly Leu
                260                 265                 270

Phe Cys Met Lys His Gln Phe Ser Gly His Gln Lys Pro Val Ser Tyr
            275                 280                 285
```

```
Met Ser Trp Ser Pro Asp Asp His Gln Leu Leu Thr Cys Gly Val Glu
290                 295                 300
Glu Val Val Arg Arg Trp Asp Ile Glu Ser Gly Cys Thr His Ile
305                 310                 315                 320
Tyr Glu Lys Asn Gly Leu Gly Leu Ile Ser Cys Gly Trp Ala Pro Asp
                325                 330                 335
Gly Lys Arg Ile Leu Cys Gly Val Thr Asp Lys Ser Ile Ser Met Trp
                340                 345                 350
Asp Leu Glu Gly Lys Glu Leu Glu Cys Trp Lys Gly His Arg Thr Ile
                355                 360                 365
Arg Ile Ser Asp Leu Gly Ile Thr Ser Asp Gly Gln His Ile Val Ser
370                 375                 380
Val Cys Lys Asp Asn Met Ile Leu Leu Phe Gly Trp Glu Ser Lys Ala
385                 390                 395                 400
Glu Lys Val Ile Gln Glu Asp Gln Thr Ile Thr Ser Phe Val Leu Ser
                405                 410                 415
Met Asp Ser Lys Tyr Leu Leu Val Ser Leu Trp Asn Gln Glu Ile His
                420                 425                 430
Leu Trp Asn Ile Glu Gly Thr Val Lys Leu Ile Ser Lys Tyr Lys Gly
                435                 440                 445
His Lys Arg Ser Arg Phe Val Val Arg Ser Cys Phe Gly Gly Leu Gly
450                 455                 460
Gln Ala Phe Val Ala Ser Gly Ser Glu Asp Ser Gln Val Tyr Ile Trp
465                 470                 475                 480
His Arg Ser Ser Gly Glu Leu Ile Glu Thr Leu Ala Gly His Ser Gly
                485                 490                 495
Thr Val Asn Cys Val Ser Trp Asn Pro Ala Asn Pro His Met Leu Ala
                500                 505                 510
Ser Ala Ser Asp Asp His Thr Ile Arg Ile Trp Gly Met Asn Gln Val
                515                 520                 525
Asn Met Lys His Tyr Asp Thr Val Ser Asn Gly Val His Tyr Cys Asn
                530                 535                 540
Gly Gly Thr
545

<210> SEQ ID NO 37
<211> LENGTH: 587
<212> TYPE: PRT
<213> ORGANISM: Nicotiana tabacum

<400> SEQUENCE: 37

Met Ala Met Val Asp Glu Pro Leu Tyr Pro Ile Ala Val Leu Ile Asp
1               5                   10                  15
Glu Leu Lys Asn Asp Asp Ile Gln Leu Arg Leu Asn Ser Ile Arg Arg
                20                  25                  30
Leu Ser Thr Ile Ala Arg Ala Leu Gly Glu Glu Arg Thr Arg Lys Glu
            35                  40                  45
Leu Ile Pro Phe Leu Ser Glu Asn Asn Asp Asp Asp Glu Val Leu
            50                  55                  60
Leu Ala Met Ala Glu Glu Leu Gly Val Phe Ile Pro Tyr Val Gly Gly
65                  70                  75                  80
Val Glu His Ala His Val Leu Leu Pro Pro Leu Glu Thr Leu Cys Thr
                85                  90                  95
```

```
Val Glu Glu Thr Cys Val Arg Asp Lys Ala Val Glu Ser Leu Cys Arg
            100                 105                 110

Ile Gly Ser Gln Met Arg Glu Ser Asp Leu Val Asp Trp Phe Val Pro
            115                 120                 125

Leu Val Lys Arg Leu Ala Ala Gly Glu Trp Phe Thr Ala Arg Val Ser
        130                 135                 140

Ala Cys Gly Leu Phe His Ile Ala Tyr Ser Ser Ala Pro Glu Met Leu
145                 150                 155                 160

Lys Ala Glu Leu Arg Ser Ile Tyr Ser Gln Leu Cys Gln Asp Asp Met
                165                 170                 175

Pro Met Val Arg Arg Ser Ala Ala Thr Asn Leu Gly Lys Phe Ala Ala
            180                 185                 190

Thr Val Glu Ser Thr Tyr Leu Lys Ser Asp Ile Met Ser Ile Phe Asp
        195                 200                 205

Asp Leu Thr Gln Asp Gln Asp Ser Val Arg Leu Leu Ala Val Glu
    210                 215                 220

Gly Cys Ala Ala Leu Gly Lys Leu Leu Glu Pro Gln Asp Cys Val Ala
225                 230                 235                 240

His Ile Leu Pro Val Ile Val Asn Phe Ser Gln Asp Lys Ser Trp Arg
                245                 250                 255

Val Arg Tyr Met Val Ala Asn Gln Leu Tyr Glu Leu Cys Glu Ala Val
            260                 265                 270

Gly Pro Glu Pro Thr Arg Thr Asp Leu Val Pro Ala Tyr Val Arg Leu
        275                 280                 285

Leu Arg Asp Asn Glu Ala Glu Val Arg Ile Ala Ala Ala Gly Lys Val
    290                 295                 300

Thr Lys Phe Cys Arg Ile Leu Ser Pro Glu Leu Ala Ile Gln His Ile
305                 310                 315                 320

Leu Pro Cys Val Lys Glu Leu Ser Ser Asp Ser Ser Gln His Val Arg
                325                 330                 335

Ser Ala Leu Ala Ser Val Ile Met Gly Met Ala Pro Val Leu Gly Lys
            340                 345                 350

Asp Ala Thr Ile Glu His Leu Leu Pro Ile Phe Leu Ser Leu Leu Lys
        355                 360                 365

Asp Glu Phe Pro Asp Val Arg Leu Asn Ile Ile Ser Lys Leu Asp Gln
    370                 375                 380

Val Asn Gln Val Ile Gly Ile Asp Leu Leu Ser Gln Ser Leu Leu Pro
385                 390                 395                 400

Ala Ile Val Glu Leu Ala Glu Asp Arg His Trp Arg Val Arg Leu Ala
                405                 410                 415

Ile Ile Glu Tyr Ile Pro Leu Leu Ala Ser Gln Leu Gly Ile Gly Phe
            420                 425                 430

Phe Asp Asp Lys Leu Gly Ala Leu Cys Met Gln Trp Leu Gln Asp Lys
        435                 440                 445

Val Tyr Ser Ile Arg Asp Ala Ala Asn Asn Leu Lys Arg Leu Ala
    450                 455                 460

Glu Glu Phe Gly Pro Glu Trp Ala Met Gln His Ile Ile Pro Gln Val
465                 470                 475                 480

Leu Asp Met Thr Thr Ser Pro His Tyr Leu Tyr Arg Met Thr Ile Leu
                485                 490                 495

Arg Ala Ile Ser Leu Leu Ala Pro Val Met Gly Ser Glu Ile Thr Cys
            500                 505                 510
```

Ser Lys Leu Leu Pro Val Val Ile Thr Ala Thr Lys Asp Arg Val Pro
515                 520                 525

Asn Ile Lys Phe Asn Val Ala Lys Val Leu Gln Ser Leu Ile Pro Ile
530                 535                 540

Val Asp His Ser Val Val Glu Lys Thr Ile Arg Pro Ser Leu Val Glu
545                 550                 555                 560

Leu Ala Glu Asp Pro Asp Val Asp Val Arg Phe Tyr Ala Asn Gln Ala
            565                 570                 575

Leu Gln Ser Ile Asp Asn Val Met Met Ser Gly
            580                 585

<210> SEQ ID NO 38
<211> LENGTH: 621
<212> TYPE: PRT
<213> ORGANISM: Nicotiana tabacum

<400> SEQUENCE: 38

Met Gly Phe Ile Glu Ser Cys Ser Gln Thr Ala Glu Met Glu Ile Arg
1               5                   10                  15

Lys Cys Ser Pro Phe Leu Glu Ser Glu Leu Leu Ser Gly Asn Gly Gly
            20                  25                  30

Leu Pro Leu Thr Glu Trp Arg Thr Val Pro Asp Ile Trp Arg Thr Ser
        35                  40                  45

Ala Glu Lys Phe Gly Asp Arg Val Ala Val Asp Pro Tyr His Asp
    50                  55                  60

Pro Pro Thr Thr Met Thr Tyr Lys Gln Leu Tyr Gln Glu Ile Val Asp
65                  70                  75                  80

Phe Ser Glu Gly Leu Arg Val Val Gly Leu Asn Pro Asn Glu Lys Ile
                85                  90                  95

Ala Leu Phe Ala Asp Asn Ser Cys Arg Trp Leu Val Ala Asp Gln Gly
            100                 105                 110

Thr Met Ala Ser Gly Ala Ile Asn Val Val Arg Gly Ser Arg Ser Ser
        115                 120                 125

Asn Gln Glu Leu Leu Gln Leu Tyr Ser His Ser Glu Ser Val Ala Leu
130                 135                 140

Ala Ile Asp Asn Pro Glu Met Tyr Asn Arg Ile Ser Asp Thr Phe Gly
145                 150                 155                 160

Ser His Thr Ala Val Arg Phe Ala Ile Leu Leu Trp Gly Glu Lys Ser
                165                 170                 175

Ser Leu Gly Arg Glu Ala Val Gln Gly Tyr Pro Val Tyr Thr Tyr Lys
            180                 185                 190

Glu Ile Ile Glu Leu Gly His Lys Ser Arg Val Asp Leu Leu Asp Ser
        195                 200                 205

Glu Asp Ala Arg Lys Gln Tyr Ser Phe Glu Ala Ile Asn Ser Asp Asp
    210                 215                 220

Val Ala Thr Ile Val Tyr Thr Ser Gly Thr Thr Gly Asn Pro Lys Gly
225                 230                 235                 240

Val Met Leu Thr His Lys Asn Leu Leu His Gln Ile Leu Asn Leu Gly
                245                 250                 255

Glu Ile Val Pro Ala Val Pro Gly Asp Arg Phe Leu Ser Met Leu Pro
            260                 265                 270

Pro Trp His Ala Tyr Glu Arg Ala Cys Glu Tyr Phe Ile Phe Thr His
        275                 280                 285

Gly Thr Glu Gln Val Tyr Thr Thr Val Lys Asn Leu Lys Pro His Tyr
    290                 295                 300

-continued

```
Leu Ile Ser Val Pro Leu Val Tyr Glu Thr Leu Tyr Ser Gly Ile Leu
305                 310                 315                 320

Lys Gln Ile Asn Ser Asn Ser Ala Ala Ser Lys Leu Ile Ala Leu Leu
            325                 330                 335

Phe Leu Arg Ile Ser Met Thr Tyr Met Glu Ala Lys Arg Ile Tyr Glu
        340                 345                 350

Ala Gly Val Ser Gly Gly Ser Leu Ser Ser His Val Asp Lys Phe
    355                 360                 365

Phe Glu Ala Ile Gly Ile Lys Ile Gln Asn Gly Tyr Gly Leu Thr Glu
370                 375                 380

Ser Ser Pro Val Ile Ser Ala Arg His Leu Ala Cys Asn Val Leu Gly
385                 390                 395                 400

Ser Val Gly His Pro Ile Arg His Val Glu Val Lys Ile Val Asn Ala
                405                 410                 415

Glu Thr Asp Glu Val Leu Pro Pro Gly Ser Arg Gly Ile Val Lys Ala
            420                 425                 430

Arg Gly Pro Leu Val Met Lys Gly Tyr Tyr Lys Asn Pro Leu Ala Thr
        435                 440                 445

Lys His Ala Ile Asp Glu Asn Gly Trp Leu Asn Thr Gly Asp Leu Gly
    450                 455                 460

Trp Ile Ala Pro Asp His Ser Val Gly Arg Ser Arg Lys Ser Gly Gly
465                 470                 475                 480

Val Ile Val Leu Glu Gly Arg Ala Lys Asp Thr Ile Val Leu Ser Thr
                485                 490                 495

Gly Glu Asn Val Glu Pro Ser Glu Ile Glu Glu Ala Ala Met Gly Ser
            500                 505                 510

Ser Leu Ile Gln Gln Ile Val Val Ile Gly Gln Asp Gln Arg Arg Leu
        515                 520                 525

Gly Ala Ile Ile Val Pro Asn Lys Glu Val Leu Leu Ala Ala Lys
    530                 535                 540

Lys Ser Ala Ile Val Asp Ser Glu Thr Thr Glu Val Ser Lys Glu Lys
545                 550                 555                 560

Ala Val Gly Ile Leu Tyr Glu Glu Leu Arg Lys Trp Thr Ser Gly Cys
                565                 570                 575

Ser Phe Gln Val Gly Pro Ile Leu Ile Val Asp Glu Pro Phe Thr Ile
            580                 585                 590

Asp Ser Gly Leu Leu Thr Pro Thr Met Lys Ile Lys Arg Asp Lys Ile
        595                 600                 605

Ala Ala Leu Tyr Lys Glu Gln Ile Glu Asn Leu Tyr Lys
    610                 615                 620

<210> SEQ ID NO 39
<211> LENGTH: 869
<212> TYPE: PRT
<213> ORGANISM: Nicotiana tabacum

<400> SEQUENCE: 39

Met Gly Gly Asp Glu Thr Lys Lys Thr Thr Ile Met Val Leu Lys Val
1               5                   10                  15

Asp Leu Gln Cys Ser Ser Cys Tyr Lys Lys Val Lys Lys Val Leu Cys
            20                  25                  30

Lys Phe Pro Arg Cys Gly Val Ile Lys Ser Ile Glu Ile Lys Glu Pro
        35                  40                  45
```

```
Pro Lys Pro Lys Ala Pro Glu Lys Pro Lys Glu Pro Val Lys Pro Lys
         50                  55                  60

Glu Pro Glu Lys Pro Lys Gln Pro Glu Lys Pro Lys Glu Pro Glu Lys
 65                  70                  75                  80

Pro Lys Gln Pro Glu Lys Thr Thr Val Val Ile Glu Lys Pro Lys
                 85                  90                  95

Glu Pro Glu Lys Pro Lys Ala Pro Glu Lys Ser Lys Glu Pro Glu Lys
                100                 105                 110

Pro Lys Glu Pro Glu Lys Pro Lys Glu Val Glu Lys Pro Lys Pro Lys
            115                 120                 125

Glu Pro Glu Lys Pro Lys Glu Ala Pro Lys Pro Asn Pro Val Ala Pro
            130                 135                 140

Pro Ser Gln Pro Pro Pro Pro Ala Pro Glu Pro Ile Met Val Gln
145                 150                 155                 160

Gln Tyr Pro Gln Pro Pro Leu Gly Tyr Cys Cys Gly Gln Cys Tyr Glu
                165                 170                 175

Gly His Ile Gly Gly Pro Cys Tyr Gln Trp Tyr Gly Arg Pro Val Leu
                180                 185                 190

Pro Ala Pro Cys Tyr Asp Asn Tyr Gly Tyr Asn Tyr Gly Pro Gly Pro
            195                 200                 205

Gly Pro Gly Pro Tyr Gly Tyr Gly Arg Gly Cys Tyr Val Ser Arg Cys
210                 215                 220

Asp Gln Tyr Phe Ser Glu Glu Asn Ala Thr Gly Cys Ser Ile Ile Lys
225                 230                 235                 240

Trp Glu Pro Asn Ile Val Ala Ser Lys Ala Lys Glu Val Tyr Ser Ala
                245                 250                 255

Val Trp Val Arg Leu Leu Gln Leu Pro Thr Glu Phe Tyr Asp Arg Ile
                260                 265                 270

Val Leu Ser Arg Ile Gly Asn Ser Ile Gly Arg Leu Leu Arg Ile Asp
            275                 280                 285

Ala Cys Thr Ser Ser Thr Leu Arg Arg Arg Tyr Ala Arg Leu Cys Val
            290                 295                 300

Gln Val Gln Met Asp Gln Leu Val Gln Thr Thr Ile Gln Ile Gly Ser
305                 310                 315                 320

His Ile Gln Gln Leu Val Tyr Glu Gly Glu Lys Phe Leu Cys Lys Ala
                325                 330                 335

Cys Gly Arg Leu Gly Asn Thr Thr Ser Thr Cys Ser His Thr Leu Leu
            340                 345                 350

Asp Phe Gln Lys Gln Gln Glu Glu Pro Cys Pro Asn Ser Thr Gly
            355                 360                 365

Phe Ile Gly Lys Glu Arg Gln Leu Lys Ser Asn Asp Lys Pro Ser Pro
370                 375                 380

Ser Pro Lys Val Thr Ser Gln Lys Glu Ala Gln Pro Met Asp Leu Lys
385                 390                 395                 400

Ile Lys Leu Lys Arg His Leu Gln Val Ser Met Ser Ile Phe Leu Met
                405                 410                 415

Arg His Gln Pro Ile Leu Thr Ser Asn Lys Phe Glu Ser Leu Leu Asn
                420                 425                 430

Asp Ser Ser Ile Thr Phe Pro Glu Ile Ile Glu Ser Gln Met Glu Leu
            435                 440                 445

Asp Gly Gln Asn Ser Asn Leu Ser Pro Asp Ser Lys Leu Ser Phe Ser
    450                 455                 460
```

```
Pro Arg Asn His Ser Ser Ser Leu Leu Pro Pro Leu Ser Pro Arg Gly
465                 470                 475                 480

Gln Lys Ala Thr Cys Asn Ser Asn Lys Pro His Lys Thr Ala Gly Pro
            485                 490                 495

Ser Thr Asn Pro Leu Pro Cys Thr Pro Leu Pro Thr Leu Met Thr Pro
            500                 505                 510

Ile Thr Thr Glu Asn Pro Ile Thr Asp Leu Ser Leu Thr Thr Cys Gln
            515                 520                 525

Leu Ala Met Gln Leu Asn Ser Pro Ile Leu Ala Ser Leu Arg Leu His
            530                 535                 540

Val Lys Asn Arg Thr Met His Thr Lys Phe Leu Leu Thr Asp Phe Gln
545                 550                 555                 560

Ser Leu Pro His Glu Asn Gln Ser Pro Ser Ser Pro Ser Ser Ser Pro
            565                 570                 575

Thr His Tyr Glu Ser Thr Pro Leu Leu Pro Ser Asn Glu Asn Pro Ser
            580                 585                 590

Lys Ile Thr Leu Thr Pro Pro Ser Phe Leu Asn Thr Val Gln Asn Glu
            595                 600                 605

Pro Pro Thr Pro Gly Tyr Lys Pro Ser Asp Leu His His Gln Cys Pro
610                 615                 620

Leu Thr Gly Pro Pro Thr Asn Ala Met Val Gly Thr Arg Thr Ser Gly
625                 630                 635                 640

Pro Ser Gly Phe Leu His Ser Gln Tyr Pro Lys Ser Arg Ser Pro Val
            645                 650                 655

Cys Ser Thr Glu Pro Thr Gly Pro Ser Ser Ile Asn Leu Gly Gly Tyr
            660                 665                 670

Glu Ala Ser Asn Val Glu Leu His Gln Pro Pro Leu Val Asp Lys Cys
            675                 680                 685

Ser Arg Ala His Ser Pro Thr Leu Ala Pro Ala Leu Leu His Asn Met
            690                 695                 700

Gln Ala His Trp Asn Pro Pro His Phe Asn Pro Leu Gln Asn Met
705                 710                 715                 720

Gln Leu Phe Tyr Gln Leu Pro Phe Phe Ala Pro Gln Asp Gln Asn Thr
            725                 730                 735

Pro Pro Leu Ile His Ala Trp Gln Pro Ile Pro Gln His Tyr Pro Ala
            740                 745                 750

Pro Met Asp Phe His His Thr His Ser His Pro His His Ser Ala Pro
            755                 760                 765

Val Pro Gly Glu Gln Glu Met Glu Thr Gln Asn Gln Thr Ile Pro Pro
            770                 775                 780

Leu Asn Ile Thr Ser Tyr Thr Glu Asn Ser Asn Leu His Glu Val Lys
785                 790                 795                 800

Ile Leu Leu Phe Gln Ala Met Glu Glu Lys Lys Tyr Val Arg Lys Cys
            805                 810                 815

Pro Thr Glu Leu Tyr Lys Cys Ser Leu Asp Ile Arg Pro Pro Leu Asn
            820                 825                 830

Ala Ala Val Gly Asn Phe Ala Val Ile Leu Ser Pro Ser Leu Asn Gly
            835                 840                 845

Leu Pro Val Pro Pro Met Gly Ser Gln Phe Asn Val Thr Pro Gln Pro
            850                 855                 860

Thr Pro Ile Asn Asp
865
```

```
<210> SEQ ID NO 40
<211> LENGTH: 369
<212> TYPE: PRT
<213> ORGANISM: Nicotiana tabacum

<400> SEQUENCE: 40
```

| | | | | | | | | | | | | | | |
|---|---|---|---|---|---|---|---|---|---|---|---|---|---|---|
| Met | His | Ile | Leu | Tyr | Thr | Cys | Pro | Leu | Ile | Leu | Phe | Met | Ala | Leu | Leu |
| 1 | | | | 5 | | | | | 10 | | | | | 15 | |
| Phe | Ala | Tyr | Ala | Ala | Ala | Thr | Ala | Ala | Asp | Leu | Glu | Thr | Asn | Gly | Ala |
| | | | 20 | | | | | 25 | | | | | 30 | | |
| Glu | Lys | Ala | Gly | Ala | Asp | Ala | Gly | Ile | Leu | Ser | Ser | Asn | Ser | Ser | Val |
| | | | | 35 | | | | | 40 | | | | | 45 | |
| Asn | Glu | Asn | Leu | Asp | Leu | Ile | Asn | Met | Asn | Arg | Lys | Lys | Asp | Gly | His |
| | 50 | | | | | 55 | | | | | 60 | | | | |
| Leu | Asp | Asn | Asp | Ser | Ser | Asn | Val | Gly | Asp | Gln | Asn | Lys | Ser | Asn | Asp |
| 65 | | | | | 70 | | | | | 75 | | | | | 80 |
| Ser | Ser | Ala | Lys | Lys | Gly | Asp | Asp | Arg | Glu | Gly | Leu | Lys | Glu | Ala | Glu |
| | | | | 85 | | | | | 90 | | | | | 95 | |
| Val | Glu | Lys | Lys | Arg | Ile | Asp | Ser | Gly | Ser | Lys | Arg | Asp | Asp | Arg | Lys |
| | | | 100 | | | | | 105 | | | | | 110 | | |
| Glu | Glu | Thr | Lys | Glu | Ala | Glu | Gln | Gln | Asp | Lys | Ala | Lys | Asp | Ile | Ser |
| | | | | 115 | | | | | 120 | | | | | 125 | |
| Ser | Glu | Lys | Gln | Gly | Glu | Met | Glu | Lys | Ile | Leu | Pro | Asp | Gly | Ile | Gln |
| | 130 | | | | | 135 | | | | | 140 | | | | |
| Ser | Arg | Glu | Glu | Ile | Leu | Pro | Thr | Arg | Lys | Glu | Ser | Phe | His | Gly | Glu |
| 145 | | | | | 150 | | | | | 155 | | | | | 160 |
| Glu | Cys | Asp | Ser | Ser | Tyr | Ser | Cys | Thr | Ile | Glu | Lys | Ala | Val | Val |
| | | | | 165 | | | | | 170 | | | | | 175 | |
| Ala | Cys | Leu | Arg | Val | Pro | Gly | Asn | Glu | Ser | Pro | Asp | Leu | Ser | Leu | Leu |
| | | | 180 | | | | | 185 | | | | | 190 | | |
| Val | Gln | Asn | Asn | Gly | Lys | Gly | Thr | Val | Asn | Ile | Leu | Ile | Lys | Ala | Pro |
| | | | | 195 | | | | | 200 | | | | | 205 | |
| Glu | Phe | Val | Gln | Leu | Glu | Lys | Glu | Lys | Ile | Glu | Leu | Gln | Gly | Lys | Glu |
| | 210 | | | | | 215 | | | | | 220 | | | | |
| Asn | Gln | Arg | Met | Lys | Val | Ser | Ile | Arg | Asn | Ala | Gly | Asn | Asp | Asn | Asn |
| 225 | | | | | 230 | | | | | 235 | | | | | 240 |
| Ile | Ile | Leu | Lys | Ala | Gly | Asp | Gly | Gln | Cys | Thr | Leu | Asp | Phe | Arg | Gly |
| | | | | 245 | | | | | 250 | | | | | 255 | |
| Leu | Ile | Asp | Asn | Ala | Asp | Lys | Thr | Ser | Gln | Phe | Lys | Tyr | Gly | Phe | Leu |
| | | | 260 | | | | | 265 | | | | | 270 | | |
| Ser | Phe | Ala | Ile | Met | Cys | Leu | Ala | Ala | Ile | Ala | Leu | Val | Ala | Thr | Val |
| | | | | 275 | | | | | 280 | | | | | 285 | |
| Leu | Met | Tyr | Phe | Lys | Arg | Arg | Leu | Leu | Val | Ser | Ser | Gly | His | Lys | Tyr |
| | 290 | | | | | 295 | | | | | 300 | | | | |
| Gln | Lys | Leu | Asp | Met | Asp | Leu | Pro | Val | Ser | Ser | Gly | Arg | Lys | Thr | Glu |
| 305 | | | | | 310 | | | | | 315 | | | | | 320 |
| Thr | Leu | Ser | Thr | Asp | Gly | Trp | Asp | Asn | Ser | Trp | Asp | Asp | Trp | Asp |
| | | | | 325 | | | | | 330 | | | | | 335 | |
| Asp | Glu | Glu | Ala | Pro | Lys | Ala | Pro | Ser | Val | Pro | Val | Thr | Pro | Ser | Phe |
| | | | 340 | | | | | 345 | | | | | 350 | | |
| Ser | Ser | Lys | Ser | Ile | Thr | Ser | Arg | Arg | Ser | Ser | Lys | Glu | Ser | Trp | Lys |
| | | | | 355 | | | | | 360 | | | | | 365 | |
| Asp | | | | | | | | | | | | | | | |

```
<210> SEQ ID NO 41
<211> LENGTH: 957
<212> TYPE: DNA
<213> ORGANISM: Nicotiana tabacum

<400> SEQUENCE: 41
atgtgtgtgt actccaattg taacaaaaaa cgtgggagag ggagagagag aggagtcgtg      60
attcaaggga agacagcagt tggcaataat aagactacaa attactatct ctactttctg     120
attttcgctc cttcactcac atccacagca catcgcttct ccgatccaaa aaagttgcg      180 aagatgaacg acgcagatgt atcgaagcag atccagcaga tggtcagatt catccgccag     240
gaagccgaag aaaaagccta tggatttccg tctccgccga agaagtattg gcctatttct     300
tattctattg atcaattagc tttagttaga ctaattttga gtaataatgt gcgcattgaa     360
gaagaattca acatcgagaa gttgcagcta gtggaactgg agaagaagaa gatcaggcag     420
gaatacgagc gtaaggagaa acaagtcgat gttcgcaaga aaattgagta ctccatgcaa     480
ctcaacgcct ctcgaatcaa ggttcttcaa gctcaggatg acttggtcaa ctccatgaag     540
gaggcagcat caaggagct tttaaacgtc agccatcacc agaaccacca tatttataag      600
aagcttctgc aggatcttat tgttcagagt ttgctcagac ttaaagagcc ttgcgtccta     660
ctacgttgtc gggaagatga tgtttccttg gtagaagggg tcttggatgc agcaaaagag     720
gagtatgcag aaaaagctca ggttcactca ccggaggtca taattgacca aatctacctt     780
ccatcagctc catcacatca caatgctcat ggctcttctt gctatggagg agtagttttg     840
gcttctcgag atgggaaaat tgtatgtgaa aatacacttg atgccagatt ggaagttgtg     900
ttccgtaaga aactaccgga gattcgcaag tgtctatttg gtcaggttgc tgcctaa       957

<210> SEQ ID NO 42
<211> LENGTH: 1980
<212> TYPE: DNA
<213> ORGANISM: Nicotiana tabacum

<400> SEQUENCE: 42
atgattactc caaagctatc tctcctttgc atacaaaatc ctggcactca gacaaggtct      60
ccaagtggct atgcaaatga atctcatacc accggaagtg aaaatttgac tcaactgagg     120
ttattactgt ccggaatggg aagccaagg attatgcata actccaggga aggaaatgaa      180
gtagcccacc tactggctaa gagacaatc aatcaatcta acatggatca tctcgtctat      240
ctggcaattt ctccttctct tgttgagacc aaggtgttgt cagacaaaga tggagaatct     300
tctctaaaat ttgttgtaga cgatgcttgt aggatgtcca atatggattt catgaaggta     360
ttcgatcaaa cagttcgcga aataaagagg gaggtgaatt tgaaagtgtt gaaggttcct     420
gagattgagc agaaggtatt ggacgctacg gatgatgaac cttggggccc ccatggtact     480
gcattggctg agatagctca ggctacaaaa aaattctctg agtgtcagat ggttatgaat     540
gtcctgtgga caagattgac tgaaacagga agaattggc gttatgttta taagtctttg      600
gctgttgttg agtatttggt ggctcacgga tctgaacgcg ctgttgatga gatcgtagaa     660
catacctatc agatatcttc tctcacaagt ttcgagtatg ttgaacccaa tgggaaagat     720
atggggatca atgtgaggaa gaaagcagaa aatattgtgg cactattgaa taacaaggaa     780
aagatcgaag acgctagaaa taaagctgct gcaaatcgcg acaagtactt tggattgtca     840
tcttctggag taacatttaa atcgagctct gcctccctaa atagcagcag caactttcag     900
agtggtgatc gatatggagg tttttggaaat aaaagtgatg gcgattcatt taaggatagt     960
```

| | |
|---|---:|
| tacagggaaa aggatcggta tggtgaagat aaatttgacc agtttaaatc aaagaagggg | 1020 |
| tcttctcgtt atggaagcaa tgttcaagac actgtttcat ctagtggatc aaagacgtca | 1080 |
| aagagggtag gtaaacctga taaagctact tctaatcctc cacatagtgc agctgtatca | 1140 |
| tcaagcaaat atgaggaaga ttttgatgat tttgatcctc gagggacttc aagtactaag | 1200 |
| ccttccaccg aaaaatctga ccaagtagat ctatttggac aaaatttgat tggtgacctc | 1260 |
| ttggatgtac caacacctgt tccagctgat aattctactg tctccagtca tccatcagag | 1320 |
| gttgatttat ttgctgatgc caattttgca ttggcgaaac cacagtctga gataagtgta | 1380 |
| gatctgtttg cttctcagcc tgcctcttca tctgcagctc cttcaaccat agatttttt | 1440 |
| tctgcaccag atcctgttgt acaatccgat atcagatctc ctaaatcaga caagataaat | 1500 |
| gctactacgg ttgatccgtt tgctgcagtt ccactaaata cctttgatag ttctgatccc | 1560 |
| tttggtacat ttgtttctca tgctgatcct gtatcagtag ccagtgaaaa tgctaatcgt | 1620 |
| ggtgggaatc aggaggagac tcctagcaaa ttagataaat cttctgtcga agctaagccc | 1680 |
| gcaccaaaga aggatgattt tcaagtcagg tctggaatat gggctgattc attgagccgt | 1740 |
| ggactgattg atctgaatat ctctgcaccc aaaaaggtca accttgcaga cataggcatc | 1800 |
| gtgggtggat tgaccgatgg gtcagatgtg aaagaaaaag gcctactac attttacatg | 1860 |
| ggcagagcca tgggtcaagg aaccgggctt ggccaatccg ggttcacgtc cacatcaacg | 1920 |
| ggtggagatg acttttttc aagtcaccag aactatcaat ttggcagctt ccaaaagtga | 1980 |

<210> SEQ ID NO 43
<211> LENGTH: 855
<212> TYPE: DNA
<213> ORGANISM: Nicotiana tabacum

<400> SEQUENCE: 43

| | |
|---|---:|
| atggcgatgg atgacaattt ccataggcaa cgactagggg cacatgcacc tccgggttac | 60 |
| tttgtccgct tggagaacgg aagggctaaa gacgatcttt acttgagaaa gggaggaagg | 120 |
| atgagaaagt ggctctgctg cacctgccaa gtagaggagt ctgacccatc gcatgaaaac | 180 |
| gagctccaca aaagccccaa gaacaatttt gatggatatc agaaagggtc aaaagcatca | 240 |
| gttcctgcca aggctgaagt gcaaaaggca ataccaacta tagaggtccc tgcattgtct | 300 |
| ttggatgaac tgaaagagga aactgacaat ttggatcga aggcattaat tggtgaagga | 360 |
| tcttacggaa gagtatacta tgctaatcta acaatggca agccgtggc tgtaaaaaag | 420 |
| cttgatgttt catctgagcc tgagactaat gttgacttcc tgagccaggt ctctatggtt | 480 |
| tcaagattga agcatgtaaa tctggttgat ttgcttggtt actgtgtgga agggaaccttt | 540 |
| cgtgtattag cttatgagaa aggagtacaa ggagcacaac ctggacctac acttgattgg | 600 |
| atgcaacggg taaaaattgc tgttgatgct gcaaggggcc ttgagtattt gcatgagaag | 660 |
| gtccagcctc caataataca cagggatatc agatcaagca atgtccttct ctttgaagac | 720 |
| tacaaagcaa aattgctgat tttaatctgt caaatcagtc tcctgacatg gctgctcgcc | 780 |
| ttcattctac acgagttttg ggaacatttg gttatcatgc accagagtaa tgtcttgcac | 840 |
| cttactcttc tttga | 855 |

<210> SEQ ID NO 44
<211> LENGTH: 1458
<212> TYPE: DNA
<213> ORGANISM: Nicotiana tabacum

<400> SEQUENCE: 44

```
atgccaccgc cgccgtccac catctccgac gatgattcct cttacttcca cgtcagcact    60
cttctacctc tatatcgagc tcgcctccgc aaaaaactta atctgagaag gttgagaaat   120
ggaacttgta gggcagagtt tgcaaacgac gcgccaatcg ccgtcgctat cggtgcttgc   180
attttcagct cgttggtttt tccgactact tacacggagg atgatgacgg ggactccgtg   240
attgattctg ctgatgcgag gtttgctgtt atgggaatta tcagcttcat tccgtatttt   300
aattggatga gttgggtttt cgcgtggttg gatactggga agcagcgtta cgctgtttat   360
gctcttgtgt atttggctcc atatttaaga accaatctgt ctctttctcc tgaagacagc   420
tggctaccaa ttgctagcat cctcttgtgc atcttccaca ttcaactaga agtaagtatc   480
aaaaatggag attttcaggc attgaacaaa tttactggga ctggagagga actatcatca   540
gtttctagga agaaagatga tagcatctct gaagaggata tgattgctgg ggatgtcgtg   600
aatccagacc acatagatgt ggggtttgat tcgattgggg ggcttggtgg gattaaggat   660
actttgtttc agctggccat tttacctctg cgaaggcctg aattgttttg tcatgggaaa   720
ttgcttggtc caatgaaagg ggttctgttg tatggaccac ctgggacagg gaagacaatg   780
cttgctaaag ccattgctaa agagtctggt gctgtgttca ttaatgtgaa ggtttctact   840
ctcatgagca gtggtttgg tgatgcgcaa aagcttgttg ctgctatttt ggtttggcc    900
tataagctcc agcctgctat aatatttatt gatgaagttg acagcttttt gggccagcgt   960
cgtgcaagtg agactgaaat gctgactagc atgaaaactg agttcatggc cttatgggat  1020
ggttttacta ctgatcagaa tgctagagtt atggtcctgg cagcaaccaa tcgcccaact  1080
gaccttgatg aggcaatact taggcgcttt tctcagtcat ttgagattgg gaaaccttcc  1140
cttagtgata gaacaaagat atttaaggta gtattgaagg gtgagagaat tgaagataac  1200
gttgactttg atcgacttgc tggcttgtgt gagggataca ctggttcaga cattctcgag  1260
gcctgcaagc tagctgcctt tattcctctt agggagtatt tgcaagatga aagaaagga   1320
aagcaatcac aggctccaag gccattgtca cagtctgatc tagagacagc tttggctcaa  1380
tcaaagaaga ccaagattac tgctaggaaa cctgctgtag tgagctttcg gttggatgat  1440
tatgaggatt tagactga                                                 1458
```

<210> SEQ ID NO 45
<211> LENGTH: 1335
<212> TYPE: DNA
<213> ORGANISM: Nicotiana tabacum

<400> SEQUENCE: 45

```
atgagctcac acgatatacg ccgcccgttc aaacggccgg cgatctcaga ccaacaaaga    60
cgccgagaac tttcattgct ccggcagtgc caaaaccgcc gcgacgctca gttacaagcc   120
cgtcgtttag cttccacagt cctctctctt caacccacgc aagacgatga ctacaagtcc   180
gcttccgaag agcaacagct ggatatagaa gttgcttccg tccccgaagt tgattccttt   240
ccggatgaaa ccgacgccga ttttggacat cctaggacg cacatgatat tcgtcaagct    300
actaagctca gaggacctga agctcgtcag tggttcgcca agcagcttat gcttcctgaa   360
tggatgattg atgttcctga taacttgaac acggattggt atgtatttgc taggccagct   420
ggaaagagat gttttgttgt tcttcaaac ggaacaacaa tcagtagact gcgcaatgga    480
attcgcttgc accgtttttcc ttctgctcta cctaacggtg ccagaattaa taacagtaaa   540
```

| | |
|---|---|
| tctgctcaat catactgtat tctcgattgc atatttcacg agtctgatga aacatattat | 600 |
| gtcattgacg gtgtatgttg ggcgggactt tcgttatatg agtgcacggc ggaattcaga | 660 |
| ttcttttggt taaacagcaa gcttgctgag acgggggctt gtgatgctcc ctctacttat | 720 |
| catagatata aatttagtac acttcctgtc tacaactgtg acaaagaagg actacacaca | 780 |
| gcttatgtag acaagttcc atatgtcaag gatggattac tgttttacaa caagcatgca | 840 |
| cattaccaaa caggaaatac accgttaaca ttggtttgga aggatgagaa ctgtagccag | 900 |
| tatgtcattg atacagataa tagaggacaa gttccaagtc aacaacaggt agttttggag | 960 |
| ctcctagatg atagcagact ggctacatct gatgatcctc ctgtcatatt tggttgcttg | 1020 |
| cttggggaat tcatacaaaa gacagaactt cagcgtggag atcttataaa gtttgctata | 1080 |
| ggtgaaggcg gattagtttt tgttgacagt aaactggaga aagctgatct acaatacttg | 1140 |
| ggcaaatcca atcgtgctcg tgcttttgct gatagttact cgaaggtctt gttccagtac | 1200 |
| gctgctcgac attctcctct gagaattgaa catcttttg catcaatcag ttcatgtgtc | 1260 |
| gaagatggaa gatcaaactc aagatgcaga tatggctggt taaagtgcca tgcacgggaa | 1320 |
| acttttttca actaa | 1335 |

<210> SEQ ID NO 46
<211> LENGTH: 2490
<212> TYPE: DNA
<213> ORGANISM: Nicotiana tabacum

<400> SEQUENCE: 46

| | |
|---|---|
| atggctcagc ctctcctgaa gaaagacgac gatcgcgatg acgaagcgga gtactctccg | 60 |
| tttatgggga ttgagaaggg ggctgtgctt caggaagcta gggttttcaa tgatccgcaa | 120 |
| ttggatgcac gcagatgctc acaggtcatt acaaagcttc tgtatcttct gaatcagggt | 180 |
| gagacgttta caaaggttga agctacagaa gtgttctttg ctgtcacaaa actctttcag | 240 |
| tcaaaggatc ttggtctaag gagaatggta tacttgatga taaaagagct ttctcccctca | 300 |
| gctgatgagg taatcatcgt tactagctct cttatgaagg acatgaatag cagtacagat | 360 |
| atgtatcgtg caaatgctat tcgagtcctc tgccgaatca cagatgggac tcttctcaca | 420 |
| caaattgaga gatacttgaa acaagcgatt gttgacaaaa accctgttgt tgcaagtgct | 480 |
| gcccttgtta gtggaatcca tttgcttcag acaaacccgg agattgtgaa agatgtggagc | 540 |
| aatgaggtcc aagaagctgt tcagtcaagg gcagctctcg ttcaattcca tgcactggcg | 600 |
| ctgctgcacc agataaggca aaatgaccgt ttagctgtga gcaagcttgt taccagtttg | 660 |
| acaagaggaa ctgttcgctc acctctagct caatgcctct tgattcgtta tactagtcag | 720 |
| gttataagag aggctgccat gagtaatcaa acaggggata ggccattcta tgactatcta | 780 |
| gagggttgcc tacgtcacaa agcagaaatg gttattttg aagctgccag ggcaatcaca | 840 |
| gagcttagtg gtgtgactag tcgagaatta actcctgcaa tcactgttct acagctcttt | 900 |
| ttaagctctt ccaagccagt tcttaggttt gctgctgttc gaaccttgaa taaggtggca | 960 |
| atgacacatc ctatggctgt gacaaactgc aacatagata tggagagctt gatttctgat | 1020 |
| cagaatagga gcatagcaac tcttgccata acgactcttc ttaagaccgg caatgaatca | 1080 |
| agtgttgatc gtttgatgaa gcagataact aattttatgt ccgacattgg tgatgagttc | 1140 |
| aagattgttg tggtggaagc cattagatca ttgtgtttga agtttcccct gaagtacaga | 1200 |
| tctttgatga atttcttaag caatattttg agggaagaag gaggatttga gtacaaaaag | 1260 |
| gctattgttg actcaattgt gatcctgatc agagacattc cagatgctaa agaaagtggg | 1320 |

```
ctgcttcact tgtgtgaatt tattgaggac tgtgaattta catacctttc tactcagata    1380
ctacattttc ttggaaatga aggacctaag acatcagacc ccagtaagta catacgatat    1440
atatacaata gagttatact tgagaatgca acagttcggg ccagtgcagt gagcaccttt    1500
gctaagtttg gtgccttggt tgattcattg aagccccgta tatttgtgct attgaaacgt    1560
tgcctattcg acggtgatga tgaggttcgc gatagggcaa cactgtattt gaatacccct    1620
ggaggtgatg gtgcagttgt tgaaactgat gatgaggtga agagttcct attcgggtca    1680 ctcggtgtcc ctctaaccaa tctggagaca agtttaaaga actatgagcc atcagaggag    1740
gcgtttgata ttttttctgt tcccaaggaa gttaaatctc agcctttggc agagaagaaa    1800
gcaccgggta aaaagccaac tggtttgggt gctccacctg tcggcccac ctctactgtt    1860 gattcatatg aaagattact gtcctctatc ccagaattcg ctagctatgg aagcttttc    1920 aagtcatcgg cgccagtgga gctcacagaa gctgaaacag agtatgcagt taatgtcgtg    1980 aagcacatttt tgatagtca tgtagtgttc cagtacaact gcaccaatac cattcctgag    2040
caattgttgg aaaatggcag acatttgtgg cttttgagaa aacctgaagg agtccctgct    2100
gttgggaaat tctcgaacac actaagattc attgttaaag aggttgatcc aaccactggt    2160
gaggctgaag atgatggtgt tgaagatgaa taccaactag aagaccttga ggttgtcact    2220
gcagattaca tgctgaaatt gggagtctcc aatttttagga atgcatggga gagcttggga    2280
ccagattgtg aacgcggcac tgaggtagtc ccaagcaact caagatcgca cacatgttta    2340
ttatctggtg tatacattgg cagcgtaaag gtacttgttc ggttatcatt tggattggat    2400
ggggcaaagg aggttgcaat gaagctggct gttaggtcag aagatatatc tgtaagtgat    2460
gcaattcatg aagttgttgc aagcggctag                                    2490

<210> SEQ ID NO 47
<211> LENGTH: 1701
<212> TYPE: DNA
<213> ORGANISM: Nicotiana tabacum

<400> SEQUENCE: 47
atgaaaatga ggggctattc attctttact gctactctca ttcttgttgc tgtttctatt      60
tttcttagct caatccatac tgatgctta ccaagagata cttcaagtc tattttaggg     120 gagggaaatc tggaatcatg gaagaatgga gtattggact cagcaggtat ggcacaagcg     180
ccaggtcctg ccgatgggca tgttggcacg cttgtgctag cgggaaacag gacgaggaga     240
ccggactttc tttctggttt ccacaaatac agaggtggat gggatattgc caataaacac     300
tactgggctt ctgttggttt tacaggcctt gctggtatca tacttgctct gctttggttt     360
atttcatttg gcttggctct cgtcgtgcat tattgctgcg gatggaaatt caatatcaga     420
ggcagagaat ggcatttttc acagaatatt tgcctgggcg tgcttattgt cttgacatgc     480
gctgcagcga ttggatgcgt cctactttct gttgacaag atgactttca tgctgaagca     540
ttggacactt taaatatgt tgtaaatcag tcagattata ctgtgcagac attgagaaat     600
gtaacgcaat acttgttact cgcaaaaact gtaaatgtgg cccagatttt cctcccttca     660
gatgtaaaag atgatatcga tcacctaaat ggcgatctag attctgcagc ggataaactt     720
gaggataaaa caaatgaaaa ctcaggaaag atacgaaggg tcttcaatgc tgtgcgttca     780
gctttgatca ctattgccat cgtcatgctc ctcatctcta ttcttggtct ttgcctctct     840
atccttggcc atcaacacgc aattcacata tttatcatta gtggatggtt actggtggca     900
```

| | |
|---|---|
| gttacattcg ttctctatgg agttttttgtc atcataaaca gtgcaatttc agatacttgt | 960 |
| atggcgatgg gagagtgggt ggacaatccg catgctgaaa gtgctcttag caacatcctt | 1020 |
| ccatgtgttg acccgagaac tacaaaccgg acgctgttca agagcaaaca agtcactgtt | 1080 |
| gatcttgtaa atattgtcaa cggatttatc gacacatatg caaattccaa tccatctaat | 1140 |
| catgccaatt caaattacta taatcagtca ggacccgtta tgccacatct ctgctatcca | 1200 |
| tatgactccc aattgcaaga tcttccgtgc cctgctgatc aagtttctat ggcaaattct | 1260 |
| tcaatggttt ggcagaactt tacttgcaac gtatctgcag ctgcaatatg cactagtgtc | 1320 |
| gggaggctga ctcctgacat gtacggacag ttggtggcga cggtcaacat tagctatgca | 1380 |
| cttgaacatt atgcaccacc gttgcttaat ctccagaact gtgatttcgt tcgtgataca | 1440 |
| tttaggaaca tcacggtcaa ccactgccct ccgttggaac accatcttcg ggttgttaat | 1500 |
| gcaggattag ctgtcatatc agtcggagtc atgctaagtc tcgcattgtg gatagtatat | 1560 |
| gcaaaccgcc cccaaaggga ggaagtgttt gcgaagctct cttcgcgaat aaagagcagc | 1620 |
| tgtaacggca agaatattag ctgcagtaat agtaatattg atttgtcatc aagaggtaca | 1680 |
| actccaaaga ctggagtgta g | 1701 |

<210> SEQ ID NO 48
<211> LENGTH: 843
<212> TYPE: DNA
<213> ORGANISM: Nicotiana tabacum

<400> SEQUENCE: 48

| | |
|---|---|
| atgttggacg cgtcagcagt agcatatatt cagattgcta gcattgccat agcagaccag | 60 |
| gttgcacgtg gtcagatcga actagcaaaa aatgtaagac agaggctgac atctcccagt | 120 |
| gttgctgctc caccattgag tactggaaag caaaagggcg gcagcagctc ttgctgcaaa | 180 |
| cttgctgctt caacatcttc tgctcaaatg ttgacctctg ttctttcgtc tcttgttgct | 240 |
| gaagaagctg cgtcactgag cagtggattg aaatcagctg gtttttcttc tagcttacct | 300 |
| tttgcatctc cagagaaacg gctcaagtta gacaagccaa tgacttttc tgatatgaac | 360 |
| agttccgaag ggggtaattc cacttacttc acttcatcac agcaaccgat tactagcatt | 420 |
| cctcttgccc cttcctcagg cttacaatcg tcaaaccaga tacaagctcc gtttccacca | 480 |
| cctccacctc caccaccacc tttacctcca gcaaattccc ctggaagtca gttaggtcag | 540 |
| tctgcagcta tgatgatggg gatgatgccc tatggatata gtgccggcag ccttcagcca | 600 |
| cctcaaattg caatgggact gaggccacct ccaccactac cccagcaagc acaacagctg | 660 |
| catctccaga ctcagcagcc acaatctcaa cagcagcctg ccaatggtgg attttatcgt | 720 |
| cctctggtat tggattctat ggacagacca atcagcagac aacaccagca gcacccaggc | 780 |
| agtaaatccc tttggaatag ggagcacatg ttacattgta cattaatagt aaaagtagac | 840 |
| tag | 843 |

<210> SEQ ID NO 49
<211> LENGTH: 678
<212> TYPE: DNA
<213> ORGANISM: Nicotiana tabacum

<400> SEQUENCE: 49

| | |
|---|---|
| atggaatccg atgctcattt tctagcaaag gaagacggga tcatagcagg aattgcactt | 60 |
| gctgagatga tattcgcgga agttgatcct tcattaaagg aaatggcaga tgctgcacac | 120 |
| cctgcttaca tcttggagac taggaaaact gctcctggat tacgtttggt ggataaatgg | 180 |

```
gcggtattga tcggtggggg gaagaatcac agaatgggct tatttgatat ggtaatgata    240
aaagacaatc acatatctgc tgctggaggt gtcggcaaag ctctaaaatc tgtggatcag    300
tatttggagc aaaataaact tcaaataggg gttgaggttg aaaccaggac aattgaagaa    360
gtacgtgagg ttctagacta tgcatctcaa acaaagactt cgttgactag gataatgctg    420
gacaatatgg ttgttccatt atctaacgga gatattgatg tatccatgct taaggaggct    480
gtagaattga tcaatgggag gtttgatacg gaggcttcag gaaatgttac ccttgaaaca    540
gtacacaaga ttggacaaac tggtgttacc tacatttcta gtggtgccct gacgcattcc    600
gtgaaagcac ttgacatttc cctgaagatc gatacagagc tcgcccttga agttggaagg    660
cgtacaaaac gagcatga                                                 678

<210> SEQ ID NO 50
<211> LENGTH: 2154
<212> TYPE: DNA
<213> ORGANISM: Nicotiana tabacum

<400> SEQUENCE: 50
atgacggaag tggcgacgag caacgttgtg cacgacgtct tagggcgacg agctgaagat     60
gtagatcagc cgattattga ctatataatc aatgttctag ccgatgaaga tttcgatttt    120
ggacttgacg gtgaaggtgc ttttgaagcc ctcggcgaat tactcgtaga ttctggttgc    180
gttgctgact cccccgaatg tcgtgcggtt tgtagcaagt tgtctgagaa gttagagaag    240
catggattgg ttaaacctca accaactgtg agaagcttaa aaatgccgct gagaatgtat    300
gatggaatgg atgaagagga agctccaaag aataaaaagc cagaaccagt tgatggtcct    360
ttgctcacag aacgtgacaa gattaagatc gaaaggagga gaggaaagat gaacgcctg    420 agagaggcag aataccaagc cacttgaaa gaagtggaag aagtgaaagc tggtatgccg    480
ttagtgtgtg tgaatcatga tggtcagggt gatggaccaa ctgttaagga tatccgtatg    540
gaaaatttca atatatctgt tgctggtcgt gaccttattg tcgatggttc tgttacgctt    600
tcttttggaa gacactatgg ccttattgga gaaacggta cggggaaaac aactctccta    660
agacacatgg ctatgcacgc tatttgatggt attcccaaga actgccagat attgcatgtt    720
gagcaagaag tggttggtga tgatacctca gttttgcaat gtattcttaa cactgatatg    780
gagagaaccc aacttctgga agaagagggt cgtctgcttg aattacagag agaaattgac    840
ctagaaggcg aagctggaaa gagtgataag ttgaatgggg agatcgacaa aaatgccctc    900 gcgaaaggc ttgaagagat atacaaaaga cttgatttca ttgatgctta ctcggctgag    960
tcacgtgcag caactatact ttcgggtttg agcttcacta cagaaatgca aaagagagca   1020
actaaaacat tttctggagg atggagaatg agaatagctc ttgctcgggc gttgttcatt   1080
gaacctgatc tattgttgct tgatgaaccc acgaatcatc ttgatctaca tgctgtctta   1140
tggctggaaa cttacctggt gaagtggccg aagacattta tagttgtctc tcatgctaga   1200
gagttcttga atactgtagt cacagacatt atccatctac aaaatcagaa attgagtacc   1260
tacaaaggag actatgatac attcgaaagg acacgagatg aacaagttaa gaatcaacag   1320
aaggcgttcg aggcgaatga acgtacaagg gcccacatgc agacctttat tgataagttc   1380
cggtacaatg caaagcgtgc atctcttgtt caatctagaa ttaaggcact ggaacgaatt   1440
ggtcgtgtgg atgaagtcat caatgatcct gactacaagt tgagttccc ttctcctgat   1500 gatagacctg gtgctcctat tataagcttc agtgatgcat cctttggata tcctgggggc   1560
```

| | |
|---|---|
| ccattattgt tcaaaaattt gaattttgga atagatctgg atagccgagt agcaatggtt | 1620 |
| ggtcctaatg gtattggaaa gtcaacaata cttaagctta tttctgggga gcttcaacca | 1680 |
| acttcaggaa ctgttttccg ctctgctaag gtccgaattg ctgtatttag tcagcatcat | 1740 |
| gttgatgggc tggatctgtc ctcaaatccc ctcttataca tgatgcgttg ctttccagga | 1800 |
| gtgcctgaac aaaaattacg tggtcatcta ggttcatttg gtatcactgg aaatcttgct | 1860 |
| cttcagccca tgtacacttt gtctggtggc caaaaaagca gagttgcatt tgcaaagata | 1920 |
| accttcaaga agcctcacat attgcttctt gatgagccat caaatcactt ggatcttgac | 1980 |
| gctgtggagg ctctgataca aggtcttgtc ttgttccaag gaggcgtact gatggtcagt | 2040 |
| cacgatgaac atttaatatc tggtagtgtt gatcaactct gggccgtctc tgagggcagg | 2100 |
| gtgacgcctt tcgacgggac attccaggat tacaagaaaa ttctgcaatc ataa | 2154 |

<210> SEQ ID NO 51
<211> LENGTH: 1155
<212> TYPE: DNA
<213> ORGANISM: Nicotiana tabacum

<400> SEQUENCE: 51

| | |
|---|---|
| atgggtgctc agatatccgt atctaagctt gccaatttgt cctttgtccc cagaatacgc | 60 |
| gttcctgtgc ctaacataag tgttccaagt cccagcatca gttctggttt tgtttcaaat | 120 |
| ctttcgtgtt ctgccatagg catttcttcc gtgttggtca ttttttatca atcagcatca | 180 |
| ttggctaagt cggcaaatcc atcaacatat acttatacag ttccttcttc gccttcagag | 240 |
| gtgttgtata gatggcattt accagagcca aatgtcgttg atatatcagg gaattatgat | 300 |
| tgttcatcag taaagtctag gactgtggta gtactgttgg gatggttagg tgcaaaacag | 360 |
| aagcatctaa agagatatgc agagtggtat gcctcagcag gatatcatgt cattacatt | 420 |
| actttcccaa tgtctgagat tcttagctat caagtcgggg gaaaggcaga gcaggatata | 480 |
| gaactgcttg tgaaccatct tgttgattgg ttggaagaag agcatggaaa gaacttggtc | 540 |
| ttccacactt tcagtaacac gggatggtta acttatggtg tcattttgga gaagtttcag | 600 |
| aaacaagatc ctgtttttaat gacaaggatc aaaggttgta ttgttgattc tgctcctgta | 660 |
| gctgctcccg atccacaggt atgggcttct ggattctctg ctgccttttt gaagaagaat | 720 |
| agtgttgcaa ccaaacacat catgactata acaacaaag atgcagatgt gacaatagaa | 780 |
| accaaaactt cttcggatgc tacacctgca gtaactgaag cagcttttgct agtagtactg | 840 |
| gagaagttct tgaggtggt tttgagcctt cccgccgtaa ataggagact ttctgatgtt | 900 |
| ctagatctat tgacatccca gcaaccaagt tgcccacaat tgtacatata cagcagtgca | 960 |
| gacagagtga ttcctgcgat ttctgttgag tcctttgtag aggagcaacg aagaattggt | 1020 |
| cgcaacgtta gagcttgcaa cttcatttct acacctcatg ttgatcattt cagaaatgac | 1080 |
| ccagaattat atactttaca gcttacccaa tttcttgagg actccgttct aagctcttgc | 1140 |
| aaacagtctt cctga | 1155 |

<210> SEQ ID NO 52
<211> LENGTH: 1644
<212> TYPE: DNA
<213> ORGANISM: Nicotiana tabacum

<400> SEQUENCE: 52

| | |
|---|---|
| atgggaggtg cagaggatgc tgaaccacca tccaaacgtg tgaaagtatc ctctgggaaa | 60 |
| ccaggagatc tttcaaacgg cacatttcct agagatcctg caagttgctc attgaatgac | 120 |

```
ttgatggctc gccccctggt ttgtcaaggg gacgatgagg ttgttggtac aaaagggggtc      180 atcaagaaag ttgaatttgt gcgaatttta gctgaggcat tatattctct tggttataac      240
aaaactgggg cacatctaga agaagagtct gggatacctt tgcaatctgc tgtggtaaag      300
ttatttatgc agcaagtcct tgatggtaaa tgggatgaaa tgtagccac attacgtaaa       360 atcggtctag tggatgaaaa ggttgttcaa ttggcatcat ttctgatatt ggaacagaag      420
ttttttgaac tgttggatga aaaaaagtc atggatgctt tgaagacatt gagcactgag       480
attggacctc tttgcataaa cactgataga gtccgtgagc tttctttgtg cattttatca      540
cctttgcagc aggttcgtgc tgtggtgtca ggtcaagttg ttgtgagagc aaagccacga      600
agaaagctac tagaggaatt gcaaaaattg cttcccccaa cagttataat tcctgaacaa      660
agattgatac gtcttgttga acaggctctt gacttgcaac tagatgcttg taggtttcac      720
aactctttgg taggtgagat gtctttgctc actgatcatc agtgcggaag ggatcaaatt      780
ccttctcaaa ctttgcaggt gaaattggat ggtttgttct gcatgaagca ccagttttct      840
ggtcaccaga aacctgtctc ctatatgtca tggagtcctg atgaccatca gcttctcact      900
tgtggagtag aggaagttgt cagacggtgg gatattgaat caggtgaatg tacacatatt      960
tatgagaaaa atggtcttgg tctgatctca gtggatggg ctcctgatgg caaaaggata       1020
ttatgcggtg ttacggacaa gagcattagc atgtgggatc tggaagggaa agagttggag      1080
tgttggaaag gccatcgaac tattagaata tctgacttgg ggataactag tgatgggcag      1140
catatagtct ctgtttgcaa agataatatg atattactat ttggatggga atcaaaagca      1200
gagaaagtaa ttcaggagga tcaaacaata acttcatttg tattgtccat ggacagtaag      1260
tatttattgg ttagtctttg gaatcaagaa atccatctgt ggaatataga gggaactgta      1320
aagctcatat ccaaatataa agggcataaa cgttcacgct tgttgtaag gtcttgctttg      1380 ggcggactgg gtcaagcatt tgttgccagt ggaagtgagg actcacaggt ttatatatgg      1440
catagaagct caggagaact cattgagaca ttggctggac attctggtac agtaaactgt      1500
gttagctgga acccagcaaa tcctcatatg ttggcatctg caagtgatga tcatactatt      1560
cgcatatggg gcatgaatca agtaaacatg aaacactatg acacagttag taatggcgtg      1620
cattactgca atggcggaac ttag                                             1644
```

<210> SEQ ID NO 53
<211> LENGTH: 1764
<212> TYPE: DNA
<213> ORGANISM: Nicotiana tabacum

<400> SEQUENCE: 53

```
atggcaatgg tagatgagcc attgtacccc atagccgtgt taatagatga acttaagaac      60
gatgatatac aattacggtt gaattcaatt aggaggttat cgactattgc acgtgcccctt     120 ggtgaggaaa gaactcgaaa ggaattgatc cctttttttga gtgaaaacaa tgatgatgat     180
gatgaggtgt tattggcaat ggctgaagag cttggtgtgt ttatccctta tgttggaggt     240
gtagagcatg ctcatgtttt gctcccgccg ttggagacgc tttgtactgt tgaggagacc     300
tgtgtgaggg ataaagctgt tgaatcgttg tgtaggatta gatctcagat gagggagagt     360
gatttggttg attggttcgt ccctcttgtg aagaggctgg cagctggtga atggttcaca     420
gctagagttt ctgcctgtgg actctttcat attgcttact caagtgcccc agagatgttg     480
aaggcagaac ttcggtctat ttacagtcaa ttgtgtcaag acgacatgcc tatggtgcga     540
```

| | |
|---|---|
| agatcagctg ccacaaactt ggggaagttt gctgctactg ttgaatctac ttacctcaag | 600 |
| agtgacatca tgtcaatatt tgatgatctt acacaggatg atcaggattc tgtacgctta | 660 |
| ttagctgttg agggctgtgc tgcacttggc aagctgttgg agccccagga ttgtgttgca | 720 |
| cacatcctgc ctgtcattgt caacttctct caggacaagt cttggcgcgt ccgctacatg | 780 |
| gttgctaacc agttgtacga actatgtgaa gctgtagggc ctgagcccac taggacggat | 840 |
| ttggtgcctg cctatgtccg tttgcttcga gataatgaag ctgaagttcg catagctgct | 900 |
| gcagggaaag tcaccaaatt ctgtcggatt cttagtcccg agcttgctat tcagcatatt | 960 |
| cttccctgtg tgaaggaatt atcatcagac tcttcacagc atgtcagatc tgctttggct | 1020 |
| tctgttataa tggggatggc tcctgttttg gaaaggatg caaccattga gcatcttctt | 1080 |
| ccaatatttc tttcccttct gaaggacgag tttcctgatg tgcgcctgaa catcattagc | 1140 |
| aagcttgatc aagtcaatca ggtgattgga attgattta tatcccaatc tttgttgcca | 1200 |
| gctattgttg agctagcaga ggacaggcat tggcgagtcc gtcttgcaat aatagaatac | 1260 |
| atacctctat tggcaagtca attgggcata ggattttttg atgataagct tggtgcccctt | 1320 |
| tgtatgcaat ggttacagga caaggtttat tcaatcagag atgctgctgc taataaccta | 1380 |
| aagcgtcttg cagaagaatt tggtccagag tgggcaatgc agcatataat tcctcaggtc | 1440 |
| ttggatatga ctaccagtcc acattatttg tatagaatga caattcttag agcaatttca | 1500 |
| ttgcttgcac ctgtaatggg ctctgaaata acttgttcta aattgctgcc tgtggttatt | 1560 |
| actgcaacaa aggatagagt gcccaacatt aaatttaatg tggcaaaggt gttgcaatcc | 1620 |
| cttataccta ttgttgacca ctcggtggtg gagaaaacca ttcgccctag tttagtagag | 1680 |
| ctagctgaag accctgatgt tgatgttcgc ttttatgcca atcaagcact tcagtcaatt | 1740 |
| gataacgtca tgatgtcagg ctag | 1764 |

<210> SEQ ID NO 54
<211> LENGTH: 1866
<212> TYPE: DNA
<213> ORGANISM: Nicotiana tabacum

<400> SEQUENCE: 54

| | |
|---|---|
| atgggattca tcgaatcatg ttcccagact gcagaaatgg aaatcaggaa gtgctcgcct | 60 |
| tttctggaaa gtgaattgtt gtccggtaat ggtgggttgc ccttgacaga gtggagaact | 120 |
| gttcccgaca tttggcggac ttcggcagag aagtttggtg accgtgtagc agttgtggac | 180 |
| ccatatcatg atcctcctac aaccatgact tataaacagc tttatcagga gattgtggat | 240 |
| ttctctgaag gtttgagagt tgttgggcta aacccaaatg agaagattgc gcttttttgct | 300 |
| gataattcat gtcgatggct tgttgcagat caaggtacga tggcgagtgg ggctatcaac | 360 |
| gttgtgaggg gttcaaggtc atcaaatcaa gagctattgc aattatacag ccactctgaa | 420 |
| agtgtcgctc ttgctattga caatcctgag atgtacaacc ggatttcaga caccttttggt | 480 |
| tcccacacag ctgtacgatt tgctatttta ctttggggcg agaaatcaag ccttggaaga | 540 |
| gaagccgtgc agggatatcc tgtatatact tataaggaga ttatagaatt gggtcacaag | 600 |
| agtcgtgtgg atctgcttga ttctgaagat gccaggaaac aatattcatt tgaggcaatc | 660 |
| aactctgatg atgtggctac aattgtctat accagtggaa ccaccggtaa tccaaaaggt | 720 |
| gtcatgctta cgcataaaaa tctgcttcac cagattttga atctggggga gattgtacct | 780 |
| gctgtacctg gggacagatt tctaagcatg cttccgcctt ggcatgcata tgagcgtgct | 840 |
| tgtgaatatt tcatattcac acatggaaca gagcaagtgt acacaactgt gaaaaatttg | 900 |

```
aagccacatt acttgataag tgttccttta gtttatgaga cattatacag tggaattcta    960
aagcagatca attcaaactc tgctgctagt aaactcattg ccctattatt tttaaggatc   1020
agtatgactt acatggaggc aaaaaggatt tacgaggctg gcgtaagtgg aggtggtagt   1080
ctttcttcac atgttgacaa gttctttgag gcaattggca taaagattca gaatggatat   1140
ggtctgactg agtcatctcc cgtgatttct gcccgtcatc ttgcgtgtaa tgtacttggc   1200
tcagttgggc atcccattcg gcatgtagaa gtaaaaattg taaatgctga aacagatgag   1260
gtccttcctc ctggctcaag gggcattgtc aaagccagag ggccactagt aatgaagggc   1320
tactataaga atccgttggc aacaaaacac gctattgatg agaatggatg ctgaacact    1380 ggtgatcttg gttggattgc gcctgatcat tctgtagggc gaagtcgtaa agtgggggt    1440 gtaatagtcc ttgaaggccg tgcaaaggat accatagtcc tttcaactgg cgagaatgtt   1500
gaaccatcag agattgaaga agctgcaatg ggaagtagtc tgatccagca gattgttgtc   1560
attggccagg atcaacgacg tcttggagct ataattgtac caaataagga ggaggttctg   1620
ttagcagcta aaaaatcagc tattgtggat tctgaaacca ctgaagttag caaggaaaaa   1680
gcagttggca tattatatga ggagttaaga aaatggactt caggttgctc atttcaagtt   1740
ggacctatcc ttattgtcga tgaaccttc acgattgata gtggcttact aacaccaacc   1800
atgaaaatca gagagacaa aattgcagct ctatacaaag agcaaattga gaacttgtac   1860
aaatga                                                              1866

<210> SEQ ID NO 55
<211> LENGTH: 2610
<212> TYPE: DNA
<213> ORGANISM: Nicotiana tabacum

<400> SEQUENCE: 55
atgggtggtg acgaaactaa aaagaccact ataatggtgc tcaaggttga tcttcagtgc     60
tccagctgct ataagaaggt caaaaaagtt ctctgtaaat tccctcgatg tggagtaatt    120
aagagcattg aaatcaaaga acctccaaag cccaaagctc ctgaaaagcc caaggagcct    180
gtgaaaccaa agaacccga aagcccaaa caaccggaga agcccaagga gcccgaaaag    240
cctaaacaac ctgagaagac tacggttgtc gtcattgaaa agcccaagga gcccgagaag    300
cctaaggcac cggaaaagtc aaaagagccc gagaagccca agaaccaga aaagccgaaa    360 gaagttgaaa agcccaagcc caagagccc gaaaagccca agaagctcc taaacctaat    420 ccagtggctc caccatcaca accaccacca ccgccagcac cagagccaat aatggttcaa    480 caatacctc agccaccact aggatattgt tgtggacaat gctacgaggg tcatatcggg    540
ggcccatgtt atcaatggta cggaagacct gtccttccgg ccccatgtta cgataactat    600
gggtataact atgggcctgg gcctgggcct gggccgtatg gctacggaag gggttgttat    660
gtgagtagat gtgaccaata ctttagtgaa gaaaatgcca caggatgctc aattataaag    720
tgggagccaa atattgtggc tagcaaagct aaagaagtct actccgccgt ttgggttcgc    780
ctcctccaat tacccacaga attctatgat agaattgtcc ttagtagaat tggaaactca    840
attggccgac tactacgcat agatgcttgt acaagttcaa cgcttagaag gaggtacgcg    900
cgactgtgtg tgcaagtgca aatggaccaa ctagtccaaa caacaatcca gattggctcc    960
catatacaac aactggtata tgaaggagaa aaatttcttt gtaaggcctg tgggcgactg   1020
ggaaacacga catcaacatg ctcccacact ctacttgact tccaaaagca acaacaagaa   1080
```

```
gagccatgtc ctaactcgac tggcttcata ggcaaggaaa ggcaattgaa gagcaatgac    1140
aaaccgtctc cttccccaaa ggtaacaagc caaaagagg cacaaccaat ggatctcaaa     1200
ataaaactca agcgacacct ccaggtatca atgtcaatat ttttgatgcg gcatcagccc    1260
atccttacat ctaataaatt cgaatcactt cttaatgata gcagtattac attcccggaa    1320
ataattgaat cccaaatgga attggatggg caaaactcta acctctcccc agactctaaa    1380
ctgtcgttct ctccaagaaa ccattcctct tccctgctcc ctcctctctc tccacgtggc    1440
caaaaggcta catgcaactc caataaacca cacaaaacag cgggcccatc cactaatcct    1500
ctaccatgca cgccacttcc cacactaatg acacctatta ccactgaaaa ccctataact    1560
gacttgtcac ttaccacctg ccaattggcc atgcaactca actctccaat actggctagt    1620
ctaaggttgc acgttaaaaa tcgaaccatg cacacaaaat ttctactaac agattttcaa    1680
tcattacctc acgaaaacca atccccctca tccccttcat cttctcctac acactatgaa    1740
tctactccac tcctcccatc aaacgaaaat ccctctaaaa taactctcac accaccatcg    1800
ttcctcaata ctgtccagaa tgaacccacc actcctggat acaaaccttc cgatctacat    1860
caccaatgcc ctctcactgg accaccaacc aacgccatgg ttggaacaag gacttcaggt    1920
ccaagtggct ttcttcactc tcaatatcca aaatcacgaa gtcctgtttg ttctacagaa    1980
cccacaggtc ctagctcaat taatctcgga gggtatgagg ctagcaatgt cgaactacat    2040
caaccacctt tagttgacaa atgttctaga gcccatagcc ccaccctagc accagccctt    2100
cttcacaaca tgcaagccca ctggaatcca ccacatcact tcaatcccct acaaaacatg    2160 caacttttt accaacttcc cttttttgct ccacaggatc aaaacacccc acccttgatc    2220
catgcatggc aacccatccc tcaacactac ccagctccga tggattttca ccacacacat    2280
tcccatcccc atcacagtgc acctgtacca ggagagcaag aaatggaaac ccaaaatcaa    2340
accatcccac cactaaatat aacatcgtac acagaaaatt caaacctaca cgaggtcaaa    2400
atcttgttat tccaagcgat ggaagaaaag aagtatgtcc gcaaatgtcc cacagagcta    2460
tacaaatgct ccctcgacat aaggccccca ctcaatgcag cagtaggcaa tttcgccgta    2520
atactcagtc catcattgaa tggtcttcct gttccaccaa tggggagcca gttcaatgtc    2580
accccccagc caacacccat caatgactag                                    2610
```

<210> SEQ ID NO 56
<211> LENGTH: 1110
<212> TYPE: DNA
<213> ORGANISM: Nicotiana tabacum

<400> SEQUENCE: 56

```
atgcatatat tgtatacttg tccgctgatt ctgtttatgg ctttactctt tgcttatgct     60
gctgctactg ctgctgattt agagaccaat ggagctgaaa aggcgggtgc ggatgcagga    120
attttgagta gtaatagcag tgtgaatgag aatttagacc tgataaatat gaatagaaaa    180
aaggatggtc atttggataa cgatagttcg aatgttgggg atcaaaacaa gtccaatgat    240
agtagtgcga aaagggtga cgacagagaa gggttgaaag aagctgaggt ggaaaagaaa    300
agaattgata gtggttctaa gagagatgac aggaaggagg agacgaaaga agctgaacag    360
caagacaaag caaaagatat tagttccgag aagcagggtg agatggaaaa gattctgccg    420
gatggaattc agtcgagaga ggagattttg cctacaagaa aggagagttt ccatggtgaa    480
gaatgcgatt catcttatag ttgcacgata gaggaaaaag cagtggttgc atgtcttaga    540
gttccgggca atgaatctcc agacctttca cttttggttc aaaacaatgg aaaaggaact    600
```

```
gtcaatatttt tgattaaggc tcctgagttt gtacaactgg agaaagagaa gattgaactg      660
caaggaaagg aaaatcagag gatgaaggtt tctataagga atgcaggaaa tgacaacaat      720
atcattctaa aggccgggga tggccaatgc actcttgatt tcagggtct gattgacaat       780 gctgataaaa catctcaatt caagtatggt ttcctatctt ttgcaataat gtgtttggct      840
gctattgcat tagtggccac agtcttgatg tactttaaac ggaggcttct agtaagtagc      900
ggccacaagt atcaaaagtt ggacatggat ttaccagttt ccagtggcag aaagacggag      960
acactctcaa ctgatggatg ggacaatagc tgggatgacg attgggatga tgaggaggcg     1020
cccaaagcac catccgtgcc agtcactcct tccttctcgt ctaaaagcat tacctcacga     1080
cggtctagta aggaaagctg gaaagactag                                       1110
```

<210> SEQ ID NO 57
<211> LENGTH: 314
<212> TYPE: DNA
<213> ORGANISM: Nicotiana tabacum

<400> SEQUENCE: 57

```
cttttctcaa gaaacatatt tattaaataa tttcttttc gttacattca tttttataat        60
ctattccttt atgttctctt agagaaaagt atactattct aaaatacatt tatcccaaaa      120
aatagaaaaa tgaatgtagt attcatktac tcaagcgtgt tatattttgt caataaaatg      180
tctcccaaaa tattcaaatc ttgttcaata ccacatttcg tgataatcct tcctgtatat      240
taattaaaat ctattttacc ccagaattgt actaaaaaag tcagctaggt gtactaccta     300
tttcgcattc atgc                                                        314
```

<210> SEQ ID NO 58
<211> LENGTH: 160
<212> TYPE: DNA
<213> ORGANISM: Nicotiana tabacum

<400> SEQUENCE: 58

```
agcccgattt gtcgtgagga tttgatatgt ctccctccaa aggtagcagc tagttttrgga      60 aatatcggtc ctcttgtgat ctgcaccaaa gtgagcaaca atattgcttt attagayccg      120
tttactctga ggcattgttt cttggatgct gatcagtact                             160
```

<210> SEQ ID NO 59
<211> LENGTH: 322
<212> TYPE: DNA
<213> ORGANISM: Nicotiana tabacum

<400> SEQUENCE: 59

```
aaaagtgcga tctaaaacga tgcagtaacc aaaccgaagg ggcctgttgc ccatatccac        60
caagtttcag gacgtgttta acatttagct aacaaattct ctcatgagat ttaactcgag      120
ttagagcttc aacctgcatg ggcataagtg tacaatacat crggtatgtt actggtgacc      180
aagagtttaa gactgaaaaa ttggagggcg acaataagag tactatacct tttgcaggca     240
ccacaaccac aaatttcaga catgtcatga agatgcgta gcctcctact gtggcagagg      300
aaagcatgca tggttaattt gg                                               322
```

<210> SEQ ID NO 60
<211> LENGTH: 71
<212> TYPE: DNA
<213> ORGANISM: Nicotiana tabacum

```
<400> SEQUENCE: 60
cataaatttt gtccaacatg aagtatata ggtcamgttg tagttgattt caaacacttg      60
ttagaaaagt a                                                          71

<210> SEQ ID NO 61
<211> LENGTH: 71
<212> TYPE: DNA
<213> ORGANISM: Nicotiana tabacum

<400> SEQUENCE: 61
tttcccgctg gggatttcag ttgtattcct ctctgytgtt tctttacttc gggctcgact      60
tgtggtcttc c                                                          71

<210> SEQ ID NO 62
<211> LENGTH: 71
<212> TYPE: DNA
<213> ORGANISM: Nicotiana tabacum

<400> SEQUENCE: 62
acagtaaatt ttctcactct tgattctgca tcaaayacac ttcttgtgct gttaagattc      60
ttcatagttg t                                                          71

<210> SEQ ID NO 63
<211> LENGTH: 71
<212> TYPE: DNA
<213> ORGANISM: Nicotiana tabacum

<400> SEQUENCE: 63
cgcctgtgca taatgaggcg catatggtgg gtatgsttta ttttagaaag gaatatgaga      60
gttcatctgg a                                                          71

<210> SEQ ID NO 64
<211> LENGTH: 71
<212> TYPE: DNA
<213> ORGANISM: Nicotiana tabacum

<400> SEQUENCE: 64
ttgtaattat tatgatagaa ttagtattgc tttatwtatt gtattttat ccctttaaaa      60 gtcaactgct g                                                          71

<210> SEQ ID NO 65
<211> LENGTH: 11801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
tgagcgtcgc aaaggcgctc ggtcttgcct tgctcgtcgg tgatgtactt caccagctcc      60
gcgaagtcgc tcttcttgat ggagcgcatg ggacgtgct tggcaatcac gcgcaccccc     120
cggccgtttt agcggctaaa aaagtcatgg ctctgccctc gggcggacca cgcccatcat     180
gaccttgcca agtcgtcct gcttctcttc gatcttcgcc agcagggcga ggatcgtggc     240
atcaccgaac cgcgccgtgc gcgggtcgtc ggtgagccag agtttcagca ggccgcccag     300
gcggcccagg tcgccattga tgcgggccag ctcgcggacg tgctcatagt ccacgacgcc     360
cgtgattttg tagccctggc cgacggccag caggtaggcc gacaggctca tgccggccgc     420
```

```
cgccgccttt tcctcaatcg ctcttcgttc gtctggaagg cagtacacct tgataggtgg      480
gctgcccttc ctggttggct tggtttcatc agccatccgc ttgccctcat ctgttacgcc      540
ggcggtagcc ggccagcctc gcagagcagg attcccgttg agcaccgcca ggtgcgaata      600
agggacagtg aagaaggaac acccgctcgc gggtgggcct acttcaccta tcctgcccgg      660
ctgacgccgt tggatacacc aaggaaagtc tacacgaacc ctttggcaaa atcctgtata      720
tcgtgcgaaa aaggatggat ataccgaaaa aatcgctata atgacccega agcagggtta      780
tgcagcggaa aagcgccacg cttcccgaag ggagaaaggc ggacaggtat ccggtaagcg      840
gcagggtcgg aacaggagag cgcacgaggg agcttccagg gggaaacgcc tggtatcttt      900
atagtcctgt cgggtttcgc cacctctgac ttgagcgtcg attttttgtga tgctcgtcag      960
gggggcggag cctatggaaa aacgccagca acgcggcctt tttacggttc ctggccttt      1020
gctggccttt tgctcacatg ttctttcctg cgttatcccc tgattctgtg gataaccgta      1080
ttaccgcctt tgagtgagct gataccgctc gccgcagccg aacgaccgag cgcagcgagt      1140
cagtgagcga ggaagcggaa gagcgccaga aggccgccag agaggccgag cgcggccgtg      1200
aggcttggac gctagggcag ggcatgaaaa agcccgtagc gggctgctac gggcgtctga      1260
cgcggtggaa agggggaggg gatgttgtct acatggctct gctgtagtga gtgggttgcg      1320
ctccggcagc ggtcctgatc aatcgtcacc ctttctcggt ccttcaacgt tcctgacaac      1380
gagcctcctt ttcgccaatc catcgacaat caccgcgagt ccctgctcga acgctgcgtc      1440
cggaccggct tcgtcgaagg cgtctatcgc ggcccgcaac agcggcgaga gcggagcctg      1500
ttcaacggtg ccgccgcgct cgccggcatc gctgtcgccg gctgctcct caagcacggc      1560
cccaacagtg aagtagctga ttgtcatcag cgcattgacg gcgtccccgg ccgaaaaacc      1620
cgcctcgcag aggaagcgaa gctgcgcgtc ggccgtttcc atctgcggtg cgcccggtcg      1680
cgtgccggca tggatgcgcg cgccatcgcg gtaggcgagc agcgcctgcc tgaagctgcg      1740
ggcattcccg atcagaaatg agcgccagtc gtcgtcggct ctcggcaccg aatgcgtatg      1800
attctccgcc agcatggctt cggccagtgc gtcgagcagc gcccgcttgt tcctgaagtg      1860
ccagtaaagc gccggctgct gaaccccccaa ccgttccgcc agtttgcgtg tcgtcagacc      1920
gtctacgccg acctcgttca acaggtccag ggcggcacgg atcactgtat tcggctgcaa      1980
ctttgtcatg cttgacactt tatcactgat aaacataata tgtccaccaa cttatcagtg      2040
ataaagaatc cgcgcgttca atcggaccag cggaggctgg tccggaggcc agacgtgaaa      2100
cccaacatac ccctgatcgt aattctgagc actgtcgcgc tcgacgctgt cggcatcggc      2160
ctgattatgc cggtgctgcc gggcctcctg cgcgatctgg ttcactcgaa cgacgtcacc      2220
gcccactatg gcattctgct ggcgctgtat gcgttggtgc aatttgcctg cgcacctgtg      2280
ctgggcgcgc tgtcggatcg tttcgggcgg cggccaatct tgctcgtctc gctggccggc      2340
gccagatctg gggaaccctg tggttggcat gcacatacaa atggacgaac ggataaacct      2400
tttcacgccc ttttaaatat ccgattattc taataaacgc tcttttctct taggtttacc      2460
cgccaatata tcctgtcaaa cactgatagt ttaaactgaa ggcgggaaac gaagcttcca      2520
gaaggtaatt atccaagatg tagcatcaag aatccaatgt ttacgggaaa aactatggaa      2580
gtattatgtg agctcagcaa gaagcagatc aatatgcggc acatatgcaa cctatgttca      2640
aaaatgaaga atgtacagat acaagatcct atactgccag aatacgaaga gaatacgta      2700
gaaattgaaa agaagaacc aggcgaagaa aagaatcttg aagacgtaag cactgacgac      2760
aacaatgaaa agaagaagat aaggtcggtg attgtgaaag agacatagag gacacatgta      2820
```

```
aggtggaaaa tgtaagggcg gaaagtaacc ttatcacaaa ggaatcttat cccccactac    2880 ttatccttt  atattttccc gtgtcatttt tgcccttgag ttttcctata taaggaacca    2940
agttcggcat tgtgaaaac  aagaaaaaat ttggtgtaag ctattttctt tgaagtactg    3000
aggatacaac ttcagagaaa tttgtaagtt tgtggatcct gcaggctagc gtgcactcta    3060
gactcgacga actgacgagc tcgaatttcc ccgatcgttc aaacatttgg caataaagtt    3120
tcttaagatt gaatcctgtt gccggtcttg cgatgattat catataattt ctgttgaatt    3180
acgttaagca tgtaataatt aacatgtaat gcatgacgtt atttatgaga tgggttttta    3240
tgattagagt cccgcaatta tacatttaat acgcgataga aaacaaaata tagcgcgcaa    3300
actatgataa attatcgcgc gcggtgtcat ctatgttact agatcgggaa ttcctcgagc    3360 aactatttt  atgtatgcaa gagtcagcat atgtataatt gattcagaat cgttttgacg    3420
agttcggatg tagtagtagc cattatttaa tgtacatact aatcgtgaat agtgaatatg    3480
atgaaacatt gtatcttatt gtataaatat ccataaacac atcatgaaag cactttctt    3540 tcacggtctg aattaattat gatacaattc taatagaaaa cgaattaaat tacgttgaat    3600
tgtatgaaat ctaattgaac aagccaacca cgacgacgac taacgttgcc tggattgact    3660
cggtttaagt taaccactaa aaaaacggag ctgtcatgta acacgcggat cgagcaggtc    3720
acagtcatga agccatcaaa gcaaagaac  taatccaagg gctgagatga ttaattagtt    3780 taaaattag  ttaacacgag ggaaaaggct gtctgacagc caggtcacgt tatctttacc    3840
tgtggtcgaa atgattcgtg tctgtcgatt ttaattattt ttttgaaagg ccgaaaataa    3900
agttgtaaga gataaacccg cctatataaa ttcatatatt ttcctctccg ctttgaattg    3960
tctcgttgtc ctcctcactt tcatcagccg ttttgaatct ccggcgactt gacagagaag    4020
aacaaggaag aagactaaga gagaaagtaa gagataatcc aggagattca ttctccgttt    4080
tgaatcttcc tcaatctcat cttcttccgc tctttctttc caaggtaata ggaacttcct    4140
ggatctactt tatttgctgg atctcgatct tgttttctca atttccttga gatctggaat    4200
tcgtttaatt tggatctgtg aacctccact aaatcttttg gttttactag aatcgatcta    4260
agttgaccga tcagttagct cgattatagc taccagaatt tggcttgacc ttgatggaga    4320
gatccatgtt catgttacct gggaaatgat ttgtatatgt gaattgaaat ctgaactgtt    4380
gaagttagat tgaatctgaa cactgtcaat gttagattga atctgaacac tgtttaaggt    4440
tagatgaagt ttgtgtatag attcttcgaa actttaggat tgtagtgtc  gtacgttgaa    4500 cagaaagcta tttctgattc aatcagggtt tatttgactg tattgaactc ttttttgtgtg   4560 tttgcagctc ataaaaggta ccaaacaatg attgaacaag atggattgca cgcaggttct    4620
ccggccgctt gggtggagag gctattcggc tatgactggg cacaacagac aatcggctgc    4680
tctgatgccg ccgtgttccg gctgtcagcg caggggcgcc cggttctttt tgtcaagacc    4740
gacctgtccg gtgccctgaa tgaactgcag gacgaggcag cgcggctatc gtggctggcc    4800
acgacgggcg ttccttgcgc agctgtgctc gacgttgtca ctgaagcggg aagggactgg    4860
ctgctattgg gcgaagtgcc ggggcaggat ctcctgtcat ctcaccttgc tcctgccgag    4920
aaagtatcca tcatggctga tgcaatgcgg cggctgcata cgcttgatcc ggctacctgc    4980
ccattcgacc accaagcgaa acatcgcatc gagcgagcac gtactcggat ggaagccggt    5040
cttgtcgatc aggatgatct ggacgaagag catcaggggc tcgcgccagc cgaactgttc    5100
gccaggctca aggcgcgcat gcccgacggc gaggatctcg tcgtgaccca tggcgatgcc    5160
```

```
tgcttgccga atatcatggt ggaaaatggc cgcttttctg gattcatcga ctgtggccgg    5220
ctgggtgtgg cggaccgcta tcaggacata gcgttggcta cccgtgatat tgctgaagag    5280
cttggcggcg aatgggctga ccgcttcctc gtgctttacg gtatcgccgc tcccgattcg    5340
cagcgcatcg ccttctatcg ccttcttgac gagttctttt gagcgggact ctggcgatcg    5400
ccccgatcgt tcaaacattt ggcaataaag tttcttaaga ttgaatcctg ttgccggtct    5460
tgcgatgatt atcatataat ttctgttgaa ttacgttaag catgtaataa ttaacatgta    5520
atgcatgacg ttatttatga gatgggtttt tatgattaga gtcccgcaat tatacattta    5580
atacgcgata gaaaacaaaa tatagcgcgc aaactaggat aaattatcgc gcgcggtgtc    5640
atctatgtta ctagatcggg actagtttac accacaatat atcctgccac cagccagcca    5700
acagctcccc gaccggcagc tcggcacaaa atcaccactc gatacaggca gcccatcagt    5760
ccgggacggc gtcagcggga gagccgttgt aaggcggcag actttgctca tgttaccgat    5820
gctattcgga agaacggcaa ctaagctgcc gggtttgaaa cacgatgat ctcgcggagg    5880 gtagcatgtt gattgtaacg atgacagagc gttgctgcct gtgatcaaat atcatctccc    5940
tcgcagagat ccgaattatc agccttctta ttcatttctc gcttaaccgt gacaggctgt    6000
cgatcttgag aactatgccg acataatagg aaatcgctgg ataaagccgc tgaggaagct    6060
gagtggcgct atttctttag aagtgaacgt tgacgatatc aactcccta tccattgctc    6120 accgaatggt acaggtcggg gacccgaagt tccgactgtc ggcctgatgc atccccggct    6180
gatcgacccc agatctgggg ctgagaaagc ccagtaagga aacaactgta ggttcgagtc    6240
gcgagatccc ccggaaccaa aggaagtagg ttaaacccgc tccgatcagg ccgagccacg    6300
ccaggccgag aacattggtt cctgtaggca tcgggattgg cggatcaaac actaaagcta    6360
ctggaacgag cagaagtcct ccggccgcca gttgccaggc ggtaaaggtg agcagaggca    6420
cgggaggttg ccacttgcgg gtcagcacgg ttccgaacgc catggaaacc gccccgcca    6480 ggcccgctgc gacgccgaca ggatctagcg ctgcgtttgg tgtcaacacc aacagcgcca    6540
cgcccgcagt tccgcaaata gccccagga ccgccatcaa tcgtatcggg ctacctagca    6600
gagcggcaga gatgaacacg accatcagcg gctgcacagc gcctaccgtc gccgcgaccc    6660
cgcccggcag gcggtagacc gaaataaaca acaagctcca gaatagcgaa atattaagtg    6720
cgccgaggat gaagatgcgc atccaccaga ttcccgttgg aatctgtcgg acgatcatca    6780
cgagcaataa acccgccggc aacgcccgca gcagcatacc ggcgacccct cggcctcgct    6840
gttcgggctc cacgaaaacg ccggacagat gcgccttgtg agcgtccttg gggccgtcct    6900
cctgtttgaa gaccgacagc ccaatgatct cgccgtcgat gtaggcgccg aatgccacgg    6960
catctcgcaa ccgttcagcg aacgcctcca tgggcttttt ctcctcgtgc tcgtaaacgg    7020
acccgaacat ctctggagct ttcttcaggg ccgacaatcg gatctcgcgg aaatcctgca    7080
cgtcggccgc tccaagccgt cgaatctgag ccttaatcac aattgtcaat tttaatcctc    7140
tgtttatcgg cagttcgtag agcgcgccgt gcgtcccgag cgatactgag cgaagcaagt    7200
gcgtcgagca gtgcccgctt gttcctgaaa tgccagtaaa gcgctggctg ctgaaccccc    7260
agccggaact gaccccacaa ggccctagcg tttgcaatgc accaggtcat cattgaccca    7320
ggcgtgttcc accaggccgc tgcctcgcaa ctcttcgcag gcttcgccga cctgctcgcg    7380
ccacttcttc acgcgggtgg aatccgatcg gcacatgagg cggaaggttt ccagcttgag    7440
cgggtacggc tccggtgcg agctgaaata gtcgaacatc cgtcgggccg tcggcgacag    7500
cttgcggtac ttctcccata tgaatttcgt gtagtggtcg ccagcaaaca gcacgacgat    7560
```

```
ttcctcgtcg atcaggacct ggcaacggga cgttttcttg ccacggtcca ggacgcggaa    7620
gcggtgcagc agcgacaccg attccaggtg cccaacgcgg tcggacgtga agcccatcgc    7680
cgtcgcctgt aggcgcgaca ggcattcctc ggccttcgtg taataccggc cattgatcga    7740
ccagcccagg tcctggcaaa gctcgtagaa cgtgaaggtg atcggctcgc cgataggggt    7800
gcgcttcgcg tactccaaca cctgctgcca caccagttcg tcatcgtcgg cccgcagctc    7860
gacgccggtg taggtgatct tcacgtcctt gttgacgtgg aaaatgacct tgttttgcag    7920
cgcctcgcgc gggatttttct tgttgcgcgt ggtgaacagg gcagagcggg ccgtgtcgtt    7980
tggcatcgct cgcatcgtgt ccggccacgg cgcaatatcg aacaaggaaa gctgcatttc    8040
cttgatctgc tgcttcgtgt gtttcagcaa cgcggcctgc ttggcctcgc tgacctgttt    8100
tgccaggtcc tcgccggcgg ttttttcgctt cttggtcgtc atagttcctc gcgtgtcgat    8160
ggtcatcgac ttcgccaaac ctgccgcctc ctgttcgaga cgacgcgaac gctccacggc    8220
ggccgatggc gcgggcaggg caggggggagc cagttgcacg ctgtcgcgct cgatcttggc    8280
cgtagcttgc tggaccatcg agccgacgga ctggaaggtt tcgcggggcg cacgcatgac    8340
ggtgcggctt gcgatggttt cggcatcctc ggcggaaaac cccgcgtcga tcagttcttg    8400
cctgtatgcc ttccggtcaa acgtccgatt cattcaccct ccttgcggga ttgccccgac    8460
tcacgccggg gcaatgtgcc cttattcctg atttgacccg cctggtgcct tggtgtccag    8520
ataatccacc ttatcggcaa tgaagtcggt cccgtagacc gtctggccgt ccttctcgta    8580
cttggtattc cgaatcttgc cctgcacgaa taccagcgac cccttgccca aatacttgcc    8640
gtgggcctcg gcctgagagc caaaacactt gatgcggaag aagtcggtgc gctcctgctt    8700
gtcgccggca tcgttgcgcc acatctaggt actaaaacaa ttcatccagt aaaatataat    8760
attttatttt ctcccaatca ggcttgatcc ccagtaagtc aaaaaatagc tcgacatact    8820
gttcttcccc gatatcctcc ctgatcgacc ggacgcagaa ggcaatgtca taccacttgt    8880
ccgccctgcc gcttctccca agatcaataa agccacttac tttgccatct ttcacaaaga    8940
tgttgctgtc tcccaggtcg ccgtgggaaa agacaagttc ctcttcgggc tttttccgtct    9000
ttaaaaaatc atacagctcg cgcggatctt taaatggagt gtcttcttcc cagttttcgc    9060
aatccacatc ggccagatcg ttattcagta agtaatccaa ttcggctaag cggctgtcta    9120
agctattcgt ataggacaa tccgatatgt cgatggagtg aaagagcctg atgcactccg    9180
catacagctc gataatcttt tcagggcttt gttcatcttc atactcttcc gagcaaagga    9240
cgccatcggc ctcactcatg agcagattgc tccagccatc atgccgttca agtgcagga    9300
cctttggaac aggcagcttt ccttccagcc atagcatcat gtcctttttcc cgttccacat    9360
cataggtggt ccctttatac cggctgtccg tcattttttaa atataggttt tcattttctc    9420
ccaccagctt atataccttaa gcaggagaca ttccttccgt atcttttacg cagcggtatt    9480
tttcgatcag ttttttttcaat tccggtgata ttctcatttt agccatttat tatttccttc    9540
ctctttttcta cagtatttaa agataccccca agaagctaat tataacaaga cgaactccaa    9600
ttcactgttc cttgcattct aaaaccttaa ataccagaaa acagcttttt caaagttgtt    9660
ttcaaagttg gcgtataaca tagtatcgac ggagccgatt ttgaaccac aatttatgggt    9720
gatgctgcca acttactgat ttagtgtatg atggtgtttt tgaggtgctc cagtggcttc    9780
tgtgtctatc agctgtccct cctgttcagc tactgacggg gtggtgcgta acggcaaaag    9840
caccgccgga catcagcgct atctctgctc tcactgccgt aaaacatggc aactgcagtt    9900
```

```
cacttacacc gcttctcaac ccggtacgca ccagaaaatc attgatatgg ccatgaatgg    9960
cgttggatgc cgggcaacag cccgcattat gggcgttggc ctcaacacga ttttacgtca   10020
cttaaaaaac tcaggccgca gtcggtaacc tcgcgcatac agccgggcag tgacgtcatc   10080
gtctgcgcgg aaatggacga acagtggggc tatgtcgggg ctaaatcgcg ccagcgctgg   10140
ctgttttacg cgtatgacag tctccggaag acggttgttg cgcacgtatt cggtgaacgc   10200
actatggcga cgctggggcg tcttatgagc ctgctgtcac cctttgacgt ggtgatatgg   10260
atgacggatg gctggccgct gtatgaatcc cgcctgaagg gaaagctgca cgtaatcagc   10320
aagcgatata cgcagcgaat tgagcggcat aacctgaatc tgaggcagca cctggcacgg   10380
ctgggacgga agtcgctgtc gttctcaaaa tcggtggagc tgcatgacaa agtcatcggg   10440
cattatctga acataaaaca ctatcaataa gttggagtca ttacccaatt atgatagaat   10500
ttacaagcta taaggttatt gtcctgggtt tcaagcatta gtccatgcaa gtttttatgc   10560
tttgcccatt ctatagatat attgataagc gcgctgccta tgccttgccc cctgaaatcc   10620
ttacatacgg cgatatcttc tatataaaag atatattatc ttatcagtat tgtcaatata   10680
ttcaaggcaa tctgcctcct catcctcttc atcctcttcg tcttggtagc ttttttaaata   10740
tggcgcttca tagagtaatt ctgtaaaggt ccaattctcg ttttcatacc tcggtataat   10800
cttacctatc acctcaaatg gttcgctggg tttatcgcac ccccgaacac gagcacggca   10860
cccgcgacca ctatgccaag aatgcccaag gtaaaaattg ccggccccgc catgaagtcc   10920
gtgaatgccc cgacggccga agtgaagggc aggccgccac ccaggccgcc gccctcactg   10980
cccggcacct ggtcgctgaa tgtcgatgcc agcacctgcg gcacgtcaat gcttccgggc   11040
gtcgcgctcg ggctgatcgc ccatcccgtt actgccccga tcccggcaat ggcaaggact   11100
gccagcgctg ccattttggg ggtgaggccg ttcgcggccg aggggcgcag cccctggggg   11160
gatgggaggc ccgcgttagc gggccgggag ggttcgagaa gggggggcac cccccttcgg   11220
cgtgcgcggt cacgcgcaca gggcgcagcc ctggttaaaa acaaggttta taaatattgg   11280
tttaaaagca ggttaaaaga caggttagcg gtggccgaaa acgggcggaa aacccttgca   11340
aatgctggat tttctgcctg tggacagccc ctcaaatgtc aataggtgcg cccctcatct   11400
gtcagcactc tgcccctcaa gtgtcaagga tcgcgcccct catctgtcag tagtcgcgcc   11460
cctcaagtgt caataccgca gggcacttat ccccaggctt gtccacatca tctgtgggaa   11520
actcgcgtaa aatcaggcgt tttcgccgat ttgcgaggct ggccagctcc acgtcgccgg   11580
ccgaaatcga gcctgcccct catctgtcaa cgccgcgccg ggtgagtcgg cccctcaagt   11640
gtcaacgtcc gcccctcatc tgtcagtgag ggccaagttt ccgcgaggt atccacaacg   11700
ccggcggccg cggtgtctcg cacacggctt cgacggcgtt tctggcgcgt ttgcagggcc   11760
atagacggcc gccagcccag cggcgagggc aaccagcccg g                      11801
```

METHODS AND COMPOSITIONS RELATED TO IMPROVED NITROGEN UTILIZATION EFFICIENCY IN TOBACCO

CROSS-REFERENCE TO RELATED APPLICATIONS

This application is a continuation of U.S. patent application Ser. No. 16/119,366, filed Aug. 31, 2018, which claims the benefit of U.S. Provisional Application No. 62/553,501, filed Sep. 1, 2017, both of which are incorporated by reference in their entireties herein.

INCORPORATION OF SEQUENCE LISTING

A sequence listing contained in the file named "P34523US02_SL.TXT" which is 188,452 bytes (measured in MS-Windows®) and created on Dec. 9, 2020, is filed electronically herewith and incorporated by reference in its entirety.

FIELD

The present disclosure provides compositions and methods useful for making and identifying tobacco plants comprising improved nitrogen utilization efficiency via breeding, transgenic approaches, and cisgenic approaches.

BACKGROUND

Fertilizer is a major cost for tobacco growers, and increased fertilization has been tied to higher levels of alkaloids and tobacco-specific nitrosamines (TSNAs) in plant tissues. Different tobacco varieties require different levels of nitrogen fertilizer input to achieve the maximum yield for each variety. For example, Maryland tobacco varieties typically require approximately 25% less nitrogen input to achieve maximum yield as compared to Burley tobacco varieties.

Improving Nitrogen Utilization Efficiency (NUE) in tobacco would increase tobacco harvestable yield per unit of input nitrogen fertilizer. Nitrogen utilization efficiency improvement also allows decreases in on-farm input costs, decreased use and dependence on the non-renewable energy sources required for nitrogen fertilizer production, and reduces the environmental impact of nitrogen fertilizer manufacturing and agricultural use.

Methods and compositions for improving the nitrogen utilization efficiency of tobacco are provided herein.

SUMMARY

In one aspect, the present disclosure provides for, and includes, a method of determining the NUE of a tobacco line comprising obtaining at least one metabolite from a tobacco plant of a tobacco line, determining the amount of the obtained metabolites, and determining the NUE of the tobacco line based on the amount of the metabolites identified.

In one aspect, the present specification provides for, and includes, a method of determining the NUE of a tobacco line using a metabolite signature comprising isolating a metabolite signature from a tobacco plant of a tobacco line, determining the amount of each metabolite comprising a metabolite signature, and determining the NUE of a tobacco line by comparing the metabolite signature to a control metabolite signature from a control tobacco line comprising a known NUE.

In one aspect, the current specification provides for, and includes, a method of breeding a tobacco line comprising a metabolite signature associated with enhanced NUE comprising determining the metabolite signature of a first tobacco plant from a first tobacco line, where a first tobacco plant comprises enhanced NUE as compared to a control tobacco plant lacking the metabolite signature, crossing the first plant with a second plant of a second tobacco line, and obtaining at least one progeny seed from the crossing, where a progeny plant grown from at least one progeny seed comprises the metabolite signature, and where the progeny plant comprises enhanced NUE as compared to a control plant lacking the metabolite signature.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a higher amount of at least one metabolite as compared to a control tobacco plant. In a further aspect of this method, a selected tobacco plant comprises an enhanced NUE as compared to a control tobacco plant.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a lower amount of at least one metabolite as compared to a control tobacco plant.

In one aspect, the present specification provides for, and includes, a method of screening a tobacco plant for a first metabolite signature associated with enhanced NUE comprising isolating a first metabolite signature associated with enhanced NUE from a tobacco plant, determining the amount of at least one metabolite that comprises that first metabolite signature, comparing the first metabolite signature to a second metabolite signature of a control tobacco plant comprising a known NUE, and determining if the first metabolite signature is associated with enhanced NUE.

In one aspect, the present specification provides for, and includes, a modified tobacco seed, or tobacco plant grown therefrom, comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions.

In one aspect, the present specification provides for, and includes, a recombinant DNA construct comprising a heterologous promoter operably linked to a polynucleotide encoding a polypeptide at least 70% identical or similar to a polypeptide selected from the group consisting of SEQ ID NOs:1 to 8.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions.

In one aspect, the present specification provides for, and includes, a greenhouse, growth chamber, or field comprising the modified tobacco seed or plant disclosed herein.

In one aspect, the present specification provides for, and includes, a modified tobacco seed, or tobacco plant grown therefrom, comprising at least one mutation in an endogenous locus encoding a polypeptide selected from the group consisting of SEQ ID NOs:25 to 40, and where a modified tobacco seed or tobacco plant comprises enhanced nitrogen utilization efficiency as compared to an unmodified control tobacco plant lacking at least one mutation when grown under the same conditions.

In one aspect, the present specification provides for, and includes, a recombinant DNA construct comprising a heterologous promoter operably linked to a guide RNA comprising at least 18 contiguous nucleotides identical or complementary to a polynucleotide encoding a polypeptide selected from the group consisting of SEQ ID NOs:25 to 40.

In one aspect, the present specification provides for, and includes, cured tobacco material, or a tobacco product comprising the cured tobacco material, where the cured tobacco material is made from a tobacco plant comprising at least one mutation in an endogenous locus encoding a polypeptide selected from the group consisting of SEQ ID NOs:25 to 40, and where the modified tobacco seed or tobacco plant comprises enhanced NUE as compared to an unmodified control tobacco plant lacking the at least one mutation when grown under the same conditions.

In one aspect, the present specification provides for, and includes, a modified tobacco seed, or tobacco plant grown therefrom, comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions.

In one aspect, the present specification provides for, and includes, a recombinant DNA construct comprising a heterologous promoter operably linked to a polynucleotide encoding a small RNA (sRNA) at least 85% identical or complementary to a polynucleotide selected from the group consisting of SEQ ID NOs:41 to 56.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a polynucleotide encoding a sRNA at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions.

In one aspect, the present specification provides for, and includes, a method of enhancing the NUE of a tobacco plant comprising introducing a cisgenic nucleic acid molecule into a tobacco cell, and regenerating a modified tobacco plant from that tobacco cell where the modified tobacco plant comprises enhanced NUE as compared to a tobacco plant lacking the cisgenic nucleic acid molecule.

In one aspect, the present specification provides for, and includes, a method of enhancing the NUE of a tobacco plant comprising introducing a modification to a nucleic acid molecule encoding a gene having a sequence selected from the group consisting of SEQ ID NOs:41 to 56 in a tobacco cell and regenerating a modified tobacco plant from the tobacco cell, where the modified tobacco plant comprises enhanced NUE as compared to a tobacco plant lacking the modification.

In one aspect, the present specification provides for, and includes, a method of enhancing the NUE of a tobacco plant comprising introducing a nucleic acid encoding a small RNA (sRNA) homologous to at least 18 contiguous nucleic acids of a nucleic acid molecule encoding a gene having a sequence selected from the group consisting of SEQ ID NOs:41 to 56 in a tobacco cell, and regenerating a modified tobacco plant from the tobacco cell, where the modified tobacco plant comprises enhanced NUE as compared to a tobacco plant lacking the sRNA.

In one aspect, the present specification provides for, and includes, a method comprising providing a first population of tobacco plants comprising enhanced NUE, genotyping a first population of tobacco plants for the presence of a molecular marker within 20 cM of an enhanced NUE locus; and selecting one or more tobacco plants genotyped and found to comprise the molecular marker.

In one aspect, the present specification provides for, and includes, a method comprising providing a first population of tobacco plants, genotyping the first population of tobacco plants for the presence of an enhanced NUE allele of a locus encoded by a sequence selected from the group consisting of SEQ ID NOs:9 to 16; and selecting one or more genotyped tobacco plants that comprise an enhanced NUE allele.

In one aspect, the present specification provides for, and includes, a method of introgressing an enhanced NUE trait into a tobacco variety comprising crossing a first tobacco variety comprising an enhanced nitrogen utilization efficiency trait with a second tobacco variety lacking the enhanced nitrogen utilization efficiency trait, obtaining progeny seed from the cross, genotyping at least one progeny seed for a molecular marker linked to an enhanced nitrogen utilization efficiency trait, where the molecular marker is within 20 cM of a locus having a sequence selected from the group consisting of SEQ ID NOs:9 to 16; and selecting a progeny seed comprising an enhanced nitrogen utilization efficiency trait.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a locus selected from the group consisting of SEQ ID NOs:9 to 16, and selecting a tobacco plant comprising an enhanced NUE trait.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a marker selected from the group consisting of SEQ ID NOs:57 to 64, and selecting a tobacco plant comprising an enhanced NUE trait.

BRIEF DESCRIPTION OF THE SEQUENCES

SEQ ID NOs: 1 to 8 are amino acid sequences of genes positively correlated with enhanced NUE in root tissue, leaf tissue, or both.

SEQ ID NOs: 9 to 16 are nucleotide sequences of genes positively correlated with enhanced NUE in root tissue, leaf tissue, or both.

SEQ ID NOs: 17 to 19 are nucleotide sequences of promoter regions for genes with leaf-preferred expression.

SEQ ID NOs: 20 to 24 are nucleotide sequences of promoter regions for genes with root-preferred expression.

SEQ ID NOs: 25 to 40 are amino acid sequences of genes negatively correlated with enhanced NUE in root tissue, leaf tissue, or both.

SEQ ID NOs: 41 to 56 are nucleotide sequences of genes negatively correlated with enhanced NUE in root tissue, leaf tissue, or both.

SEQ ID NOs:57 to 64 are nucleotide sequences of SNP markers comprising polymorphisms associated with enhanced NUE.

SEQ ID NO: 65 is the backbone sequence for expression vector p45-2-7.

DETAILED DESCRIPTION

Figure 1:
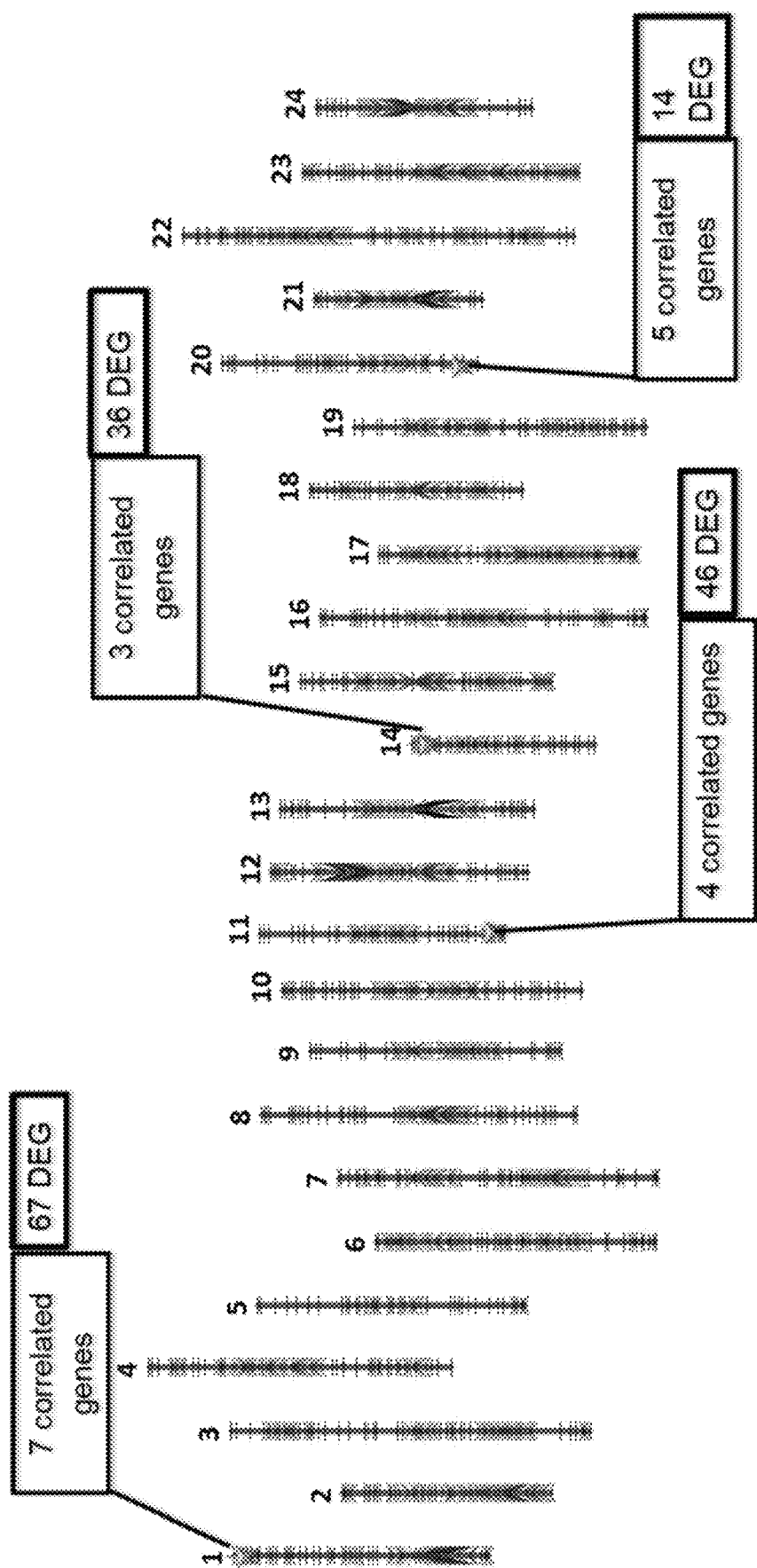
FIG. 1 depicts four gene clusters associated with NUE in the tobacco genome. Genes differentially expressed between low and normal nitrogen conditions in plants with an NUE metabolite fingerprint are indicated (correlated genes). The total number of differentially expressed genes (DEG), regardless of NUE metabolic fingerprinting, is also indicated.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of this disclosure includes, unless otherwise indicated, conventional techniques of biochemistry, chemistry, molecular biology, microbiology, cell biology, genomics, biotechnology, metabolomics, plant breeding, and genetics, which are within the skill of the art. See, for example, Green and Sambrook, Molecular Cloning: A Laboratory Manual, 4th edition (2012); Current Protocols In Molecular Biology (F. M. Ausubel, et al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

As used herein, the term "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." An alignment of two or more sequences may be performed using any suitable computer program. For example, a widely used and accepted computer program for performing sequence alignments is CLUSTALW v1.6 (Thompson, et al. (1994) Nucl. Acids Res., 22: 4673-4680).

As used herein, the term "complementary" in reference to a nucleic acid molecule refers to pairing of nucleotide bases such that adenine is complementary to thymine or uracil, and guanine is complementary to cytosine. Two complementary nucleic acid molecules are capable of hybridizing with each other. As an example, the two strands of double stranded DNA are complementary to each other.

A specific polynucleotide of at least three nucleotides in length may be referred to as an "oligonucleotide". Nucleic acid molecules provided herein include deoxyribonucleic acids (DNA) and ribonucleic acids (RNA) and functional analogues thereof, such as complementary DNA (cDNA). Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. The symbol "R" can be used to represent a purine (e.g., A or G) nucleotide base. The symbol "Y" can be used to represent a pyrimidine (e.g., a C or T) nucleotide base. The symbol "W" can be used to represent an A or a T nucleotide base. The symbol S can be used to represent a G or a C nucleotide base. The symbol "M" can be used to represent an A or a C nucleotide base. The symbol The symbol "K" can be used to represent a G or a T nucleotide base. The symbol "B" can be used to represent a G, C, or T nucleotide base. The symbol "H" can be used to represent an A, C, or T nucleotide base. The symbol "D" can be used to represent an A, G, or T nucleotide base. The symbol "V" can be used to represent an A, G, or C nucleotide base. The symbol "N" can be used to represent any nucleotide base (e.g., A, G, C, T, or U).

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids. Polypeptides can be encoded by polynucleotides provided herein.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In one aspect, an isolated polynucleotide provided herein can contain less than 10000 nucleotides, less than 5000 nucleotides, less than 4000 nucleotides, less than 3000 nucleotides, less than 2000 nucleotides, less than 1000 nucleotides, less than 500 nucleotides, or less than 100 nucleotides of nucleic acid sequence that naturally flank the polynucleotide in genomic DNA of the cell from which the polynucleotide is derived. In one aspect, an isolated polynucleotide provided herein can contain 100 to 10000 nucleotides, 500 to 10000 nucleotides, 1000 to 10000 nucleotides, 2000 to 10000 nucleotides, 3000 to 10000 nucleotides, 4000 to 10000 nucleotides, 1 to 500 nucleotides, 1 to 1000 nucleotides, 1 to 2000 nucleotides, 1 to 3000 nucleotides, 1 to 4000 nucleotides, 1 to 5000 nucleotides, 1 to 10000 nucleotides, 100 to 500 nucleotides, 100 to 1000 nucleotides, 100 to 2000 nucleotides, 100 to 3000 nucleotides, or 100 to 4000 nucleotides of nucleic acid sequence that naturally flank the polynucleotide in genomic DNA of the cell from which the polynucleotide is derived. In another aspect, an isolated polypeptide provided herein is substantially free of cellular material in preparations having less than 30%, less than 20%, less than 10%, less than 5%, or less than 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least 20 nucleotides, at least 50 nucleotides, at least 70 nucleotides, at least 100 nucleotides, at least 150 nucleotides, at least 200 nucleotides, at least 250 nucleotides, at least 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

As used herein, the phrase "associated with" or "linked to" refers to a recognizable and/or assayable relationship between two entities. For example, the phrase "associated with enhanced NUE" refers to a trait, locus, gene, allele, marker, phenotype, etc., or the expression thereof, the presence or absence of which can influence an extent, degree, and/or rate at which a plant or a part of interest thereof that has an enhanced NUE trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced NUE allele" refers to a marker whose presence or absence can be used to predict whether and to what extent a plant will display enhanced NUE phenotype.

As used herein, a "centimorgan" (cM) is a unit of measure of recombination frequency and genetic distance between two loci. One cM is equal to a 1% chance that a marker at one genetic locus will be separated from a marker at a second locus due to crossing over in a single generation.

As used herein, "closely linked" means that the marker or locus is within about 20 cM, 15 cM, 10 cM, 5 cM, 4 cM, 3 cM, 2 cM, 1 cM, 0.5 cM, or less than 0.5 cM of another marker or locus. For example, 20 cM means that recombination occurs between the marker and the locus with a frequency of equal to or less than about 20%.

As used herein, "plant" refers to a whole plant. A cell or tissue culture derived from a plant can comprise any plant components or plant organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, a tobacco plant can be from any plant from the *Nicotiana tabacum* genus including, but not limited to *Nicotiana tabacum tabacum*; *Nicotiana tabacum amplexicaulis* PI 271989; *Nicotiana tabacum benthamiana* PI 555478; *Nicotiana tabacum bigelovii* PI 555485; *Nicotiana tabacum debneyi*; *Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica*; *Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

As used herein, "modified" refers to plants, seeds, plant components, plant cells, and plant genomes that have been subjected to mutagenesis, genome editing, genetic transformation, or a combination thereof.

As used herein, "cisgenesis" or "cisgenic" refers to genetic modification of a plant, plant cell, or plant genome in which all components (e.g., promoter, donor nucleic acid, selection gene) have only plant origins (e.g., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences.

As used herein, a "functional fragment" or "functional fragment thereof" refers to a nucleotide or amino acid sequence of any size that retains the function of the full length sequence to which it refers. In an aspect, a functional fragment can be at least 5, at least 10, at least 25, at least 50, at least 75, at least 100, at least 150, at least 200, at least 250, at least 300, at least 400, at least 500, at least 600, at least 700, at least 800, at least 900, at least 1000, at least 2000, at least 3000, at least 4000, at least 5000, or more than 5000 nucleotides in length. In an aspect, a functional fragment can be at least 5, at least 10, at least 25, at least 50, at least 75, at least 100, at least 150, at least 200, at least 250, at least 300, at least 400, at least 500, at least 600, at least 700, at least 800, at least 900, at least 1000, at least 2000, or more than 2000 amino acids in length. In an aspect, a functional fragment can be between 5 and 5000 nucleotides, between 10 and 4000 nucleotides, between 25 and 3000 nucleotides, between 50 and 2000 nucleotides, between 75 and 1000 nucleotides, between 100 and 900 nucleotides, between 150 and 800 nucleotides, between 200 and 700 nucleotides, between 250 and 600 nucleotides, or between 300 and 500 nucleotides in length. In an aspect, a functional fragment can be between 5 and 2000 amino acids, between 10 and 1000 amino acids, between 25 and 900 amino acids, between 50 and 800 amino acids, between 50 and 800 amino acids, between 75 and 700 amino acids, between 100 and 600 amino acids, between 150 and 500 amino acids, between 200 and 400 amino acids, or between 250 and 300 amino acids in length. In a further aspect, the polynucleotides described herein are envisioned in their entirety and as any functional fragments thereof. In a further aspect, the polypeptides described herein are envisioned in their entirety and as any functional fragments thereof. In a further aspect, the polynucleotides having the sequence of SEQ ID NOs: 9 to 24 and 41 to 56 are envisioned in their entirety and as any functional fragments thereof. In a further aspect, the polypeptides having the sequence of SEQ ID NOs: 1 to 8 and 25 to 40 are envisioned in their entirety and as any functional fragments thereof.

As used herein, the term "nitrogen utilization efficiency" (NUE) refers to the ability of a plant to absorb, assimilate and/or use nitrogen (e.g., from soil, water and/or nitrogen fertilizer). NUE genes affect yield and have utility for improving the use of nitrogen in crop plants. Enhanced nitrogen utilization efficiency can result from improved uptake and assimilation of nitrogen fertilizer and/or the subsequent remobilization and reutilization of accumulated nitrogen reserves, as well as increased tolerance of plants to stress situations such as low nitrogen environments. NUE genes can be used to alter the genetic composition of a plant, rendering it more productive with current fertilizer application standards or maintaining its productive rates with significantly reduced fertilizer or reduced nitrogen availability.

NUE has been defined in various ways, but yield per unit of nitrogen available in the soil integrates all key parameters for evaluating fitness of crop cultivars and it is a common measure of NUE. See, for example, Ladha et al. 2005. *Advances in Agronomy*, 87:85-156, which is incorporated herein in its entirety. This indicator is sometimes referred to as "agricultural NUE." As another measure of NUE, the ratio of the plant product (e.g., tobacco leaf tissue) to above-ground nitrogen in the plant can be determined (sometimes referred to as "physiological NUE.") Enhanced NUE is related to three key components: 1) yield is not significantly different when grown on 25% normal nitrogen content compared to a plant grown at 100% normal nitrogen content); 2) the rate of chlorophyll loss is reduced compared to plants without enhanced NUE; and 3) cured leaf quality is not significantly different when grown on 25% normal nitrogen content compared to a plant grown at 100% normal nitrogen content. In a preferred aspect, a plant with enhanced NUE is capable of generating similar yields and leaf quality when grown under 25% of the Burley fertilization rate as compared to a Burley plant grown under 100% of the normal Burley fertilization rate.

At least five approaches and indices of NUE are used in the art and are discussed below.

(1) Partial factor productivity (PFP) from applied nitrogen (N) is a measure of how much yield is produced for each unit of nitrogen applied:

$PFP_N$=kilograms of yield/kilograms of N applied $$PFP_N = Y_{+N}/FN$$

Where $Y_{+N}$ is the yield (kilograms/hectare; kg/ha) and FN is the amount of fertilizer applied (kg/ha).

(2) Agronomic efficiency (AE) of applied nitrogen (N) is a measure of how much additional yield is produced for each unit of nitrogen applied:

$AE_N$=kilograms of yield increase/kilograms of N applied $$AE_N = (Y_{+N} - Y_{0N})/FN$$

Where $Y_{+N}$ is the yield in a treatment with N application (kg/ha); $Y_{0N}$ is the yield in a control treatment without N application (kg/ha); and FN is the amount of N fertilizer applied (kg/ha).

(3) Recovery efficiency (RE) of applied nitrogen (N) is a measure of how much of the nitrogen that was applied was recovered and taken up by the crop.

$RE_N$=kilograms of N taken up/kilograms of N applied $$RE_N = (UN_{+N} - UN_{0N})/FN$$

Where $UN_{+N}$ is the total plant N uptake measured in above-ground biomass at physiological maturity (kg/ha) in plots that received applied N at the rate of FN (kg/ha); and $UN_{0N}$ is the total N uptake of a control plot without the addition of N.

(4) Physiological efficiency (PE) of applied nitrogen (N) is a measure of how much additional yield is produced for each additional unit of nitrogen uptake.

$PE_N$=kilograms of yield increase/kilograms of fertilizer N taken up $$PE_N = (Y_{+N} - Y_{0N})/(UN_{+N} - UN_{0N})$$

Where $Y_{+N}$ is the yield (kg/ha) in a treatment with N application; $Y_{0N}$ is the yield (kg/ha) in a control treatment without N application; $UN_{+N}$ is the total N uptake (kg/ha) in the treatment that receives fertilizer N application; and $UN_{0N}$ is the total N uptake (kg/ha) in the treatment without fertilizer N application.

(5) Internal efficiency (IE) of nitrogen (N) addresses how much yield is produced per unit N taken up from both fertilizer and indigenous (e.g., soil) nutrient sources:

$IE_N$=kilograms of yield/kilograms of N taken up $$IE_N = Y/UN$$

s Where Y is the yield (kg/ha); and UN is the total N uptake (kg/ha).

Nitrogen can be in any form, including organic and/or inorganic forms. Without being limiting, forms of nitrogen include nitrate (e.g, ammonium nitrate, calcium nitrate, potassium nitrate), nitrite, ammonia, aqua ammonia, anhydrous ammonia, ammonium sulfate, diammonium phosphate, a low-pressure nitrogen solution, a pressureless nitrogen solution, urea, and urea-ammonium nitrate (UAN). In an aspect, nitrogen is in a form that is immediately available to a plant (e.g., ammonia and/or nitrate) and/or can be readily converted to a form that is available to a plant (e.g., urea).

In an aspect, a modified tobacco plant comprising enhanced NUE provided herein comprises increased nitrogen uptake as compared to a control tobacco plant. In another aspect, a modified tobacco plant comprising enhanced NUE provided herein comprises increased nitrogen assimilation as compared to a control tobacco plant. In a further aspect, a modified tobacco plant comprising enhanced NUE provided herein comprises increased yield as compared to a control tobacco plant. In still another aspect, a modified tobacco plant comprising enhanced NUE provided herein comprises increased yield under low nitrogen conditions as compared to a control tobacco plant. In a preferred aspect, low nitrogen conditions as used in the field are approximately 25% nitrogen compared to levels typically used by those skilled in the art. In another aspect, low nitrogen conditions as used in the field can be between approximately 5% and 50% nitrogen compared to levels typically used by those skilled in the art. In a greenhouse setting, low nitrogen conditions are approximately 25 parts per million (ppm) and normal nitrogen conditions are approximately 100 ppm. In another aspect, low nitrogen conditions as used in a greenhouse can be between 5 ppm and 50 ppm.

In an aspect, a modified tobacco plant comprising enhanced NUE provided herein comprises a yield increase of at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 200%, at least 300%, at least 400%, or at least 500% as compared to a control tobacco plant grown under similar growth conditions. In an aspect, a modified tobacco plant comprising enhanced NUE provided herein comprises a yield increase of between 5% and 100%, between 10% and 100%, between 20% and 100%, between 30% and 100%, between 40% and 100%, between 50% and 100%, between 60% and 100%, between 70% and 100%, between 80% and 100%, between 90% and 100%, between 10% and 200%, between 10% and 300%, between 10% and 400%, between 10% and 500%, or between 5% and 500% as compared to a control tobacco plant grown under similar growth conditions.

In an aspect, a population of modified tobacco plants comprising enhanced NUE provided herein comprises a yield increase of at least 0.25 kg/ha, at least 0.5 kg/ha, at least 0.75 kg/ha, at least 1 kg/ha, at least 2 kg/ha, at least 3 kg/ha, at least 4 kg/ha, at least 5 kg/ha, at least 6 kg/ha, at least 7 kg/ha, at least 8 kg/ha, at least 9 kg/ha, at least 10 kg/ha, at least 15 kg/ha, at least 20 kg/ha, at least 25 kg/ha, at least 30 kg/ha, at least 35 kg/ha, at least 40 kg/ha, at least 45 kg/ha, at least 50 kg/ha, at least 75 kg/ha, at least 100 kg/ha, at least 200 kg/ha, at least 300 kg/ha, at least 400 kg/ha, or at least 500 kg/ha as compared to a population of control tobacco plants grown under similar growth conditions. In another aspect, a population of modified tobacco plant comprising enhanced NUE provided herein comprises a yield increase of between 0.25 kg/ha and 100 kg/ha, between 0.5 kg/ha and 100 kg/ha, between 0.75 kg/ha and 100 kg/ha, between 1 kg/ha and 100 kg/ha, between 2 kg/ha and 100 kg/ha, between 3 kg/ha and 100 kg/ha, between 4 kg/ha and 100 kg/ha, between 5 kg/ha and 100 kg/ha, between 6 kg/ha and 100 kg/ha, between 7 kg/ha and 100 kg/ha, between 8 kg/ha and 100 kg/ha, between 9 kg/ha and 100 kg/ha, between 10 kg/ha and 100 kg/ha, between 15 kg/ha and 100 kg/ha, between 20 kg/ha and 100 kg/ha, between 30 kg/ha and 100 kg/ha, between 40 kg/ha and 100 kg/ha, between 50 kg/ha and 100 kg/ha, between 75 kg/ha and 100 kg/ha, between 100 kg/ha and 500 kg/ha, between 100 kg/ha and 400 kg/ha, between 100 and 300 kg/ha, or between 100 kg/ha and 200 kg/ha as compared to a population of control tobacco plants when grown under similar growth conditions. As used herein, a "population" of tobacco plants can be of any size for example, 5, 10, 15, 20, 25, 30, 35, 40, 50, 100, 500, 1000, 5000, 10000, 25000, 50000, 100000, 500000, or more. A population can be from a single variety, cultivar, or line. A population can be created using any breeding techniques known in the art.

In an aspect, a modified tobacco plant comprising enhanced NUE provided herein comprises at least 1, at least 2, at least 3, at least 4, at least 5, at least 6, at least 7, at least 8, at least 9, at least 10, at least 11, at least 12, at least 13, at least 14, at least 15, at least 20, or at least 25 more leaves as compared to a control tobacco plant grown under similar growth conditions. In another aspect, a modified tobacco plant comprising enhanced NUE provided herein comprises between 1 and 25, between 2 and 25, between 3 and 25, between 4 and 25, between 5 and 25, between 6 and 25, between 7 and 25, between 8 and 25, between 9 and 25, between 10 and 25, between 11 and 25, between 12 and 25, between 13 and 25, between 14 and 25, between 15 and 25, or between 20 and 25 more leaves as compared to a control tobacco plant grown under similar growth conditions.

As used herein, "comparable conditions" "similar conditions" or "similar growth conditions" refers to similar environmental conditions, agronomic practices, and/or curing process for growing or curing tobacco and making meaningful comparisons between two or more plant genotypes so that neither environmental conditions nor agronomic practices (including curing process) would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, suckering, and curing. See Chapters 4B and 4C of Tobacco, Production, Chemistry and Technology, Davis & Nielsen, eds., Blackwell Publishing, Oxford (1999), pp. 70-103.

In one aspect, a modified plant, seed, plant part, or plant cell provided herein comprises one or more non-naturally occurring mutations. In one aspect, a mutation provided herein improves nitrogen utilization efficiency in a plant. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, methods provided herein are capable of producing a tobacco plant with enhanced nitrogen utilization efficiency as compared to a control tobacco plant. Mutagenesis methods include, without limitation, chemical mutagenesis, for example, treatment of seeds with ethyl methylsulfate (EMS) (Hildering and Verkerk, In, The use of induced mutations in plant breeding. Pergamon Press, pp. 317-320, 1965); or UV-irradiation, X-rays, electron beams, ion beams (e.g., carbon ion beam, helium ion beam, neon ion beam), and fast neutron irradiation (see, for example, Verkerk, *Neth. J. Agric. Sci.* 19:197-203, 1971; Poehlman, Breeding Field Crops, Van Nostrand Reinhold, New York (3.sup.rd ed.), 1987; and Tanaka, *J. Radiat. Res.* 51:223-233, 2010); transposon tagging (Fedoroff et al., 1984; U.S. Pat. Nos. 4,732,856 and 5,013,658); and T-DNA insertion methodologies (Hoekema et al., 1983; U.S. Pat. No. 5,149,645). EMS-induced mutagenesis consists of chemically inducing random point mutations over the length of a genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene.

In addition, a fast and automatable method for screening for chemically induced mutations, TILLING (Targeting Induced Local Lesions In Genomes), using denaturing high performance liquid chromatography (HPLC) or selective endonuclease digestion of selected PCR products is also applicable to the present disclosure. See, McCallum et al. (2000) *Nat. Biotechnol.* 18:455-457. Mutations that impact gene expression or that interfere with the function of genes provided herein can be determined using methods that are well known in the art. Insertional mutations in gene exons usually result in null-mutants. Mutations in conserved residues can be particularly effective in inhibiting the function of a protein.

The screening and selection of mutagenized tobacco plants can be through any methodologies known to those having ordinary skill in the art. Examples of screening and selection methodologies include, but are not limited to, Southern blots, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454), enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

In one aspect, a plant genome provided herein is mutated (edited) by a nuclease selected from the group consisting of a meganuclease, a zinc-finger nuclease (ZFN), a transcription activator-like effector nuclease (TALEN), a CRISPR/Cas9 nuclease, a CRISPR/Cpf1, or a CRISPR/Cmx1 nuclease. In another aspect, a plant genome provided herein is mutated by a CRISPR/CasX or a CRISPR/CasY nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence.

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of a plant cell and is capable of being inherited by the progeny thereof. "Transient transformation" is intended to mean that a sequence is introduced into a plant or plant cell and is only temporally expressed or is only transiently present in the plant or plant cell.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, a modified plant, seed, plant component, plant cell, or plant genome provided herein comprises one or more transgenes. In one aspect, a transgene provided herein improves nitrogen utilization efficiency in a tobacco plant. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found. Therefore, a transgene can also be a cisgene under appropriate circumstances.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NPTII) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* $T_1$ plasmid or derived from an *Agrobacterium* $T_1$ plasmid. In still another aspect, a vector provided herein is a viral vector.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. In one aspect, a vector provided herein comprises all or part of SEQ ID NO: 65. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6× His tag, glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149, 645, 5,177,010, 5,231,019, 5,463,174, 5,464,763, 5,469,976, 4,762,785, 5,004,863, 5,159,135, 5,563,055, and 5,981, 840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein. It is appreciated that many different species of bacterial cells can comprise a recombinant DNA construct or recombinant vector, I including, but not limited to, *Agrobacterium tumefaciens, Escherichia coli*. Yeast cells (e.g., *Saccharomyces cerevisiae*) comprising a recombinant DNA construct or recombinant vector provided herein are also provided.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

As commonly understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetically produced, varied or derived from a known or naturally occurring promoter sequence or other promoter sequence (e.g., as provided herein). A promoter may also include a chimeric promoter comprising a combination of two or more heterologous sequences. A promoter of the present invention may thus include variants of promoter sequences that are similar in composition, but not identical to or complimentary to, other promoter sequence(s) known or provided herein. As used herein, a "heterologous promoter" in the context of a DNA construct refers to either: (i) a promoter that is derived from a source distinct from the operably linked structural gene or coding region or (ii) a promoter derived from the same source as the operably linked structural gene or coding region, where the promoter's sequence is modified from its original form. As used herein, the term "operably linked" refers to a functional linkage between a promoter or other regulatory element and an associated transcribable polynucleotide sequence or coding sequence of a gene (or transgene), such that the promoter, etc., operates to initiate, assist, affect, cause, and/or promote the transcription and expression of the associated coding or transcribable polynucleotide sequence, at least in particular tissue(s), developmental stage(s), and/or under certain condition(s). A "plant expressible promoter" refers to a promoter that may be used to express in a plant, plant cell and/or plant tissue an associated coding sequence, transgene or transcribable polynucleotide sequence that is operably linked to the promoter.

A promoter may be classified according to a variety of criteria relating to the pattern of expression of a coding sequence or gene (including a transgene) operably linked to the promoter, such as constitutive, developmental, tissue-specific, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "heterologous" may refer more broadly to a combination of two or more DNA molecules or sequences when such a combination is not normally found in nature. For example, two or more DNA molecules or sequences would be heterologous with respect to each other if they are normally found in different genomes or at different loci in the same genome, or if they are not identically combined in nature.

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

As used herein, a "leaf" promoter includes any promoter that initiates, causes, drives, etc., transcription or expression of its associated gene, transgene or transcribable DNA sequence in leaf tissue derived from any part of a plant. Such a "leaf" promoter may be further defined as initiating, causing, driving, etc., transcription or expression of its associated gene/transgene or transcribable DNA sequence in one or more tissue(s) of a plant, such as one or more floral tissue(s). Such a "leaf" promoter may be further defined as a "leaf preferred" promoter that initiates, causes, drives, etc., transcription or expression of its associated gene, transgene or transcribable DNA sequence at least preferentially or mostly, if not exclusively, in leaf tissue derived from any part of a plant (as opposed to floral tissue). However, a "leaf" and a "leaf preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more vegetative or reproductive tissue(s). In fact, a "leaf" promoter may even initiate, cause, drive, etc., transcription or expression of its associated gene, transgene or transcribable DNA sequence in one or more reproductive or vegetative tissues at a greater level or extent than in leaf tissue(s).

As used herein, a "root" promoter includes any promoter that initiates, causes, drives, etc., transcription or expression of its associated gene, transgene or transcribable DNA sequence in root tissue derived from any part of a plant. Such a "root" promoter may be further defined as initiating, causing, driving, etc., transcription or expression of its associated gene/transgene or transcribable DNA sequence in one or more tissue(s) of a plant, such as one or more floral tissue(s). Such a "root" promoter may be further defined as a "root preferred" promoter that initiates, causes, drives, etc., transcription or expression of its associated gene, transgene or transcribable DNA sequence at least preferentially or mostly, if not exclusively, in root tissue derived from any part of a plant (as opposed to floral tissue). However, a "root" and a "root preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more vegetative or reproductive tissue(s). In fact, a "root" promoter may even initiate, cause, drive, etc., transcription or expression of its associated gene, transgene or transcribable DNA sequence in one or more reproductive or vegetative tissues at a greater level or extent than in root tissue(s).

Additional exemplary tissue-preferred promoters include those disclosed in Yamamoto et al. (1997) Plant J. 12(2): 255-265; Kawamata et al. (1997) Plant Cell Physiol. 38(7): 792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

In one aspect, inhibition of the expression of one or more polypeptides provided herein may be obtained by RNA interference (RNAi) by expression of a polynucleotide provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), an intron-containing hairpin RNA (ihpRNA), and guide RNA. In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

As used herein, the terms "down-regulate," "suppress," "inhibit," "inhibition," and "inhibiting" are defined as any method known in the art or described herein that decreases the expression or function of a gene product of interest (e.g., an mRNA, a protein, a non-coding RNA). "Inhibition" can be in the context of a comparison between two plants, for example, a modified plant versus a control plant. Alternatively, inhibition of expression or function of a target gene product can be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA. An inhibitory sequence may range from at least 20 nucleotides, at least 50 nucleotides, at least 70 nucleotides, at least 100 nucleotides, at least 150 nucleotides, at least 200 nucleotides, at least 250 nucleotides, at least 300 nucleotides, at least 350 nucleotides, at least 400 nucleotides, and up to the full-length polynucleotide encoding the proteins of the present disclosure, depending upon the desired outcome. In one aspect, an inhibitory sequence can be a fragment of between 50 and 400 nucleotides, between 70 and 350 nucleotides, between 90 and 325 nucleotides, between 90 and 300 nucleotides, between 90 and 275 nucleotides, between 100 and 400 nucleotides, between 100 and 350 nucleotides, between 100 and 325 nucleotides, between 100 and 300 nucleotides, between 125 and 300 nucleotides, or between 125 and 275 nucleotides in length.

MicroRNAs (miRNAs) are non-protein coding RNAs, generally of between 19 to 25 nucleotides (commonly 20 to 24 nucleotides in plants), that guide cleavage in trans of target transcripts, negatively regulating the expression of genes involved in various regulation and development pathways (Bartel (2004) Cell, 116:281-297). In some cases, miRNAs serve to guide in-phase processing of siRNA primary transcripts (see Allen et al. (2005) Cell, 121:207-221).

Many microRNA genes (MIR genes) have been identified and made publicly available in a database ("miRBase", available on line at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript; see, for example, Parizotto et al. (2004) Genes Dev., 18:2237-2242. Recognition sites of miRNAs have been validated in all regions of an mRNA, including the 5' untranslated region, coding region, and 3' untranslated region, indicating that the position of the miRNA target site relative to the coding sequence may not necessarily affect suppression. Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are known. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST® (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "$\Delta\Delta G$"). Preferably 19-mers are selected that have all or most of the following characteristics: (1) a Reynolds score>4, (2) a GC content between 40% to 60%, (3) a negative $\Delta\Delta G$, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna.chem.t.u-tokyo.ac.jp/siexplorer.htm; (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein reduces or eliminates RNA transcription or protein translation of a target gene.

In one aspect, a miRNA or an artificial miRNA provided herein is under the control of a tissue specific promoter. In a further aspect, a miRNA or an artificial miRNA provided herein is under the control of a tissue-preferred promoter. In a further aspect, a miRNA or an artificial miRNA provided herein is under the control of a constitutive promoter.

Tobacco material obtained from modified tobacco lines, varieties or hybrids of the present disclosure can be used to make tobacco products. As used herein, "tobacco product" is defined as any product made or derived from tobacco that is intended for human use or consumption. In an aspect, a tobacco product provided herein comprises cured components from a modified tobacco plant provided herein. In another aspect, a tobacco product provided herein comprises cured tobacco leaves from a modified tobacco plant provided herein.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, chewing tobacco, moist smokeless tobacco, fine cut chewing tobacco, long cut chewing tobacco, pouched chewing tobacco), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a bidi cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff.

In yet another aspect, a tobacco product of the present disclosure is selected from the group consisting of an electronically heated cigarette, an e-cigarette, an electronic vaporing device. In one aspect, a method provided herein comprises preparing a tobacco product using a cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Also provided herein is cured tobacco material made from tobacco plants or plant components provided herein. "Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

The present disclosure further provides a method manufacturing a tobacco product comprising tobacco material from tobacco plants provided herein. In one aspect, methods provided herein comprise conditioning aged tobacco material made from tobacco plants provided herein to increase its moisture content from between 12.5% and 13.5% to 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, Burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of 10 cuts/inch up to 110 cuts/inch and lengths of 0.1 inches up to 1 inch. Double cut tobacco fibers can have a range of particle sizes such that 70% of the double cut tobacco fibers falls between the mesh sizes of −2 0 mesh and 80 mesh.

Tobacco material provided herein can be processed to have a total oven volatiles content of 10% by weight or greater; 20% by weight or greater; 40% by weight or greater; 15% by weight to 25% by weight; 20% by weight to 30% by weight; 30% by weight to 50% by weight; 45% by weight to 65% by weight; or 50% by weight to 60% by weight. Those of skill in the art will appreciate that "moist" tobacco typically refers to tobacco that has an oven volatiles content of between 40% by weight and 60% by weight (e.g., 45% by weight to 55% by weight, or 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, and Galpão tobacco. In one aspect, a tobacco plants or seed provided herein is a hybrid plants or seed. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

Flue-cured tobaccos (also called Virginia of bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In one aspect, modified tobacco plants or seeds provided herein are in a flue-cured tobacco background selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, modified tobacco plants, seeds, hybrids, varieties, or lines provided herein are in any flue cured background selected from the group consisting of K326, K346, and NC196.

Air-cured tobaccos include Burley, Md., and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In one aspect, modified tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HBO4P, Ky 14×L 8, Kt 200, Newton 98, Pedigo 561, Pf561 and Va 509. In further aspects, modified tobacco plants, seeds, hybrids, varieties, or lines provided herein are in any Burley background selected from the group consisting of TN 90, KT 209, KT 206, KT212, and HB 4488. In another aspect, modified tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of chewing tobacco and snuff. In one aspect, modified tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In one aspect, modified tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In one aspect, modified tobacco plants or seeds provided herein are in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In one aspect, modified tobacco plants, seeds, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L.8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

All foregoing mentioned specific varieties of dark air-cured, Burley, Md., dark fire-cured, or Oriental type are only listed for exemplary purposes. Any additional dark air-cured, Burley, Md., dark fire-cured, Oriental varieties are also contemplated in the present application.

Also provided herein are populations of tobacco plants described herein. In one aspect, a population of tobacco plants provided herein has a planting density of between 5,000 and 8000, between 5,000 and 7,600, between 5,000 and 7,200, between 5,000 and 6,800, between 5,000 and 6,400, between 5,000 and 6,000, between 5,000 and 5,600, between 5,000 and 5,200, between 5,200 and 8,000, between 5,600 and 8,000, between 6,000 and 8,000, between 6,400 and 8,000, between 6,800 and 8,000, between 7,200 and 8,000, or between 7,600 and 8,000 plants per acre.

Also provided herein are containers of seeds from tobacco plants described herein. A container of tobacco seeds of the present disclosure may contain any number, weight, or volume of seeds. For example, a container can contain at least or greater than 10 seeds; at least or greater than 25 seeds; at least or greater than 50 seeds; at least, or greater than, 100 seeds; at least, or greater than, 200 seeds; at least, or greater than, 300 seeds; at least, or greater than, 400 seeds; at least, or greater than, 500 seeds; at least, or greater than, 600 seeds; at least, or greater than, 700 seeds; at least, or greater than, 800 seeds; at least, or greater than, 900 seeds; at least, or greater than, 1000 seeds; at least, or greater than, 1500 seeds; at least, or greater than, 2000 seeds; at least, or greater than, 2500 seeds; at least, or greater than, 3000 seeds; at least, or greater than, 3500 seeds; at least, or greater than, 4000 seeds; or at least, or greater than 5000 seeds. Alternatively, the container can contain at least, or greater than, 1 ounce of seeds; at least, or greater than, 5 grams of seeds; at least, or greater than, 10 grams of seeds; at least, or greater than, 30 grams of seeds; at least, or greater than, 50 grams of seeds; at least, or greater than, 100 grams of seeds; at least, or greater than, 500 grams of seeds; at least, or greater than, 1 kilogram of seeds; at least, or greater than 1.5 kilograms of seeds; at least, or greater than 2 kilograms of seeds; at least, or greater than, 5 kilograms of seeds; or at least, or greater than, 10 kilograms of seeds. Containers of tobacco seeds may be any container available in the art. By way of non-limiting example, a container may be a box, a bag, a packet, a pouch, a tape roll, a tube, or a bottle.

In one aspect, present disclosure provides cured leaf from a modified tobacco plant comprising a reduced level of one or more TSNAs. In one aspect, reduced one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In one aspect, the level of total TSNAs or an individual TSNA is measured based on a freeze-dried cured leaf sample using liquid chromatograph with tandem mass spectrometry (LC/MS/MS).

In one aspect, present disclosure provides cured leaf from a modified tobacco plant comprising a reduced level of one or more alkaloids. In one aspect, reduced one or more alkaloids are selected from the group consisting of nicotine, nornicotine, anabasine, anatabine.

The present disclosure also provides methods for breeding tobacco lines, cultivars, or varieties comprising enhanced nitrogen utilization efficiency. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using $F_1$ hybrid plants provided herein or further crossing the $F_1$ hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. In one aspect, a recurrent parent provided herein is TN90. In another aspect, a recurrent parent provided herein is MD609. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety exhibits enhanced nitrogen utilization efficiency compared to a control tobacco plant of the same variety grown under comparable conditions; and selecting for progeny tobacco plants that exhibit enhanced nitrogen utilization efficiency compared to a control tobacco plant of the same cross grown under comparable conditions. In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes into a tobacco variety, the method comprising: (a) crossing a first tobacco variety comprising one or more transgenes with a second tobacco variety without the one or more transgenes to produce one or more progeny tobacco plants; (b) genotyping the one or more progeny tobacco plants for the one or more transgenes; and (c) selecting a progeny tobacco plant comprising the one or more transgenes. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes. In one aspect, the second tobacco variety is an elite variety.

In one aspect, the present disclosure provides a method of introgressing one or more mutations into a tobacco variety, the method comprising: (a) crossing a first tobacco variety comprising one or more mutations with a second tobacco variety without the one or more mutations to produce one or more progeny tobacco plants; (b) genotyping the one or more progeny tobacco plants for the one or more mutations; and (c) selecting a progeny tobacco plant comprising the one or more mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more mutations. In one aspect, the second tobacco variety is an elite variety.

In one aspect, the present disclosure provides a method of growing a population of modified tobacco plants comprising enhanced nitrogen utilization efficiency, where the method comprises planting a population of tobacco seeds comprising one or more mutations, one or more transgenes, or both, where the one or more modified tobacco plants exhibit enhanced nitrogen utilization efficiency compared to control tobacco plants of the same variety when grown under comparable conditions.

In one aspect, this disclosure provides a method for manufacturing a modified seed, comprising introducing a recombinant DNA construct provided herein into a plant cell; screening a population of plant cells for the recombinant DNA construct; selecting one or more plant cells from the population; generating one or more modified plants from the one or more plant cells; and collecting one or more modified seeds from the one or more modified plants.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (e.g., the second sister chromosome does not contain the inserted transgene).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "BC1" refers to the second use of the recurrent parent, "BC2" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested. Additionally, female sterile plants can also be used to prevent self-fertilization.

Plants can be used to form single-cross tobacco $F_1$ hybrids. Pollen from a male parent plant is manually transferred to an emasculated female parent plant or a female parent plant that is male sterile to form $F_1$ seed. Alternatively, three-way crosses can be carried out where a single-cross $F_1$ hybrid is used as a female parent and is crossed with a different male parent. As another alternative, double-cross hybrids can be created where the $F_1$ progeny of two different single-crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

In one aspect, the present disclosure provides for, and includes, a method of determining the NUE of a tobacco line comprising obtaining at least one metabolite from a tobacco plant of a tobacco line, determining the amount of the at least one obtained metabolites, and determining the NUE of the tobacco line based on the amount of the at least one metabolite determined. In a further aspect, the at least one metabolite is obtained from a plant tissue selected from the group consisting of root tissue, leaf tissue, floral tissue, meristem tissue, and stem tissue. In a further aspect of this method, at least two metabolites are obtained. In a further aspect of this method, at least three metabolites are obtained. In a further aspect of this method, at least four metabolites are obtained. In a further aspect of this method, at least five metabolites are obtained. In a further aspect of this method, at least six metabolites are obtained. In a further aspect of this method, at least seven metabolites are obtained. In a further aspect of this method, at least eight metabolites are obtained. In a further aspect of this method, at least nine metabolites are obtained. In a further aspect of this method, at least ten metabolites are obtained. In a further aspect of this method, the amount of at least two metabolites is determined. In a further aspect of this method, the amount of at least three metabolites is determined. In a further aspect of this method, the amount of at least four metabolites is determined. In a further aspect of this method, the amount of at least five metabolites is determined. In a further aspect of this method, the amount of at least six metabolites is determined. In a further aspect of this method, the amount of at least seven metabolites is determined. In a further aspect of this method, the amount of at least eight metabolites is determined. In a further aspect of this method, the amount of at least nine metabolites is determined. In a further aspect of this method, the amount of at least ten metabolites is determined.

In another aspect of a method provided herein, the amount of a metabolite selected from the group consisting of X-2357, N-acetylmuramate, X-23319, X-23852, X-23330, alpha-ketoglutarate, X-21756, 4-hydroxy-2-oxoglutaric acid, D-23937, X-23937, X-23916, 1-methyladenine, 4-guanidinobutanoate, syringaldehyde, thiamin, p-hydroxybenzaldehyde, X-23453, X-11429, X-21796, N'-methylnicotinamide, cotinine, X-23389, N-acetylarginine, X-23366, N-acetylphenylalanine, naringenin, X-23454, X-23580, and X-23852 is determined.

In another aspect of a method provided herein, a tobacco plant with enhanced NUE comprises enhanced NUE as compared to a tobacco plant that comprises a lower amount of at least one metabolite in at least one tissue. In a further aspect, a tobacco plant with enhanced NUE comprises a lower amount of at least two metabolites in at least one tissue. In a further aspect, a tobacco plant with enhanced NUE comprises a lower amount of at least three metabolites in at least one tissue. In a further aspect, a tobacco plant with enhanced NUE comprises a lower amount of at least four metabolites in at least one tissue. In a further aspect, a tobacco plant with enhanced NUE comprises a lower amount of at least five metabolites in at least one tissue. In a further aspect, a tobacco plant with enhanced NUE comprises a lower amount of at least one metabolite in two tissues. In a further aspect, a tobacco plant with enhanced NUE comprises a lower amount of at least two metabolites in at least two tissues. In a further aspect, a tobacco plant with enhanced NUE comprises a lower amount of at least three metabolites in at least two tissues. In a further aspect, a tobacco plant with enhanced NUE comprises a lower amount of at least four metabolites in at least two tissues. In a further aspect, a tobacco plant with enhanced NUE comprises a lower amount of at least five metabolites in at least two tissues. In a further aspect, a tobacco plant with enhanced NUE comprises a lower amount of at least one metabolite in three tissues. In a further aspect, a tobacco plant with enhanced NUE comprises a lower amount of at least two metabolites in at least three tissues. In a further aspect, a tobacco plant with enhanced NUE comprises a lower amount of at least three metabolites in at least three tissues. In a further aspect, a tobacco plant with enhanced NUE comprises a lower amount of at least four metabolites in at least three tissues. In a further aspect, a tobacco plant with enhanced NUE comprises a lower amount of at least five metabolites in at least three tissues. In a further aspect, a tobacco plant with enhanced NUE comprises a lower amount of at least one metabolite in four tissues. In a further aspect, a tobacco plant with enhanced NUE comprises a lower amount of at least two metabolites in at least four tissues. In a further aspect, a tobacco plant with enhanced NUE comprises a lower amount of at least three metabolites in at least four tissues. In a further aspect, a tobacco plant with enhanced NUE comprises a lower amount of at least four metabolites in at least four tissues. In a further aspect, a tobacco plant with enhanced NUE comprises a lower amount of at least five metabolites in at least four tissues. In a further aspect, a tobacco plant with enhanced NUE comprises a lower amount of at least one metabolite in five tissues. In a further aspect, a tobacco plant with enhanced NUE comprises a lower amount of at least two metabolites in at least five tissues. In a further aspect, a tobacco plant with enhanced NUE comprises a lower amount of at least three metabolites in at least five tissues. In a further aspect, a tobacco plant with enhanced NUE comprises a lower amount of at least four metabolites in at least five tissues. In a further aspect, a tobacco plant with enhanced NUE comprises a lower amount of at least five metabolites in at least five tissues.

In another aspect of a method provided herein, a tobacco plant with enhanced NUE comprises enhanced NUE as compared to a tobacco line that comprises a higher amount of at least one metabolite in at least one tissue. In a further aspect, a tobacco plant with enhanced NUE comprises a higher amount of at least two metabolites in at least one tissue. In a further aspect, a tobacco plant with enhanced NUE comprises a higher amount of at least three metabolites in at least one tissue. In a further aspect, a tobacco plant with enhanced NUE comprises a higher amount of at least four metabolites in at least one tissue. In a further aspect, a tobacco plant with enhanced NUE comprises a higher amount of at least five metabolites in at least one tissue. In a further aspect, a tobacco plant with enhanced NUE comprises a higher amount of at least one metabolite in two tissues. In a further aspect, a tobacco plant with enhanced NUE comprises a higher amount of at least two metabolites in at least two tissues. In a further aspect, a tobacco plant with enhanced NUE comprises a higher amount of at least three metabolites in at least two tissues. In a further aspect, a tobacco plant with enhanced NUE comprises a higher amount of at least four metabolites in at least two tissues. In a further aspect, a tobacco plant with enhanced NUE comprises a higher amount of at least five metabolites in at least two tissues. In a further aspect, a tobacco plant with enhanced NUE comprises a higher amount of at least one metabolite in three tissues. In a further aspect, a tobacco plant with enhanced NUE comprises a higher amount of at least two metabolites in at least three tissues. In a further aspect, a tobacco plant with enhanced NUE comprises a higher amount of at least three metabolites in at least three tissues. In a further aspect, a tobacco plant with enhanced NUE comprises a higher amount of at least four metabolites in at least three tissues. In a further aspect, a tobacco plant with enhanced NUE comprises a higher amount of at least five metabolites in at least three tissues. In a further aspect, a tobacco plant with enhanced NUE comprises a higher amount of at least one metabolite in four tissues. In a further aspect, a tobacco plant with enhanced NUE comprises a higher amount of at least two metabolites in at least four tissues. In a further aspect, a tobacco plant with enhanced NUE comprises a higher amount of at least three metabolites in at least four tissues. In a further aspect, a tobacco plant with enhanced NUE comprises a higher amount of at least four metabolites in at least four tissues. In a further aspect, a tobacco plant with enhanced NUE comprises a higher amount of at least five metabolites in at least four tissues. In a further aspect, a tobacco plant with enhanced NUE comprises a higher amount of at least one metabolite in five tissues. In a further aspect, a tobacco plant with enhanced NUE comprises a higher amount of at least two metabolites in at least five tissues. In a further aspect, a tobacco plant with enhanced NUE comprises a higher amount of at least three metabolites in at least five tissues. In a further aspect, a tobacco plant with enhanced NUE comprises a higher amount of at least four metabolites in at least five tissues. In a further aspect, a tobacco plant with enhanced NUE comprises a higher amount of at least five metabolites in at least five tissues.

In another aspect of a method provided herein, a tobacco plant with enhanced NUE comprises enhanced NUE as compared to a tobacco line that comprises an equal amount of at least one metabolite in at least one tissue. In a further aspect, a tobacco plant with enhanced NUE comprises an equal amount of at least two metabolites in at least one tissue. In a further aspect, a tobacco plant with enhanced NUE comprises an equal amount of at least three metabolites in at least one tissue. In a further aspect, a tobacco plant with enhanced NUE comprises an equal amount of at least four metabolites in at least one tissue. In a further aspect, a tobacco plant with enhanced NUE comprises an equal amount of at least five metabolites in at least one tissue. In a further aspect, a tobacco plant with enhanced NUE comprises an equal amount of at least one metabolite in two tissues. In a further aspect, a tobacco plant with enhanced NUE comprises an equal amount of at least two metabolites in at least two tissues. In a further aspect, a tobacco plant with enhanced NUE comprises an equal amount of at least three metabolites in at least two tissues. In a further aspect, a tobacco plant with enhanced NUE comprises an equal amount of at least four metabolites in at least two tissues. In a further aspect, a tobacco plant with enhanced NUE comprises an equal amount of at least five metabolites in at least two tissues. In a further aspect, a tobacco plant with enhanced NUE comprises an equal amount of at least one metabolite in three tissues. In a further aspect, a tobacco plant with enhanced NUE comprises an equal amount of at least two metabolites in at least three tissues. In a further aspect, a tobacco plant with enhanced NUE comprises an equal amount of at least three metabolites in at least three tissues. In a further aspect, a tobacco plant with enhanced NUE comprises an equal amount of at least four metabolites in at least three tissues. In a further aspect, a tobacco plant with enhanced NUE comprises an equal amount of at least five metabolites in at least three tissues. In a further aspect, a tobacco plant with enhanced NUE comprises an equal amount of at least one metabolite in four tissues. In a further aspect, a tobacco plant with enhanced NUE comprises an equal amount of at least two metabolites in at least four tissues. In a further aspect, a tobacco plant with enhanced NUE comprises an equal amount of at least three metabolites in at least four tissues. In a further aspect, a tobacco plant with enhanced NUE comprises an equal amount of at least four metabolites in at least four tissues. In a further aspect, a tobacco plant with enhanced NUE comprises an equal amount of at least five metabolites in at least four tissues. In a further aspect, a tobacco plant with enhanced NUE comprises an equal amount of at least one metabolite in five tissues. In a further aspect, a tobacco plant with enhanced NUE comprises an equal amount of at least two metabolites in at least five tissues. In a further aspect, a tobacco plant with enhanced NUE comprises an equal amount of at least three metabolites in at least five tissues. In a further aspect, a tobacco plant with enhanced NUE comprises an equal amount of at least four metabolites in at least five tissues. In a further aspect, a tobacco plant with enhanced NUE comprises an equal amount of at least five metabolites in at least five tissues.

In another aspect of a method provided herein, a tobacco plant with enhanced NUE comprises decreased NUE as compared to a tobacco line that comprises a lower amount of at least one metabolite in at least one tissue. In a further aspect, a tobacco plant with enhanced NUE comprises a lower amount of at least two metabolites in at least one tissue. In a further aspect, a tobacco plant with enhanced NUE comprises a lower amount of at least three metabolites in at least one tissue. In a further aspect, a tobacco plant with enhanced NUE comprises a lower amount of at least four metabolites in at least one tissue. In a further aspect, a tobacco plant with enhanced NUE comprises a lower amount of at least five metabolites in at least one tissue. In a further aspect, a tobacco plant with enhanced NUE comprises a lower amount of at least one metabolite in two tissues. In a further aspect, a tobacco plant with enhanced NUE comprises a lower amount of at least two metabolites in at least two tissues. In a further aspect, a tobacco plant with enhanced NUE comprises a lower amount of at least three metabolites in at least two tissues. In a further aspect, a tobacco plant with enhanced NUE comprises a lower amount of at least four metabolites in at least two tissues. In a further aspect, a tobacco plant with enhanced NUE comprises a lower amount of at least five metabolites in at least two tissues. In a further aspect, a tobacco plant with enhanced NUE comprises a lower amount of at least one metabolite in three tissues. In a further aspect, a tobacco plant with enhanced NUE comprises a lower amount of at least two metabolites in at least three tissues. In a further aspect, a tobacco plant with enhanced NUE comprises a lower amount of at least three metabolites in at least three tissues. In a further aspect, a tobacco plant with enhanced NUE comprises a lower amount of at least four metabolites in at least three tissues. In a further aspect, a tobacco plant with enhanced NUE comprises a lower amount of at least five metabolites in at least three tissues. In a further aspect, a tobacco plant with enhanced NUE comprises a lower amount of at least one metabolite in four tissues. In a further aspect, a tobacco plant with enhanced NUE comprises a lower amount of at least two metabolites in at least four tissues. In a further aspect, a tobacco plant with enhanced NUE comprises a lower amount of at least three metabolites in at least four tissues. In a further aspect, a tobacco plant with enhanced NUE comprises a lower amount of at least four metabolites in at least four tissues. In a further aspect, a tobacco plant with enhanced NUE comprises a lower amount of at least five metabolites in at least four tissues. In a further aspect, a tobacco plant with enhanced NUE comprises a lower amount of at least one metabolite in five tissues. In a further aspect, a tobacco plant with enhanced NUE comprises a lower amount of at least two metabolites in at least five tissues. In a further aspect, a tobacco plant with enhanced NUE comprises a lower amount of at least three metabolites in at least five tissues. In a further aspect, a tobacco plant with enhanced NUE comprises a lower amount of at least four metabolites in at least five tissues. In a further aspect, a tobacco plant with enhanced NUE comprises a lower amount of at least five metabolites in at least five tissues.

In another aspect of a method provided herein, a tobacco plant with enhanced NUE comprises decreased NUE as compared to a tobacco line that comprises a higher amount of at least one metabolite in at least one tissue. In a further aspect, a tobacco plant with enhanced NUE comprises a higher amount of at least two metabolites in at least one tissue. In a further aspect, a tobacco plant with enhanced NUE comprises a higher amount of at least three metabolites in at least one tissue. In a further aspect, a tobacco plant with enhanced NUE comprises a higher amount of at least four metabolites in at least one tissue. In a further aspect, a tobacco plant with enhanced NUE comprises a higher amount of at least five metabolites in at least one tissue. In a further aspect, a tobacco plant with enhanced NUE comprises a higher amount of at least one metabolite in two tissues. In a further aspect, a tobacco plant with enhanced NUE comprises a higher amount of at least two metabolites in at least two tissues. In a further aspect, a tobacco plant with enhanced NUE comprises a higher amount of at least three metabolites in at least two tissues. In a further aspect, a tobacco plant with enhanced NUE comprises a higher amount of at least four metabolites in at least two tissues. In a further aspect, a tobacco plant with enhanced NUE comprises a higher amount of at least five metabolites in at least two tissues. In a further aspect, a tobacco plant with enhanced NUE comprises a higher amount of at least one metabolite in three tissues. In a further aspect, a tobacco plant with enhanced NUE comprises a higher amount of at least two metabolites in at least three tissues. In a further aspect, a tobacco plant with enhanced NUE comprises a higher amount of at least three metabolites in at least three tissues. In a further aspect, a tobacco plant with enhanced NUE comprises a higher amount of at least four metabolites in at least three tissues. In a further aspect, a tobacco plant with enhanced NUE comprises a higher amount of at least five metabolites in at least three tissues. In a further aspect, a tobacco plant with enhanced NUE comprises a higher amount of at least one metabolite in four tissues. In a further aspect, a tobacco plant with enhanced NUE comprises a higher amount of at least two metabolites in at least four tissues. In a further aspect, a tobacco plant with enhanced NUE comprises a higher amount of at least three metabolites in at least four tissues. In a further aspect, a tobacco plant with enhanced NUE comprises a higher amount of at least four metabolites in at least four tissues. In a further aspect, a tobacco plant with enhanced NUE comprises a higher amount of at least five metabolites in at least four tissues. In a further aspect, a tobacco plant with enhanced NUE comprises a higher amount of at least one metabolite in five tissues. In a further aspect, a tobacco plant with enhanced NUE comprises a higher amount of at least two metabolites in at least five tissues. In a further aspect, a tobacco plant with enhanced NUE comprises a higher amount of at least three metabolites in at least five tissues. In a further aspect, a tobacco plant with enhanced NUE comprises a higher amount of at least four metabolites in at least five tissues. In a further aspect, a tobacco plant with enhanced NUE comprises a higher amount of at least five metabolites in at least five tissues.

In another aspect of a method provided herein, a tobacco plant with enhanced NUE comprises decreased NUE as compared to a tobacco line that comprises an equal amount of at least one metabolite in at least one tissue. In a further aspect, a tobacco plant with enhanced NUE comprises an equal amount of at least two metabolites in at least one tissue. In a further aspect, a tobacco plant with enhanced NUE comprises an equal amount of at least three metabolites in at least one tissue. In a further aspect, a tobacco plant with enhanced NUE comprises an equal amount of at least four metabolites in at least one tissue. In a further aspect, a tobacco plant with enhanced NUE comprises an equal amount of at least five metabolites in at least one tissue. In a further aspect, a tobacco plant with enhanced NUE comprises an equal amount of at least one metabolite in two tissues. In a further aspect, a tobacco plant with enhanced NUE comprises an equal amount of at least two metabolites in at least two tissues. In a further aspect, a tobacco plant with enhanced NUE comprises an equal amount of at least three metabolites in at least two tissues. In a further aspect, a tobacco plant with enhanced NUE comprises an equal amount of at least four metabolites in at least two tissues. In a further aspect, a tobacco plant with enhanced NUE comprises an equal amount of at least five metabolites in at least two tissues. In a further aspect, a tobacco plant with enhanced NUE comprises an equal amount of at least one metabolite in three tissues. In a further aspect, a tobacco plant with enhanced NUE comprises an equal amount of at least two metabolites in at least three tissues. In a further aspect, a tobacco plant with enhanced NUE comprises an equal amount of at least three metabolites in at least three tissues. In a further aspect, a tobacco plant with enhanced NUE comprises an equal amount of at least four metabolites in at least three tissues. In a further aspect, a tobacco plant with enhanced NUE comprises an equal amount of at least five metabolites in at least three tissues. In a further aspect, a tobacco plant with enhanced NUE comprises an equal amount of at least one metabolite in four tissues. In a further aspect, a tobacco plant with enhanced NUE comprises an equal amount of at least two metabolites in at least four tissues. In a further aspect, a tobacco plant with enhanced NUE comprises an equal amount of at least three metabolites in at least four tissues. In a further aspect, a tobacco plant with enhanced NUE comprises an equal amount of at least four metabolites in at least four tissues. In a further aspect, a tobacco plant with enhanced NUE comprises an equal amount of at least five metabolites in at least four tissues. In a further aspect, a tobacco plant with enhanced NUE comprises an equal amount of at least one metabolite in five tissues. In a further aspect, a tobacco plant with enhanced NUE comprises an equal amount of at least two metabolites in at least five tissues. In a further aspect, a tobacco plant with enhanced NUE comprises an equal amount of at least three metabolites in at least five tissues. In a further aspect, a tobacco plant with enhanced NUE comprises an equal amount of at least four metabolites in at least five tissues. In a further aspect, a tobacco plant with enhanced NUE comprises an equal amount of at least five metabolites in at least five tissues.

In another aspect, a method provided herein comprises determining the amount of a metabolite using a method selected from the group consisting of liquid chromatography/mass spectrometry (LC/MS), high-performance liquid chromatography (HPLC), ultra HPLC (UHPLC), mass spectrometry (MS), tandem mass spectrometry (MS/MS), matrix assisted laser desorption/ionization mass spectrometry (MALDI-MS), X-ray fluorescence spectrometry (XRF), ion chromatography (IC), gas chromatography (GC), gas chromatography/mass spectrometry (GC/MS), capillary electrophoresis/mass spectrometry (CE-MS), ion mobility spectrometry/mass spectrometry (IMS/MS), X-ray diffraction, nuclear magnetic resonance (NMR), emission spectral analysis, polarography, ultraviolet-visual spectrometry, infrared spectrometry, and thin-layer chromatography.

In one aspect, the present specification provides for, and includes, a method of determining the NUE of a tobacco line using a metabolite signature comprising isolating a metabolite signature from a tobacco plant of a tobacco line, determining the amount of each metabolite comprising a metabolite signature, and determining the NUE of a tobacco line by comparing the metabolite signature to a control metabolite signature from a control tobacco line comprising a known NUE. In a further aspect of this method, NUE comprises enhanced NUE as compared to a control tobacco line. In another aspect of this method, a metabolite signature is isolated from a plant tissue selected from the group consisting of root tissue, leaf tissue, floral tissue, meristem tissue, and stem tissue.

In an aspect of a method provided herein, a metabolite signature comprises at least two metabolites. In a further aspect, a metabolite signature comprises at least three metabolites. In a further aspect, a metabolite signature comprises at least four metabolites. In a further aspect, a metabolite signature comprises at least five metabolites. In a further aspect, a metabolite signature comprises at least six metabolites. In a further aspect, a metabolite signature comprises at least seven metabolites. In a further aspect, a metabolite signature comprises at least eight metabolites. In a further aspect, a metabolite signature comprises at least nine metabolites. In a further aspect, a metabolite signature comprises at least ten metabolites. In a further aspect, a metabolite signature comprises at least eleven metabolites. In a further aspect, a metabolite signature comprises at least twelve metabolites. In a further aspect, a metabolite signature comprises at least thirteen metabolites. In a further aspect, a metabolite signature comprises at least fourteen metabolites. In a further aspect, a metabolite signature comprises at least fifteen metabolites. In a further aspect, a metabolite signature comprises at least twenty metabolites. In a further aspect, a metabolite signature comprises at least twenty-five metabolites. In a further aspect, a metabolite signature comprises at least thirty metabolites. In a further aspect, a metabolite signature comprises at least thirty-five metabolites. In a further aspect, a metabolite signature comprises at least forty metabolites. In a further aspect, a metabolite signature comprises at least forty-five metabolites. In a further aspect, a metabolite signature comprises at least fifty metabolites. In a further aspect, metabolite signature comprises between two and fifty metabolites. In a further aspect, metabolite signature comprises between three and forty-five metabolites. In a further aspect, metabolite signature comprises between three and forty metabolites. In a further aspect, metabolite signature comprises between four and thirty-five metabolites. In a further aspect, metabolite signature comprises between five and thirty metabolites. In a further aspect, metabolite signature comprises between six and twenty-five metabolites. In a further aspect, metabolite signature comprises between seven and twenty metabolites. In a further aspect, metabolite signature comprises between eight and fifteen metabolites. In a further aspect, metabolite signature comprises between nine and fourteen metabolites. In a further aspect, metabolite signature comprises between ten and thirteen metabolites. In a further aspect, metabolite signature comprises between ten and twelve metabolites.

In one aspect, the current specification provides for, and includes, a method of breeding a tobacco line comprising a metabolite signature associated with enhanced NUE comprising determining the metabolite signature of a first tobacco plant from a first tobacco line, where a first tobacco plant comprises enhanced NUE as compared to a control tobacco plant lacking the metabolite signature, crossing the first plant with a second plant of a second tobacco line, and obtaining at least one progeny seed from the crossing, where a progeny plant grown from at least one progeny seed comprises the metabolite signature, and where the progeny plant comprises enhanced NUE as compared to a control plant lacking the metabolite signature. In a further aspect of this method, a progeny plant is crossed to third plant that is from the first tobacco line. In another aspect, a first tobacco line is selected from the group consisting of MD609, MD601, Banket A1, K326, K346, K358, K394, K399, K730, NC196, NC37NF, NC471, NC55, NC92, NC2326, NC95, NC925. In another aspect, a second tobacco line is selected from the group consisting of TN86, TN86LC, TN90, TN90LC, TN97, TN97LC. In a further aspect, a metabolite signature comprises a leaf metabolite signature. In a further aspect, a metabolite signature comprises a root metabolite signature. In another aspect, a metabolite signature comprises higher amounts of 4-guanidinobutanoate, syringaldehyde, thiamin, p-hydroxybenzaldehyde, X-23454, X-23580, X-23852, or any combination thereof as compared to the metabolite signature of a control tobacco plant. In another aspect, a metabolite signature comprises lower amounts of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof as compared to the metabolite signature of a control tobacco plant.

In another aspect, a method provided herein comprises tobacco plants comprising enhanced NUE where enhanced NUE comprises an increased partial factor productivity (PFP) compared to a tobacco plant lacking enhanced NUE grown in the same conditions. In a further aspect, enhanced NUE comprises an increased agronomic efficiency (AE) compared to a tobacco plant lacking enhanced NUE grown in the same conditions. In a further aspect, enhanced NUE comprises an increased recovery efficiency (RE) compared to a tobacco plant lacking enhanced NUE grown in the same conditions. In a further aspect, enhanced NUE comprises an increased physiological efficiency (PE) compared to a tobacco plant lacking said enhanced NUE grown in the same conditions. In a further aspect, enhanced NUE comprises an increased internal efficiency (IE) compared to a tobacco plant lacking said enhanced NUE grown in the same conditions.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a higher amount of at least one metabolite as compared to a control tobacco plant. In a further aspect of this method, a selected tobacco plant comprises enhanced NUE as compared to a control tobacco plant. In a further aspect of this method, at least one metabolite is selected from the group consisting of 4-guanidinobutanoate, syringaldehyde, thiamin, p-hydroxybenzaldehyde, X-23454, X-23580, X-23852, or any combination thereof. In a further aspect of this method, a metabolite is isolated from a plant tissue selected from the group consisting of root tissue, leaf tissue, floral tissue, meristem tissue, and stem tissue.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a lower amount of at least one metabolite as compared to a control tobacco plant. In a further aspect of this method, a selected tobacco plant comprises a enhanced NUE as compared to a control tobacco plant. In a further aspect of this method, at least one metabolite is selected from the group consisting of X-2357, N-acetylmuramate, X-23319, X-23852, X-23330, alpha-ketoglutarate, X-21756, 4-hydroxy-2-oxoglutaric acid, X-23937, X-23916, 1-methyl adenine, X-23453, X-11429, X-21796, N'-methylnicotinamide, cotinine, X-23389, N-acetylarginine, N-23366, N-acetylphenylalanine, naringenin, or any combination thereof. In a further aspect of this method, a metabolite is isolated from a plant tissue selected from the group consisting of root tissue, leaf tissue, floral tissue, meristem tissue, and stem tissue.

In one aspect, the present specification provides for, and includes, a method of screening a tobacco plant for a first metabolite signature associated with enhanced NUE comprising isolating a first metabolite signature from a tobacco plant, determining the amount of at least one metabolite that comprises that first metabolite signature, comparing the first metabolite signature to a second metabolite signature of a control tobacco plant comprising a known NUE, and determining if the first metabolite signature is associated with enhanced NUE.

In one aspect, the present specification provides for, and includes, a modified tobacco seed, or tobacco plant grown therefrom, comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions. In a further aspect, a modified tobacco seed or tobacco plant comprises a heterologous promoter that is selected from the group consisting of a constitutive promoter, an inducible promoter, a tissue-preferred promoter, and a tissue-specific promoter. In another aspect, a heterologous promoter comprises a polynucleotide sequence from a tobacco genome. In another aspect, a heterologous promoter comprises a polynucleotide sequence from a plant genome. In another aspect, a tissue-preferred promoter is a leaf-preferred promoter. In another aspect, a tissue-preferred promoter is a root-preferred promoter. In a further aspect, a modified tobacco seed or tobacco plant is of a Burley variety.

In a further aspect, a modified tobacco seed or tobacco plant of the present specification comprises lower amounts of TSNAs as compared to an unmodified tobacco plant lacking the cisgenic polynucleotide when grown under the same conditions. In a further aspect, a modified tobacco seed or tobacco plant comprises lower amount N'-nitrosonornicotine (NNN) as compared to an unmodified tobacco plant lacking the cisgenic polynucleotide when grown under the same conditions. In a further aspect, a modified tobacco seed or tobacco plant comprises lower amount 4-methylnitrosoamino-1-(3-pyridyl)-1-butanone (NNK) as compared to an unmodified tobacco plant lacking the cisgenic polynucleotide when grown under the same conditions. In a further aspect, a modified tobacco seed or tobacco plant comprises lower amount N'-nitrosoanatabine (NAT) as compared to an unmodified tobacco plant lacking the cisgenic polynucleotide when grown under the same conditions. In a further aspect, a modified tobacco seed or tobacco plant comprises lower amount N'-nitrosoanabasine (NAB) as compared to an unmodified tobacco plant lacking the cisgenic polynucleotide when grown under the same conditions. In a further aspect, a modified tobacco seed or tobacco plant comprises lower amounts of alkaloids as compared to an unmodified tobacco plant lacking the cisgenic polynucleotide when grown under the same conditions. In a further aspect, a modified tobacco seed or tobacco plant comprises lower amounts of nicotine as compared to an unmodified tobacco plant lacking the cisgenic polynucleotide when grown under the same conditions. In a further aspect, a modified tobacco seed or tobacco plant comprises lower amounts of nornicotine as compared to an unmodified tobacco plant lacking the cisgenic polynucleotide when grown under the same conditions. In a further aspect, a modified tobacco seed or tobacco plant comprises lower amounts of anabasine as compared to an unmodified tobacco plant lacking the cisgenic polynucleotide when grown under the same conditions. In a further aspect, a modified tobacco seed or tobacco plant comprises lower amounts of anatabine as compared to an unmodified tobacco plant lacking the cisgenic polynucleotide when grown under the same conditions.

In a further aspect, a modified tobacco seed or tobacco plant of the present specification comprises a coding region encoding a polypeptide that is at least 70% identical or similar to a sequence selected from the group consisting of SEQ ID NOs:1 to 8. In a further aspect, a modified tobacco seed or tobacco plant comprises a coding region encoding a polypeptide that is at least 75% identical or similar to a sequence selected from the group consisting of SEQ ID NOs:1 to 8. In a further aspect, a modified tobacco seed or tobacco plant comprises a coding region encoding a polypeptide that is at least 80% identical or similar to a sequence selected from the group consisting of SEQ ID NOs:1 to 8. In a further aspect, a modified tobacco seed or tobacco plant comprises a coding region encoding a polypeptide that is at least 85% identical or similar to a sequence selected from the group consisting of SEQ ID NOs:1 to 8. In a further aspect, a modified tobacco seed or tobacco plant comprises a coding region encoding a polypeptide that is at least 90% identical or similar to a sequence selected from the group consisting of SEQ ID NOs:1 to 8. In a further aspect, a modified tobacco seed or tobacco plant comprises a coding region encoding a polypeptide that is at least 95% identical or similar to a sequence selected from the group consisting of SEQ ID NOs:1 to 8. In a further aspect, a modified tobacco seed or tobacco plant comprises a coding region encoding a polypeptide that is at least 96% identical or similar to a sequence selected from the group consisting of SEQ ID NOs:1 to 8. In a further aspect, a modified tobacco seed or tobacco plant comprises a coding region encoding a polypeptide that is at least 97% identical or similar to a sequence selected from the group consisting of SEQ ID NOs:1 to 8. In a further aspect, a modified tobacco seed or tobacco plant comprises a coding region encoding a polypeptide that is at least 98% identical or similar to a sequence selected from the group consisting of SEQ ID NOs:1 to 8. In a further aspect, a modified tobacco seed or tobacco plant comprises a coding region encoding a polypeptide that is at least 99% identical or similar to a sequence selected from the group consisting of SEQ ID NOs:1 to 8. In a further aspect, a modified tobacco seed or tobacco plant comprises a coding region encoding a polypeptide that is 100% identical to a sequence selected from the group consisting of SEQ ID NOs:1 to 8.

In a further aspect, a modified tobacco seed or tobacco plant of the present specification comprises a coding region encoding a polynucleotide that is at least 70% identical or similar to a sequence selected from the group consisting of SEQ ID NOs:9 to 16. In a further aspect, a modified tobacco seed or tobacco plant comprises a coding region encoding a polynucleotide that is at least 75% identical or similar to a sequence selected from the group consisting of SEQ ID NOs:9 to 16. In a further aspect, a modified tobacco seed or tobacco plant comprises a coding region encoding a polynucleotide that is at least 80% identical or similar to a sequence selected from the group consisting of SEQ ID NOs:9 to 16. In a further aspect, a modified tobacco seed or tobacco plant comprises a coding region encoding a polynucleotide that is at least 85% identical or similar to a sequence selected from the group consisting of SEQ ID NOs:9 to 16. In a further aspect, a modified tobacco seed or tobacco plant comprises a coding region encoding a polynucleotide that is at least 90% identical or similar to a sequence selected from the group consisting of SEQ ID NOs:9 to 16. In a further aspect, a modified tobacco seed or tobacco plant comprises a coding region encoding a polynucleotide that is at least 95% identical or similar to a sequence selected from the group consisting of SEQ ID NOs:9 to 16. In a further aspect, a modified tobacco seed or tobacco plant comprises a coding region encoding a polynucleotide that is at least 96% identical or similar to a sequence selected from the group consisting of SEQ ID NOs:9 to 16. In a further aspect, a modified tobacco seed or tobacco plant comprises a coding region encoding a polynucleotide that is at least 97% identical or similar to a sequence selected from the group consisting of SEQ ID NOs:9 to 16. In a further aspect, a modified tobacco seed or tobacco plant comprises a coding region encoding a polynucleotide that is at least 98% identical or similar to a sequence selected from the group consisting of SEQ ID NOs:9 to 16. In a further aspect, a modified tobacco seed or tobacco plant comprises a coding region encoding a polynucleotide that is at least 99% identical or similar to a sequence selected from the group consisting of SEQ ID NOs:9 to 16. In a further aspect, a modified tobacco seed or tobacco plant comprises a coding region encoding a polynucleotide that is identical to a sequence selected from the group consisting of SEQ ID NOs:9 to 16.

In a further aspect, a modified tobacco seed or tobacco plant comprises a leaf-preferred promoter that is encoded by a sequence at least 70% identical to a sequence selected from the group consisting of SEQ ID NOs:17 to 19, or a functional fragment thereof. In a further aspect, a leaf-preferred promoter is encoded by a sequence at least 75% identical to a sequence selected from the group consisting of SEQ ID NOs:17 to 19, or a functional fragment thereof. In a further aspect, a leaf-preferred promoter is encoded by a sequence at least 80% identical to a sequence selected from the group consisting of SEQ ID NOs:17 to 19, or a functional fragment thereof. In a further aspect, a leaf-preferred promoter is encoded by a sequence at least 85% identical to a sequence selected from the group consisting of SEQ ID NOs:17 to 19, or a functional fragment thereof. In a further aspect, a leaf-preferred promoter is encoded by a sequence at least 90% identical to a sequence selected from the group consisting of SEQ ID NOs:17 to 19, or a functional fragment thereof. In a further aspect, a leaf-preferred promoter is encoded by a sequence at least 95% identical to a sequence selected from the group consisting of SEQ ID NOs:17 to 19, or a functional fragment thereof. In a further aspect, a leaf-preferred promoter is encoded by a sequence at least 96% identical to a sequence selected from the group consisting of SEQ ID NOs:17 to 19, or a functional fragment thereof. In a further aspect, a leaf-preferred promoter is encoded by a sequence at least 97% identical to a sequence selected from the group consisting of SEQ ID NOs:17 to 19, or a functional fragment thereof. In a further aspect, a leaf-preferred promoter is encoded by a sequence at least 98% identical to a sequence selected from the group consisting of SEQ ID NOs:17 to 19, or a functional fragment thereof. In a further aspect, a leaf-preferred promoter is encoded by a sequence at least 99% identical to a sequence selected from the group consisting of SEQ ID NOs:17 to 19, or a functional fragment thereof. In a further aspect, a leaf-preferred promoter is encoded by to a sequence selected from the group consisting of SEQ ID NOs:17 to 19, or a functional fragment thereof.

In a further aspect, a modified tobacco seed or tobacco plant comprises a root-preferred promoter that is encoded by a sequence at least 70% identical to a sequence selected from the group consisting of SEQ ID NOs:20 to 24, or a functional fragment thereof. In a further aspect, a leaf-preferred promoter is encoded by a sequence at least 75% identical to a sequence selected from the group consisting of SEQ ID NOs:20 to 24, or a functional fragment thereof. In a further aspect, a leaf-preferred promoter is encoded by a sequence at least 80% identical to a sequence selected from the group consisting of SEQ ID NOs:20 to 24, or a functional fragment thereof. In a further aspect, a leaf-preferred promoter is encoded by a sequence at least 85% identical to a sequence selected from the group consisting of SEQ ID NOs:20 to 24, or a functional fragment thereof. In a further aspect, a leaf-preferred promoter is encoded by a sequence at least 90% identical to a sequence selected from the group consisting of SEQ ID NOs:20 to 24, or a functional fragment thereof. In a further aspect, a leaf-preferred promoter is encoded by a sequence at least 95% identical to a sequence selected from the group consisting of SEQ ID NOs:20 to 24, or a functional fragment thereof. In a further aspect, a leaf-preferred promoter is encoded by a sequence at least 96% identical to a sequence selected from the group consisting of SEQ ID NOs:20 to 24, or a functional fragment thereof. In a further aspect, a leaf-preferred promoter is encoded by a sequence at least 97% identical to a sequence selected from the group consisting of SEQ ID NOs:20 to 24, or a functional fragment thereof. In a further aspect, a leaf-preferred promoter is encoded by a sequence at least 98% identical to a sequence selected from the group consisting of SEQ ID NOs:20 to 24, or a functional fragment thereof. In a further aspect, a leaf-preferred promoter is encoded by a sequence at least 99% identical to a sequence selected from the group consisting of SEQ ID NOs:20 to 24, or a functional fragment thereof. In a further aspect, a leaf-preferred promoter is encoded by to a sequence selected from the group consisting of SEQ ID NOs:20 to 24, or a functional fragment thereof.

In a further aspect, a modified tobacco plant of the present specification comprising a cisgenic polynucleotide comprises higher levels of a metabolite selected from the group consisting of 4-guanidinobutanoate, syringaldehyde, thiamin, and p-hydroxybenzaldehyde in root tissue as compared to an unmodified tobacco plant lacking the cisgenic polynucleotide when grown under the same conditions.

In a further aspect, a modified tobacco plant of the present specification comprising a cisgenic polynucleotide comprises higher levels of a metabolite selected from the group consisting of 4-guanidinobutanoate, X-23454, X-23580, and X-23852 in leaf tissue as compared to an unmodified tobacco plant lacking the cisgenic polynucleotide when grown under the same conditions.

In a further aspect, a modified tobacco plant of the present specification comprising a cisgenic polynucleotide comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking the cisgenic polynucleotide when grown under the same conditions.

In a further aspect, a modified tobacco plant of the present specification comprising a cisgenic polynucleotide comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking the cisgenic polynucleotide when grown under the same conditions.

In one aspect, the present specification provides for, and includes, a recombinant DNA construct comprising a heterologous promoter operably linked to a polynucleotide encoding a polypeptide at least 70% identical or similar to a polypeptide selected from the group consisting of SEQ ID NOs:1 to 8. In a further aspect, a recombinant DNA construct comprises a polynucleotide encoding a polypeptide at least 75% identical or similar to a polypeptide selected from the group consisting of SEQ ID NOs:1 to 8. In a further aspect, a recombinant DNA construct comprises a polynucleotide encoding a polypeptide at least 80% identical or similar to a polypeptide selected from the group consisting of SEQ ID NOs:1 to 8. In a further aspect, a recombinant DNA construct comprises a polynucleotide encoding a polypeptide at least 85% identical or similar to a polypeptide selected from the group consisting of SEQ ID NOs:1 to 8. In a further aspect, a recombinant DNA construct comprises a polynucleotide encoding a polypeptide at least 90% identical or similar to a polypeptide selected from the group consisting of SEQ ID NOs:1 to 8. In a further aspect, a recombinant DNA construct comprises a polynucleotide encoding a polypeptide at least 95% identical or similar to a polypeptide selected from the group consisting of SEQ ID NOs:1 to 8. In a further aspect, a recombinant DNA construct comprises a polynucleotide encoding a polypeptide at least 96% identical or similar to a polypeptide selected from the group consisting of SEQ ID NOs:1 to 8. In a further aspect, a recombinant DNA construct comprises a polynucleotide encoding a polypeptide at least 97% identical or similar to a polypeptide selected from the group consisting of SEQ ID NOs:1 to 8. In a further aspect, a recombinant DNA construct comprises a polynucleotide encoding a polypeptide at least 98% identical or similar to a polypeptide selected from the group consisting of SEQ ID NOs:1 to 8. In a further aspect, a recombinant DNA construct comprises a polynucleotide encoding a polypeptide at least 99% identical or similar to a polypeptide selected from the group consisting of SEQ ID NOs:1 to 8. In a further aspect, a recombinant DNA construct comprises a polynucleotide encoding a polypeptide 100% identical to a polypeptide selected from the group consisting of SEQ ID NOs:1 to 8.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a coding region, where the modified tobacco plant comprises enhanced nitrogen utilization efficiency as compared to an unmodified control tobacco plant lacking the cisgenic polynucleotide when grown under the same conditions.

In one aspect, the present specification provides for, and includes, a greenhouse, growth chamber, or field comprising the modified tobacco seed or plant disclosed herein. In one aspect, the present specification provides for, and includes, a method to grow tobacco plants of the present specification in a greenhouse, growth chamber, or field.

In one aspect, the present specification provides for, and includes, a modified tobacco seed, or tobacco plant grown therefrom, comprising at least one mutation in an endogenous locus encoding a polypeptide selected from the group consisting of SEQ ID NOs: 25 to 40, and where a modified tobacco seed or tobacco plant comprises enhanced nitrogen utilization efficiency as compared to an unmodified control tobacco plant lacking at least one mutation when grown under the same conditions. In a further aspect, a mutation in an endogenous locus is selected from the group consisting of an insertion, a deletion, a substitution, and an inversion. In another aspect, a mutation in an endogenous locus is a silent mutation, a non-silent mutation, or a null mutation. In a further aspect, a modified tobacco seed or modified tobacco plant is of a Burley variety.

In a further aspect, a modified tobacco plant comprises higher levels of a metabolite selected from the group consisting of 4-guanidinobutanoate, syringaldehyde, thiamin, and p-hydroxybenzaldehyde in root tissue as compared to an unmodified tobacco plant when grown under the same conditions. In a further aspect, a modified tobacco plant comprises higher levels of a metabolite selected from the group consisting of 4-guanidinobutanoate, X-23454, X-23580, and X-23852 in leaf tissue as compared to an unmodified tobacco plant when grown under the same conditions. In a further aspect, a modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking when grown under the same conditions. In a further aspect, a modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant when grown under the same conditions.

In one aspect, the present specification provides for, and includes, a recombinant DNA construct comprising a heterologous promoter operably linked to a guide RNA comprising at least 18 contiguous nucleotides identical or complementary to a polynucleotide encoding a polypeptide selected from the group consisting of SEQ ID NOs:25 to 40. In a further aspect, a guide RNA comprises at least 19 contiguous nucleotides identical or complementary to a polynucleotide encoding a polypeptide selected from the group consisting of SEQ ID NOs:25 to 40. In a further aspect, a guide RNA comprises at least 20 contiguous nucleotides identical or complementary to a polynucleotide encoding a polypeptide selected from the group consisting of SEQ ID NOs:25 to 40. In a further aspect, a guide RNA comprises at least 21 contiguous nucleotides identical or complementary to a polynucleotide encoding a polypeptide selected from the group consisting of SEQ ID NOs:25 to 40. In a further aspect, a guide RNA comprises at least 22 contiguous nucleotides identical or complementary to a polynucleotide encoding a polypeptide selected from the group consisting of SEQ ID NOs:25 to 40. In a further aspect, a guide RNA comprises at least 23 contiguous nucleotides identical or complementary to a polynucleotide encoding a polypeptide selected from the group consisting of SEQ ID NOs:25 to 40. In a further aspect, a guide RNA comprises at least 24 contiguous nucleotides identical or complementary to a polynucleotide encoding a polypeptide selected from the group consisting of SEQ ID NOs:25 to 40. In a further aspect, a guide RNA comprises at least 25 contiguous nucleotides identical or complementary to a polynucleotide encoding a polypeptide selected from the group consisting of SEQ ID NOs:25 to 40. In a further aspect, a guide RNA comprises at least 26 contiguous nucleotides identical or complementary to a polynucleotide encoding a polypeptide selected from the group consisting of SEQ ID NOs:25 to 40. In a further aspect, a guide RNA comprises at least 27 contiguous nucleotides identical or complementary to a polynucleotide encoding a polypeptide selected from the group consisting of SEQ ID NOs:25 to 40. In a further aspect, a guide RNA comprises at least 28 contiguous nucleotides 100% identical or complementary to a polynucleotide encoding a polypeptide selected from the group consisting of SEQ ID NOs:25 to 40.

In one aspect, the present specification provides for, and includes, cured tobacco material, or a tobacco product comprising the cured tobacco material, where the cured tobacco material is made from a tobacco plant comprising at least one mutation in an endogenous locus encoding a polypeptide selected from the group consisting of SEQ ID NOs:25 to 40, and where the modified tobacco seed or tobacco plant comprises enhanced NUE as compared to an unmodified control tobacco plant lacking at least one mutation when grown under the same conditions. In a further aspect, a tobacco plant comprises at least two mutations in an endogenous locus encoding a polypeptide selected from the group consisting of SEQ ID NOs:25 to 40. In a further aspect, a tobacco plant comprises at least three mutations in an endogenous locus encoding a polypeptide selected from the group consisting of SEQ ID NOs:25 to 40. In a further aspect, a tobacco plant comprises at least four mutations in an endogenous locus encoding a polypeptide selected from the group consisting of SEQ ID NOs:25 to 40. In a further aspect, a tobacco plant comprises at least five mutations in an endogenous locus encoding a polypeptide selected from the group consisting of SEQ ID NOs:25 to 40. In a further aspect, a tobacco plant comprises at least six mutations in an endogenous locus encoding a polypeptide selected from the group consisting of SEQ ID NOs:25 to 40. In a further aspect, a tobacco plant comprises at least seven mutations in an endogenous locus encoding a polypeptide selected from the group consisting of SEQ ID NOs:25 to 40. In a further aspect, a tobacco plant comprises at least eight mutations in an endogenous locus encoding a polypeptide selected from the group consisting of SEQ ID NOs:25 to 40. In a further aspect, a tobacco plant comprises at least nine mutations in an endogenous locus encoding a polypeptide selected from the group consisting of SEQ ID NOs:25 to 40. In a further aspect, a tobacco plant comprises at least ten mutations in an endogenous locus encoding a polypeptide selected from the group consisting of SEQ ID NOs:25 to 40.

In one aspect, the present specification provides for, and includes, a modified tobacco seed, or tobacco plant grown therefrom, comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions. In a further aspect, a cisgenic polynucleotide comprises a polynucleotide encoding a sRNA at least 90% identical or complementary to a polynucleotide selected from the group consisting of SEQ ID NOs:41 to 56. In a further aspect, a cisgenic polynucleotide comprises a polynucleotide encoding a sRNA at least 91% identical or complementary to a polynucleotide selected from the group consisting of SEQ ID NOs:41 to 56. In a further aspect, a cisgenic polynucleotide comprises a polynucleotide encoding a sRNA at least 92% identical or complementary to a polynucleotide selected from the group consisting of SEQ ID NOs:41 to 56. In a further aspect, a cisgenic polynucleotide comprises a polynucleotide encoding a sRNA at least 93% identical or complementary to a polynucleotide selected from the group consisting of SEQ ID NOs:41 to 56. In a further aspect, a cisgenic polynucleotide comprises a polynucleotide encoding a sRNA at least 94% identical or complementary to a polynucleotide selected from the group consisting of SEQ ID NOs:41 to 56. In a further aspect, a cisgenic polynucleotide comprises a polynucleotide encoding a sRNA at least 95% identical or complementary to a polynucleotide selected from the group consisting of SEQ ID NOs:41 to 56. In a further aspect, a cisgenic polynucleotide comprises a polynucleotide encoding a sRNA at least 96% identical or complementary to a polynucleotide selected from the group consisting of SEQ ID NOs:41 to 56. In a further aspect, a cisgenic polynucleotide comprises a polynucleotide encoding a sRNA at least 97% identical or complementary to a polynucleotide selected from the group consisting of SEQ ID NOs:41 to 56. In a further aspect, a cisgenic polynucleotide comprises a polynucleotide encoding a sRNA at least 98% identical or complementary to a polynucleotide selected from the group consisting of SEQ ID NOs:41 to 56. In a further aspect, a cisgenic polynucleotide comprises a polynucleotide encoding a sRNA at least 99% identical or complementary to a polynucleotide selected from the group consisting of SEQ ID NOs:41 to 56. In a further aspect, a cisgenic polynucleotide comprises a polynucleotide encoding a sRNA 100% identical or complementary to a polynucleotide selected from the group consisting of SEQ ID NOs:41 to 56. In a further aspect, a heterologous promoter is selected from the group consisting of a constitutive promoter, an inducible promoter, a tissue-preferred promoter, and a tissue-specific promoter. In a further aspect, a tissue-preferred promoter is a leaf-preferred promoter. In a further aspect, a tissue-preferred promoter is a root-preferred promoter.

In a further aspect, a sRNA having at least 18 nucleotides. In a further aspect, a sRNA comprises at least 19 nucleotides. In a further aspect, a sRNA comprises at least 20 nucleotides. In a further aspect, a sRNA comprises at least 21 nucleotides. In a further aspect, a sRNA comprises at least 22 nucleotides. In a further aspect, a sRNA comprises at least 23 nucleotides. In a further aspect, a sRNA comprises at least 24 nucleotides. In a further aspect, a sRNA comprises at least 25 nucleotides. In a further aspect, a sRNA comprises at least 26 nucleotides. In a further aspect, a sRNA comprises at least 27 nucleotides. In a further aspect, a sRNA comprises at least 28 nucleotides. In a further aspect, a sRNA is selected from the group consisting of a microRNA, a small-interfering RNA (siRNA), a trans-acting siRNA, and precursors thereof. In a further aspect, a sRNA down-regulates the expression or translation of a polynucleotide selected from the group consisting of SEQ ID NOs:41 to 56.

In one aspect, the present specification provides for, and includes, a recombinant DNA construct comprising a heterologous promoter operably linked to a polynucleotide encoding a small RNA (sRNA) at least 85% identical or complementary to a polynucleotide selected from the group consisting of SEQ ID NOs:41 to 56. In a further aspect, a recombinant DNA construct comprises a polynucleotide encoding a sRNA at least 90% identical or complementary to a polynucleotide selected from the group consisting of SEQ ID NOs:41 to 56. In a further aspect, a recombinant DNA construct comprises a polynucleotide encoding a sRNA at least 91% identical or complementary to a polynucleotide selected from the group consisting of SEQ ID NOs:41 to 56. In a further aspect, a recombinant DNA construct comprises a polynucleotide encoding a sRNA at least 92% identical or complementary to a polynucleotide selected from the group consisting of SEQ ID NOs:41 to 56. In a further aspect, a recombinant DNA construct comprises a polynucleotide encoding a sRNA at least 93% identical or complementary to a polynucleotide selected from the group consisting of SEQ ID NOs:41 to 56. In a further aspect, a recombinant DNA construct comprises a polynucleotide encoding a sRNA at least 94% identical or complementary to a polynucleotide selected from the group consisting of SEQ ID NOs:41 to 56. In a further aspect, a recombinant DNA construct comprises a polynucleotide encoding a sRNA at least 95% identical or complementary to a polynucleotide selected from the group consisting of SEQ ID NOs:41 to 56. In a further aspect, a recombinant DNA construct comprises a polynucleotide encoding a sRNA at least 96% identical or complementary to a polynucleotide selected from the group consisting of SEQ ID NOs:41 to 56. In a further aspect, a recombinant DNA construct comprises a polynucleotide encoding a sRNA at least 97% identical or complementary to a polynucleotide selected from the group consisting of SEQ ID NOs:41 to 56. In a further aspect, a recombinant DNA construct comprises a polynucleotide encoding a sRNA at least 98% identical or complementary to a polynucleotide selected from the group consisting of SEQ ID NOs:41 to 56. In a further aspect, a recombinant DNA construct comprises a polynucleotide encoding a sRNA at least 99% identical or complementary to a polynucleotide selected from the group consisting of SEQ ID NOs:41 to 56. In a further aspect, a recombinant DNA construct comprises a polynucleotide encoding a sRNA 100% identical or complementary to a polynucleotide selected from the group consisting of SEQ ID NOs:41 to 56.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a polynucleotide encoding a sRNA at least 85% identical or complementary to a polynucleotide selected from the group consisting of SEQ ID NOs:41 to 56, and where the modified tobacco seed or tobacco plant comprises enhanced NUE as compared to an unmodified control tobacco plant lacking the cisgenic polynucleotide when grown under the same conditions. In a further aspect, a cisgenic polynucleotide encodes a sRNA at least 90% identical or complementary to a polynucleotide selected from the group consisting of SEQ ID NOs:41 to 56. In a further aspect, a cisgenic polynucleotide encodes a sRNA at least 91% identical or complementary to a polynucleotide selected from the group consisting of SEQ ID NOs:41 to 56. In a further aspect, a cisgenic polynucleotide encodes a sRNA at least 92% identical or complementary to a polynucleotide selected from the group consisting of SEQ ID NOs:41 to 56. In a further aspect, a cisgenic polynucleotide encodes a sRNA at least 93% identical or complementary to a polynucleotide selected from the group consisting of SEQ ID NOs:41 to 56. In a further aspect, a cisgenic polynucleotide encodes a sRNA at least 94% identical or complementary to a polynucleotide selected from the group consisting of SEQ ID NOs:41 to 56. In a further aspect, a cisgenic polynucleotide encodes a sRNA at least 95% identical or complementary to a polynucleotide selected from the group consisting of SEQ ID NOs:41 to 56. In a further aspect, a cisgenic polynucleotide encodes a sRNA at least 96% identical or complementary to a polynucleotide selected from the group consisting of SEQ ID NOs:41 to 56. In a further aspect, a cisgenic polynucleotide encodes a sRNA at least 97% identical or complementary to a polynucleotide selected from the group consisting of SEQ ID NOs:41 to 56. In a further aspect, a cisgenic polynucleotide encodes a sRNA at least 98% identical or complementary to a polynucleotide selected from the group consisting of SEQ ID NOs:41 to 56. In a further aspect, a cisgenic polynucleotide encodes a sRNA at least 99% identical or complementary to a polynucleotide selected from the group consisting of SEQ ID NOs:41 to 56. In a further aspect, a cisgenic polynucleotide encodes a sRNA 100% identical or complementary to a polynucleotide selected from the group consisting of SEQ ID NOs:41 to 56.

In one aspect, the present specification provides for, and includes, a method of enhancing the NUE of a tobacco plant comprising introducing a cisgenic nucleic acid molecule into a tobacco cell, and regenerating a modified tobacco plant from that tobacco cell where the modified tobacco plant comprises enhanced NUE as compared to a tobacco plant lacking the cisgenic nucleic acid molecule. In another aspect, the method further comprises crossing the modified tobacco plant with a second tobacco plant or self-pollinating the modified tobacco plant.

In one aspect, the present specification provides for, and includes, a method of enhancing the NUE of a tobacco plant comprising introducing a modification to a nucleic acid molecule encoding a gene having a sequence selected from the group consisting of SEQ ID NOs:41 to 56 in a tobacco cell and regenerating a modified tobacco plant from the tobacco cell, where the modified tobacco plant comprises enhanced NUE as compared to a tobacco plant lacking the modification. In another aspect, the method further comprises crossing the modified tobacco plant with a second tobacco plant or self-pollinating the modified tobacco plant. In a further aspect, a modification is introducing via a method comprising the use of an RNA-guided nuclease. In a further aspect, a RNA-guided nuclease is selected from the group consisting of a Cas9 nuclease, a Cpf1 nuclease, a CasX nuclease, a CasY nuclease, and functional homologues thereof. In a further aspect, the modification is selected from the group consisting of an insertion, a substitution, an inversion, and a deletion In one aspect, the present specification provides for, and includes, a method of enhancing the NUE of a tobacco plant comprising introducing a nucleic acid encoding a small RNA (sRNA) homologous to at least 18 contiguous nucleic acids of a nucleic acid molecule encoding a gene having a sequence selected from the group consisting of SEQ ID NOs:41 to 56 in a tobacco cell, and regenerating a modified tobacco plant from the tobacco cell, where the modified tobacco plant comprises enhanced NUE as compared to a tobacco plant lacking the sRNA. In another aspect, the method further comprises crossing the modified tobacco plant with a second tobacco plant or self-pollinating the modified tobacco plant. In a further aspect, the method comprises introducing a sRNA selected from the group consisting of a microRNA, a small-interfering RNA (siRNA), a trans-acting siRNA, and precursors thereof.

In one aspect, the present specification provides for, and includes, a method comprising providing a first population of tobacco plants comprising enhanced NUE, genotyping a first population of tobacco plants for the presence of a molecular marker within 20 cM of an enhanced NUE locus; and selecting one or more tobacco plants genotyped and found to comprise the molecular marker. In a further aspect, a method disclosed herein comprises genotyping a first population of tobacco plants for the presence of a molecular marker within 15 cM of an enhanced NUE locus. In a further aspect, a method disclosed herein comprises genotyping a first population of tobacco plants for the presence of a molecular marker within 10 cM of an enhanced NUE locus. In a further aspect, a method disclosed herein comprises genotyping a first population of tobacco plants for the presence of a molecular marker within 9 cM of an enhanced NUE locus. In a further aspect, a method disclosed herein comprises genotyping a first population of tobacco plants for the presence of a molecular marker within 8 cM of an enhanced NUE locus. In a further aspect, a method disclosed herein comprises genotyping a first population of tobacco plants for the presence of a molecular marker within 7 cM of an enhanced NUE locus. In a further aspect, a method disclosed herein comprises genotyping a first population of tobacco plants for the presence of a molecular marker within 6 cM of an enhanced NUE locus. In a further aspect, a method disclosed herein comprises genotyping a first population of tobacco plants for the presence of a molecular marker within 5 cM of an enhanced NUE locus. In a further aspect, a method disclosed herein comprises genotyping a first population of tobacco plants for the presence of a molecular marker within 4 cM of an enhanced NUE locus. In a further aspect, a method disclosed herein comprises genotyping a first population of tobacco plants for the presence of a molecular marker within 3 cM of an enhanced NUE locus. In a further aspect, a method disclosed herein comprises genotyping a first population of tobacco plants for the presence of a molecular marker within 2 cM of an enhanced NUE locus. In a further aspect, a method disclosed herein comprises genotyping a first population of tobacco plants for the presence of a molecular marker within 1 cM of an enhanced NUE locus. In a further aspect, a method disclosed herein comprises genotyping a first population of tobacco plants for the presence of a molecular marker within 0.5 cM of an enhanced NUE locus. In a further aspect, the method comprises crossing one or more selected tobacco plants to a second tobacco plant; and obtaining progeny seed from that cross. In a further aspect, a molecular marker is selected from the group consisting of a SNP marker, an INDEL marker, an RFLP marker, an SSR marker, an AFLP marker, and a RAPD marker.

In a further aspect, a method provided herein comprises a tobacco plant comprising an enhanced NUE locus comprising a polynucleotide encoding a polypeptide at least 70% identical or similar to a polypeptide selected from the group consisting of SEQ ID NOs:1 to 8. In a further aspect, a polynucleotide encodes a polypeptide at least 75% identical or similar to a polypeptide selected from the group consisting of SEQ ID NOs:1 to 8. In a further aspect, a polynucleotide encodes a polypeptide at least 80% identical or similar to a polypeptide selected from the group consisting of SEQ ID NOs:1 to 8. In a further aspect, a polynucleotide encodes a polypeptide at least 85% identical or similar to a polypeptide selected from the group consisting of SEQ ID NOs:1 to 8. In a further aspect, a polynucleotide encodes a polypeptide at least 90% identical or similar to a polypeptide selected from the group consisting of SEQ ID NOs:1 to 8. In a further aspect, a polynucleotide encodes a polypeptide at least 95% identical or similar to a polypeptide selected from the group consisting of SEQ ID NOs:1 to 8. In a further aspect, a polynucleotide encodes a polypeptide at least 96% identical or similar to a polypeptide selected from the group consisting of SEQ ID NOs:1 to 8. In a further aspect, a polynucleotide encodes a polypeptide at least 97% identical or similar to a polypeptide selected from the group consisting of SEQ ID NOs:1 to 8. In a further aspect, a polynucleotide encodes a polypeptide at least 98% identical or similar to a polypeptide selected from the group consisting of SEQ ID NOs:1 to 8. In a further aspect, a polynucleotide encodes a polypeptide at least 99% identical or similar to a polypeptide selected from the group consisting of SEQ ID NOs:1 to 8. In a further aspect, a polynucleotide encodes a polypeptide 100% identical to a polypeptide selected from the group consisting of SEQ ID NOs:1 to 8. In a further aspect, an enhanced NUE locus is genetically linked to a polynucleotide sequence selected from the group consisting of SEQ ID NOs:57 to 64. In another aspect, an enhanced NUE locus is genetically linked to a G nucleotide at position 57 of SEQ ID NOs: 58. In another aspect, an enhanced NUE locus is genetically linked to a C nucleotide at position 117 of SEQ ID NOs: 58. In another aspect, an enhanced NUE locus is genetically linked to a G nucleotide at position 57 and a C nucleotide at position 117 of SEQ ID NOs: 58. In another aspect, an enhanced NUE locus is genetically linked to a T nucleotide at position 147 of SEQ ID NO:57. In another aspect, an enhanced NUE locus is genetically linked to a G nucleotide at position 162 of SEQ ID NO:59. In another aspect, an enhanced NUE locus is genetically linked to a C nucleotide at position 36 of SEQ ID NO:60. In another aspect, an enhanced NUE locus is genetically linked to a T nucleotide at position 36 of SEQ ID NO:61. In another aspect, an enhanced NUE locus is genetically linked to a T nucleotide at position 36 of SEQ ID NO:62. In another aspect, an enhanced NUE locus is genetically linked to a G nucleotide at position 36 of SEQ ID NO:63. In another aspect, an enhanced NUE locus is genetically linked to a T nucleotide at position 36 of SEQ ID NO:64.

In a further aspect of a method provided herein, a first population of tobacco plants is of a Maryland variety. In a further aspect, a method provided herein comprises a first population of tobacco plants of a variety selected from the group consisting of MD609, MD601, Banket A1, K326, K346, K358, K394, K399, K730, NC196, NC37NF, NC471, NC55, NC92, NC2326, NC95, NC925. In a further aspect, a method provided herein comprises a second population of tobacco plants of the Burley variety In a further aspect, a method provided herein comprises a second population of tobacco plants of a variety selected from the group consisting of TN86, TN86LC, TN90, TN90LC, TN97, TN97LC.

In a further aspect, a method provided herein comprises progeny seed comprising molecular markers. In a further aspect, a method provided herein comprises progeny seed comprising enhanced NUE. In a further aspect, a method provided herein comprises progeny seed comprising a molecular marker within 20 cM of an enhanced NUE efficiency locus provided herein. In a further aspect, a method provided herein comprises progeny seed comprising a molecular marker within 15 cM of an enhanced NUE efficiency locus provided herein. In a further aspect, a method provided herein comprises progeny seed comprising a molecular marker within 10 cM of an enhanced NUE efficiency locus provided herein. In a further aspect, a method provided herein comprises progeny seed comprising a molecular marker within 9 cM of an enhanced NUE efficiency locus provided herein. In a further aspect, a method provided herein comprises progeny seed comprising a molecular marker within 8 cM of an enhanced NUE efficiency locus provided herein. In a further aspect, a method provided herein comprises progeny seed comprising a molecular marker within 7 cM of an enhanced NUE efficiency locus provided herein. In a further aspect, a method provided herein comprises progeny seed comprising a molecular marker within 6 cM of an enhanced NUE efficiency locus provided herein. In a further aspect, a method provided herein comprises progeny seed comprising a molecular marker within 5 cM of an enhanced NUE efficiency locus provided herein. In a further aspect, a method provided herein comprises progeny seed comprising a molecular marker within 4 cM of an enhanced NUE efficiency locus provided herein. In a further aspect, a method provided herein comprises progeny seed comprising a molecular marker within 3 cM of an enhanced NUE efficiency locus provided herein. In a further aspect, a method provided herein comprises progeny seed comprising a molecular marker within 2 cM of an enhanced NUE efficiency locus provided herein. In a further aspect, a method provided herein comprises progeny seed comprising a molecular marker within 1 cM of an enhanced NUE efficiency locus provided herein. In a further aspect, a method provided herein comprises progeny seed comprising a molecular marker within 0.5 cM of an enhanced NUE efficiency locus provided herein.

In one aspect, the present specification provides for, and includes, a method comprising providing a first population of tobacco plants, genotyping the first population of tobacco plants for the presence of an enhanced NUE allele of a locus encoded by a sequence selected from the group consisting of SEQ ID NOs:9 to 16; and selecting one or more genotyped tobacco plants that comprise an enhanced NUE allele. In a further aspect, the method further comprises crossing the one or more selected tobacco plants to a second tobacco plant; and obtaining progeny seed from the cross.

In one aspect, the present specification provides for, and includes, a method of introgressing an enhanced NUE trait into a tobacco variety comprising crossing a first tobacco variety comprising an enhanced nitrogen utilization efficiency trait with a second tobacco variety lacking the enhanced nitrogen utilization efficiency trait, obtaining progeny seed from the cross, genotyping at least one progeny seed for a molecular marker linked to an enhanced nitrogen utilization efficiency trait, where the molecular marker is within 20 cM of a locus having a sequence selected from the group consisting of SEQ ID NOs:9 to 16; and selecting a progeny seed comprising an enhanced nitrogen utilization efficiency trait.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a locus having a sequence selected from the group consisting of SEQ ID NOs:9 to 16, and selecting a tobacco plant comprising an enhanced NUE trait. In a further aspect, the method further comprises crossing the one or more selected tobacco plants to a second tobacco plant; and obtaining progeny seed from the cross.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a marker selected from the group consisting of SEQ ID NOs:57 to 64, and selecting a tobacco plant comprising an enhanced NUE trait. In a further aspect, a method disclosed herein comprises assaying isolated nucleic acids for one or more markers located within 15 cM of a marker selected from the group consisting of SEQ ID NOs: 58. In a further aspect, a method disclosed herein comprises assaying isolated nucleic acids for one or more markers located within 10 cM of a marker selected from the group consisting of SEQ ID NOs:57 to 64. In a further aspect, a method disclosed herein comprises assaying isolated nucleic acids for one or more markers located within 9 cM of a marker selected from the group consisting of SEQ ID NOs:57 to 64. In a further aspect, a method disclosed herein comprises assaying isolated nucleic acids for one or more markers located within 8 cM of a marker selected from the group consisting of SEQ ID NOs:57 to 64. In a further aspect, a method disclosed herein comprises assaying isolated nucleic acids for one or more markers located within 7 cM of a marker selected from the group consisting of SEQ ID NOs:57 to 64. In a further aspect, a method disclosed herein comprises assaying isolated nucleic acids for one or more markers located within 6 cM of a marker selected from the group consisting of SEQ ID NOs:57 to 64. In a further aspect, a method disclosed herein comprises assaying isolated nucleic acids for one or more markers located within 5 cM of a marker selected from the group consisting of SEQ ID NOs:57 to 64. In a further aspect, a method disclosed herein comprises assaying isolated nucleic acids for one or more markers located within 4 cM of a marker selected from the group consisting of SEQ ID NOs:57 to 64. In a further aspect, a method disclosed herein comprises assaying isolated nucleic acids for one or more markers located within 3 cM of a marker selected from the group consisting of SEQ ID NOs:57 to 64. In a further aspect, a method disclosed herein comprises assaying isolated nucleic acids for one or more markers located within 2 cM of a marker selected from the group consisting of SEQ ID NOs:57 to 64. In a further aspect, a method disclosed herein comprises assaying isolated nucleic acids for one or more markers located within 1 cM of a marker selected from the group consisting of SEQ ID NOs:57 to 64. In a further aspect, a method disclosed herein comprises assaying isolated nucleic acids for one or more markers located within 0.5 cM of a marker selected from the group consisting of SEQ ID NOs:57 to 64. In a further aspect, a method disclosed herein comprises assaying isolated nucleic acids for a marker selected from the group consisting of SEQ ID NOs:57 to 64. In another aspect, an allele associated with enhanced NUE comprises a G nucleotide at position 57 of SEQ ID NO:58. In another aspect an allele associated with enhanced NUE comprises a C nucleotide at position 117 of SEQ ID NO:58. In another aspect, an allele associated with enhanced NUE comprises a G nucleotide at position 57 and a C nucleotide at position 117 of SEQ ID NO:58. In another aspect, an allele associated with enhanced NUE comprises a T nucleotide at position 147 of SEQ ID NO:57. In another aspect, an allele associated with enhanced NUE comprises a G nucleotide at position 162 of SEQ ID NO:59. In another aspect, an allele associated with enhanced NUE comprises a C nucleotide at position 36 of SEQ ID NO:60. In another aspect, an allele associated with enhanced NUE comprises a T nucleotide at position 36 of SEQ ID NO:61. In another aspect, an allele associated with enhanced NUE comprises a T nucleotide at position 36 of SEQ ID NO:62. In another aspect, an allele associated with enhanced NUE comprises a G nucleotide at position 36 of SEQ ID NO:63. In another aspect, an allele associated with enhanced NUE comprises a T nucleotide at position 36 of SEQ ID NO:64. In a further aspect, a tobacco plant can be selected comprising any combination of alleles associated with enhanced NUE disclosed herein.

The following are exemplary embodiments

Embodiment 1. A method of determining the nitrogen utilization efficiency (NUE) of a tobacco line comprising:
 a. obtaining at least one metabolite from a tobacco plant of said tobacco line;
 b. determining the amount of said at least one metabolite; and
 c. determining the nitrogen utilization efficiency of said tobacco line based on the amount of said at least one metabolite identified in step (b).

Embodiment 2. The method of embodiment 1, wherein said at least one metabolite is obtained from a plant tissue selected from the group consisting of root tissue, leaf tissue, floral tissue, meristem tissue, and stem tissue.

Embodiment 3. The method of embodiment 1 or 2, wherein said plant tissue comprises leaf tissue.

Embodiment 4. The method of any one of embodiments 1 to 3, wherein said plant tissue comprises root tissue.

Embodiment 5. The method of any one of embodiments 1 to 4, wherein said at least one metabolite is selected from the group consisting of X-2357, N-acetylmuramate, X-23319, X-23852, X-23330, alpha-ketoglutarate, X-21756, 4-hydroxy-2-oxoglutaric acid, D-23937, X-23937, X-23916, 1-methyladenine, 4-guanidinobutanoate, syringaldehyde, thiamin, p-hydroxybenzaldehyde, X-23453, X-11429, X-21796, N'-methylnicotinamide, cotinine, X-23389, N-acetylarginine, X-23366, N-acetylphenylalanine, naringenin, X-23454, X-23580, and X-23852.

Embodiment 6. The method of any one of embodiments 1 to 5, wherein said NUE comprises enhanced NUE as compared to a tobacco line that comprises a lower amount of said at least one metabolite in said at least one tissue.

Embodiment 7. The method of any one of embodiments 1 to 6, wherein said NUE comprises enhanced NUE as compared to a tobacco line that comprises an equal amount of said at least one metabolite in said at least one tissue.

Embodiment 8. The method of any one of embodiments 1 to 7, wherein said NUE comprises enhanced NUE as compared to a tobacco line that comprises an equal amount of said at least one metabolite in said at least one tissue.

Embodiment 9. The method of any one of embodiments 1 to 8, wherein said NUE comprises decreased NUE as compared to a tobacco line that comprises a lower amount of said at least one metabolite in said at least one tissue.

Embodiment 10. The method of any one of embodiments 1 to 9, wherein said NUE comprises decreased NUE as compared to a tobacco line that comprises an equal amount of said at least one metabolite in said at least one tissue.

Embodiment 11. The method of any one of embodiments 1 to 10, wherein said NUE comprises decreased NUE as compared to a tobacco line that comprises an equal amount of said at least one metabolite in said at least one tissue.

Embodiment 12. The method of any one of embodiments 1 to 11, wherein said determining the amount of said at least one metabolite comprises a method selected from the group consisting of liquid chromatography/mass spectrometry (LC/MS), high-performance liquid chromatography (HPLC), ultra HPLC (UHPLC), mass spectrometry (MS), tandem mass spectrometry (MS/MS), matrix assisted laser desorption/ionization mass spectrometry (MALDI-MS), X-ray fluorescence spectrometry (XRF), ion chromatography (IC), gas chromatography (GC), gas chromatography/mass spectrometry (GC/MS), capillary electrophoresis/mass spectrometry (CE-MS), ion mobility spectrometry/mass spectrometry (IMS/MS), X-ray diffraction, nuclear magnetic resonance (NMR), emission spectral analysis, polarography, ultraviolet-visual spectrometry, infrared spectrometry, thin-layer chromatography.

Embodiment 13. The method of any one of embodiments 1 to 12, wherein said at least one metabolite comprises at least two metabolites.

Embodiment 14. The method of any one of embodiments 1 to 13, wherein said at least one metabolite comprises at least five metabolites.

Embodiment 15. The method of any one of embodiments 1 to 14, wherein said at least one metabolite comprises at least ten metabolites.

Embodiment 16. A method of determining the nitrogen utilization efficiency (NUE) of a tobacco line using a metabolite signature comprising:
  a. isolating said metabolite signature from a tobacco plant of said tobacco line;
  b. determining the amount of each metabolite comprising said metabolite signature;
  c. determining said NUE of said tobacco line by comparing said metabolite signature to a control metabolite signature from a control tobacco line comprising a known NUE.

Embodiment 17. The method of embodiment 16, wherein said metabolite signature comprises at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, or at least 50 metabolites.

Embodiment 18. The method of embodiments 16 or 17, wherein said NUE comprises enhanced NUE as compared to said control tobacco line.

Embodiment 19. The method of any one of embodiments 16 to 18, wherein said NUE comprises reduced NUE as compared to said control tobacco line.

Embodiment 20. The method of any one of embodiments 16 to 19, wherein said metabolite signature is isolated from a plant tissue selected from the group consisting of root tissue, leaf tissue, floral tissue, meristem tissue, and stem tissue.

Embodiment 21. A method of breeding a tobacco line comprising a metabolite signature associated with enhanced nitrogen utilization efficiency (NUE) comprising:
  a. determining the metabolite signature of a first tobacco plant from a first tobacco line, wherein said first tobacco plant comprises enhanced NUE as compared to a control tobacco plant lacking said metabolite signature;
  b. crossing said first plant with a second plant of a second tobacco line; and
  c. obtaining at least one progeny seed from the crossing of step (a), wherein a progeny plant grown from said at least one progeny seed comprises said metabolite signature, and wherein said progeny plant comprises enhanced NUE as compared to a control plant lacking said metabolite signature.

Embodiment 22. The method of embodiment 21, wherein said method further comprises:
  d. crossing said progeny plant to a tobacco plant from said first tobacco line.

Embodiment 23. The method of embodiments 21 or 22, wherein said first tobacco line is selected from the group consisting of MD609, MD601, Banket A1, K326, K346, K358, K394, K399, K730, NC196, NC37NF, NC471, NC55, NC92, NC2326, NC95, NC925.

Embodiment 24. The method of any one of embodiments 21 to 23, wherein said second tobacco line is selected from the group consisting of TN86, TN86LC, TN90, TN90LC, TN97, TN97LC.

Embodiment 25. The method of any one of embodiments 21 to 24, wherein said metabolite signature comprises a leaf metabolite signature.

Embodiment 26. The method of any one of embodiments 21 to 25, wherein said metabolite signature comprises a root metabolite signature.

Embodiment 27. The method of any one of embodiments 21 to 26, wherein said enhanced NUE comprises an increased partial factor productivity (PFP) compared to a tobacco plant lacking said enhanced NUE grown in the same conditions.

Embodiment 28. The method of any one of embodiments 21 to 27, wherein said enhanced NUE comprises an increased agronomic efficiency (AE) compared to a tobacco plant lacking said enhanced NUE grown in the same conditions.

Embodiment 29. The method of any one of embodiments 21 to 28, wherein said enhanced NUE comprises an increased recovery efficiency (RE) compared to a tobacco plant lacking said enhanced NUE grown in the same conditions.

Embodiment 30. The method of any one of embodiments 21 to 29, wherein said enhanced NUE comprises an increased physiological efficiency (PE) compared to a tobacco plant lacking said enhanced NUE grown in the same conditions.

Embodiment 31. The method of any one of embodiments 21 to 30, wherein said enhanced NUE comprises an increased internal efficiency (IE) compared to a tobacco plant lacking said enhanced NUE grown in the same conditions.

Embodiment 32. The method of any one of embodiments 21 to 31, wherein said metabolite signature comprises equal amounts of 4-guanidinobutanoate, syringaldehyde, thiamin, p-hydroxybenzaldehyde, X-23454, X-23580, X-23852, or any combination thereof as compared to the metabolite signature of said control tobacco plant.

Embodiment 33. The method of any one of embodiments 21 to 32, wherein said metabolite signature comprises lower amounts of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof as compared to the metabolite signature of said control tobacco plant.

Embodiment 34. The method of any one of embodiments 21 to 33, wherein said metabolite signature comprises at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, or at least 50 metabolites.

Embodiment 35. A method of selecting a tobacco plant comprising:
  a. obtaining a population of tobacco plants;
  b. isolating at least one metabolite associated with enhanced nitrogen utilization efficiency (NUE) from at least one tobacco plant of said population of tobacco plants;
  c. selecting at least one tobacco plant that comprises a equal amount of said at least one metabolite as compared to a control tobacco plant.

Embodiment 36. The method of embodiment 35, wherein said tobacco plant selected in step (c) comprises a equal NUE as compared to said control tobacco plant.

Embodiment 37. The method of embodiment 35 or 36, wherein said enhanced NUE comprises an increased partial factor productivity (PFP) compared to a tobacco plant lacking said enhanced NUE grown in the same conditions.

Embodiment 38. The method of any one of embodiments 35 to 37, wherein said enhanced NUE comprises an increased agronomic efficiency (AE) compared to a tobacco plant lacking said enhanced NUE grown in the same conditions.

Embodiment 39. The method of any one of embodiments 35 to 38, wherein said enhanced NUE comprises an increased recovery efficiency (RE) compared to a tobacco plant lacking said enhanced NUE grown in the same conditions.

Embodiment 40. The method of any one of embodiments 35 to 39, wherein said enhanced NUE comprises an increased physiological efficiency (PE) compared to a tobacco plant lacking said enhanced NUE grown in the same conditions.

Embodiment 41. The method of any one of embodiments 35 to 40, wherein said enhanced NUE comprises an increased internal efficiency (IE) compared to a tobacco plant lacking said enhanced NUE grown in the same conditions.

Embodiment 42. The method of any one of embodiments 35 to 41, wherein said at least one metabolite is selected from the group consisting of 4-guanidinobutanoate, syringaldehyde, thiamin, p-hydroxybenzaldehyde, X-23454, X-23580, X-23852, or any combination thereof.

Embodiment 43. The method of any one of embodiments 35 to 42, wherein said at least one metabolite is isolated from leaf tissue or root tissue.

Embodiment 44. The method of any one of embodiments 35 to 43, wherein said at least one metabolite is isolated from a plant tissue selected from the group consisting of root tissue, leaf tissue, floral tissue, meristem tissue, and stem tissue.

Embodiment 45. A method of selecting a tobacco plant comprising:
  a. obtaining a population of tobacco plants;
  b. isolating at least one metabolite associated with enhanced nitrogen utilization efficiency (NUE) from at least one tobacco plant of said population of tobacco plants;
  c. selecting at least one tobacco plant that comprises a lower amount of said at least one metabolite as compared to a control tobacco plant.

Embodiment 46. The method of embodiment 45, wherein said tobacco plant selected in step (c) comprises a equal NUE as compared to said control tobacco plant.

Embodiment 47. The method of embodiment 45 or 46, wherein said enhanced NUE comprises an increased partial factor productivity (PFP) compared to a tobacco plant lacking said enhanced NUE grown in the same conditions.

Embodiment 48. The method of any one of embodiments 45 to 47, wherein said enhanced NUE comprises an increased agronomic efficiency (AE) compared to a tobacco plant lacking said enhanced NUE grown in the same conditions.

Embodiment 49. The method of any one of embodiments 45 to 48, wherein said enhanced NUE comprises an increased recovery efficiency (RE) compared to a tobacco plant lacking said enhanced NUE grown in the same conditions.

Embodiment 50. The method of any one of embodiments 45 to 49, wherein said enhanced NUE comprises an increased physiological efficiency (PE) compared to a tobacco plant lacking said enhanced NUE grown in the same conditions.

Embodiment 51. The method of any one of embodiments 45 to 50, wherein said enhanced NUE comprises an increased internal efficiency (IE) compared to a tobacco plant lacking said enhanced NUE grown in the same conditions.

Embodiment 52. The method of any one of embodiments 45 to 51, wherein said at least one metabolite is selected from the group consisting of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof.

Embodiment 53. The method of any one of embodiments 45 to 52, wherein said at least one metabolite is isolated from leaf tissue or root tissue.

Embodiment 54. The method of any one of embodiments 45 to 53, wherein said at least one metabolite is isolated from a plant tissue selected from the group consisting of root tissue, leaf tissue, floral tissue, meristem tissue, and stem tissue.

Embodiment 55. A method of screening a tobacco plant for a metabolite signature associated with enhanced nitrogen utilization efficiency (NUE) comprising:
  a. isolating a first metabolite signature associated with enhanced NUE from said tobacco plant;
  b. determining the amount of at least one metabolite comprising said first metabolite signature;
  c. comparing said first metabolite signature to a second metabolite signature of a control tobacco plant that comprises a known NUE; and
  d. determining if said first metabolite signature is associated with enhanced NUE.

Embodiment 56. The method of embodiment 55, wherein said enhanced NUE comprises an increased partial factor productivity (PFP) compared to a tobacco plant lacking said enhanced NUE grown in the same conditions.

Embodiment 57. The method of embodiment 55 or 56, wherein said enhanced NUE comprises an increased agronomic efficiency (AE) compared to a tobacco plant lacking said enhanced NUE grown in the same conditions.

Embodiment 58. The method of any one of embodiments 55 to 57, wherein said enhanced NUE comprises an increased recovery efficiency (RE) compared to a tobacco plant lacking said enhanced NUE grown in the same conditions.

Embodiment 59. The method of any one of embodiments 55 to 58, wherein said enhanced NUE comprises an increased physiological efficiency (PE) compared to a tobacco plant lacking said enhanced NUE grown in the same conditions.

Embodiment 60. The method of any one of embodiments 55 to 59, wherein said enhanced NUE comprises an increased internal efficiency (IE) compared to a tobacco plant lacking said enhanced NUE grown in the same conditions.

Embodiment 61. A modified tobacco seed, or tobacco plant grown therefrom, comprising a cisgenic polynucleotide comprising a heterologous promoter operably linked to a coding region, wherein said modified tobacco plant comprises enhanced nitrogen utilization efficiency as compared to an unmodified control tobacco plant lacking said cisgenic polynucleotide when grown under the same conditions.

Embodiment 62. The modified tobacco seed or tobacco plant of embodiment 61, wherein said coding region encodes a polypeptide at least 70% identical or similar to a sequence selected from the group consisting of SEQ ID NOs:1 to 8.

Embodiment 63. The modified tobacco seed or tobacco plant of embodiment 61 or 62, wherein said coding region comprises a polynucleotide sequence at least 70% identical or complementary to a polynucleotide sequence selected from the group consisting of SEQ ID NOs:9 to 16.

Embodiment 64. The modified tobacco seed or tobacco plant of any one of embodiments 61 to 63, wherein said heterologous promoter is selected from the group consisting of a constitutive promoter, an inducible promoter, a tissue-preferred promoter, and a tissue-specific promoter.

Embodiment 65. The modified tobacco seed or tobacco plant of any one of embodiments 61 to 64, wherein said heterologous promoter comprises a polynucleotide sequence from a tobacco genome.

Embodiment 66. The modified tobacco seed or tobacco plant of any one of embodiments 61 to 65, wherein said heterologous promoter comprises a polynucleotide sequence from a plant genome.

Embodiment 67. The modified tobacco seed or tobacco plant of any one of embodiments 61 to 66, wherein said tissue-preferred promoter is a leaf-preferred promoter.

Embodiment 68. The modified tobacco seed or tobacco plant of any one of embodiments 61 to 67, wherein said tissue-preferred promoter is a root-preferred promoter.

Embodiment 69. The modified tobacco seed or tobacco plant of any one of embodiments 61 to 68, wherein said leaf-preferred promoter is encoded by a sequence at least 70% identical or complementary to a sequence selected from the group consisting of SEQ ID NOs:17 to 19, or a functional fragment thereof.

Embodiment 70. The modified tobacco seed or tobacco plant of any one of embodiments 61 to 69, wherein said root-preferred promoter is encoded by a sequence at least 70% identical or complementary to a sequence selected from the group consisting of SEQ ID NOs:20 to 24, or a functional fragment thereof.

Embodiment 71. The modified tobacco plant of any one of embodiments 61 to 70, wherein said modified tobacco plant comprises equal levels of a metabolite selected from the group consisting of 4-guanidinobutanoate, syringaldehyde, thiamin, and p-hydroxybenzaldehyde in root tissue as compared to an unmodified tobacco plant lacking said cisgenic polynucleotide when grown under the same conditions.

Embodiment 72. The modified tobacco plant of any one of embodiments 61 to 71, wherein said modified tobacco plant comprises equal levels of a metabolite selected from the group consisting of 4-guanidinobutanoate, X-23454, X-23580, and X-23852 in leaf tissue as compared to an unmodified tobacco plant lacking said cisgenic polynucleotide when grown under the same conditions.

Embodiment 73. The modified tobacco plant of any one of embodiments 61 to 72, wherein said modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking said cisgenic polynucleotide when grown under the same conditions.

Embodiment 74. The modified tobacco plant of any one of embodiments 61 to 73, wherein said modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking said cisgenic polynucleotide when grown under the same conditions.

Embodiment 75. The modified tobacco seed or plant of any one of embodiments 61 to 74, wherein said modified tobacco seed or plant is of a Burley variety.

Embodiment 76. The modified tobacco seed or plant of any one of embodiments 61 to 75, wherein said modified tobacco seed or plant comprises lower amounts of TSNAs as compared to an unmodified tobacco plant lacking said cisgenic polynucleotide when grown under the same conditions.

Embodiment 77. A recombinant DNA construct comprising a heterologous promoter operably linked to a polynucleotide encoding a polypeptide at least 70% identical or similar to a polypeptide selected from the group consisting of SEQ ID NOs:1 to 8.

Embodiment 78. Cured tobacco material, or a tobacco product comprising said cured tobacco material, wherein said cured tobacco material is made from a tobacco plant comprising a cisgenic polynucleotide comprising a heterologous promoter operably linked to a coding region, wherein said modified tobacco plant comprises enhanced nitrogen utilization efficiency as compared to an unmodified control tobacco plant lacking said cisgenic polynucleotide when grown under the same conditions.

Embodiment 79. A greenhouse, growth chamber, or field comprising the modified tobacco seed or plant of any one of embodiments 61 to 76.

Embodiment 80. A modified tobacco seed, or tobacco plant grown therefrom, comprising at least one mutation in an endogenous locus encoding a polypeptide selected from the group consisting of SEQ ID NOs:25 to 40, and wherein said modified tobacco seed or tobacco plant comprises enhanced nitrogen utilization efficiency as compared to an unmodified control tobacco plant lacking said at least one mutation when grown under the same conditions.

Embodiment 81. The modified tobacco seed or tobacco plant of embodiment 80, wherein said at least one mutation is selected from the group consisting of an insertion, a deletion, a substitution, and an inversion.

Embodiment 82. The modified tobacco seed or tobacco plant of embodiment 80 or 81, wherein said at least one mutation is a null mutation.

Embodiment 83. The modified tobacco plant of any one of embodiments 80 to 82, wherein said modified tobacco plant comprises equal levels of a metabolite selected from the group consisting of 4-guanidinobutanoate, syringaldehyde, thiamin, and p-hydroxybenzaldehyde in root tissue as compared to an unmodified tobacco plant lacking said at least one mutation when grown under the same conditions.

Embodiment 84. The modified tobacco plant of any one of embodiments 80 to 83, wherein said modified tobacco plant comprises equal levels of a metabolite selected from the group consisting of 4-guanidinobutanoate, X-23454, X-23580, and X-23852 in leaf tissue as compared to an unmodified tobacco plant lacking said at least one mutation when grown under the same conditions.

Embodiment 85. The modified tobacco plant of any one of embodiments 80 to 84, wherein said modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking said at least one mutation when grown under the same conditions.

Embodiment 86. The modified tobacco plant of any one of embodiments 80 to 85, wherein said modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking said at least one mutation when grown under the same conditions.

Embodiment 87. The modified tobacco seed or plant of any one of embodiments 80 to 86, wherein said modified tobacco seed or plant is of a Burley variety.

Embodiment 88. The modified tobacco seed or plant of any one of embodiments 80 to 87, wherein said modified tobacco seed or plant comprises lower amounts of TSNAs as compared to an unmodified tobacco plant lacking said at least one mutation when grown under the same conditions.

Embodiment 89. A recombinant DNA construct comprising a heterologous promoter operably linked to a guide RNA comprising at least 18, at least 19, at least 20, at least 21, at least 22, at least 23, at least 24, at least 25, at least 26, at least 27, or at least 28 contiguous nucleotides identical or complementary to a polynucleotide encoding a polypeptide selected from the group consisting of SEQ ID NOs:25 to 40.

Embodiment 90. Cured tobacco material, or a tobacco product comprising said cured tobacco material, wherein said cured tobacco material is made from a tobacco plant comprising at least one mutation in an endogenous locus encoding a polypeptide selected from the group consisting of SEQ ID NOs:25 to 40, and wherein said modified tobacco seed or tobacco plant comprises enhanced nitrogen utilization efficiency as compared to an unmodified control tobacco plant lacking said at least one mutation when grown under the same conditions.

Embodiment 91. A modified tobacco seed, or tobacco plant grown therefrom, comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and wherein said modified tobacco seed or tobacco plant comprises enhanced nitrogen utilization efficiency as compared to an unmodified control tobacco plant lacking said cisgenic polynucleotide when grown under the same conditions.

Embodiment 92. The modified tobacco seed or tobacco plant of embodiment 91, wherein said sRNA comprises at least 18, at least 19, at least 20, at least 21, at least 22, at least 23, at least 24, at least 25, at least 26, at least 27, or at least 28 nucleotides.

Embodiment 93. The modified tobacco seed or tobacco plant of embodiment 91 or 92, wherein said sRNA is selected from the group consisting of a microRNA, a small-interfering RNA (siRNA), a trans-acting siRNA, and precursors thereof.

Embodiment 94. The modified tobacco seed or tobacco plant of any one of embodiments 91 to 93, wherein said sRNA down-regulates the expression or translation of a polynucleotide selected from the group consisting of SEQ ID NOs:41 to 56.

Embodiment 95. The modified tobacco seed or tobacco plant of any one of embodiments 91 to 94, wherein said heterologous promoter is selected from the group consisting of a constitutive promoter, an inducible promoter, a tissue-preferred promoter, and a tissue-specific promoter.

Embodiment 96. The modified tobacco seed or tobacco plant of any one of embodiments 91 to 95, wherein said tissue-preferred promoter is a leaf-preferred promoter.

Embodiment 97. The modified tobacco seed or tobacco plant of any one of embodiments 91 to 96, wherein said tissue-preferred promoter is a root-preferred promoter.

Embodiment 98. The modified tobacco seed or tobacco plant of any one of embodiments 91 to 97, wherein said leaf-preferred promoter is encoded by a sequence at least 70% identical or complementary to a sequence selected from the group consisting of SEQ ID NOs:17 to 19, or a functional fragment thereof.

Embodiment 99. The modified tobacco seed or tobacco plant of any one of embodiments 91 to 98, wherein said root-preferred promoter is encoded by a sequence at least 70% identical or complementary to a sequence selected from the group consisting of SEQ ID NOs:20 to 24, or a functional fragment thereof.

Embodiment 100. The modified tobacco seed or tobacco plant of any one of embodiments 91 to 99, wherein said heterologous promoter comprises a polynucleotide sequence from a tobacco genome.

Embodiment 101. The modified tobacco seed or tobacco plant of any one of embodiments 91 to 100, wherein said heterologous promoter comprises a polynucleotide sequence from a plant genome.

Embodiment 102. The modified tobacco plant of any one of embodiments 91 to 101, wherein said modified tobacco plant comprises equal levels of a metabolite selected from the group consisting of 4-guanidinobutanoate, syringaldehyde, thiamin, and p-hydroxybenzaldehyde in root tissue as compared to an unmodified tobacco plant lacking said cisgenic polynucleotide when grown under the same conditions.

Embodiment 103. The modified tobacco plant of any one of embodiments 91 to 102, wherein said modified tobacco plant comprises equal levels of a metabolite selected from the group consisting of 4-guanidinobutanoate, X-23454, X-23580, and X-23852 in leaf tissue as compared to an unmodified tobacco plant lacking said cisgenic polynucleotide when grown under the same conditions.

Embodiment 104. The modified tobacco plant of any one of embodiments 91 to 103, wherein said modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking said cisgenic polynucleotide when grown under the same conditions.

Embodiment 105. The modified tobacco plant of any one of embodiments 91 to 104, wherein said modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking said cisgenic polynucleotide when grown under the same conditions.

Embodiment 106. The modified tobacco seed or plant of any one of embodiments 91 to 105, wherein said modified tobacco seed or plant is of a Burley variety.

Embodiment 107. The modified tobacco seed or plant of any one of embodiments 91 to 106, wherein said modified tobacco seed or plant comprises lower amounts of TSNAs as compared to an unmodified tobacco plant lacking said cisgenic polynucleotide when grown under the same conditions.

Embodiment 108. A recombinant DNA construct comprising a heterologous promoter operably linked to a polynucleotide encoding a small RNA (sRNA) at least 85% identical or complementary to a polynucleotide selected from the group consisting of SEQ ID NOs:41 to 56.

Embodiment 109. Cured tobacco material, or a tobacco product comprising said cured tobacco material, wherein said cured tobacco material is made from a tobacco plant comprising a cisgenic polynucleotide comprising a heterologous promoter operably linked to a polynucleotide encoding a small RNA (sRNA) at least 85% identical or complementary to a polynucleotide selected from the group consisting of SEQ ID NOs:41 to 56, and wherein said modified tobacco seed or tobacco plant comprises enhanced nitrogen utilization efficiency as compared to an unmodified control tobacco plant lacking said cisgenic polynucleotide when grown under the same conditions.

Embodiment 110. A method of enhancing the nitrogen utilization efficiency (NUE) of a tobacco plant comprising:
a. introducing a cisgenic nucleic acid molecule into a tobacco cell; and
b. regenerating a modified tobacco plant from said tobacco cell, wherein said modified tobacco plant comprises enhanced NUE as compared to a tobacco plant lacking said cisgenic nucleic acid molecule.

Embodiment 111. The method of embodiment 110, wherein said method further comprises:
c. crossing said modified tobacco plant with a second tobacco plant or self-pollinating said modified tobacco plant.

Embodiment 112. The method of embodiment 110 or 111, wherein said enhanced NUE comprises an increased partial factor productivity (PFP) compared to a tobacco plant lacking said enhanced NUE grown in the same conditions.

Embodiment 113. The method of any one of embodiments 110 to 112, wherein said enhanced NUE comprises an increased agronomic efficiency (AE) compared to a tobacco plant lacking said enhanced NUE grown in the same conditions.

Embodiment 114. The method of any one of embodiments 110 to 113, wherein said enhanced NUE comprises an increased recovery efficiency (RE) compared to a tobacco plant lacking said enhanced NUE grown in the same conditions.

Embodiment 115. The method of any one of embodiments 110 to 114, wherein said enhanced NUE comprises an increased physiological efficiency (PE) compared to a tobacco plant lacking said enhanced NUE grown in the same conditions.

Embodiment 116. The method of any one of embodiments 110 to 115, wherein said enhanced NUE comprises an increased internal efficiency (IE) compared to a tobacco plant lacking said enhanced NUE grown in the same conditions.

Embodiment 117. A method of enhancing the nitrogen utilization efficiency (NUE) of a tobacco plant comprising:
a. introducing a modification to a nucleic acid molecule encoding a gene having sequence selected from the group consisting of SEQ ID NOs:41 to 56 in a tobacco cell;
b. regenerating a modified tobacco plant from said tobacco cell, wherein said modified tobacco plant comprises enhanced NUE as compared to a tobacco plant lacking said modification.

Embodiment 118. The method of embodiment 117, wherein said introduction comprises the use of an RNA-guided nuclease.

Embodiment 119. The method of embodiment 117 or 118, wherein said RNA-guided nuclease is selected from the group consisting of a Cas9 nuclease, a Cpf1 nuclease, a CasX nuclease, a CasY nuclease, and functional homologues thereof.

Embodiment 120. The method of any one of embodiments 117 to 119, wherein said modification is selected from the group consisting of an insertion, a substitution, an inversion, and a deletion.

Embodiment 121. The method of any one of embodiments 117 to 120, wherein said enhanced NUE comprises an increased partial factor productivity (PFP) compared to a tobacco plant lacking said enhanced NUE grown in the same conditions.

Embodiment 122. The method of any one of embodiments 117 to 121, wherein said enhanced NUE comprises an increased agronomic efficiency (AE) compared to a tobacco plant lacking said enhanced NUE grown in the same conditions.

Embodiment 123. The method of any one of embodiments 117 to 122, wherein said enhanced NUE comprises an increased recovery efficiency (RE) compared to a tobacco plant lacking said enhanced NUE grown in the same conditions.

Embodiment 124. The method of any one of embodiments 117 to 123, wherein said enhanced NUE comprises an increased physiological efficiency (PE) compared to a tobacco plant lacking said enhanced NUE grown in the same conditions.

Embodiment 125. The method of any one of embodiments 117 to 124, wherein said enhanced NUE comprises an increased internal efficiency (IE) compared to a tobacco plant lacking said enhanced NUE grown in the same conditions.

Embodiment 126. The method of any one of embodiments 117 to 125, wherein said method further comprises:
c. crossing said modified tobacco plant with a second tobacco plant or self-pollinating said modified tobacco plant.

Embodiment 127. A method of enhancing the nitrogen utilization efficiency (NUE) of a tobacco plant comprising:
a. introducing a nucleic acid encoding a small RNA (sRNA) homologous to at least 18 contiguous nucleic acids of a nucleic acid molecule encoding a gene having sequence selected from the group consisting of SEQ ID NOs:41 to 56 in a tobacco cell;
b. regenerating a modified tobacco plant from said tobacco cell, wherein said modified tobacco plant comprises enhanced NUE as compared to a tobacco plant lacking said sRNA.

Embodiment 128. The method of embodiment 127, wherein said sRNA is selected from the group consisting of a microRNA, a small-interfering RNA (siRNA), a trans-acting siRNA, and precursors thereof.

Embodiment 129. The method of embodiment 127 or 128, wherein said enhanced NUE comprises an increased partial factor productivity (PFP) compared to a tobacco plant lacking said enhanced NUE grown in the same conditions.

Embodiment 130. The method of any one of embodiments 127 to 129, wherein said enhanced NUE comprises an increased agronomic efficiency (AE) compared to a tobacco plant lacking said enhanced NUE grown in the same conditions.

Embodiment 131. The method of any one of embodiments 127 to 130, wherein said enhanced NUE comprises an increased recovery efficiency (RE) compared to a tobacco plant lacking said enhanced NUE grown in the same conditions.

Embodiment 132. The method of any one of embodiments 127 to 131, wherein said enhanced NUE comprises an increased physiological efficiency (PE) compared to a tobacco plant lacking said enhanced NUE grown in the same conditions.

Embodiment 133. The method of any one of embodiments 127 to 132, wherein said enhanced NUE comprises an increased internal efficiency (IE) compared to a tobacco plant lacking said enhanced NUE grown in the same conditions.

Embodiment 134. The method of any one of embodiments 127 to 133, wherein said method further comprises:
c. crossing said modified tobacco plant with a second tobacco plant or self-pollinating said modified tobacco plant.

Embodiment 135. A method comprising:
a. providing a first population of tobacco plants comprising enhanced nitrogen utilization efficiency;
b. genotyping said first population of tobacco plants for the presence of a molecular marker within 20 cM of an enhanced nitrogen utilization efficiency locus; and
c. selecting one or more tobacco plants genotyped in step (b) that comprise said molecular marker.

Embodiment 136. The method of embodiment 135, wherein said method further comprises:
d. crossing one or more tobacco plants selected in step (c) to a second tobacco plant; and
e. obtaining progeny seed from the cross of step (d).

Embodiment 137. The method of embodiment 135 or 136, wherein said molecular marker is selected from the group consisting of a SNP marker, an INDEL marker, an RFLP marker, an SSR marker, an AFLP marker, and a RAPD marker.

Embodiment 138. The method of any one of embodiments 135 to 137, wherein said enhanced nitrogen utilization efficiency locus comprises a polynucleotide encoding a polypeptide at least 70% identical or similar to a polypeptide selected from the group consisting of SEQ ID NOs:1 to 8.

Embodiment 139. The method of any one of embodiments 135 to 138, wherein said enhanced nitrogen utilization efficiency locus comprises a polynucleotide sequence selected from the group consisting of SEQ ID NOs:9 to 16.

Embodiment 140. The method of any one of embodiments 135 to 139, wherein said molecular marker is selected from the group consisting of SEQ ID NOs:57 to 64.

Embodiment 141. The method of any one of embodiments 135 to 140, wherein said molecular marker comprises a G nucleotide at position 57 of SEQ ID NO:58.

Embodiment 142. The method of any one of embodiments 135 to 141, wherein said molecular marker comprises a C nucleotide at position 117 of SEQ ID NO:58.

Embodiment 143. The method of any one of embodiments 135 to 142, wherein said molecular marker comprises a G nucleotide at position 57 and a C nucleotide at position 117 of SEQ ID NO:58.

Embodiment 144. The method of any one of embodiments 135 to 143, wherein said molecular marker comprises a T nucleotide at position 14 of SEQ ID NO:57.

Embodiment 145. The method of any one of embodiments 135 to 144, wherein said molecular marker comprises a G nucleotide at position 162 of SEQ ID NO:59.

Embodiment 146. The method of any one of embodiments 135 to 145, wherein said molecular marker comprises a C nucleotide at position 36 of SEQ ID NO:60.

Embodiment 147. The method of any one of embodiments 135 to 146, wherein said molecular marker comprises a T nucleotide at position 36 of SEQ ID NO:61.

Embodiment 148. The method of any one of embodiments 135 to 147, wherein said molecular marker comprises a T nucleotide at position 36 of SEQ ID NO:62.

Embodiment 149. The method of any one of embodiments 135 to 148, wherein said molecular marker comprises a G nucleotide at position 36 of SEQ ID NO:63.

Embodiment 150. The method of any one of embodiments 135 to 149, wherein said molecular marker comprises a T nucleotide at position 36 of SEQ ID NO:64.

Embodiment 151. The method of any one of embodiments 135 to 150, wherein said first population of tobacco plants is of a Maryland variety.

Embodiment 152. The method of any one of embodiments 135 to 151, wherein said first population of tobacco plants is of a variety selected from the group consisting of MD609, MD601, Banket A1, K326, K346, K358, K394, K399, K730, NC196, NC37NF, NC471, NC55, NC92, NC2326, NC95, NC925.

Embodiment 153. The method of any one of embodiments 135 to 152, wherein said second tobacco plant is of a variety selected from the group consisting of TN86, TN86LC, TN90, TN90LC, TN97, TN97LC.

Embodiment 154. The method of any one of embodiments 135 to 153, wherein said progeny seed comprises said molecular marker.

Embodiment 155. The method of any one of embodiments 135 to 154, wherein said progeny seed comprises said enhanced nitrogen utilization efficiency.

Embodiment 156. The method of any one of embodiments 135 to 155, wherein said molecular marker is within 15 cM of said enhanced nitrogen utilization efficiency locus.

Embodiment 157. The method of any one of embodiments 135 to 156, wherein said molecular marker is within 10 cM of said enhanced nitrogen utilization efficiency locus.

Embodiment 158. The method of any one of embodiments 135 to 157, wherein said molecular marker is within 5 cM of said enhanced nitrogen utilization efficiency locus.

Embodiment 159. The method of any one of embodiments 135 to 158, wherein said molecular marker is within 2 cM of said enhanced nitrogen utilization efficiency locus.

Embodiment 160. The method of any one of embodiments 135 to 159, wherein said molecular marker is within 1 cM of said enhanced nitrogen utilization efficiency locus.

Embodiment 161. The method of any one of embodiments 135 to 160, wherein said molecular marker is within 0.5 cM of said enhanced nitrogen utilization efficiency locus.

Embodiment 162. A method comprising:
a. providing a first population of tobacco plants;
b. genotyping said first population of tobacco plants for the presence of an enhanced nitrogen utilization efficiency allele of a locus encoded by a sequence selected from the group consisting of SEQ ID NOs:9 to 16; and
c. selecting one or more tobacco plants genotyped in step (b) that comprise said enhanced nitrogen utilization efficiency allele.

Embodiment 163. The method of embodiment 161 or 162, wherein said method further comprises:
d. crossing the one or more tobacco plants selected in step (c) to a second tobacco plant; and
e. obtaining progeny seed from the crossing of step (d).

Embodiment 164. The method of any one of embodiments 161 to 163, wherein said first population of tobacco plants is of a Maryland variety.

Embodiment 165. The method of any one of embodiments 161 to 164, wherein said first population of tobacco plants is of a variety selected from the group consisting of MD609, MD601, Banket A1, K326, K346, K358, K394, K399, K730, NC196, NC37NF, NC471, NC55, NC92, NC2326, NC95, NC925.

Embodiment 166. The method of any one of embodiments 161 to 165, wherein said second tobacco plant is of a variety selected from the group consisting of TN86, TN86LC, TN90, TN90LC, TN97, TN97LC.

Embodiment 167. The method of any one of embodiments 161 to 166, wherein said progeny seed comprises said molecular marker.

Embodiment 168. The method of any one of embodiments 161 to 167, wherein said progeny seed comprises said enhanced nitrogen utilization efficiency.

Embodiment 169. A method of introgressing an enhanced nitrogen utilization efficiency trait into a tobacco variety comprising:
a. crossing a first tobacco variety comprising said enhanced nitrogen utilization efficiency trait with a second tobacco variety lacking said enhanced nitrogen utilization efficiency trait;
b. obtaining progeny seed from the cross of step (a);
c. genotyping at least one of said progeny seed obtained in step (b) for a molecular marker linked to said enhanced nitrogen utilization efficiency trait, wherein said molecular marker is within 20 cM of a locus selected from the group consisting of SEQ ID NOs:9 to 16; and
d. selecting a progeny seed comprising said enhanced nitrogen utilization efficiency trait.

Embodiment 170. The method of embodiment 169, wherein said first tobacco variety is a Maryland tobacco variety.

Embodiment 171. The method of embodiment 169 or 170, wherein said first tobacco variety is selected from the group consisting of MD609, MD601, Banket A1, K326, K346, K358, K394, K399, K730, NC196, NC37NF, NC471, NC55, NC92, NC2326, NC95, NC925.

Embodiment 172. The method of any one of embodiments 169 to 171, wherein said second tobacco variety is a Burley tobacco variety.

Embodiment 173. The method of any one of embodiments 169 to 172, wherein said second tobacco variety is selected from the group consisting of TN86, TN86LC, TN90, TN90LC, TN97, TN97LC.

Embodiment 174. The method of any one of embodiments 169 to 173, wherein said enhanced NUE comprises an increased partial factor productivity (PFP) compared to a tobacco plant lacking said enhanced NUE grown in the same conditions.

Embodiment 175. The method of any one of embodiments 169 to 174, wherein said enhanced NUE comprises an increased agronomic efficiency (AE) compared to a tobacco plant lacking said enhanced NUE grown in the same conditions.

Embodiment 176. The method of any one of embodiments 169 to 175, wherein said enhanced NUE comprises an increased recovery efficiency (RE) compared to a tobacco plant lacking said enhanced NUE grown in the same conditions.

Embodiment 177. The method of any one of embodiments 169 to 176, wherein said enhanced NUE comprises an increased physiological efficiency (PE) compared to a tobacco plant lacking said enhanced NUE grown in the same conditions.

Embodiment 178. The method of any one of embodiments 169 to 177, wherein said enhanced NUE comprises an increased internal efficiency (IE) compared to a tobacco plant lacking said enhanced NUE grown in the same conditions.

Embodiment 179. The method of any one of embodiments 169 to 178, wherein said molecular marker is within 15 cM of said locus.

Embodiment 180. The method of any one of embodiments 169 to 179, wherein said molecular marker is within 10 cM of said locus.

Embodiment 181. The method of any one of embodiments 169 to 180, wherein said molecular marker is within 5 cM of said locus.

Embodiment 182. The method of any one of embodiments 169 to 181, wherein said molecular marker is within 2 cM of said locus.

Embodiment 183. The method of any one of embodiments 169 to 182, wherein said molecular marker is within 1 cM of said locus.

Embodiment 184. The method of any one of embodiments 169 to 183, wherein said molecular marker is within 0.5 cM of said locus.

Embodiment 185. A method of selecting a tobacco plant comprising an enhanced nitrogen utilization efficiency trait comprising:
a. isolating nucleic acids from a collection of tobacco germplasm;
b. assaying said nucleic acids for one or more markers located within 20 cM of a locus selected from the group consisting of SEQ ID NOs:9 to 16; and
c. selecting said tobacco plant comprising said enhanced nitrogen utilization efficiency trait.

Embodiment 186. The method of embodiment 185, wherein said method further comprises:
d. crossing said tobacco plant selected in step (c) with a second tobacco plant; and
e. obtaining progeny seed from the cross of step (d).

Embodiment 187. The method of embodiment 185 or 186, wherein said molecular marker is within 15 cM of said locus.

Embodiment 188. The method of any one of embodiments 185 to 187, wherein said molecular marker is within 10 cM of said locus.

Embodiment 189. The method of any one of embodiments 185 to 188, wherein said molecular marker is within 5 cM of said locus.

Embodiment 190. The method of any one of embodiments 185 to 189, wherein said molecular marker is within 2 cM of said locus.

Embodiment 191. The method of any one of embodiments 185 to 190, wherein said molecular marker is within 1 cM of said locus.

Embodiment 192. The method of any one of embodiments 185 to 191, wherein said molecular marker is within 0.5 cM of said locus.

Embodiment 193. A method of selecting a tobacco plant comprising an enhanced nitrogen utilization efficiency trait comprising:
  a. isolating nucleic acids from a collection of tobacco germplasm;
  b. assaying said nucleic acids for one or more markers located within 20 cM of SNP marker selected from the group consisting of SEQ ID NOs:57 to 64; and
  c. selecting said tobacco plant comprising said enhanced nitrogen utilization efficiency trait.

Embodiment 194. The method of embodiment 193, wherein said assaying comprises assaying for a G nucleotide at position 57 of SEQ ID NO:58.

Embodiment 195. The method of embodiment 193 or 194, wherein said assaying comprises assaying for a C nucleotide at position 117 of SEQ ID NO:58.

Embodiment 196. The method of any one of embodiments 193 to 195, wherein said assaying comprises assaying for a G nucleotide at position 57 and a C nucleotide at position 117 of SEQ ID NO:58.

Embodiment 197. The method of embodiment 193 to 196, wherein said assaying comprises assaying for a T nucleotide at position 14 of SEQ ID NO:57.

Embodiment 198. The method of any one of embodiments 193 to 197, wherein said assaying comprises assaying for a G nucleotide at position 162 of SEQ ID NO:59.

Embodiment 199. The method of any one of embodiments 193 to 198, wherein said assaying comprises assaying for a C nucleotide at position 36 of SEQ ID NO:60.

Embodiment 200. The method of any one of embodiments 193 to 199, wherein said assaying comprises assaying for a T nucleotide at position 36 of SEQ ID NO:61.

Embodiment 201. The method of any one of embodiments 193 to 200, wherein said assaying comprises assaying for a T nucleotide at position 36 of SEQ ID NO:62.

Embodiment 202. The method of any one of embodiments 193 to 201, wherein said assaying comprises assaying for a G nucleotide at position 36 of SEQ ID NO:63.

Embodiment 203. The method of any one of embodiments 193 to 202, wherein said assaying comprises assaying for a T nucleotide at position 36 of SEQ ID NO:64.

EXAMPLES

Example 1. Field Production Practices

Field grown tobacco plants are generated using standard field production practices. Each test plot comprises up to 40 rows of transplanted seedlings. Seedlings are germinated in a greenhouse before transplantation. For testing NUE traits, a test plot receives a nitrogen rate of 60 pounds of nitrogen per acre. Plants are topped using standard procedures when 50% of the plants in a test plot reach the elongated button stage. Pesticide application follows standard protocols. Leaves are harvested at maturity and sorted into 3 sticks per plot with 5 plants per stick for curing. Leaves are sampled from the sticks at the takedown/stripping stage. Five leaves are harvested from three different sticks per experimental variety for 15 leaves per sample. Half of the lamina from the fourth leaf from the top of each plant is harvested for sampling. Analytical analysis of alkaloids, TSNA and $NO_3$ are conducted using routine methods known in the art.

Example 2. Identification of Metabolites Associated with Enhanced Nitrogen Utilization Efficiency Maryland tobacco varieties require approximately 25% less nitrogen fertilizer input as compared to Burley tobacco varieties. In order to identify metabolites associated with high nitrogen efficiency (Maryland) and low nitrogen efficiency (Burley) tobacco varieties, differences in metabolite levels were examined in the Maryland tobacco variety MD609 and the Burley tobacco variety TN90.

MD609 and TN90 seedlings were germinated from seed and grown without the addition of nitrogen for six weeks. After six weeks, the seedlings from each variety were split into two groups: Group A comprised plants that were provided with 100 parts per million nitrogen or the normal greenhouse fertilization; and Group B comprised plants that were provided with 25 ppm or 25% of the normal greenhouse fertilization rate. Metabolites were extracted using methanol from root leaf tissue at 10 and 14 weeks after seeding.

The isolated metabolites were analyzed using three different LC/MS approaches (UHPLC-MS/MS (+ESI), UHPLC-MS/MS (−ESI), and GC-MS (+EI)) to separate and identify individual metabolites. Metabolites were identified by comparing the obtained mass spectra to standard spectral databases (Metabolon Inc, Morrisville, N.C.). Peaks were quantified using area-under-the-curve. Each compound was scaled by registering the medians to equal one (1.00) and normalizing each data point proportionately (termed the "block correction"). The molecular mass of unknown metabolites is provided in Table 1. Discriminant metabolites are shown below in Tables 2 to 5, along with scaled measured values for each sample. Discriminant metabolites were determined by Student's t-test comparisons between TN90 and MD609 taking into account all time points. Metabolites with a p-value less than 0.01 were included in the analysis.

TABLE 1 molecular mass in kiloDaltons for unknown metabolite compounds.

| Metabolite | Mass |
|---|---|
| X - 21756 | 247.0918 |
| X - 21796 | 138.0566 |
| X - 23319 | 299.0771 |
| X - 23330 | 251.1136 |
| X - 23366 | 189.1023 |
| X - 23389 | 157.0762 |
| X - 23453 | 161.0818 |
| X - 23454 | 319.0933 |
| X - 23576 | 267.1237 |
| X - 23580 | 311.1136 |
| X - 23852 | 374.144 |
| X - 23916 | 395.0291 |
| X - 23937 | 161.0819 |

TABLE 2

Metabolites negatively correlated with enhanced nitrogen efficiency identified in root tissue when comparing MD609 and TN90 tobacco lines at week 10 and week 14 after seeding.

| | TN90 | | | | MD609 | | | |
| --- | --- | --- | --- | --- | --- | --- | --- | --- |
| | 25% Nitrogen | | 100% Nitrogen | | 25% Nitrogen | | 100% Nitrogen | |
| Metabolite | W10 | W14 | W10 | W14 | W10 | W14 | W10 | W14 |
| X-23576 | 4.6 | 3.6 | 1.2 | 8.4 | 2.5 | 1.2 | 1 | 2.3 |
| N-acetylmuramate | 0.3 | 0.4 | 2.5 | 4 | 0.1 | 0.2 | 0.3 | 0.6 |
| X-23319 | 0.5 | 0.5 | 3.2 | 2.9 | 0.3 | 0.3 | 0.4 | 1.2 |
| X-23852 | 0.8 | 1.0 | 2.2 | 3.1 | 0.1 | 1.0 | 0.9 | 0.4 |
| X-23330 | 0.7 | 0.5 | 3.5 | 2.4 | 0.4 | 0.6 | 0.9 | 1.0 |
| Alpha-ketoglutarate | 2.1 | 1.5 | 1.5 | 0.9 | 0.8 | 0.6 | 0.8 | 0.5 |
| X-21756 | 0.6 | 0.4 | 1.9 | 1.3 | 0.2 | 0.3 | 1.0 | 0.5 |
| 4-hydroxy-2-oxoglutaric acid | 0.9 | 0.4 | 1.1 | 1.2 | 0.5 | 0.4 | 0.5 | 0.6 |
| X-23937 | 0.2 | 0.2 | 0.7 | 1.1 | 0.1 | 0.2 | 0.1 | 0.4 |
| X-23916 | 0.6 | 0.6 | 0.5 | 1.0 | 0.3 | 0.3 | 0.2 | 0.3 |
| 1-methyladenine | 1.2 | 0.9 | 1.2 | 1.1 | 1.0 | 0.8 | 0.8 | 0.7 |

TABLE 3

Metabolites positively correlated with enhanced nitrogen efficiency identified in root tissue when comparing MD609 and TN90 tobacco lines

| | TN90 | | | | MD609 | | | |
| --- | --- | --- | --- | --- | --- | --- | --- | --- |
| | 25% Nitrogen | | 100% Nitrogen | | 25% Nitrogen | | 100% Nitrogen | |
| Metabolite | W10 | W14 | W10 | W14 | W10 | W14 | W10 | W14 |
| 4-guanidinobutanoate | 0.7 | 0.7 | 0.7 | 0.6 | 1.0 | 1.1 | 0.8 | 0.7 |
| Syringaldehyde | 0.5 | 0.6 | 0.4 | 0.3 | 0.9 | 1.0 | 0.6 | 0.4 |
| Thiamin | 0.2 | 0.1 | 0.7 | 0.7 | 0.7 | 1.1 | 0.7 | 1.1 |
| p-hydroxybenzaldehyde | 0.4 | 1.0 | 0.8 | 0.9 | 0.6 | 1.6 | 1.4 | 1.5 |

TABLE 4

Metabolites negatively correlated with enhanced nitrogen efficiency identified in leaf tissue when comparing MD609 and TN90 tobacco lines

| | TN90 | | | | MD609 | | | |
| --- | --- | --- | --- | --- | --- | --- | --- | --- |
| | 25% Nitrogen | | 100% Nitrogen | | 25% Nitrogen | | 100% Nitrogen | |
| Metabolite | W10 | W14 | W10 | W14 | W10 | W14 | W10 | W14 |
| X-23453 | 1.2 | 4.9 | 2.2 | 3.9 | 0.9 | 1.3 | 1.3 | 1.9 |
| X-21756 | 1.6 | 0.8 | 2.3 | 2.5 | 0.8 | 0.3 | 1.0 | 0.8 |
| X-11429 | 1.3 | 0.6 | 2.7 | 2.4 | 0.7 | 0.2 | 1.0 | 1.0 |
| X-21796 | 0.7 | 2.0 | 0.7 | 2.0 | 0.2 | 0.6 | 0.2 | 0.5 |
| N'-methylnicotinamide | 0.7 | 1.0 | 1.9 | 1.1 | 0.9 | 0.1 | 0.1 | 0.2 |
| Cotinine | 0.5 | 1.4 | 0.3 | 1.7 | 0.4 | 0.4 | 0.1 | 0.3 |
| X-23389 | 0.9 | 1.2 | 0.4 | 1.2 | 0.5 | 0.3 | 0.1 | 0.2 |
| N-acetylarginine | 1.0 | 0.7 | 0.8 | 1.9 | 0.6 | 0.3 | 0.7 | 0.8 |
| X-23366 | 0.6 | 0.9 | 0.1 | 0.8 | 0.3 | 0.2 | 0.1 | 0.1 |
| N-acetylphenylalanine | 1.0 | 1.0 | 1.2 | 1.0 | 0.9 | 0.4 | 0.7 | 0.5 |
| Naringenin | 0.4 | 0.8 | 0.3 | 0.8 | 0.2 | 0.2 | 0.1 | 0.4 |

TABLE 5

Metabolites positively correlated with enhanced nitrogen efficiency identified in leaf tissue when comparing MD609 and TN90 tobacco lines

| | TN90 | | | | MD609 | | | |
|---|---|---|---|---|---|---|---|---|
| | 25% Nitrogen | | 100% Nitrogen | | 25% Nitrogen | | 100% Nitrogen | |
| Metabolite | W10 | W14 | W10 | W14 | W10 | W14 | W10 | W14 |
| 4-guanidinobutanoate | 0.6 | 0.8 | 1.0 | 1.1 | 1.3 | 0.9 | 1.6 | 1.6 |
| X-23454 | 0.1 | 0.1 | 0.5 | 0.1 | 0.8 | 0.1 | 1.5 | 1.5 |
| X-23580 | 1.1 | 3.6 | 1.8 | 1.5 | 4.9 | 6.0 | 3.5 | 5.3 |
| X-23852 | 0.9 | 7.7 | 3.6 | 2.1 | 9.8 | 13.2 | 7.6 | 11.0 |

Example 3. Identification of Gene Expression Associated with Enhanced Nitrogen Utilization Efficiency The same plants used in Example 1 are also subjected to RNA extraction to be used for RNAseq. RNA is extracted from leaf and root tissue at 10 weeks and 14 weeks after seeding and used for Illumina sequencing. The RNAseq data were analyzed according to methods standard in the art. Candidate genes are subsequently verified.

Seventeen genes (Tables 6 and 7) were found to negatively correlate with the enhanced nitrogen utilization efficiency phenotype of MD609, and seven genes (Tables 8 and 9) were found to positively correlate with the enhanced nitrogen utilization efficiency phenotype of MD609. The negatively correlated genes are candidates for down-regulation in Burley tobacco varieties (via mutagenesis, cisgenic transformation, or transgenic transformation), and the positively correlated genes are candidates for over-expression in Burley tobacco varieties to improve nitrogen utilization efficiency. Single nucleotide polymorphism (SNP) markers associated are provided for tracking the each candidate gene (Tables 6 to 10). The polymorphism associated with the MD609 alleles, and therefore favorable for enhanced NUE is provided (Table 10).

Figure 2:
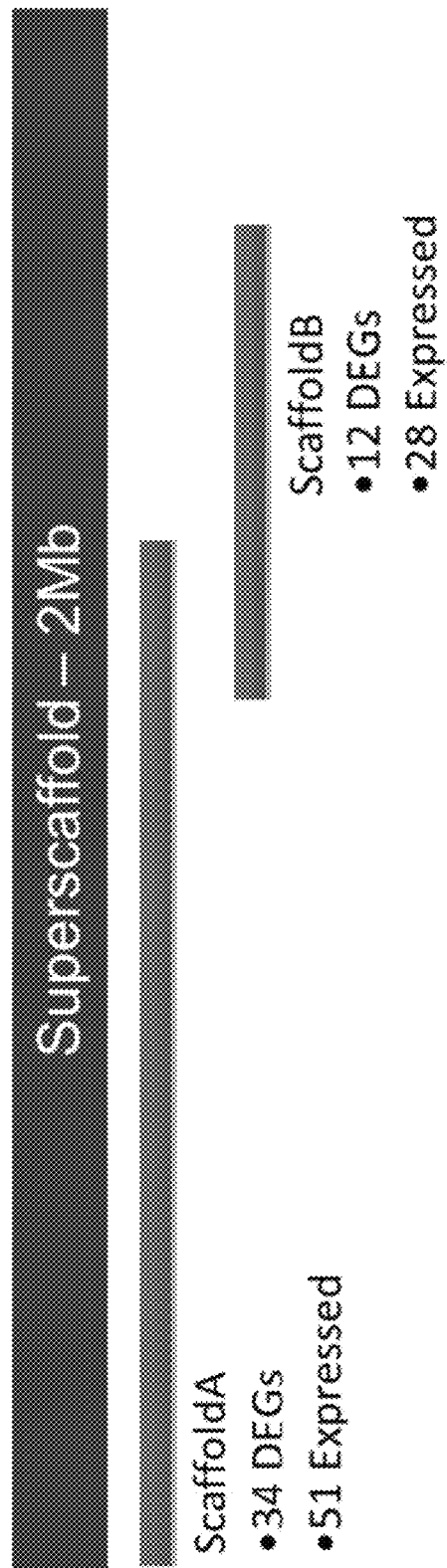
FIG. 2 depicts a 2 megabase region of tobacco chromosome 11 that is covered by superscaffold 1. Superscaffold1 is a contig of scaffolds A and B. Of the 79 expressed genes located in this region, 56 genes are differentially expressed.

Identification of the genomic location for each of the correlated genes identifies four clusters of genes associated with enhanced NUE in the tobacco genome (FIG. 1). Seven genes are similarly located on chromosome 1, four genes are similarly located on chromosome 11, three genes are similarly located on chromosome 14, and five genes are similarly located on chromosome 20 (FIG. 1). These four locations are also hotspots for genes differentially expressed between low and normal nitrogen conditions (FIG. 1). SNP markers are created to identify MD609 specific and therefore enhanced NUE polymorphisms for each of these locations (Tables 6 to 10). The area on chromosome 11 is further characterized and contains 79 total expressed genes and 46 of these genes are differentially expressed genes under low nitrogen conditions (FIG. 2).

TABLE 6

Genes identified as negatively correlated with enhanced nitrogen utilization efficiency in root tissue.

| Gene Identifier | SEQ ID NO | Gene Description | SNP marker SEQ ID NO: |
|---|---|---|---|
| G38453 | 25 | Putative vacuolar proton ATPase subunit E | 57 |
| G64360 | 26 | Clathrin interactor epsin 1-like | 63 |
| G26157 | 27 | Serine/threonine-protein kinase PBS1 | 59 |

TABLE 6-continued

Genes identified as negatively correlated with enhanced nitrogen utilization efficiency in root tissue.

| Gene Identifier | SEQ ID NO | Gene Description | SNP marker SEQ ID NO: |
|---|---|---|---|
| G54692 | 28 | ATPase family AAA domain-containing protein 1-a-like | 57 |
| G32111 | 29 | Uncharacterized protein | 57 |
| G49619 | 30 | Coatomer subunit gamma | 61 |
| G19982 | 31 | Uncharacterized protein | 60 |
| G39737 | 32 | Uncharacterized protein | 58 |
| G28894 | 33 | Putative quinolinate phosphoribosyltransferase | 60 |
| G30288 | 38 | Probable acyl-activating enzyme chloroplastic-like | 59 |
| G39762 | 39 | Alpha-1-fucosidase | 58 |
| G39442 | 40 | Uncharacterized protein | 57 |

TABLE 7

Genes identified as negatively correlated with enhanced nitrogen utilization efficiency in leaf tissue.

| Gene Identifier | SEQ ID NO | Gene Description | SNP Marker SEQ ID NO: |
|---|---|---|---|
| G41803 | 34 | ABC transporter F-family member 3-like | 57 |
| G46356 | 35 | Uncharacterized protein | 57 |
| G56420 | 36 | WD repeat-containing protein 26-like | 58 |
| G59801 | 37 | Protein phosphatase 2A | 60 |
| G30288 | 38 | Probable acyl-activating enzyme chloroplastic-like | 59 |
| G39762 | 39 | Alpha-1-fucosidase | 58 |
| G39442 | 40 | Uncharacterized protein | 57 |

TABLE 8

Genes identified as positively correlated with enhanced nitrogen utilization efficiency in root tissue.

| Gene Identifier | SEQ ID NO | Gene Description | SNP Marker SEQ ID NO: |
|---|---|---|---|
| G59318 | 1 | PR-10 type pathogenesis-related protein | 57 |
| G20580 | 2 | Uncharacterized amino acid permease | 60 |
| G30999 | 3 | TBZ17 | 62 |

TABLE 8-continued

Genes identified as positively correlated with enhanced nitrogen utilization efficiency in root tissue.

| Gene Identifier | SEQ ID NO | Gene Description | SNP Marker SEQ ID NO: |
|---|---|---|---|
| G29260 | 4 | BTB/POZ domain-containing protein (AT5G48800-like) | 64 |
| G41446 | 8 | 3-isopropylmalate dehydratase small subunit | 57 |

TABLE 9

Genes identified as positively correlated with enhanced nitrogen utilization efficiency in leaf tissue.

| Gene Identifier | SEQ ID NO | Gene Description | SNP Marker SEQ ID NO: |
|---|---|---|---|
| G41343 | 5 | Glucose-6-phosphate 1-epimerase-like | 57 |
| G53261 | 6 | Probable nitrite transporter (AT1G68570-like) | 60 |
| G42290 | 7 | Phospho-2-dehydro-3-deoxyheptonate aldolase | 58 |
| G41446 | 8 | 3-isopropylmalate dehydratase small subunit | 61 |

TABLE 10

SNP markers comprising polymorphisms associated with enhanced NUE.

| SNP marker SEQ ID NO | Positon of polymorphism | Allele associated with NUE |
|---|---|---|
| 57 | 147 | T |
| 58 | 57 | G |
|  | 117 | C |
| 59 | 162 | G |
| 60 | 36 | C |
| 61 | 36 | T |
| 62 | 36 | T |
| 63 | 36 | G |
| 64 | 36 | T |

Example 4. Identifying Tobacco Leaf- and Root-Preferred Promoters

RNA samples from 4 week old TN90 tobacco plants are obtained from 10 tissue types (axillary buds before topping; axillary buds 2 hours after topping; axillary buds 6 hours after topping; axillary buds 24 hours after topping; axillary buds 72 hours after topping; roots before topping; roots 24 hours after topping; roots 72 hours after topping; young leaf at the time of topping; and shoot apical meristem). The resulting RNA samples (three independently collected samples for each tissue type) are used as starting material for Illumina 1×100 bp sequencing.

Illumina reads are mapped and used to identify a list of candidate genes exhibiting high root or leaf expression. Tables 11 and 12 provide RPKM expression values for genes identified as having leaf-preferred or root-preferred expression. These genes are candidates for possessing leaf-preferred promoters or root-preferred promoters, respectively.

TABLE 11

Genes with leaf-preferred expression

| Promoter | Gene Description | SEQ ID NO: | Axillary Bud | | | | | Root | | | | |
|---|---|---|---|---|---|---|---|---|---|---|---|---|
| | | | 0 hr | 2 hr | 6 hr | 24 hr | 72 hr | 0 hr | 24 hr | 72 hr | SAM | Leaf |
| P16098 | Carbonic anhydrase | 17 | 4.88 | 5.94 | 7.49 | 4.67 | 16.12 | 0.45 | 0.41 | 0.52 | 2.89 | 1002.14 |
| P42207 | CP12 | 18 | 0.41 | 0.99 | 1.24 | 0.52 | 1.83 | 0.05 | 0.02 | 0.07 | 0.13 | 34.34 |
| P47582 | Chloroplast sedoheptulose-1,7-bisphosphatase | 19 | 0.32 | 0.68 | 0.91 | 0.68 | 1.96 | 0.03 | 0.03 | 0.06 | 0.06 | 96.69 |

TABLE 12

Genes with root-preferred expression

| Promoter | Gene Description | SEQ ID NO: | Axillary Bud | | | | | Root | | | | |
|---|---|---|---|---|---|---|---|---|---|---|---|---|
| | | | 0 hr | 2 hr | 6 hr | 24 hr | 72 hr | 0 hr | 24 hr | 72 hr | SAM | Leaf |
| P2862 | Putative PLA2 | 20 | 0.65 | 0.78 | 0.58 | 0.38 | 0.38 | 336.69 | 391.95 | 511.86 | 0.36 | 0.43 |
| P57190 | Uncharacterized protein | 21 | 0.38 | 0.45 | 0.29 | 0.39 | 0.35 | 198.00 | 416.84 | 384.52 | 0.47 | 0.26 |
| P49330 | Glutathione S-transferase parC | 22 | 0.35 | 0.35 | 0.27 | 0.75 | 0.38 | 196.29 | 269.39 | 417.71 | 0.23 | 0.22 |
| P3788 | PR-10 type pathogenesis-related protein | 23 | 0.29 | 0.36 | 0.45 | 0.15 | 0.23 | 192.16 | 88.51 | 193.35 | 0.26 | 0.16 |
| P77628 | Cytochrome P450 | 24 | 0.39 | 0.71 | 0.53 | 0.39 | 0.44 | 144.99 | 333.54 | 386.32 | 0.52 | 0.50 |

Example 5. Development of Modified Plants

An expression vector, p45-2-7 (SEQ ID NO: 65), is used as a backbone to generate multiple transformation vectors (See Examples X-Y). p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, Nat Protoc. 1:1105-11 and Horsch et al., 1985, Science 227:1229-1231.

TN90 tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is resuspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. Approximately 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaves are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Evaluation of enhanced nitrogen utilization efficiency phenotypes is conducted by growing modified plants ($T_0$, $T_1$, $T_2$, or later generations) and control plants. Control plants are either NLM plants that have not been transformed or NLM plants that have been transformed with an empty p45-2-7 vector.

Phenotypic screening for enhanced nitrogen utilization efficiency is conducted in a greenhouse using zero parts per million (ppm) nitrogen (no nitrogen), 25 ppm nitrogen (low nitrogen), and 100 ppm nitrogen (normal nitrogen). Initial screening is undertaken in the greenhouse with $T_1$ plants. Homozygous $T_2$ populations are then evaluated in the field using 60 pounds per acre fertilizer (~25% of the recommended rate for Burley tobacco. Seedling growth, chlorophyll loss, and final yield are measured and compared to control plants grown at normal nitrogen levels.

Figure 5:
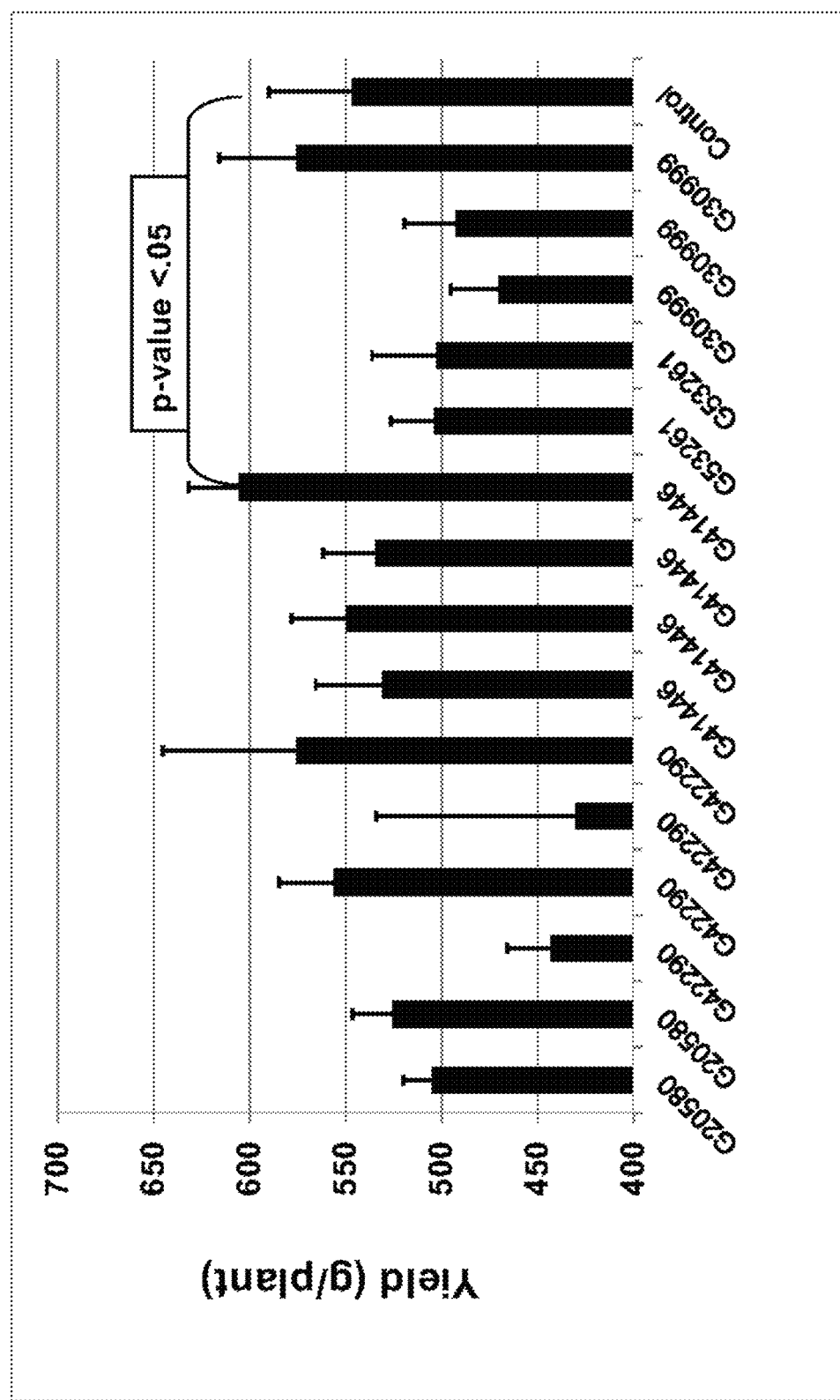
FIG. 5 depicts yield in grams fresh weight per plant of greenhouse grown $T_1$ plants overexpressing genes positively correlated with increased yield under nitrogen stress. The mean and standard deviation based on 9 plants per sample is displayed.

In the $T_1$ generation, plants overexpressing G20580 (2 independent transformants), G42290 (4 independent transformants), G41446 (4 independent transformants), G53261 (2 independent transformants), and G30999 (3 independent transformants) are grown in the greenhouse along with controls under nitrogen limiting conditions equivalent to 60 pounds of Nitrogen per acre. Nine plants per transformant are sampled and one of the lines overexpressing G41446 show a statistically significant increase in yield (grams fresh weight per plant) compared to the control (See FIG. 5).

Example 6. Creating a Cisgenic Tobacco Plant with Enhanced Nitrogen Utilization Efficiency Nitrogen utilization efficiency can be improved by modifying the expression of genes involving the genes that were identified as differentially expressed in Example 2. Similarly, genes involved in the biosynthesis or degradation of the metabolites identified in Example 1 can be modulated to improve nitrogen utilization efficiency. Genes that are positively associated with enhanced nitrogen utilization efficiency can be over-expressed using a general over-expression promoter or a tissue-preferred promoter to over-express the gene in desired tissues.

Transformation vectors are created to overexpress proteins that are positively associated with enhanced nitrogen utilization efficiency. Separate transformation vectors comprising one of SEQ ID NOs:9 to 16 are incorporated into p45-2-7 transformation vectors. Additionally transformation vectors are created comprising one of SEQ ID NOs:9 to 16.

Modified tobacco plants are generated using these transformation vectors according to Example 4. Modified tobacco plants ($T_1$ generation) and control tobacco plants are then phenotypically evaluated as described in Example 4. The modified tobacco plants exhibit enhanced nitrogen utilization efficiency as compared to control tobacco plants grown under the same conditions.

Example 7. Creating a Transgenic Tobacco Plant with Enhanced Nitrogen Utilization Efficiency Nitrogen utilization efficiency can also be enhanced by down-regulating the expression of genes identified as being negatively associated with nitrogen utilization efficiency in Example 2.

Transformation vectors comprising RNAi constructs are designed to inhibit tobacco genes whose expression is negatively associated with nitrogen utilization efficiency in Example 2. Separate transformation vectors comprise one of SEQ ID NOs:41 to 56, which are incorporated into p45-2-7 transformation vectors. Additional transformation vectors are created comprising one of SEQ ID NOs:41 to 56.

Modified tobacco plants are generated using these transformation vectors according to Example 4. Modified tobacco plants ($T_1$ generation) and control tobacco plants are then phenotypically evaluated as described in Example 4. The modified tobacco plants exhibit enhanced nitrogen utilization efficiency as compared to control tobacco plants grown under the same conditions.

Example 8. Additional Methods of Improving Nitrogen Utilization Efficiency Using Gene Editing Technologies Gene editing technologies such as CRISPR/Cas9, CRISPR/Cpf1, CRISPR/CasX, CRISPR/CasY, CRISPR/Csm1, zinc-finger nucleases (ZFN), and transcription activator-like effector nucleases (TALENs) are used to modify the coding region of a gene negatively associated with enhanced nitrogen utilization efficiency so that the gene encodes a non-functional protein or a lower-functioning protein. These gene editing technologies are also used to edit or replace an endogenous promoter sequence to drive its cognate protein expression in either leaf or root tissue to improve nitrogen utilization efficiency. For example, an endogenous G64360 is edited or replaced so the gene is only expressed in leaf tissue, where it can function to improve nitrogen utilization efficiency of the plant.

Separate CRISPR/Cas9 or CRISPR/Cpf1 guide RNAs are constructed to recognize and hybridize to the promoter sequence of each one of SEQ ID NOs:9 to 40. The engineered guide RNA and a donor polynucleotide comprising a promoter selected from the group consisting of SEQ ID NOs: 17 to 24 are provided to a tobacco plant, allowing the selected promoter to replace the endogenous promoter of the selected genes and restrict expression of endogenous to either leaf or root tissue as desired. The edited tobacco plants exhibit enhanced nitrogen utilization efficiency compared to control tobacco plants grown under similar conditions.

Example 9. Development of Novel Mutations to Improve Nitrogen Utilization Efficiency Via Random Mutagenesis Random mutagenesis of tobacco plants are performed using ethyl methanesulfonate (EMS) mutagenesis or fast neutron bombardment. EMS mutagenesis consists of chemically inducing random point mutations. Fast neutron mutagenesis consists of exposing seeds to neutron bombardment which causes large deletions through double stranded DNA breakage.

For EMS mutagenesis, one gram (approximately 10,000 seeds) of the Burley tobacco variety TN90 seeds are washed in 0.1% Tween for fifteen minutes and then soaked in 30 mL of ddH$_2$O for two hours. One hundred fifty (150) µL of 0.5% EMS (Sigma, Catalogue No. M-0880) is then mixed into the seed/ddH$_2$O solution and incubated for 8-12 hours (rotating at 30 R.P.M.) under a hood at room temperature (RT; approximately 20° C.). The liquid then is removed from the seeds and mixed into 1 M NaOH overnight for decontamination and disposal. The seeds are then washed twice with 100 mL ddH$_2$O for 2-4 hours. The washed seeds are then suspended in 0.1% agar solution.

The EMS-treated seeds in the agar solution are evenly spread onto water-soaked Carolina's Choice Tobacco Mix (Carolina Soil Company, Kinston, N.C.) in flats at ~2000 seeds/flat. The flats are then covered with plastic wrap and placed in a growth chamber. Once the seedlings emerge from the soil, the plastic wrap is punctured to allow humidity to decline gradually. The plastic wrap is completely removed after two weeks. Flats are moved to a greenhouse and fertilized with NPK fertilizer. The seedlings are replugged into a float tray and grown until transplanting size. The plants are subsequently transplanted into a field. During growth, the plants self-pollinate to form M1 seeds. At the mature stage, five capsules are harvested from each plant and individual designations are given to the set of seeds from each plant. This forms the M1 population. A composite of M1 seed from each M0 plant are grown, and plants are phenotypically evaluated for enhanced nitrogen efficiency as described in Example 4. M1 plants exhibiting enhanced nitrogen efficiency are selected and screened for mutations using DNA sequencing and gene mapping techniques known in the art.

Example 10. Using Breeding to Create a Tobacco Plant with Enhanced Nitrogen Utilization Efficiency Traditional breeding techniques can be used to introduce NUE favorable alleles provided herein into any tobacco variety to enhance NUE. A population of tobacco plants can be created by crossing a tobacco plant with at least one favorable NUE allele (See Table 10) to a tobacco plant lacking that favorable allele. Marker assisted selection, or other techniques known in the art (e.g. direct sequencing) can be used to track introgression of a favorable allele in the $F_1$ generation and can be used to determine heterozygosity or homozygosity in subsequent generations. Enhanced NUE of progeny plants can be determined using methods known in the art or described above. Multiple different NUE favorable alleles can be combined into a single line. A molecular phenotype as determined by metabolite signature can be used to track enhanced NUE during breeding. The metabolite signatures of progeny plants can be determined using methods described above. Progeny plants with metabolite signatures of parental plants with enhanced NUE are crossed to create subsequent populations of tobacco plants with enhanced NUE.

Figure 3:
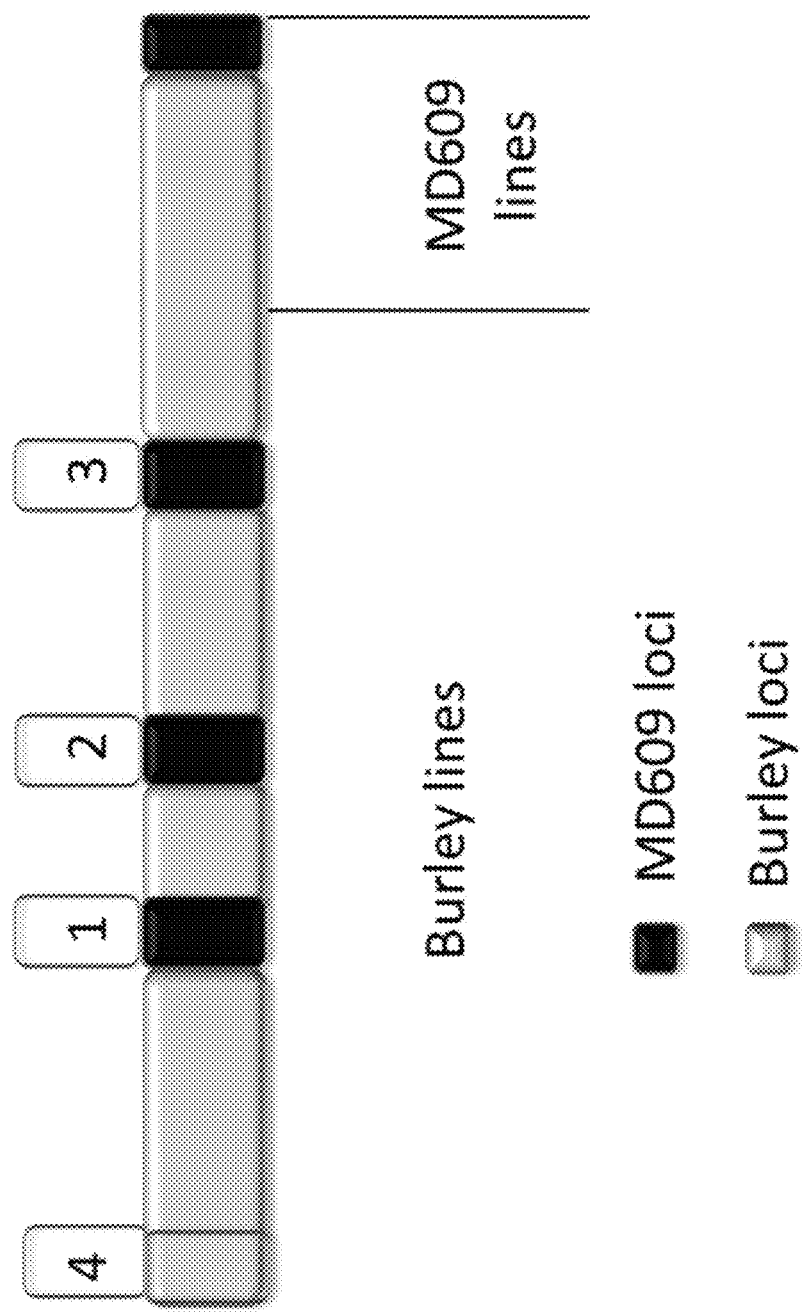
FIG. 3 depicts the allelic constitution for 23 Burley and 6 Maryland varieties at a genetic locus correlated with NUE on tobacco chromosome 11. Lines 1, 2, and 3 are Burley lines that contain a favorable Maryland allele at SEQ ID NO:58, and line 4 is a standard Burley line that contains an unfavorable Burley allele at SEQ ID NO:58.
Figure 4:
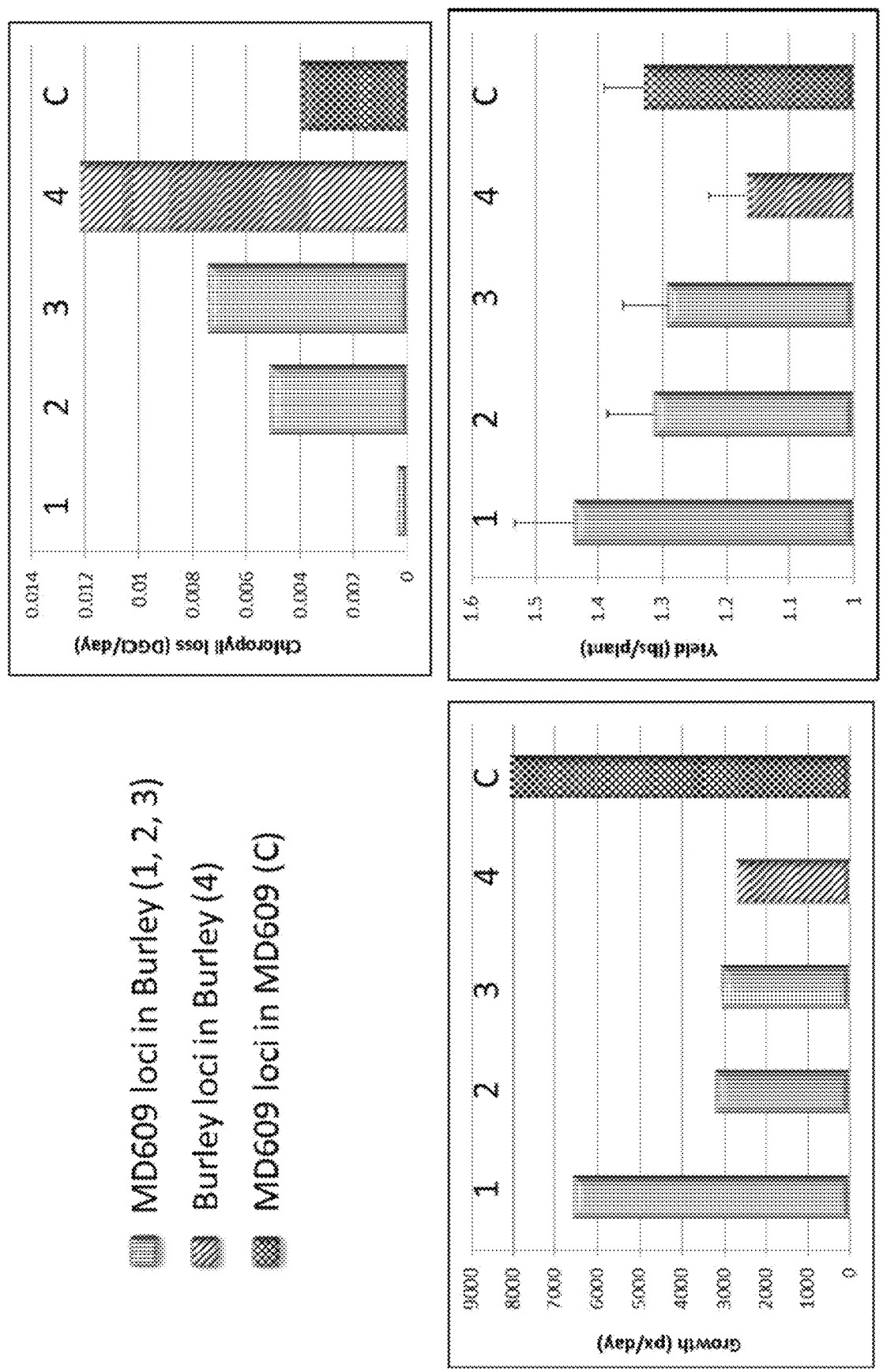
FIG. 4 depicts chlorophyll loss, growth, and yield for Lines 1 to 4 as described in FIG. 3 and a MD609 control (C). Lines 1, 2, and 3 are Burley lines that contain a favorable Maryland allele at SEQ ID NO:58 and line 4 is a standard Burley line that contains an unfavorable Burley allele at SEQ ID NO:58.

Introduction of Maryland609 loci into commercially available Burley varieties can be performed as described to develop Burley lines with enhanced NUE. Screening of 23 Burley and 6 MD609 lines identified 3 Burley lines containing the MD609 allele at SNP marker S451 (SEQ ID NO:58) (FIG. 3). The three Burley lines with the MD609 allele were tested for chlorophyll loss, growth, and yield under nitrogen limiting conditions and compared to a control TN90 Burley line and a control MD609 line (MD609 with the MD609 allele at SNP marker 5451) (FIG. 4). The Burley lines with the MD609 allele exhibit chlorophyll lose, growth, and yield more similar to the Maryland control (FIG. 4). The TN90 Burley control exhibits increased chlorophyll lose, decreased growth, and decreased yield compared to the MD609 control (FIG. 4). These results indicate that introduction of the MD609 allele at SNP marker S451 can enhance NUE.

Figure 6:
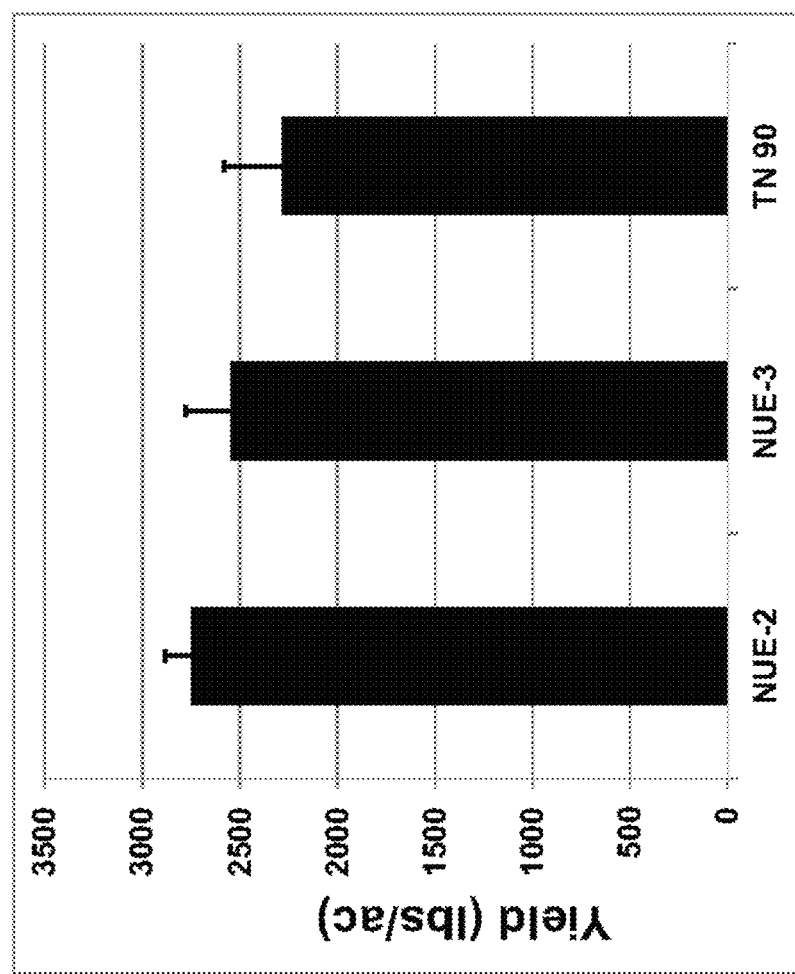
FIG. 6 depicts yield in pounds per acre after harvest for two independent field grown $F_4$ lines, NUE-2 and NUE-3. The test lines are generated from crosses of MD609 to Burley TN90 as described. The mean and standard deviation is provided in comparison to control TN90 Burley tobacco.

In order to introduce MD609 alleles into Burley, MD609 was crossed with Burley. Ft progeny from this cross were selected and subsequently selfed to produce $F_2$ seed. $F_2$ and $F_3$ plants were grown and selfed to generate $F_4$ seed. Bulked $F_4$ seed from two independent crossing schemes, identified as the NUE-2 and NUE-3 lines, are grown and harvested in the field. The genotypes of the SNP markers S451, S317, S12385, S238, S3894, and S2237 are determined for $F_4$ seed of both NUE-2 and NUE-3 lines (See Table 13). $F_4$ plants are grown using reduced nitrogen production practices described in Example 1. Both NUE-2 and NUE-3 lines demonstrate an increased yield in pounds per acre compared to the Burley control TN90 (See FIG. 6).

Alternatively, a modified tobacco plant comprising an enhanced NUE phenotype can be created using the methods described herein and crossed to a unmodified tobacco plant to propagate the modification in subsequent generations. Selection for the genetic modification can be tracked using appropriate techniques known in the art. Enhanced NUE of progeny plants can be determined using methods known in the art or described above.

TABLE 13

Genotypes of field grown plants from F₄ NUE-2 and NUE-3 lines and TN90. MD represents a MD609 allele, Burley represents a Burley allele, and HET represents a heterozygous MD609/Burley.

|  | S451 | S317 | S12835 | S238 | S3894 | S2237 |
|---|---|---|---|---|---|---|
| NUE-2 | MD | HET | MD | Burley | Burley | MD |
| NUE-3 | MD | HET | MD | Burley | Burley | MD |
| TN90 | Burley | Burley | Burley | Burley | Burley | Burley |

What is claimed is:

1. A method of producing a tobacco plant comprising an enhanced nitrogen utilization efficiency (NUE) trait, said method comprising:
   a. providing a first population of tobacco plants comprising at least one tobacco plant comprising an enhanced NUE trait;
   b. obtaining nucleic acids from said first population of tobacco plants;
   c. genotyping said nucleic acids from said first population of tobacco plants via a molecular assay for the presence of one or more molecular markers located within 10 cM of a SNP marker comprising SEQ ID NO: 58;
   d. selecting a tobacco plant comprising said one or more molecular markers and a favorable NUE allele at SEQ ID NO: 58;
   e. crossing said tobacco plant selected in step (d) with a second tobacco plant; and
   f. obtaining progeny seed from the cross of step (e) wherein a plant grown from said progeny seed comprises an enhanced NUE trait and said SNP marker.

2. The method of claim 1, wherein said SNP marker comprises a favorable NUE allele selected from the group consisting of:
   a G nucleotide at a position corresponding to position 57 of SEQ ID NO: 58, and
   a C nucleotide at a position corresponding to position 117 of SEQ ID NO: 58.

3. The method of claim 1, wherein said enhanced NUE trait is selected from the group consisting of an increased partial factor productivity (PFP), an increased agronomic efficiency (AE), an increased recovery efficiency (RE), an increased physiological efficiency (PE), and an increased internal efficiency (IE), when compared to a tobacco plant lacking said enhanced NUE trait when grown in the same conditions.

4. The method of claim 1, wherein said first population of tobacco plants is selected from the group consisting of MD609, MD601, Banket A1, K326, K346, K358, K394, K399, K730, NC196, NC37NF, NC471, NC55, NC92, NC2326, NC95, and NC925.

5. The method of claim 1, wherein said second tobacco plant is a Burley tobacco variety.

6. The method of claim 1, wherein said second tobacco plant is selected from the group consisting of TN86, TN86LC, TN90, TN90LC, TN97, and TN97LC.

7. The method of claim 1, wherein said one or more molecular markers are within 5 cM of a favorable NUE allele selected from the group consisting of:
   a G nucleotide at a position corresponding to position 57 of SEQ ID NO: 58, and
   a C nucleotide at a position corresponding to position 117 of SEQ ID NO: 58.

8. The method of claim 1, wherein said one or more molecular markers are within 3 cM of a favorable NUE allele selected from the group consisting of:
   a G nucleotide at a position corresponding to position 57 of SEQ ID NO: 58, and
   a C nucleotide at a position corresponding to position 117 of SEQ ID NO: 58.

9. The method of claim 1, wherein said one or more molecular markers are within 1 cM of a favorable NUE allele selected from the group consisting of:
   a G nucleotide at a position corresponding to position 57 of SEQ ID NO: 58, and
   a C nucleotide at a position corresponding to position 117 of SEQ ID NO: 58.

10. The method of claim 1, wherein said molecular marker is selected from the group consisting of a SNP marker, an INDEL marker, an RFLP marker, an SSR marker, an AFLP marker, and a RAPD marker.

11. A method of introgressing an enhanced NUE trait into a tobacco variety, said method comprising the steps of:
   a. crossing a first tobacco variety comprising an enhanced nitrogen utilization efficiency trait with a second tobacco variety lacking said enhanced nitrogen utilization efficiency trait;
   b. obtaining progeny seed from the cross of step (a);
   c. genotyping at least one of said progeny seed obtained in step (b) via a molecular assay for a molecular marker linked within 10 cM to a SNP marker comprising SEQ ID NO: 58; and
   d. selecting a progeny seed comprising at least one favorable NUE allele at said SNP marker and further comprising said enhanced nitrogen utilization efficiency trait.

12. The method of claim 11, wherein said SNP marker comprises a favorable NUE allele selected from the group consisting of
   a G nucleotide at a position corresponding to position 57 of SEQ ID NO: 58, and
   a C nucleotide at a position corresponding to position 117 of SEQ ID NO: 58.

13. The method of claim 11, wherein said second tobacco variety is a Burley tobacco variety.

14. The method of claim 11, wherein said second tobacco variety is selected from the group consisting of TN86, TN86LC, TN90, TN90LC, TN97, and TN97LC.

15. The method of claim 11, where said molecular marker is linked within 5 cM to a SNP marker comprising a favorable NUE allele selected from the group consisting of
   a G nucleotide at a position corresponding to position 57 of SEQ ID NO: 58, and
   a C nucleotide at a position corresponding to position 117 of SEQ ID NO: 58.

16. The method of claim 11, where said molecular marker is linked within 3 cM to a SNP marker comprising a favorable NUE allele selected from the group consisting of
   a G nucleotide at a position corresponding to position 57 of SEQ ID NO: 58, and
   a C nucleotide at a position corresponding to position 117 of SEQ ID NO: 58.

17. The method of claim 11, where said molecular marker is linked within 1 cM to a SNP marker comprising a favorable NUE allele selected from the group consisting of
   a G nucleotide at a position corresponding to position 57 of SEQ ID NO: 58, and
   a C nucleotide at a position corresponding to position 117 of SEQ ID NO: 58.

18. The method of claim 11, wherein said enhanced NUE trait is selected from the group consisting of an increased partial factor productivity (PFP), an increased agronomic efficiency (AE), an increased recovery efficiency (RE), an increased physiological efficiency (PE), and an increased internal efficiency (IE), when compared to a tobacco plant lacking said enhanced NUE trait when grown in the same conditions.

19. The method of claim 11, wherein said first population of tobacco plants is selected from the group consisting of MD609, MD601, Banket A1, K326, K346, K358, K394, K399, K730, NC196, NC37NF, NC471, NC55, NC92, NC2326, NC95, and NC925.

* * * * *